(12) United States Patent
Le et al.

(10) Patent No.: US 12,186,324 B2
(45) Date of Patent: *Jan. 7, 2025

(54) IMIDAZOPIPERAZINE INHIBITORS OF TRANSCRIPTION ACTIVATING PROTEINS

(71) Applicant: Board of Regents, The University of Texas System, Austin, TX (US)

(72) Inventors: Kang Le, Sugar Land, TX (US); Michael J. Soth, Sugar Land, TX (US); Philip Jones, Houston, TX (US); Jason Bryant Cross, Pearland, TX (US); Christopher L. Carroll, Houston, TX (US); Timothy Joseph McAfoos, Pearland, TX (US); Pijus Kumar Mandal, Sugarland, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 756 days.

This patent is subject to a terminal disclaimer.

(21) Appl. No.: 17/327,217

(22) Filed: May 21, 2021

(65) Prior Publication Data

US 2023/0008047 A1 Jan. 12, 2023

Related U.S. Application Data

(63) Continuation of application No. 16/370,404, filed on Mar. 29, 2019, now Pat. No. 11,058,688.

(60) Provisional application No. 62/650,151, filed on Mar. 29, 2018.

(51) Int. Cl.
| | | |
|---|---|---|
| C07D 487/04 | (2006.01) |
| A61K 31/4985 | (2006.01) |
| A61K 31/5377 | (2006.01) |
| C07D 471/04 | (2006.01) |
| C07D 495/04 | (2006.01) |

(52) U.S. Cl.
CPC ...... *A61K 31/5377* (2013.01); *A61K 31/4985* (2013.01); *C07D 471/04* (2013.01); *C07D 487/04* (2013.01); *C07D 495/04* (2013.01)

(58) Field of Classification Search
CPC ... C07D 471/04; C07D 487/04; C07D 495/04
See application file for complete search history.

(56) References Cited

U.S. PATENT DOCUMENTS

| | | |
|---|---|---|
| 7,732,603 B2 | 6/2010 | McKenna |
| 8,772,279 B2 | 7/2014 | Mirizzi |
| 9,145,418 B2 | 9/2015 | Casuscelli |
| 9,695,176 B2 | 7/2017 | Degnan |
| 10,899,769 B2 | 1/2021 | Le |
| 11,058,688 B2 | 7/2021 | Le |
| 2007/0004736 A1 | 1/2007 | Kubo |
| 2009/0149450 A1 | 6/2009 | Beckett |
| 2010/0093740 A1 | 4/2010 | Aissaoui |
| 2010/0240641 A1 | 9/2010 | Papillon |
| 2011/0034443 A1 | 2/2011 | Beckett |
| 2011/0190292 A1 | 8/2011 | Dhar |
| 2012/0220766 A1 | 8/2012 | Tang |
| 2016/0113893 A1 | 4/2016 | Mulvany |
| 2019/0298729 A1 | 10/2019 | Le |
| 2019/0308978 A1 | 10/2019 | Le |

FOREIGN PATENT DOCUMENTS

| | | |
|---|---|---|
| CN | 103087067 | 5/2013 |
| WO | 2008078291 | 7/2008 |
| WO | 2008157751 | 12/2008 |
| WO | 2009065298 | 5/2009 |
| WO | 2009082881 | 7/2009 |
| WO | 2009156951 | 12/2009 |
| WO | 2012019427 | 2/2012 |
| WO | 2014199171 | 12/2014 |
| WO | 2016055028 | 4/2016 |
| WO | 2016086200 | 6/2016 |
| WO | 2016113273 | 7/2016 |
| WO | 2016170323 | 10/2016 |
| WO | 2016170324 | 10/2016 |
| WO | 2017184462 | 10/2017 |
| WO | 2017205536 | 11/2017 |
| WO | 2017205538 | 11/2017 |
| WO | 2019191667 | 10/2019 |
| WO | 2019195846 | 10/2019 |

OTHER PUBLICATIONS

Lala, et al. Cancer and Metastasis Reviews (1998), 17(1), 91-106.*
Golub, et al. Science 286, 531 (1999).*
Cancer [online], [retrieved on Aug. 11, 2023]. Retrieved from the internet, URL https://medlineplus.gov/cancer.html#>.*
Bronner, S. et al., "A Unique Approach to Design Potent and Selective Cyclic Adenosine Monophosphate Response Element Binding Protein (CBP) Inhibitors", J Med Chem., 60(24):10151-71, (2017).
CA Registry No. 1069782-59-7 entered into the CA Registry File on Nov. 2, 2008 supplied by ChemBridge Corporation. (Year: 2008).
ChemBridge Product Guide, 2 pages, retrieved from the internet at http://www.chembridge.com/screening_libraries/ on Aug. 9, 2015. (Year: 2015).
Crawford, T. et al., "Discovery of a Potent and Selective In Vivo Probe (GNE-272) for the Bromodomains of CBP/EP300", J Med Chem., 59(23):10549-63, (2016).
Dörwald, F., "Side Reactions in Organic Synthesis: A Guide to Successful Sysnthesis Design", Wiley: VCH, Weinheim, pages: Preface IX, 1-16, 40-41, 278-309, (2005).

(Continued)

*Primary Examiner* — Shawquia Jackson
(74) *Attorney, Agent, or Firm* — Global Patent Group Inc.; Lauren L. Stevens; Erik M. Larsen

(57) ABSTRACT

The present disclosure relates to heterocyclic compounds and methods which may be useful as inhibitors of transcription activating proteins such as CBP and P300 for the treatment or prevention of diseases such as proliferative diseases, inflammatory disorders, autoimmune diseases, and fibrotic diseases.

26 Claims, No Drawings

(56) References Cited

OTHER PUBLICATIONS

International Application No. PCT/US2019/022727; International Search Report and Written Opinion of the International Searching Authority, date of mailing May 14, 2019; 8 pages.
International Application No. PCT/US2019/024976; International Preliminary Report on Patentability, date of issuance Oct. 8, 2020; 7 pages.
International Application No. PCT/US2019/024976; International Search Report and Written Opinion of the International Searching Authority, date of mailing Jul. 22, 2019; 11 pages.
International Application No. PCT/US2019/026379; International Preliminary Report on Patentability, date of issuance Oct. 15, 2020; 6 pages.
International Application No. PCT/US2019/026379; International Search Report and Written Opinion of the International Searching Authority, date of mailing Jul. 30, 2019; 8 pages.
Lai, K. et al., "Design and Synthesis of a Biaryl Series as Inhibitors for the Bromodomains of CBP/P300", Bioorg Med Chem Lett., 28(1):15-23, (2018).
Machine Translation for CN 103087067 (May 8, 2013). (Year: 2013).
PubChem CID: 89233298, Compound Summary ZNFWDQVOYHEDS0-UHFFFAOYSA-N Create Date: Feb. 13, 2015, 8 pages.
Romero, F. et al., "GNE-781, A Highly Advanced Potent and Selective Bromodomain Inhibitor of Cyclic Adenosine Monophosphate Response Element Binding Protein, Binding Protein (CBP)", J Med Chem., 60(22):9162-83, (2017).
Taylor, A.M. et al., "Fragment-Based Discovery of a Selective and Cell-Active Benzodiazepinone CBP/EP300 Bromodomain Inhibitor (CPI-637)", Acs. Med. Chem. Lett., 7:531-6, (2016).
U.S. Appl. No. 16/370,404; Examiner-Initiated Interview Summary, dated Oct. 28, 2020; 2 pages.
U.S. Appl. No. 16/370,404; Non-Final Office Action, dated Dec. 12, 2019; 18 pages.
U.S. Appl. No. 16/370,404; Notice of Allowance, dated Feb. 22, 2021; 5 pages.
U.S. Appl. No. 16/370,404; Notice of Allowance, dated Oct. 28, 2020; 6 pages.
U.S. Appl. No. 16/378,309; Non-Final Office Action, dated Jan. 14, 2020; 19 pages.
U.S. Appl. No. 16/378,309; Notice of Allowance, dated Aug. 26, 2020; 7 pages.
Venkatesh, S. et al., "Role of the Development Scientist in Compound Lead Selection and Optimization", J Pharm Sci., 89(2):145-54, (2000).
Bouchal, J. et al., "Transcriptional coactivators p300 and CBP stimulate estrogen receptor-beta signaling and regulate cellular events in prostate cancer", Prostate, 71(4):431-7, (2011).
Conery, A. et al., "Bromodomain inhibition of the transcriptional coactivators CBP/EP300 as a therapeutic strategy to target the IRF4 network in multiple myeloma", Elife, 5:e10483, 17 pages, (2016).
Database PubChem [online]: "3-[3-cyclopentyl-1-(4-methoxyphenyl)-6,8-dihydro-5H-imidazo[1,5-a]pyrazine-7-carbonyl]-1-methylquinolin-4-one", Database accession No. 26223485, (2009).
Database PubChem [online]: "3-Methyl-7-(2-methylpropanoyl)-6,8-dihydro-5H-imidazo [I,5-a]pyrazine-1-carbaldehyde", Database accession No. 115267846, (2016).
Database PubChem [online]: "3-Methyl-7-propanoyl-6,8-dihydro-5H-imida zo[I,5-a]pyrazine-1-carbaldehyde", Database accession No. 115267844, (2016).
Database PubChem [online]: "7-Acetyl-6,8-dihydro-5H-imidazo[I,5-a]pyr azine-I-carboxylic acid", Database accession No. 83834364, (2014).
Database PubChem [online]: "7-Propanoyl-6,8-dihydro-5H-imidazo[I,5-a] pyrazine-I-carbaldehyde", Database accession No. 115267864, (2016).
Gatla, H. et al., "Epigenetic regulation of interleukin-8 expression by class I HDAC and CBP in ovarian cancer cells", Oncotarget, 8(41):70798-810, (2017).
Geldenhuys, W. et al., "Virtual Screening to Identify Novel Antagonists for the G Protein-Coupled NK3 Receptor", J Med Chem., 53(22):8080-8, (2010).
Giotopoulos, G. et al., "The epigenetic regulators CBP and p300 facilitate leukemogenesis and represent therapeutic targets in acute myeloid leukemia", Oncogene, 35(3):279-89, (2016).
Mulvihill, M. et al., "Discovery of OSI-906: a selective and orally efficacious dual inhibitor of the IGF-1 receptor and insulin receptor", Future Med Chem., 1(6):1153-71, (2009).
Ogiwara, H. et al., "Targeting p300 Addiction in CBP-Deficient Cancers Causes Synthetic Lethality by Apoptotic Cell Death due to Abrogation of MYC Expression", Cancer Discov., 6(4):430-45, (2016).
Picaud, S. et al., "Generation of a Selective Small Molecule Inhibitor of the CBP/p300 Bromodomain for Leukemia Therapy", Cancer Res., 75(23):5106-19, (2015).
Thornber, C., "Isosterism and Molecular Modification in Drug Design", Chem Soc Rev., 4(8):563-80, (1979).
Yan, G. et al., "Selective inhibition of p300 HAT blocks cell cycle progression, induces cellular senescence, and inhibits the DNA damage response in melanoma cells", J Invest Dermatol., 133(10):2444-52, (2013).
Yang, H. et al., "Small-molecule inhibitors of acetyltransferase p300 identified by high-throughput screening are potent anticancer agents", Mol Cancer Ther., 12(5):610-20, (2013).

* cited by examiner

IMIDAZOPIPERAZINE INHIBITORS OF TRANSCRIPTION ACTIVATING PROTEINS

This application is a continuation of U.S. application Ser. No. 16/370,404, filed Mar. 29, 2019, which claims the benefit of priority of U.S. Provisional Application No. 62/650,151, filed Mar. 29, 2018, the disclosures of which are hereby incorporated by reference as if written herein in their entireties.

Disclosed herein are new imidazo[1,5-a]pyrazine compounds and compositions and their application as pharmaceuticals for the treatment of disease. Methods of inhibition of the activity of transcription activating proteins such as CBP and P300 in a human or animal subject are also provided for the treatment of diseases such as cancer.

Chromatin is a combination of DNA and protein, found in eukaryotic nuclei, that makes up chromosomes. Chromatin can be classified as either heterochromatin (condensed) and euchromatin (extended) forms. The major protein components of chromatin are termed histones, which serve as scaffolds on which DNA is packaged and compacted into a smaller volume to fit in the nucleus. Histones are implicated in the processes of mitosis and meiosis, and are thought to play important roles in the expression and replication of DNA. Importantly, histones undergo post-translational modification ("PTM") at various amino acid sites, which modulates chromatin structure and thereby affects transcription. This modification provides a mechanism for "epigenetics", or the control of gene activity and expression that does not arise from the direct alteration of the DNA sequence.

Acetylation of lysine residues is a PTM with broad relevance to cellular signaling and disease biology. Lysine acetylation, which is particularly abundant in nuclear macromolecular complexes, plays a key role in chromatin regulation and transcriptional control. In cells, the principal 'readers' of the acetyl-lysine marks are the bromodomains (BRDs), which are a diverse family of evolutionary conserved protein-protein interaction modules that specifically recognize and bind to acetylated lysine residues. The bromodomains, together with the enzymes that 'write' (Histone acetyl transferases, HATs) and 'erase' (histone deacetylases, HDACs) acetylated lysine residues on histone and non-histone proteins, critically control the regulation of gene expression and thereby cell phenotype including proliferation, cell differentiation and metabolism. Besides chromatin, many other proteins are also post-translationally modified such as p53, which could also be potentially recognized by bromodomain proteins. Because chromatin-mediated processes are often deregulated in cancer, targeting epigenetic reader proteins like BET (dual-BRD4 containing proteins), CREBBP, ATAD2A, SMARCA2/4 and Tripartite Motif-containing 24 (TRIM24) represent promising targets for drug discovery. As illustrated by the development of selective inhibitors of the BET family of bromodomains, the conserved BRD fold represents a promising pocket for the development of small pharmaceutically active molecules.

The histone acetyltransferase paralogues, cyclic adenosine monophosphate response element binding protein, binding protein (CBP, CREBBP, or CREB-binding protein) and adenoviral E1A binding protein of 300 kDa (P300 or EP300), are highly homologous and are two closely related multi-domain transcription activating proteins containing both a histone acetyl transferase (HAT) as well as a bromodomain, and have important roles in histone acetylation. They are key transcriptional co-activators that are essential for a multitude of cellular processes, and have also been implicated in several human pathological conditions, including cancer.

CBP and P300 bind to chromatin via their bromodomains, and once associated with chromatin, this complex recruits additional transcriptional machinery to modulate gene expression leading to the recruitment of various transcriptional proteins to modulate gene expression. In addition to chromatin, CBP/P300 have been shown to bind non-histone proteins; for instance, CBP has been described to recognize acetylated p53 at K382 following DNA damage. Several studies have implicated CBP/P300 in the development, maintenance, and/or progression of cancer and tumor immunity, and therefore CBP/P300 inhibitors are the target of current efforts to develop anti-cancer agents. In particular, CBP has been found to regulate expression of MYC, a transcription factor and oncogene widely up-regulated in many human cancers, which suggests a potential therapeutic strategy for targeting multiple myeloma and other lymphoid malignancies, and solid tumors.

In addition, CBP and P300 are known co-activators of the androgen receptor (AR), and have been implicated in enhancing the response to androgen. Consistent with this, CBP/P300 have been proposed to play an oncogenic role in prostate cancer, and up-regulation of both proteins has been observed in tumors. CBP inhibitors selectively inhibit proliferation in lineage-specific tumour types, including several hematological malignancies and androgen receptor-positive prostate cancer. CBP inhibitors inhibit the androgen receptor transcriptional program in both androgen-sensitive and castration-resistant prostate cancer and inhibit tumour growth in prostate cancer xenograft models.

CBP also has relevance to cancer immunotherapy, and the ability of CBP bromodomain inhibitors to impair Treg differentiation and suppressive function has been described. This activity could constitute a novel small molecule approach to enhance the response to cancer immunotherapy.

Compounds and pharmaceutical compositions, certain of which have been found to bind to and inhibit interactions of CBP and P300 have been discovered, together with methods of synthesizing and using the compounds including methods for the treatment of CBP- and P300-mediated diseases in a patient by administering the compounds.

DETAILED DESCRIPTION

Provided herein is Embodiment 1: a compound having structural Formula I:

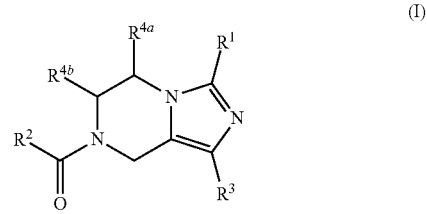

or a salt thereof, wherein:
$R^1$ is H or is chosen from alkyl, amino, alkoxy, heteroalkyl, cycloalkyl, heterocycloalkyl, halo, haloalkyl, sulfonylalkyl, aryl, and heteroaryl, any of which is optionally substituted with 1, 2, or 3 $R^5$ groups;

$R^2$ is H or is chosen from alkyl, haloalkyl, amino, alkoxy, cycloalkyl, and heterocycloalkyl, any of which is optionally substituted with 1 or 2 $R^6$ groups;

$R^3$ is chosen from alkyl, amino, alkoxy, heteroalkyl, cycloalkyl, heterocycloalkyl, carbonyl, sulfonyl, aryl, and heteroaryl, any of which is:
(a) optionally substituted with 1, 2, or 3 $R^7$ groups, and
(b) optionally substituted with 1 $R^8$ group;

$R^{4a}$ and $R^{4b}$ are independently chosen from H, alkyl, cycloalkyl and heterocycloalkyl;

each $R^5$, $R^6$, and $R^7$ is independently chosen from alkyl, alkoxy, cyano, carboxy, halo, haloalkyl, haloalkoxyl, hydroxy, and oxo;

$R^8$ is chosen from aryl, heteroaryl, and heterocycloalkyl, and is optionally substituted with 1, 2, or 3 $R^{10}$ groups; and each $R^{10}$ is independently chosen from alkyl, cycloalkyl, (cycloalkyl)alkyl, heterocycloalkyl, (heterocycloalkyl)alkyl, aryl, (aryl)alkyl, (heteroaryl)alkyl, alkoxy, cyano, carboxy, halo, haloalkyl, haloalkoxy, hydroxy, hydroxyalkyl, oxo, $CONH_2$, $CONHCH_3$, $SO_2CH_3$, and $SO_2NH_2$.

Certain compounds disclosed herein may possess useful inhibiting activity for CBP or P300, and may be used in the treatment or prophylaxis of a disease or condition in which CBP or P300 plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting CBP or P300. Other embodiments provide methods for treating a disorder mediated by CBP or P300 in a patient in need of such treatment, comprising administering to said patient a therapeutically effective amount of a compound or composition according to the present disclosure. Also provided is the use of certain compounds disclosed herein for use in the manufacture of a medicament for the treatment of a disease or condition ameliorated by the inhibition of CBP and P300.

In certain embodiments, $R^1$ is chosen from alkyl, amino, alkoxy, heteroalkyl, cycloalkyl, heterocycloalkyl, halo, haloalkyl, sulfonylalkyl, aryl, and heteroaryl, any of which is optionally substituted with 1, 2, or 3 $R^5$ groups.

In certain embodiments, $R^1$ is cycloalkyl, and is optionally substituted with 1 or 2 $R^5$ groups.

In certain embodiments, $R^1$ is cyclopropyl.

In certain embodiments, $R^2$ is chosen from alkyl, heteroalkyl, cycloalkyl, and heterocycloalkyl, any of which is optionally substituted with 1 or 2 $R^6$ groups.

In certain embodiments, $R^2$ is chosen from alkyl and cycloalkyl.

In certain embodiments, $R^2$ is chosen from $—CH_3$, $—CH_2F$, amino, and $—OCH_3$.

In certain embodiments, $R^2$ is chosen from $—CH_3$, $—CH_2F$, $—NH_2$, $—NHCH_3$, and $—OCH_3$.

In certain embodiments, $R^2$ is amino, and is optionally substituted with 1 or 2 $R^6$ groups.

In certain embodiments, $R^2$ is alkylamino.

In certain embodiments, $R^2$ is methylamino.

In certain embodiments, $R^2$ is methyl.

In certain embodiments, $R^2$ is methoxy.

In certain embodiments, $R^3$ is chosen from alkyl, amino, alkoxy, heteroalkyl, cycloalkyl, heterocycloalkyl, carbonyl, sulfonyl, aryl, and heteroaryl, any of which is:
(a) optionally substituted with 1, 2, or 3 $R^7$ groups, and
(b) substituted with 1 $R^8$ group.

In certain embodiments, $R^3$ is chosen from cycloalkyl, heterocycloalkyl, aryl, and heteroaryl, any of which is:
(a) optionally substituted with 1, 2, or 3 $R^7$ groups, and
(b) substituted with 1 $R^8$ group.

In certain embodiments, $R^3$ is chosen from aryl and heteroaryl, any of which is:
(a) optionally substituted with 1, 2, or 3 $R^7$ groups, and
(b) substituted with 1 $R^8$ group.

In certain embodiments, $R^3$ is heteroaryl, and is:
(a) optionally substituted with 1 or 2 $R^7$ groups, and
(b) substituted with 1 $R^8$ group.

In certain embodiments, $R^3$ is a nitrogen-containing heteroaryl, and is:
(a) optionally substituted with 1 or 2 $R^7$ groups, and
(b) substituted with 1 $R^8$ group.

In certain embodiments, $R^3$ is a bicyclic nitrogen-containing heteroaryl, and is:
(a) optionally substituted with 1 or 2 $R^7$ groups, and
(b) substituted with 1 $R^8$ group.

In certain embodiments, $R^3$ is a bicyclic heteroaryl containing 1 or 2 nitrogens, and is:
(a) optionally substituted with 1 or 2 $R^7$ groups, and
(b) substituted with 1 $R^8$ group.

In certain embodiments, $R^3$ is chosen from quinolinyl, isoquinolinyl, diazanaphthalenyl, 1,2,3,4-tetrahydroquinolinyl, 1,2,3,4-tetrahydroisoquinolinyl, indolyl, indazolyl, purinyl, and 7-deazapurinyl, and is:
(a) optionally substituted with 1 or 2 $R^7$ groups, and
(b) substituted with 1 $R^8$ group.

In certain embodiments, $R^{4a}$ and $R^{4b}$ are independently chosen from H and alkyl.

In certain embodiments, $R^{4a}$ and $R^{4b}$ are independently chosen from H and methyl.

In certain embodiments, at least one of $R^{4a}$ and $R^{4b}$ is H.

In certain embodiments, $R^{4a}$ and $R^{4b}$ are H.

In certain embodiments, each $R^5$, $R^6$, and $R^7$ is independently chosen from alkyl, alkoxy, halo, cyano, haloalkyl, haloalkoxy, hydroxy, and oxo.

In certain embodiments, $R^8$ is a monocyclic aryl or heteroaryl, and is optionally substituted with 1 or 2 $R^{10}$ groups.

In certain embodiments, $R^8$ is a nitrogen-containing heteroaryl, and is optionally substituted with 1 or 2 $R^{10}$ groups.

In certain embodiments, $R^8$ is chosen from pyrrolyl, isoxazolyl, thiazolyl, imidazolyl, and pyrazolyl, any of which is optionally substituted with 1 or 2 $R^{10}$ groups.

In certain embodiments, $R^8$ is chosen from pyrrolyl, imidazolyl, and pyrazolyl, any of which is optionally substituted with 1 or 2 $R^{10}$ groups.

Provided herein is Embodiment 1a: a compound having structural Formula Ia:

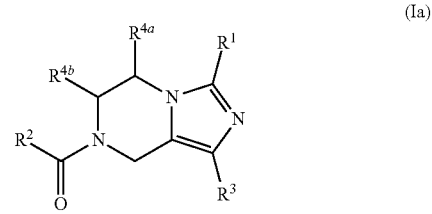

(Ia)

or a salt thereof, wherein:

$R^1$ is H or is chosen from alkyl, amino, alkoxy, heteroalkyl, cycloalkyl, heterocycloalkyl, halo, haloalkyl, sulfonylalkyl, aryl, and heteroaryl, any of which is optionally substituted with 1, 2, or 3 $R^5$ groups;

$R^2$ is H or is chosen from alkyl, haloalkyl, amino, alkoxy, cycloalkyl, and heterocycloalkyl, any of which is optionally substituted with 1 or 2 $R^6$ groups;

$R^3$ is chosen from aryl and heteroaryl, either of which is:
(a) optionally substituted with 1, 2, or 3 $R^7$ groups, and
(b) optionally substituted with 1 $R^8$ group;

$R^{4a}$ and $R^{4b}$ are independently chosen from H, alkyl, cycloalkyl and heterocycloalkyl;

each $R^5$, $R^6$, and $R^7$ is independently chosen from alkyl, alkoxy, cyano, carboxy, halo, haloalkyl, haloalkoxyl, hydroxy, and oxo;

$R^8$ is chosen from aryl, heteroaryl, and heterocycloalkyl, and is optionally substituted with 1, 2, or 3 $R^{10}$ groups; and each $R^{10}$ is independently chosen from alkyl, cycloalkyl, (cycloalkyl)alkyl, heterocycloalkyl, (heterocycloalkyl)alkyl, aryl, (aryl)alkyl, (heteroaryl)alkyl, alkoxy, cyano, carboxy, halo, haloalkyl, haloalkoxy, hydroxy, hydroxyalkyl, oxo, $CONH_2$, $CONHCH_3$, $SO_2CH_3$, and $SO_2NH_2$.

Provided herein is Embodiment 2: a compound having structural Formula II:

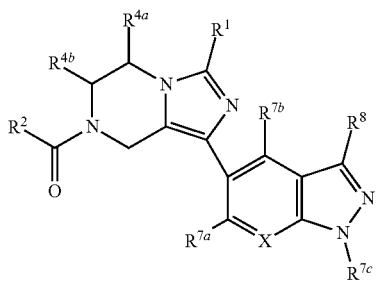

(II)

or a salt thereof, wherein:

$R^1$ is chosen from alkyl, cycloalkyl, and heterocycloalkyl, any of which is optionally substituted with 1 or 2 $R^5$ groups;

$R^2$ is H or is chosen from alkyl, haloalkyl, amino, alkoxy, cycloalkyl, and heterocycloalkyl, any of which is optionally substituted with 1 or 2 $R^6$ groups;

$R^{4a}$ and $R^{4b}$ are independently chosen from H, alkyl, cycloalkyl and heterocycloalkyl;

each $R^5$ and $R^6$ is independently chosen from alkyl, alkoxy, cyano, carboxy, halo, haloalkyl, hydroxy, and oxo;

$R^{7a}$, $R^{7b}$, and $R^{7c}$ are independently chosen from H, alkyl, alkoxy, cyano, carboxy, halo, haloalkyl, hydroxy, and oxo;

$R^8$ is chosen from aryl, heteroaryl, and heterocycloalkyl, and is optionally substituted with 1, 2, or 3 $R^{10}$ groups;

each $R^{10}$ is independently chosen from alkyl, cycloalkyl, (cycloalkyl)alkyl, heterocycloalkyl, (heterocycloalkyl)alkyl, aryl, (aryl)alkyl, (heteroaryl)alkyl, alkoxy, cyano, carboxy, halo, haloalkyl, haloalkoxy, hydroxy, hydroxyalkyl, oxo, $CONH_2$, $CONHCH_3$, $SO_2CH_3$, $SO_2NH_2$; and X is chosen from CH and N.

Embodiment 3: the compound of Embodiment 2, wherein Formula II, $R^{7a}$, $R^{7b}$, and $R^{7c}$ are independently chosen from H, alkyl, alkoxy, and haloalkyl.

Embodiment 4: the compound of either one of Embodiments 2 and 3, wherein at least one of $R^{7a}$, $R^{7b}$, and $R^{7c}$ is H.

Embodiment 5: the compound of any one of Embodiments 2-4, wherein at least two of $R^{7a}$, $R^{7b}$, and $R^{7c}$ are H.

Embodiment 6: the compound of Embodiment 5, wherein $R^{7c}$ is alkyl.

Embodiment 7: the compound of Embodiment 6, wherein $R^{7c}$ is methyl.

Embodiment 8: the compound of any one of Embodiments 2-5, wherein $R^{7a}$, $R^{7b}$, and $R^{7c}$ are H.

Embodiment 9: the compound of any one of Embodiments 2-8, wherein X is CH.

Embodiment 10: the compound of any one of Embodiments 2-8, wherein X is N.

Provided herein is Embodiment 11: a compound having structural Formula III:

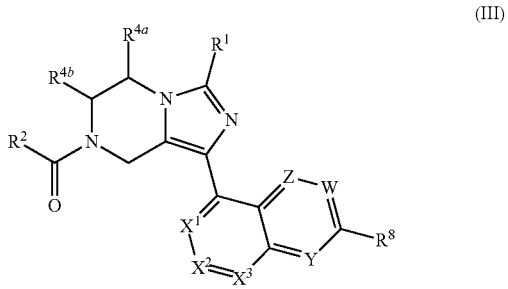

(III)

or a salt thereof, wherein:

$R^1$ is chosen from alkyl, cycloalkyl, and heterocycloalkyl, any of which is optionally substituted with 1 or 2 $R^5$ groups;

$R^2$ is H or is chosen from alkyl, haloalkyl, amino, alkoxy, cycloalkyl, and heterocycloalkyl, any of which is optionally substituted with 1 or 2 $R^6$ groups;

$R^{4a}$ and $R^{4b}$ are independently chosen from H, alkyl, cycloalkyl and heterocycloalkyl;

W is chosen from $C(R^{7a})$ and N;

$X^1$ is independently chosen from $C(R^{7b})$ and N;

$X^2$ and $X^3$ are independently chosen from C(H) and N;

Y and Z are independently chosen from CH and N;

each $R^5$ and $R^6$ is independently chosen from alkyl, alkoxy, cyano, carboxy, halo, haloalkyl, hydroxy, and oxo;

$R^{7a}$ is chosen from H, alkyl, alkoxy, cyano, carboxy, halo, haloalkyl, hydroxy, and oxo;

$R^{7b}$ is chosen from H and fluoro;

$R^8$ is chosen from aryl, heteroaryl, and heterocycloalkyl, and is optionally substituted with 1, 2, or 3 $R^{10}$ groups; and each $R^{10}$ is independently chosen from alkyl, cycloalkyl, (cycloalkyl)alkyl, heterocycloalkyl, (heterocycloalkyl)alkyl, aryl, (aryl)alkyl, (heteroaryl)alkyl, alkoxy, cyano, carboxy, halo, haloalkyl, haloalkoxy, hydroxy, hydroxyalkyl, oxo, $CONH_2$, $CONHCH_3$, $SO_2CH_3$, and $SO_2NH_2$.

Embodiment 12: the compound of Embodiment 11, wherein $R^{7b}$ is H.

Embodiment 13: the compound of Embodiment 11, wherein $R^{7b}$ is fluoro.

Embodiment 14: the compound of any one of Embodiments 11-13, wherein at least one of $X^1$, $X^2$, and $X^3$ is N.

Embodiment 15: the compound of any one of Embodiments 11-13, wherein at most one of $X^1$, $X^2$, and $X^3$ is N.

Embodiment 16: the compound of any one of Embodiments 11-13, wherein exactly one of $X^1$, $X^2$, and $X^3$ is N.

Embodiment 17: the compound of Embodiment 16, wherein:
$X^1$ is N,
$X^2$ is C(H), and
$X^3$ is C(H).

Embodiment 18: the compound of Embodiment 16, wherein:
$X^1$ is C($R^{7b}$),
$X^2$ is N, and
$X^3$ is C(H).

Embodiment 19: the compound of Embodiment 16, wherein:
$X^1$ is C($R^{7b}$),
$X^2$ is C(H), and
$X^3$ is N.

Embodiment 20: the compound of any one of Embodiments 11-19, wherein at most two of W, Y, and Z is N.

Embodiment 21: the compound of Embodiment 20, wherein exactly one of W, Y and Z is N.

Embodiment 22: the compound of any one of Embodiments 11-21, wherein W is C($R^{7a}$).

Embodiment 23: the compound of Embodiment 22, wherein Y is CH.

Embodiment 24: the compound of Embodiment 22, wherein Z is CH.

Embodiment 25: the compound of any one of Embodiments 22-24, wherein $R^{7a}$ is chosen from H, alkyl, alkoxy, cyano, and haloalkyl.

Embodiment 26: the compound of Embodiment 25, wherein $R^{7a}$ is H.

Embodiment 27: the compound of Embodiment 25, wherein $R^{7a}$ is methyl.

Embodiment 28: the compound of Embodiment 25, wherein $R^{7a}$ is cyano.

Embodiment 29: the compound of Embodiment 25, wherein $R^{7a}$ is haloalkyl.

Embodiment 30: the compound of Embodiment 29, wherein $R^{7a}$ is difluoromethyl.

Embodiment 31: the compound of Embodiment 29, wherein $R^{7a}$ is trifluoromethyl.

Embodiment 32: the compound of any one of Embodiments 11-21, wherein W is N.

Provided herein is Embodiment 33: a compound having structural Formula IV:

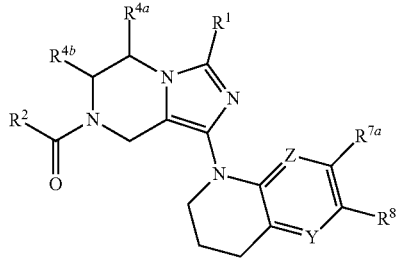

(IV)

or a salt thereof, wherein:
$R^1$ is chosen from alkyl, cycloalkyl, and heterocycloalkyl, any of which is optionally substituted with 1 or 2 $R^5$ groups;
$R^2$ is H or is chosen from alkyl, haloalkyl, amino, alkoxy, cycloalkyl, and heterocycloalkyl, any of which is optionally substituted with 1 or 2 $R^6$ groups;
$R^{4a}$ and $R^{4b}$ are independently chosen from H, alkyl, cycloalkyl and heterocycloalkyl;
each $R^5$ and $R^6$ is independently chosen from alkyl, alkoxy, cyano, carboxy, halo, haloalkyl, hydroxy, and oxo;
$R^{7a}$ is chosen from H, alkyl, alkoxy, cyano, carboxy, halo, haloalkyl, hydroxy, and oxo;
$R^8$ is chosen from aryl, heteroaryl, and heterocycloalkyl, and is optionally substituted with 1, 2, or 3 $R^{10}$ groups;
each $R^{10}$ is independently chosen from alkyl, cycloalkyl, (cycloalkyl)alkyl, heterocycloalkyl, (heterocycloalkyl)alkyl, aryl, (aryl)alkyl, (heteroaryl)alkyl, alkoxy, cyano, carboxy, halo, haloalkyl, haloalkoxy, hydroxy, hydroxyalkyl, oxo, $CONH_2$, $CONHCH_3$, $SO_2CH_3$, and $SO_2NH_2$; and
Y and Z are independently chosen from CH and N.

Embodiment 34: the compound of Embodiment 33, wherein exactly one of Y and Z is N.

Embodiment 35: the compound of Embodiment 33, wherein Y and Z are CH.

Embodiment 36: the compound of any one of Embodiments 33-34, wherein $R^{7a}$ is chosen from H, alkyl, alkoxy, cyano, and haloalkyl.

Embodiment 37: the compound of Embodiment 36, wherein $R^{7a}$ is H.

Embodiment 38: the compound of Embodiment 36, wherein $R^{7a}$ is haloalkyl.

Embodiment 39: the compound of Embodiment 38, wherein $R^{7a}$ is difluoromethyl.

Embodiment 40: the compound of Embodiment 38, wherein $R^{7a}$ is trifluoromethyl.

Provided herein is Embodiment 41: a compound having structural Formula V:

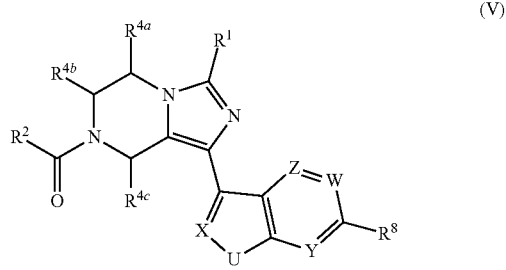

(V)

or a salt thereof, wherein:
$R^1$ is chosen from alkyl, cycloalkyl, and heterocycloalkyl, any of which is optionally substituted with 1 or 2 $R^5$ groups;
$R^2$ is H or is chosen from alkyl, haloalkyl, amino, alkoxy, cycloalkyl, and heterocycloalkyl, any of which is optionally substituted with 1 or 2 $R^6$ groups;
$R^{4a}$ and $R^{4b}$ are independently chosen from H, alkyl, cycloalkyl and heterocycloalkyl;
U is chosen from NH and S;
W is chosen from C($R^{7a}$) and N;
X is chosen from CH and N;
Y and Z are independently chosen from CH and N;
each $R^5$ and $R^6$ is independently chosen from alkyl, alkoxy, cyano, carboxy, halo, haloalkyl, hydroxy, and oxo;

$R^{7a}$ is chosen from H, alkyl, alkoxy, cyano, carboxy, halo, haloalkyl, hydroxy, and oxo;

$R^8$ is chosen from aryl, heteroaryl, and heterocycloalkyl, and is optionally substituted with 1, 2, or 3 $R^{10}$ groups; and each $R^{10}$ is independently chosen from alkyl, cycloalkyl, (cycloalkyl)alkyl, heterocycloalkyl, (heterocycloalkyl)alkyl, aryl, (aryl)alkyl, (heteroaryl)alkyl, alkoxy, cyano, carboxy, halo, haloalkyl, haloalkoxy, hydroxy, hydroxyalkyl, oxo, $CONH_2$, $CONHCH_3$, $SO_2CH_3$, and $SO_2NH_2$.

Embodiment 42: the compound of Embodiment 41, wherein U is NH.

Embodiment 43: the compound of Embodiment 41, wherein U is S.

Embodiment 44: the compound of any one of Embodiments 41-43, wherein at most two of W, Y, and Z is N.

Embodiment 45: the compound of Embodiment 44, wherein exactly one of W, Y and Z is N.

Embodiment 46: the compound of any one of Embodiments 41-45, wherein W is $C(R^{7a})$.

Embodiment 47: the compound of Embodiment 46, wherein $R^{7a}$ is chosen from H, alkyl, alkoxy, cyano, and haloalkyl.

Embodiment 48: the compound of Embodiment 47, wherein $R^{7a}$ is H.

Embodiment 49: the compound of Embodiment 47, wherein $R^{7a}$ is methyl.

Embodiment 50: the compound of Embodiment 47, wherein $R^{7a}$ is cyano.

Embodiment 51: the compound of Embodiment 47, wherein $R^{7a}$ is haloalkyl.

Embodiment 52: the compound of Embodiment 51, wherein $R^{7a}$ is difluoromethyl.

Embodiment 53: the compound of Embodiment 51, wherein $R^{7a}$ is trifluoromethyl.

Embodiment 54: the compound of any one of Embodiments 41-45, wherein W is N.

Embodiment 55: a compound of Embodiment 1, wherein $R^3$ is chosen from:

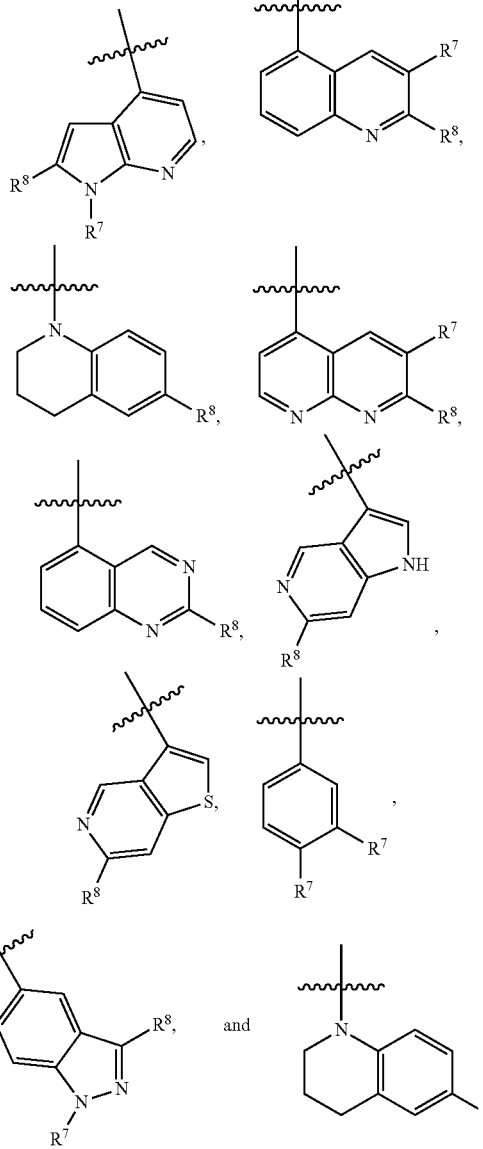

Embodiment 56: a compound of any one of Embodiments 1-55, wherein $R^3$ is substituted with 1 $R^8$ group.

Embodiment 57: a compound of Embodiment 56 wherein $R^8$ is optionally substituted with 1 or 2 $R^{10}$ groups.

Embodiment 58: a compound of Embodiment 57 wherein $R^8$ is substituted with 1 or 2 $R^{10}$ groups.

Embodiment 59: a compound of Embodiment 58 wherein $R^8$ is substituted with 1 $R^{10}$ group.

Embodiment 60: a compound of Embodiment 57 wherein $R^8$ is optionally substituted with 1 $R^{10}$ group.

Embodiment 61: a compound of any one of Embodiments 56-60 wherein each $R^{10}$ is independently chosen from alkyl, cyclopropyl, cyclobutyl, (cycloalkyl)methyl, heterocycloalkyl, aryl, (aryl)methyl, (heteroaryl)methyl, methoxy, cyano, halo, difluoromethyl, trifluoromethyl, trifluoromethoxy, hydroxy, hydroxyalkyl, oxo, $CONH_2$, and $CONHCH_3$.

Embodiment 62: a compound of Embodiment 61 wherein each $R^{10}$ is independently chosen from alkyl, cyclopropyl, methoxy, cyano, halo, difluoromethyl, trifluoromethyl, trifluoromethoxy, hydroxy, $CONH_2$, and $CONHCH_3$.

Embodiment 63: a compound of Embodiment 62 wherein each $R^{10}$ is alkyl.

Embodiment 64: a compound of Embodiment 63 wherein each $R^{10}$ is methyl.

Embodiment 65: a compound of Embodiment 60 wherein $R^8$ is not substituted with an $R^{10}$ group.

Embodiment 66: a compound of any one of Embodiments 56-65, wherein $R^8$ is heteroaryl.

Embodiment 67: a compound of Embodiment 66, wherein $R^8$ is 5-membered monocyclic heteroaryl.

Embodiment 68: a compound of Embodiment 67, wherein $R^8$ is chosen from pyrrolyl, pyrazolyl, imidazolyl, oxazolyl, isoxazolyl, furyl, thienyl, and thiazolyl.

Embodiment 69: a compound of Embodiment 66, wherein $R^8$ is 6-membered monocyclic heteroaryl.

Embodiment 70: a compound of Embodiment 69, wherein $R^8$ is chosen from pyridinyl, pyridazinyl, pyrimidinyl, and pyrazinyl.

Embodiment 71: a compound of any one of Embodiments 56-65, wherein $R^8$ is aryl.

Embodiment 72: a compound of Embodiment 71, wherein $R^8$ is phenyl.

Embodiment 73: a compound of Embodiment 56, wherein $R^8$ is chosen from:

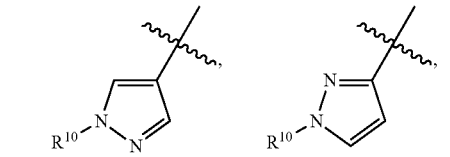
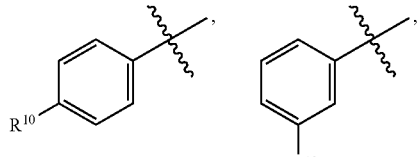
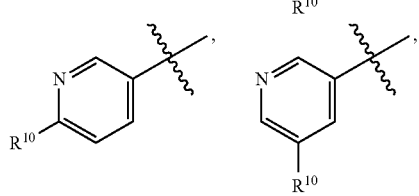
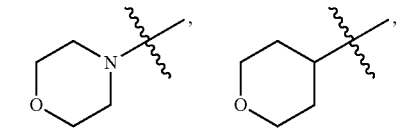
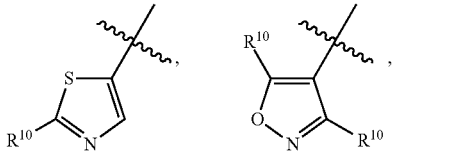
and
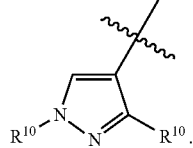

Embodiment 74: a compound of Embodiment 73, wherein $R^8$ is

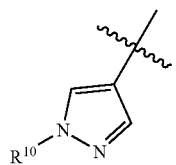

Embodiment 75: a compound of Embodiment 73, wherein $R^8$ is

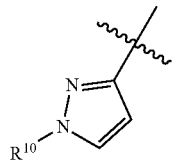

Embodiment 76: a compound of Embodiment 73, wherein $R^8$ is

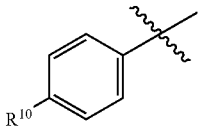

Embodiment 77: a compound of Embodiment 73, wherein $R^8$ is

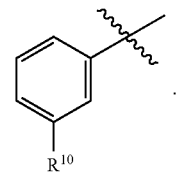

Embodiment 78: a compound of Embodiment 73, wherein $R^8$ is

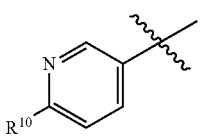

Embodiment 79: a compound of Embodiment 73, wherein $R^8$ is

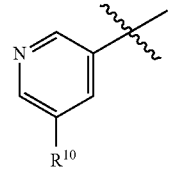

Embodiment 80: a compound of Embodiment 73, wherein R⁸ is

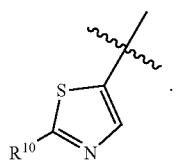

Embodiment 81: a compound of Embodiment 73, wherein R⁸ is

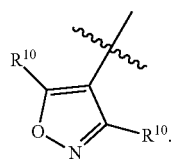

Embodiment 82: a compound of Embodiment 73, wherein R⁸ is

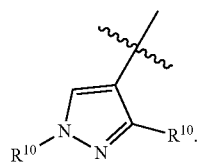

Embodiment 83: a compound of any one of Embodiments 73-82 wherein each $R^{10}$ is independently chosen from alkyl, cyclopropyl, cyclobutyl, (cycloalkyl)methyl, heterocycloalkyl, aryl, (aryl)methyl, (heteroaryl)methyl, methoxy, cyano, halo, difluoromethyl, trifluoromethyl, trifluoromethoxy, hydroxy, hydroxyalkyl, oxo, $CONH_2$, and $CONHCH_3$.

Embodiment 84: a compound of Embodiment 83 wherein each $R^{10}$ is independently chosen from alkyl, cyclopropyl, methoxy, cyano, halo, difluoromethyl, trifluoromethyl, trifluoromethoxy, hydroxy, $CONH_2$, and $CONHCH_3$.

Embodiment 85: a compound of Embodiment 84 wherein each $R^{10}$ is alkyl.

Embodiment 86: a compound of Embodiment 85 wherein each $R^{10}$ is methyl.

Embodiment 87: a compound of Embodiment 73, wherein R⁸ is

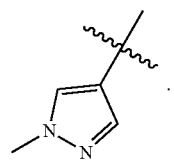

Embodiment 88: a compound of Embodiment 73, wherein R⁸ is

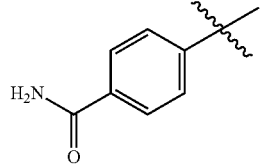

Embodiment 89: a compound of Embodiment 73, wherein R⁸ is

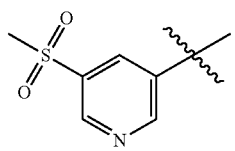

Embodiment 90: a compound of Embodiment 73, wherein R⁸ is

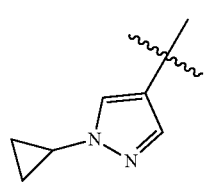

Embodiment 91: a compound of Embodiment 73, wherein R⁸ is

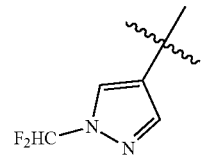

Embodiment 92: a compound of Embodiment 73, wherein R⁸ is

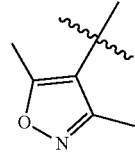

Embodiment 93: a compound of Embodiment 73, wherein R⁸ is

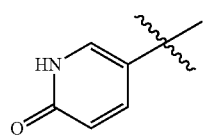

Embodiment 94: a compound of Embodiment 73, wherein R⁸ is

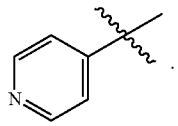

Embodiment 95: a compound of Embodiment 73, wherein R⁸ is

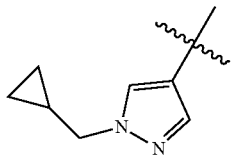

Embodiment 96: a compound of Embodiment 73, wherein R⁸ is

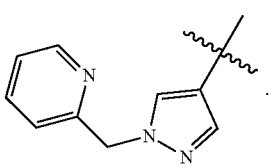 [SMILES: *c1cnn(Cc2ccccn2)c1]

Embodiment 97: a compound of Embodiment 73, wherein R⁸ is

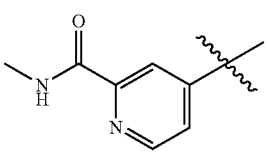

Embodiment 98: a compound of Embodiment 73, wherein R⁸ is

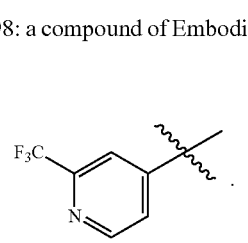

Embodiment 99: a compound of Embodiment 73, wherein R⁸ is

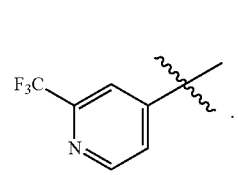 [SMILES: *c1ccnc(C(F)(F)F)c1]

Embodiment 100: a compound of Embodiment 73, wherein R⁸ is

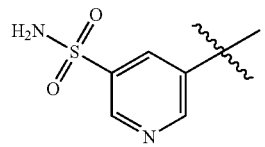

Embodiment 101: a compound of Embodiment 73, wherein R⁸ is

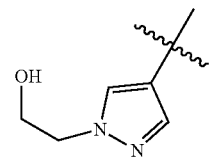

Embodiment 102: a compound of Embodiment 73, wherein R⁸ is

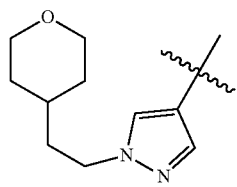

Embodiment 103: a compound of Embodiment 73, wherein R⁸ is

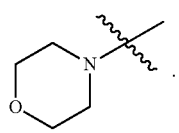

Embodiment 104: a compound of Embodiment 73, wherein R⁸ is

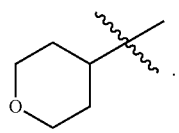 [SMILES: *C1CCOCC1]

Embodiment 105: a compound of a compound of any one of Embodiments 1-55, wherein R³ is unsubstituted with an R⁸ group.

Embodiment 106: a compound of any one of Embodiments 1-105, wherein R¹ is H or is chosen from alkyl, cycloalkyl, and heterocycloalkyl, any of which is optionally substituted with 1, 2, or 3 R⁵ groups.

Embodiment 107: a compound of Embodiment 106, wherein R¹ is chosen from alkyl, cycloalkyl, and heterocycloalkyl, any of which is optionally substituted with 1, 2, or 3 R⁵ groups.

Embodiment 108: a compound of Embodiment 106, wherein R¹ is H.

Embodiment 109: a compound of any one of Embodiments 1-107, wherein R¹ is optionally substituted with 1 or 2 R⁵ groups.

Embodiment 110: a compound of Embodiment 109, wherein $R^1$ is substituted with 1 or 2 $R^5$ groups.

Embodiment 111: a compound of Embodiment 110, wherein $R^1$ is substituted with 1 $R^5$ group.

Embodiment 112: a compound of Embodiment 109, wherein $R^1$ is optionally substituted with 1 $R^5$ group.

Embodiment 113: a compound of Embodiment 109, wherein $R^1$ is not substituted with an $R^5$ group.

Embodiment 114: a compound of Embodiment 113, wherein $R^1$ is chosen from: —$CH_3$, —$CH(CH_3)_2$,

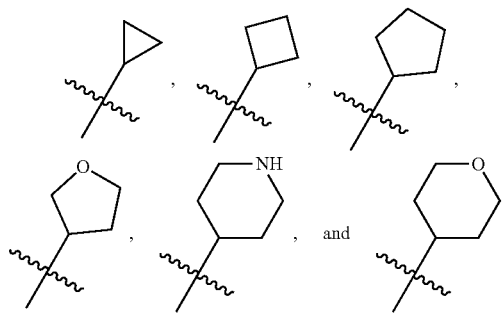

, and .

Embodiment 115: a compound of Embodiment 114, wherein $R^1$ is

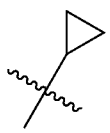

Embodiment 116: the compound of any one of Embodiments 1-115, wherein $R^2$ is H or is chosen from alkyl, haloalkyl, amino, and alkoxy, any of which is optionally substituted with 1 or 2 $R^6$ groups.

Embodiment 117: the compound of Embodiment 116, wherein $R^2$ is chosen from alkyl, haloalkyl, amino, and alkoxy, any of which is optionally substituted with 1 or 2 $R^6$ groups.

Embodiment 118: the compound of Embodiment 117, wherein $R^2$ is chosen from alkyl, fluoroalkyl, amino, and alkoxy, any of which is optionally substituted with 1 or 2 $R^6$ groups Embodiment 119: the compound of any one of Embodiments 1-118, wherein each $R^6$ is independently chosen from alkoxy, cyano, halo, haloalkyl, and hydroxy.

Embodiment 120: the compound of Embodiment 118, wherein $R^2$ is chosen from —$CH_3$, —$CH_2F$, amino, and —$OCH_3$.

Embodiment 121: the compound of Embodiment 120, wherein $R^2$ is chosen from —$CH_3$, —$CH_2F$, —$NH_2$, —$NHCH_3$, and —$OCH_3$.

Embodiment 122: the compound of Embodiment 121, wherein $R^2$ is chosen from —$CH_3$ and —$NHCH_3$.

Embodiment 123: the compound of any one of Embodiments 1-122, wherein each $R^7$ is independently chosen from methyl, ethyl, methoxy, cyano, $NH_2$, halo, difluoromethyl, trifluoromethyl, and trifluoromethoxy.

Embodiment 124: the compound of Embodiment 123, wherein each $R^7$ is independently chosen from methyl, methoxy, cyano, fluoro, difluoromethyl, trifluoromethyl, and trifluoromethoxy.

Embodiment 125: the compound of Embodiment 124, wherein each $R^7$ is independently chosen from methyl, fluoro, and difluoromethyl.

Embodiment 126: the compound of any one of 1-125, wherein at least one $R^7$ is methyl.

Embodiment 127: the compound of any one of 1-126, wherein at least one $R^7$ is fluoro.

Embodiment 128: the compound of any one of 1-127, wherein at least one $R^7$ is difluoromethyl.

Embodiment 129: the compound of any one of Embodiments 1-128, wherein $R^{4a}$ and $R^{4b}$ are chosen from H and methyl.

Embodiment 130: the compound of Embodiment 129, wherein at least one of $R^{4a}$ and $R^{4b}$ is H.

Embodiment 131: the compound of Embodiment 130, wherein $R^{4a}$ and $R^{4b}$ are H.

Also provided are embodiments wherein any embodiment above may be combined with any one or more of these embodiments, provided the combination is not mutually exclusive.

As used herein, two embodiments are "mutually exclusive" when one is defined to be something which is different than the other. For example, an embodiment wherein two groups combine to form a cycloalkyl is mutually exclusive with an embodiment in which one group is ethyl the other group is hydrogen. Similarly, an embodiment wherein one group is $CH_2$ is mutually exclusive with an embodiment wherein the same group is NH.

Also provided is a compound chosen from the Examples disclosed herein.

The present disclosure also relates to a method of inhibiting at least one function of CBP comprising the step of contacting CBP with a compound as described herein. The cell phenotype, cell proliferation, activity of CBP, change in biochemical output produced by active CBP, expression of CBP, or binding of CBP with a natural binding partner may be monitored. Such methods may be modes of treatment of disease, biological assays, cellular assays, biochemical assays, or the like.

The present disclosure also relates to a method of inhibiting at least one function of P300 comprising the step of contacting P300 with a compound as described herein. The cell phenotype, cell proliferation, activity of P300, change in biochemical output produced by active P300, expression of P300, or binding of P300 with a natural binding partner may be monitored. Such methods may be modes of treatment of disease, biological assays, cellular assays, biochemical assays, or the like.

Also provided herein is a method of treatment of a CBP-mediated disease comprising the administration of a therapeutically effective amount of a compound as disclosed herein, or a salt thereof, to a patient in need thereof.

Also provided herein is a method of treatment of a P300-mediated disease comprising the administration of a therapeutically effective amount of a compound as disclosed herein, or a salt thereof, to a patient in need thereof.

In certain embodiments, the disease is a proliferative disease.

In certain embodiments, the disease is cancer.

Also provided herein is a compound as disclosed herein for use as a medicament.

Also provided herein is a compound as disclosed herein for use as a medicament for the treatment of a CBP-mediated disease.

Also provided herein is a compound as disclosed herein for use as a medicament for the treatment of a P300-mediated disease.

Also provided is the use of a compound as disclosed herein as a medicament.

Also provided is the use of a compound as disclosed herein as a medicament for the treatment of a CBP-mediated disease.

Also provided is the use of a compound as disclosed herein as a medicament for the treatment of a P300-mediated disease.

Also provided is a compound as disclosed herein for use in the manufacture of a medicament for the treatment of a CBP-mediated disease.

Also provided is a compound as disclosed herein for use in the manufacture of a medicament for the treatment of a P300-mediated disease.

Also provided is the use of a compound as disclosed herein for the treatment of a CBP-mediated disease.

Also provided is the use of a compound as disclosed herein for the treatment of a P300-mediated disease.

Also provided herein is a method of inhibition of CBP comprising contacting CBP with a compound as disclosed herein, or a salt thereof.

Also provided herein is a method of inhibition of P300 comprising contacting P300 with a compound as disclosed herein, or a salt thereof.

Also provided herein is a method for achieving an effect in a patient comprising the administration of a therapeutically effective amount of a compound as disclosed herein, or a salt thereof, to a patient, wherein the effect is chosen from cognition enhancement.

In certain embodiments, the CBP-mediated disease is cancer.

In certain embodiments, the P300-mediated disease is cancer.

Also provided is a method of modulation of a CBP-mediated function in a subject comprising the administration of a therapeutically effective amount of a compound as disclosed herein.

Also provided is a method of modulation of a P300-mediated function in a subject comprising the administration of a therapeutically effective amount of a compound as disclosed herein.

Also provided is a pharmaceutical composition comprising a compound as disclosed herein, together with a pharmaceutically acceptable carrier.

In certain embodiments, the pharmaceutical composition is formulated for oral administration.

In certain embodiments, the pharmaceutical composition is formulated for parenteral administration.

In certain embodiments, the oral pharmaceutical composition is chosen from a tablet and a capsule.

Abbreviations and Definitions

As used herein, the terms below have the meanings indicated.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a $C(O)CH_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH═CH—),(—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 8 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, nonyl and the like. The term "alkylene," as used herein, alone or in combination, refers to a saturated aliphatic group derived from a straight or branched chain saturated hydrocarbon attached at two or more positions, such as methylene (—$CH_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH₃C(O)NH—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl(hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4=$ derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronaphthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or combinations thereof, fully saturated or containing from 1 to 3 degrees of unsaturation, consisting of the stated number of carbon atoms and from one to three heteroatoms chosen from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —CH$_2$—NH—OCH$_3$.

The term "heteroaryl", as used herein, alone or in combination, refers to a 3 to 15 membered unsaturated heteromonocyclic ring, or a fused monocyclic, bicyclic, or tricyclic ring system in which all of the fused rings are aromatic, which contains at least one atom chosen from N, O, and S. The term "heteroaryl" thus encompasses, for example, pyridine, thiophene, quinoline, and phenanthridine. The term "heteroaryl" thus does not encompass, for example, indoline, and 2,3-dihydrobenzofuran. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings, and wherein heteroaryl rings are fused with other heteroaryl rings. Examples of heteroaryl groups include pyrrolyl, pyrrolinyl, imidazolyl, pyrazolyl, pyridyl, pyrimidinyl, pyrazinyl, pyridazinyl, triazolyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, and the like. Exemplary tricyclic heterocyclic groups include carbazolyl, phenanthrolinyl, dibenzofuranyl, acridinyl, phenanthridinyl, and the like.

The terms "heterocycloalkyl" and, interchangeably, "heterocycle," as used herein, alone or in combination, each refer to a saturated, partially unsaturated, or fully unsaturated (but not fully aromatic) monocyclic, bicyclic, or tricyclic heterocyclic group containing at least one heteroatom as a ring member, wherein each said heteroatom may be independently chosen from nitrogen, oxygen, and sulfur. The term "heterocycloalkyl" thus excludes fully aromatic ring systems such as pyridine, pyrimidine, quinoline, and acridine. The term "heterocycloalkyl" thus includes partially aromatic bicyclic and larger ring systems such as 1,2,3,4-tetrahydroquinoline, 5,6,7,8-tetrahydroquinoline, and indoline. In certain embodiments, said heterocycloalkyl will comprise from 1 to 4 heteroatoms as ring members. In further embodiments, said heterocycloalkyl will comprise from 1 to 2 heteroatoms as ring members. In certain embodiments, said heterocycloalkyl will comprise from 3 to 8 ring members in each ring. In further embodiments, said heterocycloalkyl will comprise from 3 to 7 ring members in each ring. In yet further embodiments, said heterocycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydroquinolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

Certain compounds in the present disclosure can comprise diazanaphthalene groups, which will be understood as derivatives of naphthalene in which two of the non-bridgehead CH groups is replaced with N. The term "diazanaphthalene" encompasses the four isomers of benzodiazine, which have both nitrogens in the same ring, and the six isomers of naphthyridine, which have nitrogens on different rings.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms (i.e., $C_1$-$C_6$ alkyl).

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four said members may be heteroatoms chosen from N, O, and S, or 2) bicyclic heteroaryl, wherein each of the fused rings comprises five or six ring members, comprising between them one to four heteroatoms chosen from N, O, and S.

The term "lower cycloalkyl," as used herein, alone or in combination, means a monocyclic cycloalkyl having between three and six ring members (i.e., $C_3$-$C_6$ cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from N, O, and S (i.e., $C_3$-$C_6$ heterocycloalkyl). Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen and lower alkyl, either of which may be optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a X$_3$CS(O)$_2$NR— group with X is a halogen and R as defined herein.

The term "trihalomethanesulfonyl" refers to a X$_3$CS(O)$_2$— group where X is a halogen.

The term "trihalomethoxy" refers to a X$_3$CO— group where X is a halogen.

The term "trisubstituted silyl," as used herein, alone or in combination, refers to a silicone group substituted at its three free valences with groups as listed herein under the definition of substituted amino. Examples include trimethylsilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the disclosure encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present disclosure includes all cis, trans, syn, anti, entgegen (E), and zusammen (Z) isomers as well as the appropriate mixtures thereof. Additionally, compounds may exist as tautomers; all tautomeric isomers are provided by this disclosure. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"CBP inhibitor", as used herein, refers to a compound that binds to and inhibits the bromodomain of CBP with measurable affinity and activity. In certain embodiments, a CBP inhibitor exhibits an IC50 with respect to CBP activity of no more than about 100 μM and more typically not more than about 50 μM, as measured in the CBP (assay name) described generally herein. "IC50" is that concentration of inhibitor which reduces the activity of the bromodomain of CBP to half-maximal level. Certain compounds disclosed herein have been discovered to exhibit inhibition against CBP. In certain embodiments, compounds will exhibit an IC50 with respect to CBP of no more than about 20 μM; in further embodiments, compounds will exhibit an IC50 with respect to CBP of no more than about 5 μM; in yet further embodiments, compounds will exhibit an IC50 with respect to CBP of not more than about 200 nM; in yet further embodiments, compounds will exhibit an IC50 with respect to CBP of not more than about 50 nM; in yet further embodiments, compounds will exhibit an IC50 with respect to CBP of not more than about 10 nM; in yet further embodiments, compounds will exhibit an IC50 with respect to CBP of not more than about 2 nM, as measured in the CBP assay described herein.

"P300 inhibitor", as used herein, refers to a compound that binds to and inhibits the bromodomain of P300 with measurable affinity and activity. In certain embodiments, a P300 inhibitor exhibits an IC50 with respect to P300 activity of no more than about 100 μM and more typically not more than about 50 μM, as measured in the P300 (assay name) described generally herein. "IC50" is that concentration of inhibitor which reduces the activity of the bromodomain of P300 to half-maximal level. Certain compounds disclosed herein have been discovered to exhibit inhibition against P300. In certain embodiments, compounds will exhibit an IC50 with respect to P300 of no more than about 20 μM; in further embodiments, compounds will exhibit an IC50 with respect to P300 of no more than about 5 μM; in yet further embodiments, compounds will exhibit an IC50 with respect to P300 of not more than about 200 nM; in yet further embodiments, compounds will exhibit an IC50 with respect to P300 of not more than about 50 nM; in yet further embodiments, compounds will exhibit an IC50 with respect to P300 of not more than about 10 nM; in yet further embodiments, compounds will exhibit an IC50 with respect to P300 of not more than about 2 nM, as measured in the P300 assay described herein.

In some embodiments, certain compounds disclosed herein interfere with the associating of CBP and/or EP300 with histones, in particular acetylated lysines in histones. In some embodiments, certain compounds disclosed herein inhibit binding of CBP and/or EP300 to chromatin (e.g., histone associated DNA). In some embodiments, certain compounds disclosed herein inhibit and/or reduces binding of the CBP bromodomain and/or EP300 bromodomain to chromatin (e.g., histone associated DNA). In some embodiments, certain compounds disclosed herein do not affect association of other domains of CBP and/or EP300 to chromatin. In some embodiments, certain compounds disclosed herein bind to the CBP and/or EP300 primarily (e.g., solely) through contacts and/or interactions with the CBP bromodomain and/or EP300 bromodomain. In some embodiments, certain compounds disclosed herein bind to the CBP and/or EP300 through contacts and/or interactions with the CBP bromodomain and/or EP300 bromodomain as well as additional CBP and/or EP300 residues and/or domains. Methods of assaying association with chromatin are known in the art and include, but are not limited to, chromatin fractionation, BRET assay (Promega), FRAP assay, Chromatin Immunoprecipitation (ChIP), biophysical binding assay, and/or Histone Association Assay. See, e.g., Das et al., BioTechniques 37:961-969 (2004).

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present disclosure includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethanesulfonate (isethionate), lactate, maleate, malonate, DL-mandelate, mesitylenesulfonate, methanesulfonate, naphthalenesulfonate, nicotinate, 2-naphthalenesulfonate, oxalate, pamoate, pectinate, persulfate, 3-phenylpropionate, phosphonate, picrate, pivalate, propionate, pyroglutamate, succinate, sulfonate, tartrate, L-tartrate, trichloroacetate, 2,2,2-trifluoroacetate=trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and stearyl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present disclosure contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

Pharmaceutical Compositions

While it may be possible for the compounds of the subject disclosure to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject disclosure or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Oral Administration

The compounds of the present disclosure may be administered orally, including swallowing, so the compound enters the gastrointestinal tract, or is absorbed into the blood stream directly from the mouth, including sublingual or buccal administration.

Suitable compositions for oral administration include solid formulations such as tablets, pills, cachets, lozenges and hard or soft capsules, which can contain liquids, gels, powders, or granules, solutions or suspensions in an aqueous liquid or a non-aqueous liquid, or as an oil-in-water liquid emulsion or a water-in-oil liquid emulsion. The active ingredient may also be presented as a bolus, electuary or paste.

In a tablet or capsule dosage form the amount of drug present may be from about 0.05% to about 95% by weight, more typically from about 2% to about 50% by weight of the dosage form.

In addition, tablets or capsules may contain a disintegrant, comprising from about 0.5% to about 35% by weight, more typically from about 2% to about 25% of the dosage form. Examples of disintegrants include methyl cellulose, sodium or calcium carboxymethyl cellulose, croscarmellose sodium, polyvinylpyrrolidone, hydroxypropyl cellulose, starch and the like.

Suitable binders, for use in a tablet, include gelatin, polyethylene glycol, sugars, gums, starch, hydroxypropyl cellulose and the like. Suitable diluents, for use in a tablet, include mannitol, xylitol, lactose, dextrose, sucrose, sorbitol and starch.

Suitable surface active agents and glidants, for use in a tablet or capsule, may be present in amounts from about 0.1% to about 3% by weight, and include polysorbate 80, sodium dodecyl sulfate, talc and silicon dioxide.

Suitable lubricants, for use in a tablet or capsule, may be present in amounts from about 0.1% to about 5% by weight, and include calcium, zinc or magnesium stearate, sodium stearyl fumarate and the like.

Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with a liquid diluent. Dyes or pigments may be added to tablets for identification or to characterize different combinations of active compound doses.

Liquid formulations can include emulsions, solutions, syrups, elixirs and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

Compositions for oral administration may be formulated as immediate or modified release, including delayed or sustained release, optionally with enteric coating.

In another embodiment, a pharmaceutical composition comprises a therapeutically effective amount of a compound of Formula (I) or a pharmaceutically acceptable salt thereof, and a pharmaceutically acceptable carrier.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Parenteral Administration

Compounds of the present disclosure may be administered directly into the blood stream, muscle, or internal organs by injection, e.g., by bolus injection or continuous infusion. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods. The formulations may be presented in unit-dose or multi-dose containers, for example sealed ampoules and vials.

Most parenteral formulations are aqueous solutions containing excipients, including salts, buffering, suspending, stabilizing and/or dispersing agents, antioxidants, bacteriostats, preservatives, and solutes which render the formulation isotonic with the blood of the intended recipient, and carbohydrates.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions. Compositions for parenteral administration may be formulated as immediate or modified release, including delayed or sustained release. Compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Topical Administration

Compounds of the present disclosure may be administered topically (for example to the skin, mucous membranes, ear, nose, or eye) or transdermally. Formulations for topical administration can include, but are not limited to, lotions, solutions, creams, gels, hydrogels, ointments, foams, implants, patches and the like. Carriers that are pharmaceutically acceptable for topical administration formulations can include water, alcohol, mineral oil, glycerin, polyethylene glycol and the like. Topical administration can also be performed by, for example, electroporation, iontophoresis, phonophoresis and the like.

Typically, the active ingredient for topical administration may comprise from 0.001% to 10% w/w (by weight) of the formulation. In certain embodiments, the active ingredient may comprise as much as 10% w/w; less than 5% w/w; from 2% w/w to 5% w/w; or from 0.1% to 1% w/w of the formulation.

Compositions for topical administration may be formulated as immediate or modified release, including delayed or sustained release.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

Rectal, Buccal, and Sublingual Administration

Suppositories for rectal administration of the compounds of the present disclosure can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Administration by Inhalation

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Other carrier materials and modes of administration known in the pharmaceutical art may also be used. Pharmaceutical compositions of the disclosure may be prepared by any of the well-known techniques of pharmacy, such as effective formulation and administration procedures. Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. In addition, the route of administration may vary depending on the condition and its severity. The above considerations concerning effective formulations and administration procedures are well known in the art and are described in standard textbooks.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

Combinations and Combination Therapy

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of certain compounds of the invention with anti-cancer (chemotherapeutic) drugs. Classes of anti-cancer drugs include, but are not limited to: alkylating agents, anti-metabolites, antimitotics, checkpoint inhibitors, plant alkaloids and terpenoids, topoisomerase inhibitors, cytotoxic antibiotics, aromatase inhibitors, angiogenesis inhibitors, anti-steroids and anti-androgens, mTOR inhibitors, tyrosine kinase inhibitors, and others.

For use in cancer and neoplastic diseases a CBP/EP300 inhibitor may be optimally used together with one or more of the following non-limiting examples of anti-cancer agents:

(1) alkylating agents, including but not limited to carmustine, chlorambucil (LEUKERAN), cisplatin (PLATIN), carboplatin (PARAPLATIN), oxaliplatin (ELOXATIN), streptozocin (ZANOSAR), busulfan (MYLERAN), dacarbazine, ifosfamide, lomustine (CCNU), melphalan (ALKERAN), procarbazine (MATULAN), temozolomide (TEMODAR), thiotepa, and cyclophosphamide (ENDOXAN);

(2) anti-metabolites, including but not limited to cladribine (LEUSTATIN), mercaptopurine (PURINETHOL), thioguanine, pentostatin (NIPENT), cytosine arabinoside (cytarabine, ARA-C), gemcitabine (GEMZAR), fluorouracil (5-FU, CARAC), capecitabine (XELODA), leucovorin (FUSILEV), methotrexate (RHEUMATREX), raltitrexed;

(3) antimitotics, which are often plant alkaloids and terpenoids, or derivatives thereof, including but not limited to taxanes such as docetaxel (TAXITERE) and paclitaxel (ABRAXANE, TAXOL); *vinca* alkaloids such as vincristine (ONCOVIN), vinblastine, vindesine, and vinorelbine (NAVELBINE);

(4) checkpoint inhibitors, such as anti-PD-1 or PD-L1 antibodies pembrolizumab (KEYTRUDA), nivolumab (OPDIVO), MEDI4736, and MPDL3280A; anti- CTLA-4 antibody ipilimumab (YERVOY); and those that target LAG3 (lymphocyte activation gene 3 protein), KIR (killer cell immunoglobulin-like receptor), 4-1BB (tumour necrosis factor receptor superfamily member 9), TIM3 (T-cell immunoglobulin and mucin-domain containing-3) and OX40 (tumour necrosis factor receptor superfamily member 4);

(5) topoisomerase inhibitors, including but not limited to camptothecin (CTP), irinotecan (CAMPTOSAR), topotecan (HYCAMTIN), teniposide (VUMON), and etoposide (EPOSIN);

(6) cytotoxic antibiotics, including but not limited to actinomycin D (dactinomycin, COSMEGEN), bleomycin (BLENOXANE) doxorubicin (ADRIAMYCIN), daunorubicin (CERUBIDINE), epirubicin (ELLENCE), fludarabine (FLUDARA), idarubicin, mitomycin (MITOSOL), mitoxantrone (NOVANTRONE), plicamycin;

(7) aromatase inhibitors, including but not limited to aminoglutethimide, anastrozole (ARIMIDEX), letrozole (FEMARA), vorozole (RIVIZOR), exemestane (AROMASIN);

(8) angiogenesis inhibitors, including but not limited to genistein, sunitinib (SUTENT) and bevacizumab (AVASTIN);

(9) anti-steroids and anti-androgens such as aminoglutethimide (CYTADREN), bicalutamide (CASODEX), cyproterone, flutamide (EULEXIN), nilutamide (NILANDRON);

(10) tyrosine kinase inhibitors, including but not limited to imatinib (GLEEVEC), erlotinib (TARCEVA), lapatinib (TYKERB), sorafenib (NEXAVAR), and axitinib (INLYTA);

(11) mTOR inhibitors such as everolimus, temsirolimus (TORISEL), and sirolimus;

(12) monoclonal antibodies such as trastuzumab (HERCEPTIN) and rituximab (RITUXAN);

(13) other agents, such as amsacrine; *Bacillus* Calmette-Guérin (B-C-G) vaccine; buserelin (ETILAMIDE); chloroquine (ARALEN); clodronate, pamidronate, and other bisphosphonates; colchicine; demethoxyviridin; dichloroacetate; estramustine; filgrastim (NEUPOGEN); fludrocortisone (FLORINEF); goserelin (ZOLADEX); interferon; leucovorin; leuprolide (LUPRON); levamisole; lonidamine; mesna; metformin; mitotane (o,p'-DDD, LYSODREN); nocodazole; octreotide (SANDOSTATIN); perifosine; porfimer (particularly in combination with photo- and radiotherapy); suramin; tamoxifen; titanocene dichloride; tretinoin; anabolic steroids such as fluoxymesterone (HALOTESTIN); estrogens such as estradiol, diethylstilbestrol (DES), and dienestrol; progestins such as medroxyprogesterone acetate (MPA) and megestrol; and testosterone.

Where a subject is suffering from or at risk of suffering from an inflammatory condition, a CBP/EP300 inhibitor compound described herein is optionally used together with one or more agents or methods for treating an inflammatory condition in any combination. Therapeutic agents/treatments for treating an autoimmune and/or inflammatory condition include, but are not limited to any of the following examples:

(1) corticosteroids, including but not limited to cortisone, dexamethasone, and methylprednisolone;

(2) nonsteroidal anti-inflammatory drugs (NSAIDs), including but not limited to ibuprofen, naproxen, acetaminophen, aspirin, fenoprofen (NALFON), flurbiprofen (ANSAID), ketoprofen, oxaprozin (DAYPRO), diclofenac sodium (VOLTAREN), diclofenac potassium (CATAFLAM), etodolac (LODINE), indomethacin (INDOCIN), ketorolac (TORADOL), sulindac (CLINORIL), tolmetin (TOLECTIN), meclofenamate (MECLOMEN), mefenamic acid (PONSTEL), nabumetone (RELAFEN) and piroxicam (FELDENE);

(3) immunosuppressants, including but not limited to methotrexate (RHEUMATREX), leflunomide (ARAVA), azathioprine (IMURAN), cyclosporine (NEORAL, SANDIMMUNE), tacrolimus and cyclophosphamide (CYTOXAN);

(4) CD20 blockers, including but not limited to rituximab (RITUXAN);

(5) Tumor Necrosis Factor (TNF) blockers, including but not limited to etanercept (ENBREL), infliximab (REMICADE) and adalimumab (HUMIRA);

(6) interleukin-1 receptor antagonists, including but not limited to anakinra (KINERET);

(7) interleukin-6 inhibitors, including but not limited to tocilizumab (ACTEMRA);

(8) interleukin-17 inhibitors, including but not limited to AIN457;

(9) Janus kinase inhibitors, including but not limited to tasocitinib; and

(10) syk inhibitors, including but not limited to fostamatinib.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating CBP-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of CBP-mediated disorders.

Thus, in another aspect, certain embodiments provide methods for treating P300-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of P300-mediated disorders.

The compounds, compositions, and methods disclosed herein are useful for the treatment of disease. In certain embodiments, the disease is one of dysregulated cellular proliferation, including cancer. The cancer may be hormone-dependent or hormone-resistant, such as in the case of breast cancers. In certain embodiments, the cancer is a solid tumor. In other embodiments, the cancer is a lymphoma or leukemia. In certain embodiments, the cancer is and a drug resistant phenotype of a cancer disclosed herein or known in the art. Tumor invasion, tumor growth, tumor metastasis, and angiogenesis may also be treated using the compositions and methods disclosed herein. Precancerous neoplasias are also treated using the compositions and methods disclosed herein.

Cancers to be treated by the methods disclosed herein include colon cancer, breast cancer, ovarian cancer, lung cancer and prostate cancer; cancers of the oral cavity and pharynx (lip, tongue, mouth, larynx, pharynx), esophagus, stomach, small intestine, large intestine, colon, rectum, liver and biliary passages; pancreas, bone, connective tissue, skin, cervix, uterus, corpus endometrium, testis, bladder, kidney and other urinary tissues, including renal cell carcinoma (RCC); cancers of the eye, brain, spinal cord, and other components of the central and peripheral nervous systems, as well as associated structures such as the meninges; and thyroid and other endocrine glands. The term "cancer" also encompasses cancers that do not necessarily form solid tumors, including Hodgkin's disease, non-Hodgkin's lymphomas, multiple myeloma and hematopoietic malignancies including leukemias (Chronic Lymphocytic Leukemia (CLL), Acute Lymphocytic Leukemia (ALL), Chronic Myelogenous Leukemia (CML), Acute Myelogenous Leukemia (AML)) and lymphomas including lymphocytic, granulocytic and monocytic. Additional types of cancers which may be treated using the compounds and methods of the invention include, but are not limited to, adenocarcinoma, angiosarcoma, astrocytoma, acoustic neuroma, anaplastic astrocytoma, basal cell carcinoma, blastoglioma, chondrosarcoma, choriocarcinoma, chordoma, craniopharyngioma, cutaneous melanoma, cystadenocarcinoma, endotheliosarcoma, embryonal carcinoma, ependymoma, Ewing's tumor, epithelial carcinoma, fibrosarcoma, gastric cancer, genitourinary tract cancers, glioblastoma multiforme, head and neck cancer, hemangioblastoma, hepatocellular carcinoma, hepatoma, Kaposi's sarcoma, large cell carcinoma, leiomyosarcoma, leukemias, liposarcoma, lymphatic system cancer, lymphomas, lymphangiosarcoma, lymphangioendotheliosarcoma, medullary thyroid carcinoma, medulloblastoma, meningioma mesothelioma, myelomas, myxosarcoma neuroblastoma, neurofibrosarcoma, oligodendroglioma, osteogenic sarcoma, epithelial ovarian cancer, papillary carcinoma, papillary adenocarcinomas, paraganglioma, parathyroid tumours, pheochromocytoma, pinealoma, plasmacytomas, retinoblastoma, rhabdomyosarcoma, sebaceous gland carcinoma, seminoma, skin cancers, melanoma, small cell lung carcinoma, non-small cell lung carcinoma, squamous cell carcinoma, sweat gland carcinoma, synovioma, thyroid cancer, uveal melanoma, and Wilm's tumor.

In certain embodiments, the compositions and methods disclosed herein are useful for preventing or reducing tumor invasion and tumor metastasis.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Compound Synthesis

Compounds of the present disclosure can be prepared using methods illustrated in general synthetic schemes and experimental procedures detailed below. General synthetic schemes and experimental procedures are presented for purposes of illustration and are not intended to be limiting. Starting materials used to prepare compounds of the present disclosure are commercially available or can be prepared using routine methods known in the art.

LIST OF ABBREVIATIONS $Ac_2O$=acetic anhydride; AcCl=acetyl chloride; AcOH=acetic acid; AIBN=azobisisobutyronitrile; aq.=aqueous; $BPin_2$=bis(pinacolato)diboron=4,4,4',4',5,5,5', 5'-octamethyl-2,2'-bi-1,3,2-dioxaborolane; Brettphos=2-(Dicyclohexylphosphino)$_{3,6}$-dimethoxy-2',4',6'-triisopropyl-1,1'-biphenyl; $Bu_3SnH$=tributyltin hydride; CBz=carboxybenzyl=$PhCH_2OC(=O)$—; CBzCl=benzyl chloroformate=$PhCH_2OC(=O)Cl$; $CD_3OD$=deuterated methanol; $CDCl_3$=deuterated chloroform; CDI=1,1'-Carbonyldiimidazole; DAST=diethylaminosulfur trifluoride; DBU=1,8-diazabicyclo[5.4.0]undec-7-ene; DCE=1,2-dichloroethane; DCM=dichloromethane; DEAD=diethyl azodicarboxylate; DIBAL-H=di-iso-butyl aluminium hydride; DIEA=DIPEA=N,N-diisopropylethylamine; DMAP=4-dimethylaminopyridine; DMF=N,N-dimethylformamide; DMSO-$d_6$=deuterated dimethyl sulfoxide; DMSO=dimethyl sulfoxide; DPPA=diphenylphosphoryl azide; dppe=1,2-bis(diphenylphosphino)ethane; dppf=1,1'-bis(diphenylphosphino)ferrocene; EDC.HCl=EDCI.HCl=1-ethyl-3-(3-dimethylaminopropyl)carbodiimide hydrochloride; $Et_2O$=diethyl ether; EtOAc=ethyl acetate; EtOH=ethanol; h=hour; HATU=2-(1H-7-azabenzotriazol-1-yl)-1,1,3,3-tetramethyl uronium hexafluorophosphate methanaminium; HMDS=hexamethyldisilazane; HOBT=1-hydroxybenzotriazole; iPr=i-Pr=isopropyl=$(CH_3)_2CH$—; i-PrOH=isopropanol=$(CH_3)_2CH$—OH;

LAH=$LiAlH_4$=lithium aluminium hydride; LiHMDS=LiN(TMS)$_2$=Lithium bis(trimethylsilyl)amide; MeCN=acetonitrile; MeOH=methanol; MP-carbonate resin=macroporous triethylammonium methylpolystyrene carbonate resin; MsCl=mesyl chloride; MTBE=methyl tertiary butyl ether; MW=microwave irradiation; n-BuLi=n-butyllithium; NaHMDS=Sodium bis(trimethylsilyl)amide; NaOMe=sodium methoxide; NaOtBu=sodium tert-butoxide; NBS=N-bromosuccinimide; NCS=N-chlorosuccinimide; NIS=N-iodosuccinimide; NMP=N-Methyl-2-pyrrolidone; $PdCl_2$(dppf)=Pd(dppf)$Cl_2$=[1,1'-bis(diphenylphosphino)ferrocene]palladium(II) chloride; Pd(Ph$_3$)$_4$=tetrakis(triphenyl-phosphine)palladium(O); Pd$_2$(dba)$_3$=tris(dibenzylideneacetone)dipalladium(O); $PdCl_2$(PPh$_3$)$_2$=bis(triphenylphosphine)palladium(II) dichloride; PG=protecting group; prep-HPLC=preparative high-performance liquid chromatography; PyBop=(benzotriazol-1-yloxy)-tripyrrolidinophosphonium hexafluorophosphate; Pyr=pyridine; RT=room temperature; RuPhos=2-dicyclohexylphosphino-2',6'-diisopropoxybiphenyl; sat.=saturated; ss=saturated solution; tBu=t-Bu=tert-butyl=$(CH_3)_3C$—; t-BuOH=tert-butanol=$(CH_3)_3C$—OH;

T3P=Propylphosphonic Anhydride; TBS=TBDMS=tert-butyldimethylsilyl; TBSCl=TBDMSCl=tert-butyldimethylchlorosilane; TEA=$Et_3N$=triethylamine; TFA=trifluoroacetic acid; TFAA=trifluoroacetic anhydride; THF=tetrahydrofuran; Tol=toluene; TsCl=tosyl chloride; XPhos=2-dicyclohexylphosphino-2',4',6'-triisopropylbiphenyl; Xphos Pd G2=chloro(2-dicyclohexylphosphino-2',4',6'-triisopropyl-1,1'-biphenyl)[2-(2'-amino-1,1'-biphenyl)]palladium(II).

General Synthetic Methods for Preparing Compounds

The following schemes can be used to practice the present disclosure.

Scheme I

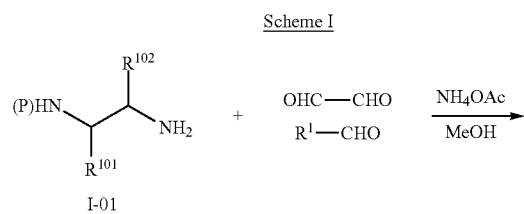

I-01

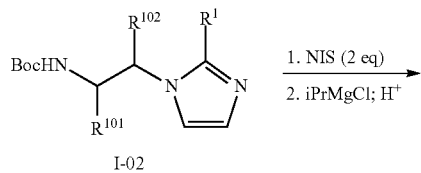

I-02

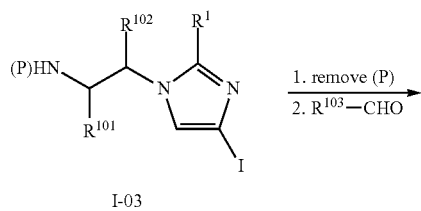

I-03

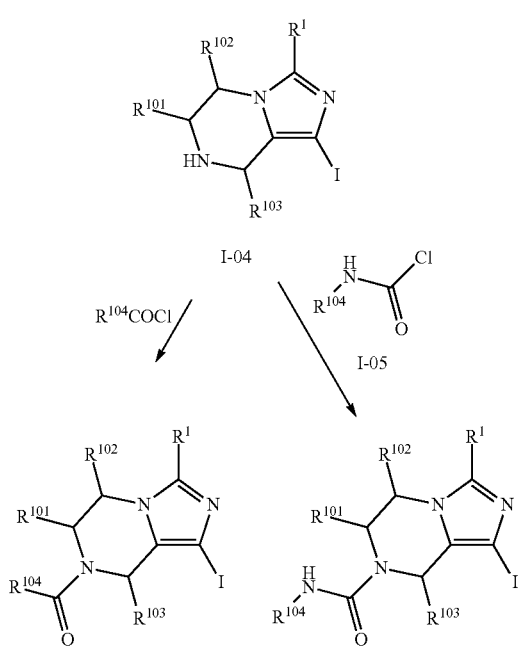

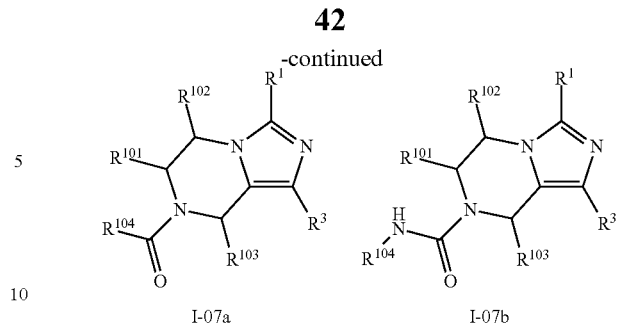

I-07a      I-07b

The Examples can be synthesized using the following general synthetic procedure set forth in Scheme I. Synthesis of imidazole I-02 begins with ethylenediamine I-01 having a suitable protecting group symbolized as (P), such as a carbamate protecting group. Compound I-01 is reacted with glyoxal and aldehyde $R^1$—CHO. Mono-iodo compound I-03 is formed through a 2-step procedure that consists of the synthesis of the 4,5-diiodoimidazole compound (not shown), followed by selective halogen/metal exchange and $H^+$ quench of the resulting organometallic. The protecting group is removed (for example, a Boc group is removed with HCl), and condensation with aldehyde $R^{103}$—CHO gives the bicyclic structure. The amino group can be functionalized either with acid chloride/acid chloroformate $R^{104}$—COCl to give amide/carbamate I-06a, or with carbamyl chloride I-05 to give urea I-06b (alternatively, the amine can be reacted with 4-nitrophenylchloroformate followed by treatment with an amine to give urea 106b). Synthesis is completed by Pd(II)-mediated coupling of I-06a or I-06b with an arylboronic acid or ester to give I-07a or I-07b, respectively.

Scheme II

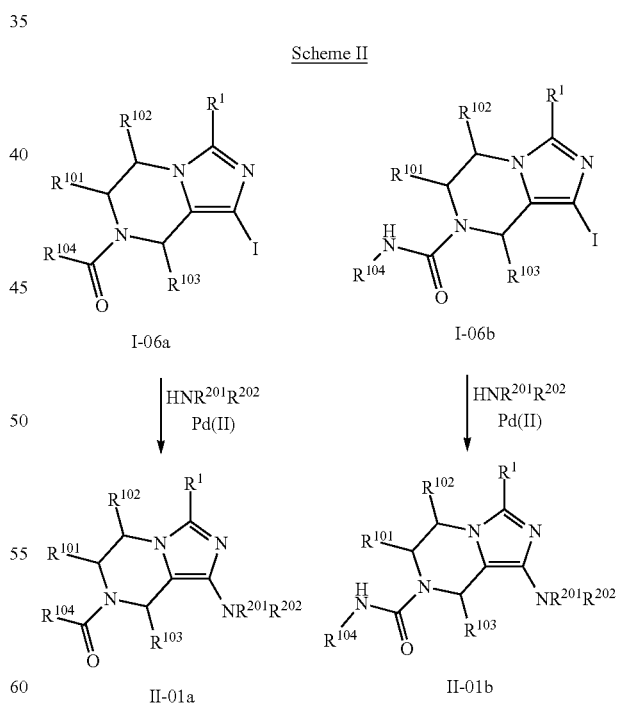

Other Examples can be synthesized using the following general synthetic procedure set forth in Scheme II. Reaction of I-06a and I-06b under Buchwald coupling conditions provides the substituted amines II-01a and II-01b, respectively.

Scheme III

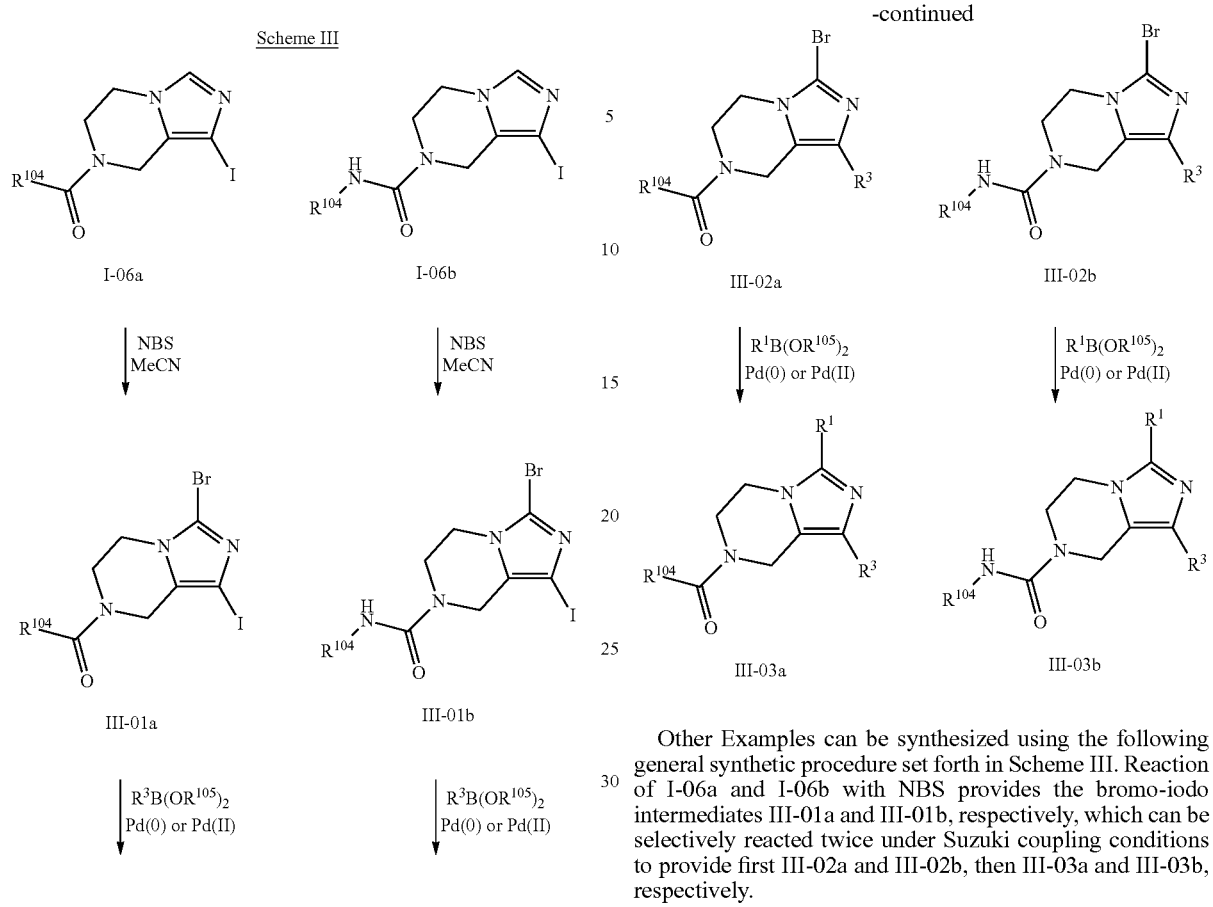

Other Examples can be synthesized using the following general synthetic procedure set forth in Scheme III. Reaction of I-06a and I-06b with NBS provides the bromo-iodo intermediates III-01a and III-01b, respectively, which can be selectively reacted twice under Suzuki coupling conditions to provide first III-02a and III-02b, then III-03a and III-03b, respectively.

Scheme IV

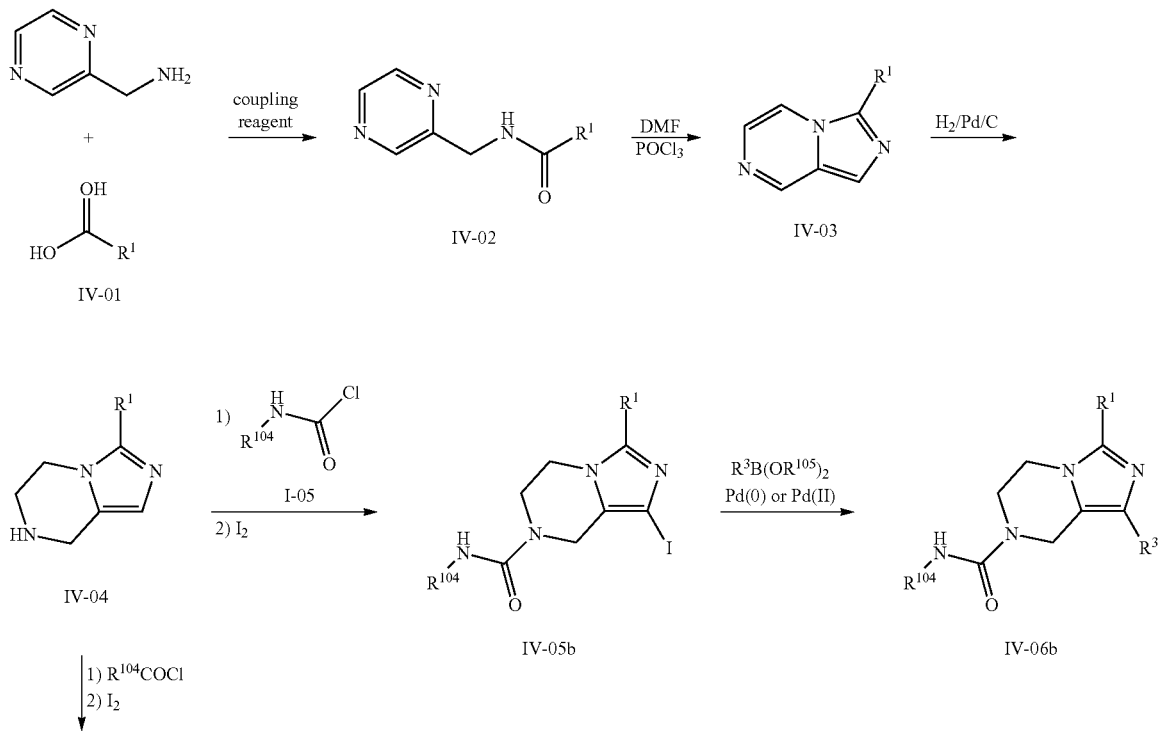

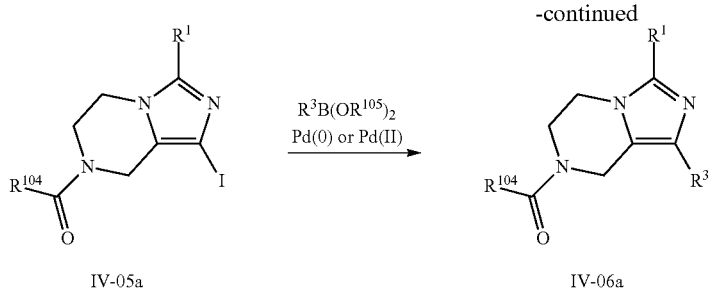
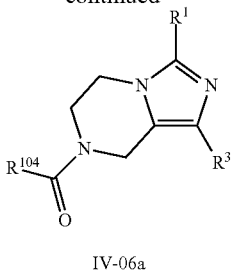

IV-05a → IV-06a

Other Examples can be synthesized using the general synthetic procedure set forth in Scheme IV. Coupling of acid IV-01 with pyrazin-2-ylmethanamine provides amide IV-02, which is cyclized to provide imidazopyrazine IV-03. Imidazopyrazine IV-03 is reduced by hydrogenation to imidazopiperazine IV-04. Imidazopiperazine IV-04 is reacted with either an acid chloride $R^{104}COCl$ followed by reaction with iodine to provide amide IV-05a, or a carbamoyl chloride I-05 followed by reaction with iodine to provide urea IV-05b. Synthesis is completed by Pd(II)-mediated coupling of IV-05a or IV-05b with an arylboronic ester or acid to give IV-06a or IV-06b, respectively.

The disclosure is further illustrated by the following examples.

Intermediate "A"

1-(3-Cyclopropyl-1-iodo-5,6-dihydroimidazo[1,5-a]pyrazin-7(8H)-yl)ethan-1-one

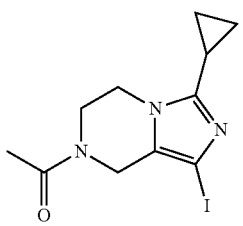 [SMILES: CC(=O)N1CCn2c(C3CC3)nc(I)c2C1]

tert-Butyl(2-(2-cyclopropyl-1H-imidazol-1-yl)ethyl)carbamate

To a solution of cyclopropanecarbaldehyde (0.70 g, 10 mmol) in MeOH (50 ml) at RT was added tert-butyl(2-aminoethyl)carbamate (1.60 g, 10 mmol) followed by NH₄OAc (0.771 g, 10.0 mmol) and 40% aqueous glyoxal (1.451 g, 10.00 mmol). The mixture was stirred at RT for 16 h, then concentrated under reduced pressure. Sat. aq. NaHCO₃ (50 mL) was added, the aqueous phase was extracted with EtOAc (3×20 mL), and the combined organic layers were washed with sat. aq. NaCl, dried over MgSO₄, filtered and concentrated under reduced pressure to give the crude title compound as a yellow foamy solid (2.51 g), which was used in the next step without further purification. MS (ES⁺) $C_{13}H_{21}N_3O_2$ requires: 251 found: 252 [M+H]⁺.

tert-Butyl(2-(2-cyclopropyl-4,5-diiodo-1H-imidazol-1-yl)ethyl)carbamate

To a solution of crude tert-butyl(2-(2-cyclopropyl-1H-imidazol-1-yl)ethyl)carbamate prepared in the previous step (2.51 g, 10.0 mmol) in DMF (30 ml) was added NIS (6.75 g, 30.0 mmol), and the resulting mixture was stirred at 80° C. for 2 h, then allowed to cool to RT. H₂O (100 mL) and sat. aq. Na₂S₂O₃ (5 ml) were added. The aqueous phase was extracted with EtOAc (3×50 mL), and the combined organic layers were washed with sat. aq. NaCl, dried over MgSO₄, filtered and concentrated under reduced pressure. The residue was purified by SiO₂ gel chromatography (0% to 50% EtOAc in hexanes) to give the title compound as a pale yellow foamy solid (2.41 g, 48%). MS (ES⁺) $C_{13}H_{19}I_2N_3O_2$ requires: 503, found: 504 [M+H]⁺.

tert-Butyl(2-(2-cyclopropyl-4-iodo-1H-imidazol-1-yl)ethyl)carbamate

To a solution of tert-butyl(2-(2-cyclopropyl-4,5-diiodo-1H-imidazol-1-yl)ethyl)carbamate (2.40 g, 4.77 mmol) in THF (20 ml) at −78° C. was added 2.0 M iPrMgCl in THF (3.58 ml, 7.16 mmol), and the resulting mixture was stirred at −78° C. for 0.5 h. Sat. aq. NH₄Cl (50 mL) was added, and the layers were separated. The aqueous phase was extracted with EtOAc (3×30 mL), and the combined organic layers were washed with sat. aq. NaCl, dried over MgSO₄, filtered and concentrated under reduced pressure. The residue was purified by SiO₂ gel chromatography (0% to 60% EtOAc in hexanes) to give the title compound as an off-white solid (1.45 g, 81%). MS (ES⁺) $C_{13}H_{20}IN_3O_2$ requires: 377, found: 378 [M+H]⁺.

1-(3-Cyclopropyl-1-iodo-5,6-dihydroimidazo[1,5-a]pyrazin-7(8H)-yl)ethan-1-one

To a solution of HCl in MeOH (made by adding AcCl (2 mL) dropwise to MeOH (10 mL)) was added tert-butyl(2-(2-cyclopropyl-4-iodo-1H-imidazol-1-yl)ethyl)carbamate (700 mg, 1.86 mmol), and the resulting mixture was stirred at RT for 1 h. The mixture was concentrated under reduced pressure, and the residue was dissolved in EtOH (10 ml). To the resulting mixture was added 50% aq. formaldehyde (2.045 ml, 37.1 mmol), and the mixture was stirred at 100° C. for 3 h then concentrated under reduced pressure. The residue was dissolved in CH₂Cl₂ (10 ml), and the resulting mixture was cooled to 0° C. then treated with iPr₂NEt (0.972 ml, 5.57 mmol) and acetyl chloride (0.198 ml, 2.78 mmol). The mixture was stirred at RT for 1 h, then concentrated under reduced pressure. The residue was treated with H₂O (20 mL), extracted with EtOAc (3×10 mL), and the combined organic layers were washed with sat. aq. NaCl, dried over MgSO₄, filtered and concentrated under reduced pressure. The residue was purified by SiO₂ gel chromatography (0% to 5% MeOH in CH₂Cl₂) to give the title compound as an off-white solid (355 mg, 58%). MS (ES⁺) $C_{11}H_{14}IN_3O$ requires: 331, found: 332 [M+H]⁺.

Intermediate "B"

3-cyclopropyl-1-iodo-N-methyl-5,6-dihydroimidazo[1,5-a]pyrazine-7(8H)-carboxamide

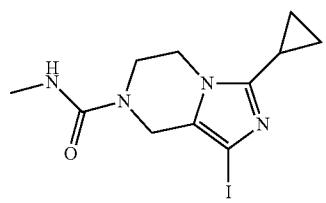 [SMILES: CNC(=O)N1CCn2c(C3CC3)nc(I)c2C1]

3-cyclopropyl-1-iodo-5,6,7,8-tetrahydroimidazo[1,5-a]pyrazine hydrochloride

To a solution of tert-butyl(2-(2-cyclopropyl-4-iodo-1H-imidazol-1-yl)ethyl)carbamate (1.4 g, 3.7 mmol) in 10 ml of $CH_2Cl_2$ was added a 4.0 M HCl in dioxane solution (10 mL, 40 mmol) and the resulting mixture was stirred at RT for 1 h then concentrated under reduced pressure. The resulting residue was dissolved in EtOH (10 ml), and to the mixture was added formaldehyde (5.5 mL, 74 mmol). The mixture was stirred at 80° C. for 3 h, then concentrated under reduced pressure. The residue was dissolved in a 1:1 water/acetonitrile mixture (10 mL) then lyophilized to give the crude title compound as an off-white solid (1.2 g, "112%"), which was used without further purification. MS (ES$^+$) $C_9H_{12}IN_3$ requires: 289, found: 290 [M+H]$^+$.

3-cyclopropyl-1-iodo-N-methyl-5,6-dihydroimidazo[1,5-a]pyrazine-7(8H)-carboxamide To a suspension of the above-prepared crude 3-cyclopropyl-1-iodo-5,6,7,8-tetrahydroimidazo[1,5-a]pyrazine hydrochloride (500 mg, 1.73 mmol) in $CH_2Cl_2$ (15 mL) were added 4-nitrophenyl chloroformate (350 mg, 1.73 mmol) and N-ethyl-N-isopropylpropan-2-amine (0.60 mL, 3.5 mmol), and the resulting mixture was stirred at RT for 2 h. To the mixture was added 10% aq. $NaHCO_3$ (10 mL), and the layers were separated. The aqueous phase was extracted with $CH_2Cl_2$ (2×5 mL), and the combined organic layers were washed with sat. aq. NaCl (10 mL), dried over $MgSO_4$, filtered and concentrated under reduced pressure to give a yellow solid (700 mg), which was then dissolved in $CH_2Cl_2$ (10 mL). To the mixture was added a 2.0 M $MeNH_2$ in THF solution (1 mL, 2 mmol), and the resulting mixture was stirred at RT for 3 h then concentrated under reduced pressure. The residue was partitioned between EtOAc (20 mL) and 10% aq. $NaHCO_3$ (10 mL), and the layers were separated. The aqueous phase was extracted with EtOAc (2×10 mL), and the combined organic layers were washed with sat. aq. NaCl (10 mL), dried over $MgSO_4$, filtered and concentrated under reduced pressure. The residue was purified by $SiO_2$ gel chromatography (0% to 20% isopropanol in $CH_2Cl_2$) to give the title compound as a light brown solid (210 mg, 35%). MS (ES$^+$) $C_{11}H_{15}IN_4O$ requires: 346, found: 347 [M+H]$^+$.

Intermediate "C"

1-Iodo-N-methyl-3-(tetrahydro-2H-pyran-4-yl)-5,6-dihydroimidazo[1,5-a]pyrazine-7(8H)-carboxamide

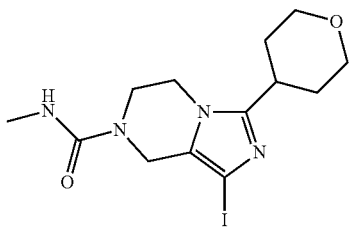

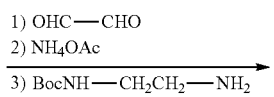

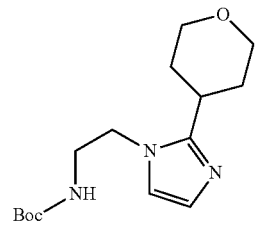

tert-Butyl 2-(2-(tetrahydro-2H-pyran-4-yl)-1H-imidazol-1-yl)ethylcarbamate

To a mixture of tetrahydro-2H-pyran-4-carbaldehyde (2.80 g, 25 mmol) and 40% aq. glyoxal (5.0 g, 34 mmol) in MeOH (100 mL) at 0° C. was added $NH_4OAc$ (3.8 g, 49 mmol), followed by tert-butyl 2-aminoethylcarbamate (3.94 g, 24.6 mmol) dropwise. The mixture was stirred at RT overnight, then concentrated under reduced pressure. The residue was diluted with $MeOH/CH_2Cl_2$ (1/10, 400 mL), and the mixture was washed with sat. aq. $NH_4Cl$ (200 mL), dried over $Na_2SO_4$, filtered and concentrated under reduced pressure to afford the crude title compound as a red oil (7.0 g, 96%). MS (ES$^+$) $C_{15}H_{25}N_3O_3$ requires: 295, found: 296 [M+H]$^+$.

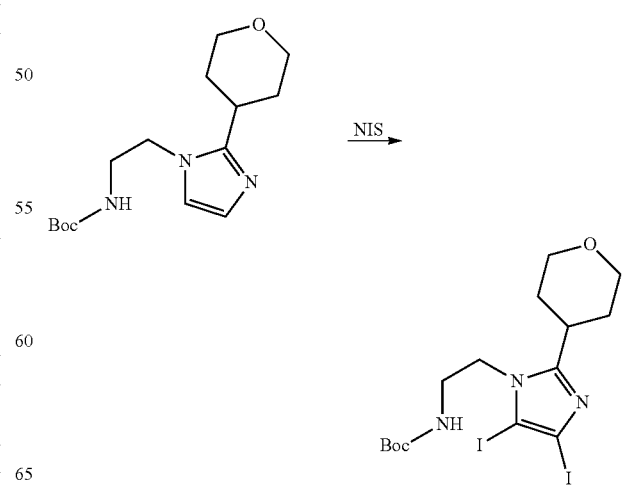

tert-Butyl 2-(4,5-diiodo-2-(tetrahydro-2H-pyran-4-yl)-1H-imidazol-1-yl)ethylcarbamate To a mixture of the product from the previous step (7.0 g, 24 mmol) in DMF (80 mL) at 0° C. was added NIS (16 g, 71 mmol) in small portions. The mixture was stirred at RT overnight, diluted with H$_2$O (800 mL), and extracted with EtOAc (300 mL×3). The combined organic layers were washed with sat. aq. NH$_4$Cl (200 mL×4), dried over Na$_2$SO$_4$, filtered and concentrated under reduced pressure. The residue was purified by SiO$_2$ gel chromatography (0% to 40% EtOAc in petroleum ether) to give the title compound as a tan solid (4.3 g, 33%). MS (ES$^+$) C$_{15}$H$_{23}$I$_2$N$_3$O$_3$ requires: 547, found: 548 [M+H]$^+$.

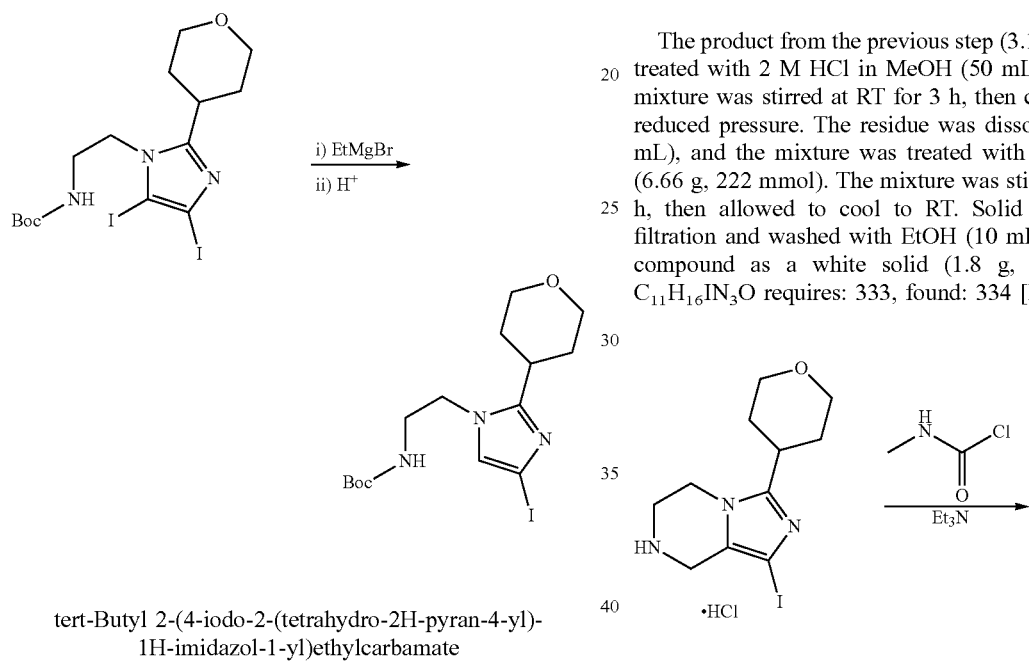

tert-Butyl 2-(4-iodo-2-(tetrahydro-2H-pyran-4-yl)-1H-imidazol-1-yl)ethylcarbamate To a mixture of the product from the previous step (4.3 g, 7.9 mmol) in THF (100 mL) at −50° C. was added, drop-wise, 1.0 M EtMgBr in THF (31.6 mL, 31.6 mmol). The mixture was stirred at −50° C. for 3 h, treated with sat. aq. NH$_4$Cl (10 mL) at low temperature, diluted with H$_2$O (200 mL), and extracted with EtOAc (100 mL×3). The combined organic phases were washed with sat. aq. NaCl (100 mL), dried over Na$_2$SO$_4$, filtered and concentrated under reduced pressure to give the crude title compound as a yellow oil (3.1 g, 93%). MS (ES$^+$) C$_{15}$H$_{24}$IN$_3$O$_3$ requires: 421, found: 422 [M+H]$^+$.

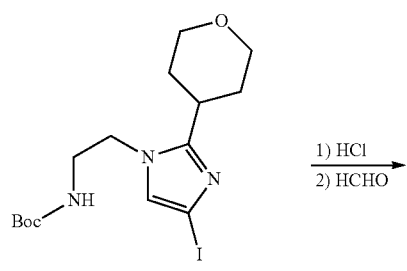

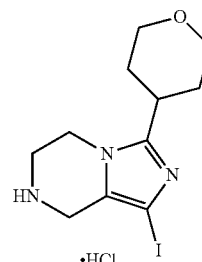

1-Iodo-3-(tetrahydro-2H-pyran-4-yl)-5,6,7,8-tetrahydroimidazo[1,5-a]pyrazine, HCl salt The product from the previous step (3.1 g, 7.4 mmol) was treated with 2 M HCl in MeOH (50 mL, 100 mmol). The mixture was stirred at RT for 3 h, then concentrated under reduced pressure. The residue was dissolved in EtOH (50 mL), and the mixture was treated with paraformaldehyde (6.66 g, 222 mmol). The mixture was stirred at reflux for 2 h, then allowed to cool to RT. Solid was collected by filtration and washed with EtOH (10 mL) to give the title compound as a white solid (1.8 g, 66%). MS (ES$^+$) C$_{11}$H$_{16}$IN$_3$O requires: 333, found: 334 [M+H]$^+$.

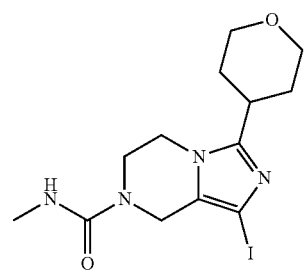

1-Iodo-N-methyl-3-(tetrahydro-2H-pyran-4-yl)-5,6-dihydroimidazo[1,5-a]pyrazine-7(8H)-carboxamide To a mixture of the product from the previous step (1.8 g, 4.9 mmol) in CH$_2$Cl$_2$ (100 mL) was added Et$_3$N (2.02 g, 20.0 mmol). The mixture was cooled to 0° C. and methylcarbamic chloride (930 mg, 10 mmol) was added in small portions. The mixture was stirred at RT for 2 h, treated with sat. aq. NaCl (200 mL), then extracted with MeOH/CH$_2$Cl$_2$ (1/10, 150 mL×6). The combined organic layers were dried over Na$_2$SO$_4$, filtered and concentrated under reduced pressure to give the title compound as a white solid (1.4 g, 73%). MS (ES$^+$) C$_{13}$H$_{19}$IN$_4$O$_2$ requires: 390, found: 391 [M+H]$^+$.

Intermediate "D"

3-(4,4-difluorocyclohexyl)-1-iodo-N-methyl-5,6-dihydroimidazo[1,5-a]pyrazine-7(8H) carboxamide

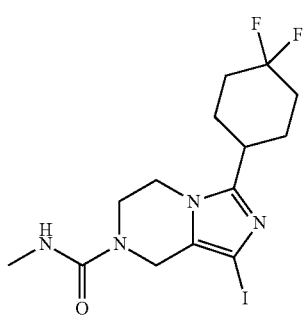

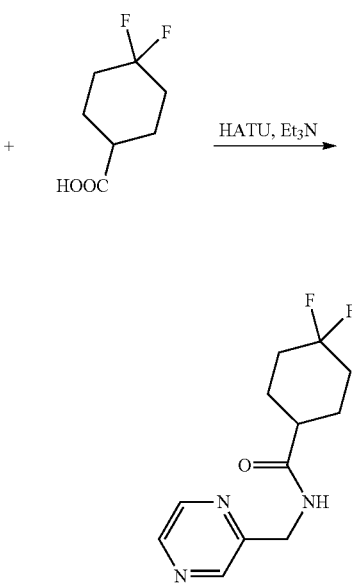

4,4-Difluoro-N-(pyrazin-2-ylmethyl)cyclohexanecarboxamide

To a mixture of pyrazin-2-ylmethanamine (5.0 g, 45.9 mmol) and 4,4-difluorocyclohexanecarboxylic acid (7.53 g, 45.9 mmol) in DMF (100 mL) were added HATU (17.4 g, 45.9 mmol) and Et$_3$N (4.64 g, 45.9 mmol). The mixture was stirred at RT overnight, diluted with H$_2$O (800 mL), and extracted with EtOAc (300 mL×3). The organic phase was washed with sat. aq. NaCl (200 mL), dried over Na$_2$SO$_4$, filtered and concentrated under reduced pressure. The residue was purified by SiO$_2$ gel chromatography (0% to 10% MeOH in CH$_2$Cl$_2$) to give the title compound as a red solid (5.0 g, 43%). MS (ES$^+$) C$_{12}$H$_{15}$F$_2$N$_3$O requires: 255, found: 256 [M+H]$^+$.

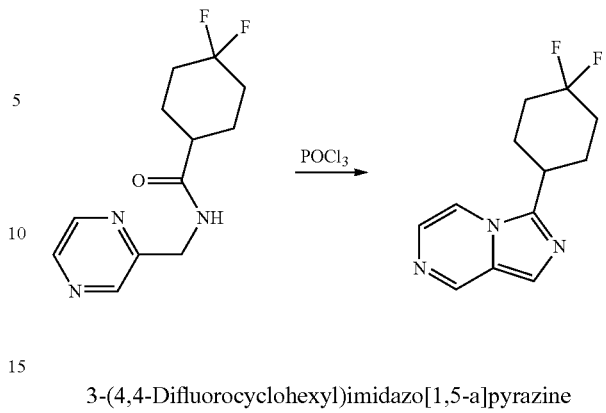

3-(4,4-Difluorocyclohexyl)imidazo[1,5-a]pyrazine

To a mixture of the product from the previous step (5.0 g, 20 mmol) in MeCN (80 mL) was added DMF (1.43 g, 19.6 mmol) then POCl$_3$ (3.00 g, 19.6 mmol) in small portions. The mixture was stirred at 80° C. for 30 min, diluted with sat. aq. KHCO$_3$ (200 mL), and extracted with EtOAc (300 mL×3). The organic phase was washed with sat. aq. NaCl (300 mL), dried over Na$_2$SO$_4$, filtered and concentrated under reduced pressure. The residue was purified by SiO$_2$ gel chromatography (0% to 10% MeOH in CH$_2$Cl$_2$) to give the title compound as a tan solid (4.0 g, 77%). MS (ES$^+$) C$_{12}$H$_{13}$F$_2$N$_3$ requires: 237, found: 238 [M+H]$^+$.

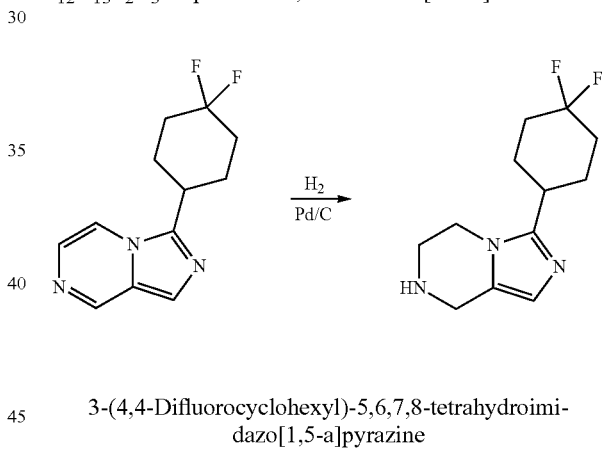

3-(4,4-Difluorocyclohexyl)-5,6,7,8-tetrahydroimidazo[1,5-a]pyrazine

To a mixture of the product from the previous step (4.0 g, 17 mmol) in MeOH (50 mL) was added 10% Pd/C (8.0 g). The mixture was stirred at RT under an atmosphere of hydrogen (balloon) for 12 h, filtered and concentrated under reduced pressure to give the title compound as a yellow solid (3.8 g, 83%). MS (ES$^+$) C$_{12}$H$_{17}$F$_2$N$_3$ requires: 241, found: 242 [M+H]$^+$.

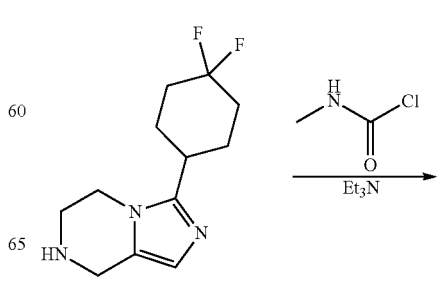

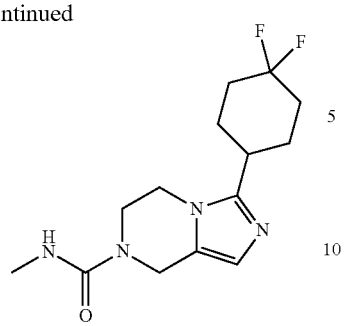

3-(4,4-Difluorocyclohexyl)-N-methyl-5,6-dihydro-imidazo[1,5-a]pyrazine-7(8H)-carboxamide To a mixture of the product from the previous step (3.8 g, 16 mmol) in CH$_2$Cl$_2$ (50 mL) were added methylcarbamic chloride (4.97 g, 47.1 mmol) and Et$_3$N (4.76 g, 47.1 mmol). The mixture was stirred at RT for 3 h, diluted with H$_2$O (200 mL), and extracted with EtOAc (300 mL×3). The combined organic layers were washed with sat. aq. NaCl (300 mL), dried over Na$_2$SO$_4$, filtered and concentrated under reduced pressure. The residue was purified by SiO$_2$ gel chromatography (0% to 10% MeOH in CH$_2$Cl$_2$) to give the title compound as a tan solid (4.0 g, 75%). MS (ES$^+$) C$_{14}$H$_{20}$F$_2$N$_4$O requires: 298, found: 299 [M+H]$^+$.

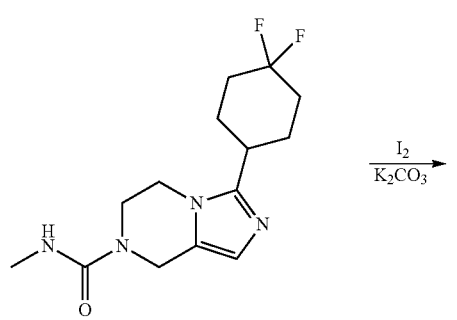

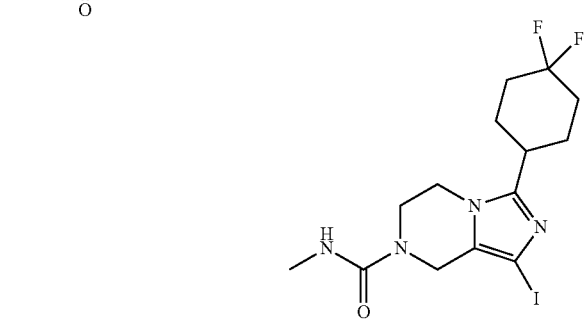

3-(4,4-Difluorocyclohexyl)-1-iodo-N-methyl-5,6-dihydroimidazo[1,5-a]pyrazine-7(8H)-carboxamide To a mixture of the product from the previous step (4.0 g, 13 mmol) in DMF (50 mL) were added I2 (3.40 g, 13.4 mmol) and K$_2$CO$_3$ (3.70 g, 26.8 mmol). The mixture was stirred at RT for 2 h, treated with sat. aq. NaCl (100 mL), and extracted with EtOAc (100 mL×6). The combined organic layers were dried over Na$_2$SO$_4$, filtered and concentrated under reduced pressure. The residue was purified by SiO$_2$ gel chromatography (0% to 10% MeOH in CH$_2$Cl$_2$) to give the title compound as a yellow solid (3.60 g, 57%). MS (ES$^+$) C$_{14}$H$_{19}$F$_2$IN$_4$O requires: 424, found: 425 [M+H]$^+$.

Intermediate "E"

3-(3,3-Difluorocyclobutyl)-1-iodo-N-methyl-5,6-dihydroimidazo[1,5-a]pyrazine-7(8H)-carboxamide

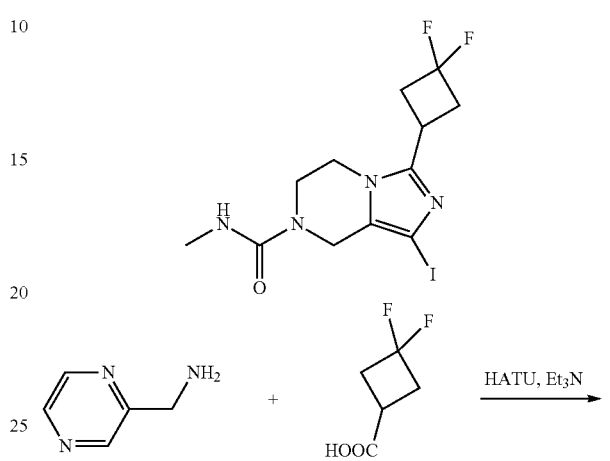

3,3-Difluoro-N-(pyrazin-2-ylmethyl)cyclobutanecarboxamide

To a mixture of pyrazin-2-ylmethanamine (5.00 g, 45.9 mmol) and 3,3-difluorocyclobutanecarboxylic acid (6.24 g, 45.9 mmol) in DMF (100 mL) were added HATU (17.4 g, 45.9 mmol) and TEA (4.64 g, 45.9 mmol). The mixture was stirred at RT overnight, diluted with H$_2$O (800 mL), and extracted with EtOAc (300 mL×3). The combined organic layers were washed with sat. aq. NaCl (200 mL), dried over Na$_2$SO$_4$, filtered and concentrated under reduced pressure. The residue was purified by SiO$_2$ gel chromatography (0% to 10% MeOH in CH$_2$Cl$_2$) to give the title compound as a red solid (5.0 g, 48%). MS (ES$^+$) C$_{10}$H$_{11}$F$_2$N$_3$O requires: 227, found: 228 [M+H]$^+$.

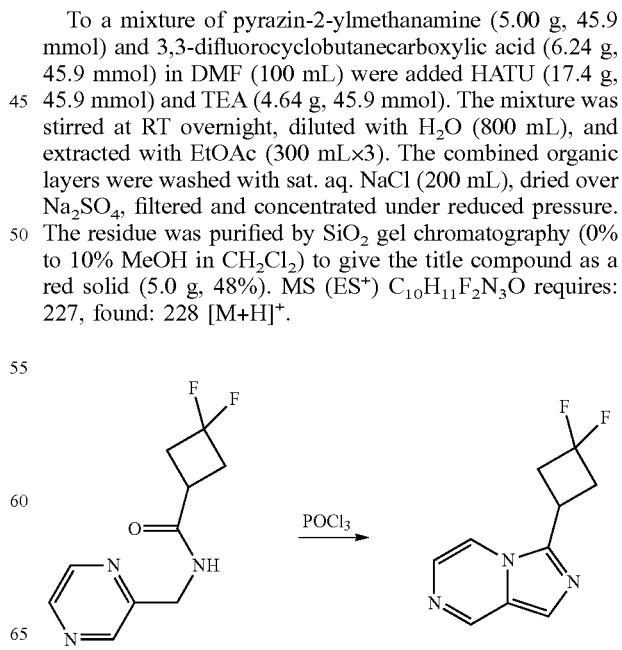

3-(3,3-Difluorocyclobutyl)imidazo[1,5-a]pyrazine

To a mixture of 3,3-difluoro-N-(pyrazin-2-ylmethyl)cyclobutanecarboxamide (5.0 g, 22 mmol) in MeCN (80 mL) was added DMF (1.61 g, 22.0 mmol) then POCl$_3$ (3.37 g, 22.0 mmol) in small portions. The mixture was stirred at 80° C. for 30 min, treated with sat. aq. KHCO$_3$ (200 mL), and extracted with EtOAc (300 mL×3). The combined organic layers were washed with sat. aq. NaCl (300 mL), dried over Na$_2$SO$_4$, filtered and concentrated under reduced pressure. The residue was purified by SiO$_2$ gel chromatography (0% to 10% MeOH in CH$_2$Cl$_2$) to give the title compound as a tan solid (4.0 g, 87%). MS (ES$^+$) C$_{10}$H$_9$F$_2$N$_3$ requires: 209, found: 210 [M+H]$^+$.

3-(3,3-Difluorocyclobutyl)-5,6,7,8-tetrahydroimidazo[1,5-a]pyrazine

To a mixture of 3-(3,3-difluorocyclobutyl)imidazo[1,5-a]pyrazine (4.0 g, 19 mmol) in MeOH (50 mL) was added 10% palladium on carbon (8.0 g). The mixture was stirred at RT under an atmosphere of hydrogen (balloon) for 12 h, filtered and concentrated under reduced pressure to give the title compound as a yellow solid (3.8 g, 93%). MS (ES$^+$) C$_{10}$H$_{13}$F$_2$N$_3$ requires: 213, found: 214 [M+H]$^+$.

3-(3,3-Difluorocyclobutyl)-N-methyl-5,6-dihydroimidazo[1,5-a]pyrazine-7(8H)-carboxamide To a mixture of 3-(3,3-difluorocyclobutyl)-5,6,7,8-tetrahydroimidazo[1,5-a]pyrazine (3.8 g, 18 mmol) in CH$_2$Cl$_2$ (50 mL) was added methylcarbamic chloride (4.97 g, 53.4 mmol) and TEA (5.39 g, 53.4 mmol). The mixture was stirred at RT for 3 h, treated with H$_2$O (200 mL), and extracted with EtOAc (300 mL×3). The combined organic layers were washed with sat. aq. NaCl (300 mL), dried over Na$_2$SO$_4$, filtered and concentrated under reduced pressure. The residue was purified by SiO$_2$ gel chromatography (0% to 10% MeOH in CH$_2$Cl$_2$) to give the title compound as a tan solid (4.0 g, 83%). MS (ES$^+$) C$_{12}$H$_{16}$F$_2$N$_4$O requires: 270, found: 271 [M+H]$^+$.

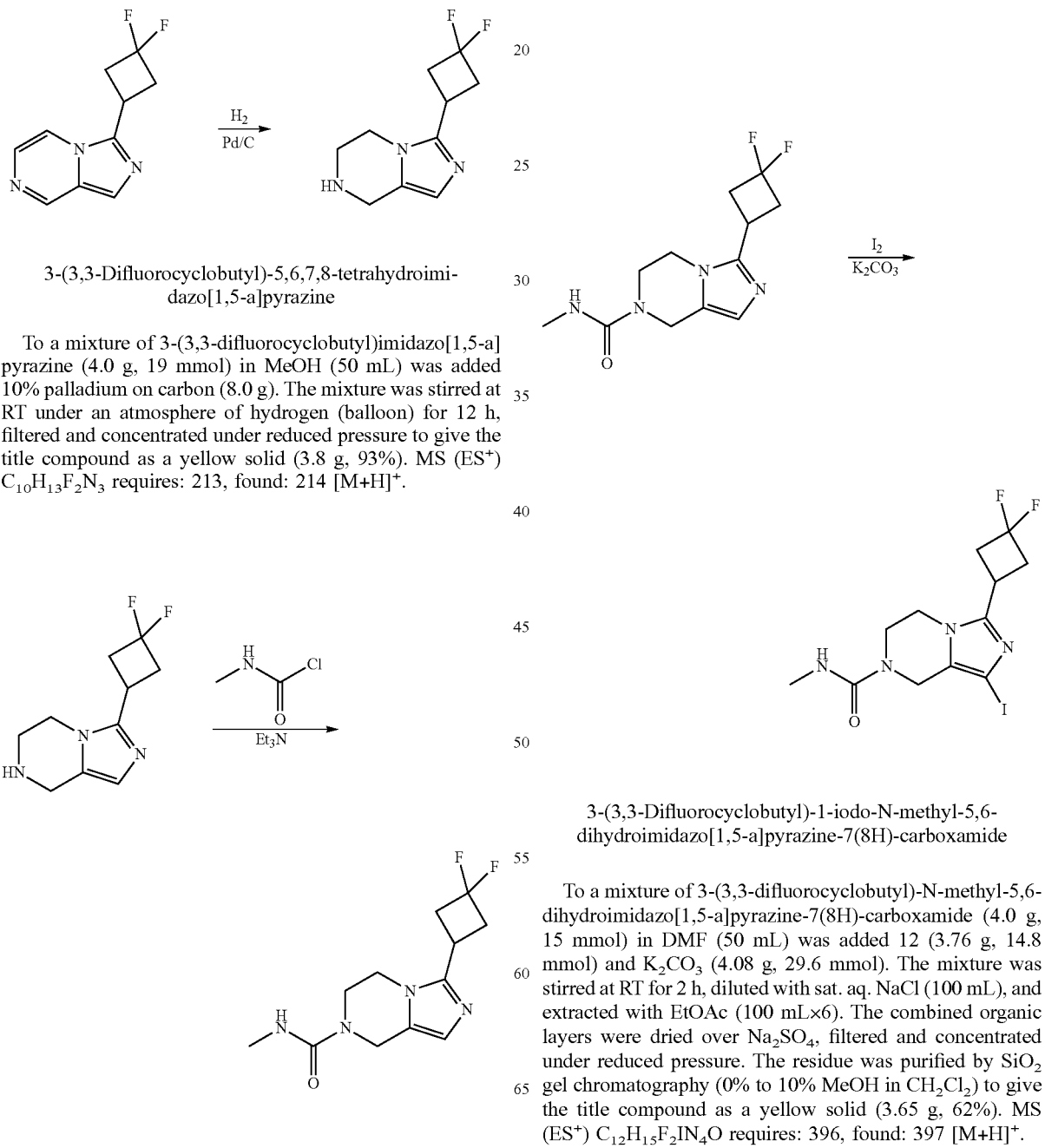

3-(3,3-Difluorocyclobutyl)-1-iodo-N-methyl-5,6-dihydroimidazo[1,5-a]pyrazine-7(8H)-carboxamide To a mixture of 3-(3,3-difluorocyclobutyl)-N-methyl-5,6-dihydroimidazo[1,5-a]pyrazine-7(8H)-carboxamide (4.0 g, 15 mmol) in DMF (50 mL) was added I2 (3.76 g, 14.8 mmol) and K$_2$CO$_3$ (4.08 g, 29.6 mmol). The mixture was stirred at RT for 2 h, diluted with sat. aq. NaCl (100 mL), and extracted with EtOAc (100 mL×6). The combined organic layers were dried over Na$_2$SO$_4$, filtered and concentrated under reduced pressure. The residue was purified by SiO$_2$ gel chromatography (0% to 10% MeOH in CH$_2$Cl$_2$) to give the title compound as a yellow solid (3.65 g, 62%). MS (ES$^+$) C$_{12}$H$_{15}$F$_2$IN$_4$O requires: 396, found: 397 [M+H]$^+$.

Example 1

1-(3-cyclopropyl-1-(1-methyl-3-(1-methyl-1H-pyrazol-4-yl)-1H-indazol-5-yl)-5,6-dihydroimidazo[1,5-a]pyrazin-7(8H)-yl)ethan-1-one

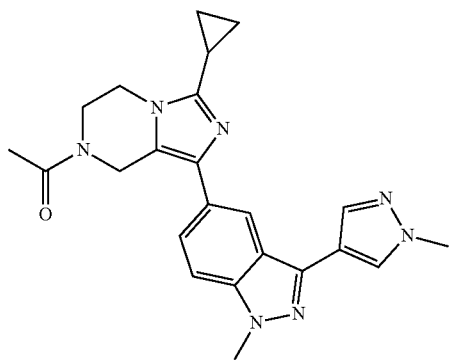

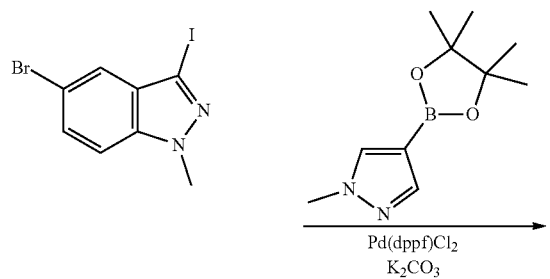

5-Bromo-3-iodo-1-methyl-1H-indazole

To a solution of 5-bromo-1-methyl-1H-indazole (800 mg, 3.79 mmol) in DMF (10 ml) was added NIS (2132 mg, 9.476 mmol), and the resulting mixture was stirred at 100° C. for 16 h. $H_2O$ (30 mL) and sat. aq. $Na_2S_2O_3$ (5 ml) were added, and the layers were separated. The aqueous phase was extracted with EtOAc (3×20 mL), and the combined organic layers were washed with sat. aq. NaCl, dried over $MgSO_4$, filtered and concentrated under reduced pressure. The residue was purified by $SiO_2$ gel chromatography (0% to 25% EtOAc in hexanes) to give the title compound as a white solid (825 mg, 65%). MS (ES+) $C_8H_6BrIN_2$ requires: 336, found: 337 [M+H]+.

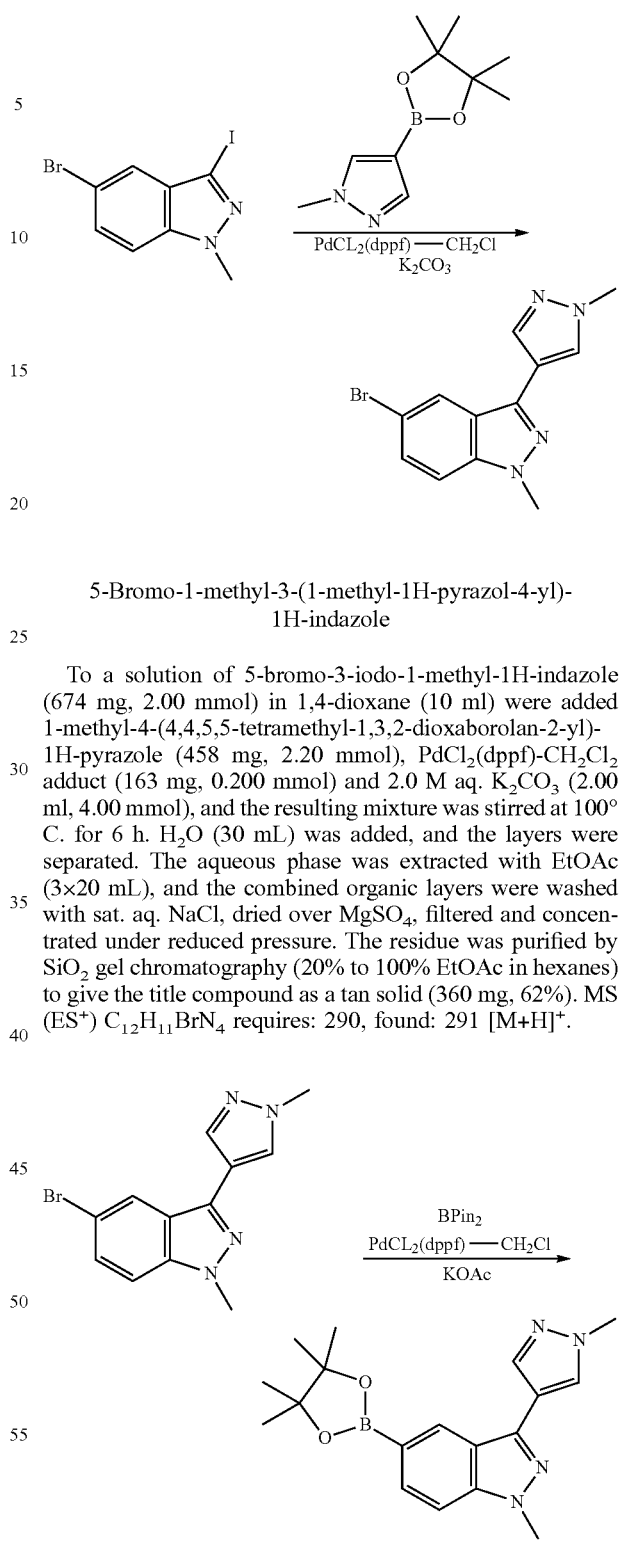

5-Bromo-1-methyl-3-(1-methyl-1H-pyrazol-4-yl)-1H-indazole

To a solution of 5-bromo-3-iodo-1-methyl-1H-indazole (674 mg, 2.00 mmol) in 1,4-dioxane (10 ml) were added 1-methyl-4-(4,4,5,5-tetramethyl-1,3,2-dioxaborolan-2-yl)-1H-pyrazole (458 mg, 2.20 mmol), $PdCl_2(dppf)$-$CH_2Cl_2$ adduct (163 mg, 0.200 mmol) and 2.0 M aq. $K_2CO_3$ (2.00 ml, 4.00 mmol), and the resulting mixture was stirred at 100° C. for 6 h. $H_2O$ (30 mL) was added, and the layers were separated. The aqueous phase was extracted with EtOAc (3×20 mL), and the combined organic layers were washed with sat. aq. NaCl, dried over $MgSO_4$, filtered and concentrated under reduced pressure. The residue was purified by $SiO_2$ gel chromatography (20% to 100% EtOAc in hexanes) to give the title compound as a tan solid (360 mg, 62%). MS (ES+) $C_{12}H_{11}BrN_4$ requires: 290, found: 291 [M+H]+.

1-Methyl-3-(1-methyl-1H-pyrazol-4-yl)-5-(4,4,5,5-tetramethyl-1,3,2-dioxaborolan-2-yl)-1H-indazole ("Intermediate "F"")

A degassed solution of 5-bromo-1-methyl-3-(1-methyl-1H-pyrazol-4-yl)-1H-indazole (360 mg, 1.24 mmol), $BPin_2$ (377 mg, 1.48 mmol), PdCl$_2$(dppf)-CH$_2$Cl$_2$ adduct (101 mg, 0.124 mmol) and KOAc (364 mg, 3.71 mmol) in 1,4-dioxane (10 ml) was stirred at 100° C. for 4 h, then allowed to cool to RT. H$_2$O (50 mL) was added, and the layers were separated. The aqueous phase was extracted with EtOAc (3×30 mL), and the combined organic layers were washed with sat. aq. NaCl, dried over MgSO$_4$, filtered and concentrated under reduced pressure. The residue was purified by SiO$_2$ gel chromatography (0% to 5% MeOH in CH$_2$Cl$_2$) to give to give the title compound as on off-white solid (410 mg, 98%). MS (ES$^+$) C$_{18}$H$_{23}$BN$_4$O$_2$ requires: 338, found: 339 [M+H]$^+$.

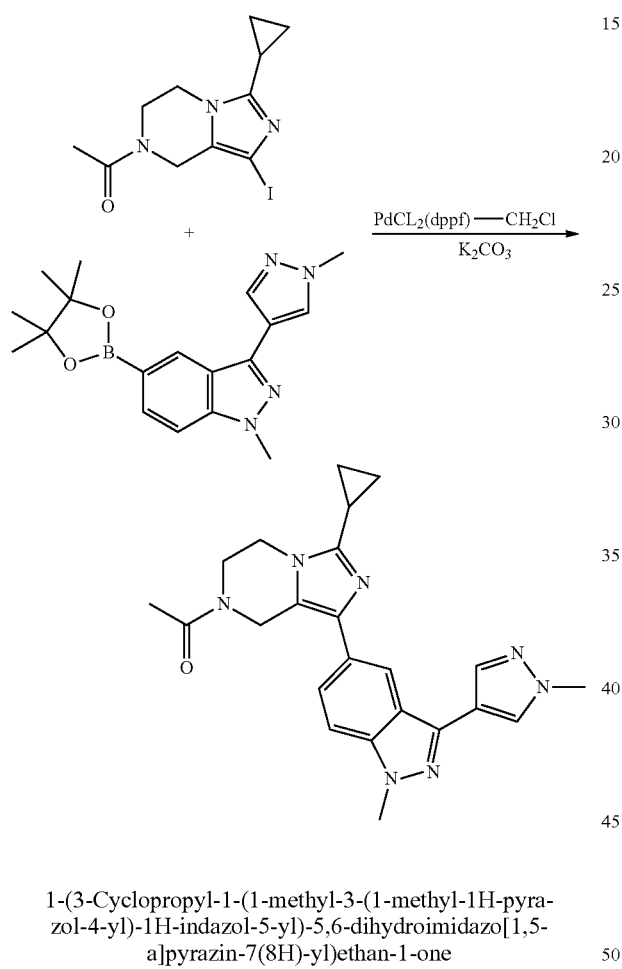

1-(3-Cyclopropyl-1-(1-methyl-3-(1-methyl-1H-pyrazol-4-yl)-1H-indazol-5-yl)-5,6-dihydroimidazo[1,5-a]pyrazin-7(8H)-yl)ethan-1-one A degassed solution of Intermediate "A" (35.0 mg, 0.106 mmol), Intermediate "F" (71.5 mg, 0.106 mmol), PdCl$_2$(dppf)-CH$_2$Cl$_2$ adduct (8.63 mg, 10.6 μmol) and 2.0 M aq. K$_2$CO$_3$ (0.106 ml, 0.212 mmol) in DMF (0.5 ml) was stirred at 90° C. for 1 h, then concentrated under reduced pressure. The residue was purified by mass-triggered preparative HPLC (Mobile phase: A=0.1% TFA/H$_2$O, B=0.1% TFA/MeCN; Gradient: B=10% to 40%; 12 min; Column: C18) to give the title compound as a TFA salt. To this salt was added sat. aq. NaHCO$_3$ (5 mL), the mixture was extracted with EtOAc (3×5 mL), and the combined organic layers were washed with sat. aq. NaCl, dried over MgSO$_4$, filtered and concentrated under reduced pressure to give the title compound as a white powder (18 mg, 41.0% yield). MS (ES$^+$) C$_{23}$H$_{25}$N$_7$O requires: 415, found: 416 [M+H]$^+$. $^1$H NMR (CD$_3$OD) δ 8.22 (s, 1H), 8.16 (d, 1H, J=9.6 Hz), 8.07 (d, 1H, J=6.0 Hz), 7.76-7.72 (m, 1H), 7.62-7.58 (m, 1H), 5.00 (s, 0.7H), 4.98 (s, 1.3H), 4.27-4.26 (m, 1.3H), 4.18-4.16 (m, 0.7H), 4.08-4.01 (m, 8H), 2.24 (s, 2H), 2.18 (s, 1H), 1.99-1.96 (m, 1H), 1.04-1.01 (m, 4H).

The disclosure is further illustrated by the following examples. All IUPAC names were generated using CambridgeSoft's ChemDraw 10.0.

Example 2

3-cyclopropyl-N-methyl-1-(7-(1-methyl-1H-pyrazol-4-yl)-6-(trifluoromethoxy)quinolin-4-yl)-5,6-dihydroimidazo[1,5-a]pyrazine-7(8H)-carboxamide

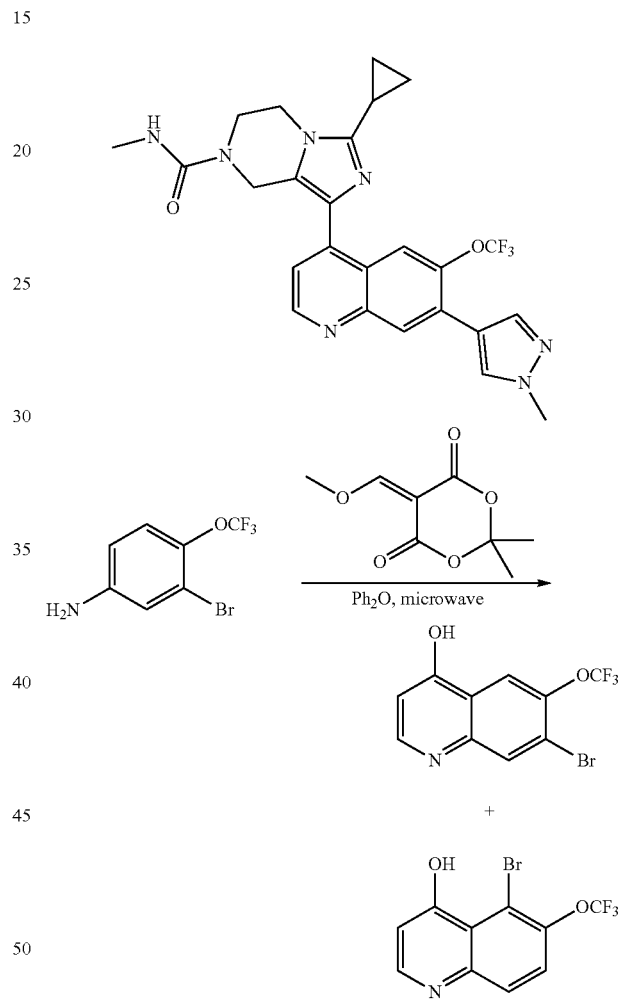

5-Bromo-6-(trifluoromethoxy)quinolin-4-ol and 7-bromo-6-(trifluoromethoxy)quinolin-4-ol A microwave vial was charged with 5-(methoxymethylene)-2,2-dimethyl-1,3-dioxane-4,6-dione (372 mg, 2.00 mmol), 3-bromo-4-(trifluoromethoxy)aniline (512 mg, 2.00 mmol) and diphenyl ether (2 ml). The vial was sealed and the reaction mixture was heated to 200° C. in the microwave reactor for 12 minutes. The reaction mixture was diluted with Et$_2$O, and solid was isolated by Büchner filtration to give an approximately 1:1 mixture of 5-bromo-6-(trifluoromethoxy)quinolin-4-ol and 7-bromo-6-(trifluoromethoxy)quinolin-4-ol as an off-white solid (198 mg, 32%). The mixture was carried to the next step without further purification. MS (ES⁺) C₁₀H₅BrF₃NO₂ requires: 307, found: 308 [M+H]⁺.

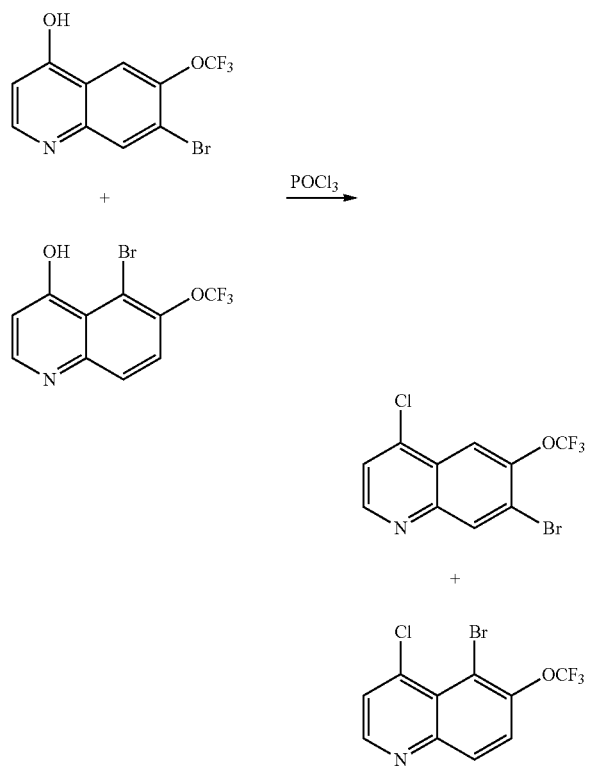

7-Bromo-4-chloro-6-(trifluoromethoxy)quinoline

To a solution of the crude regioisomer mixture from the previous step (198 mg, 0.643 mmol) in CH₃CN (5 ml) was added POCl₃ (0.120 ml, 1.28 mmol), and the resulting mixture was stirred at 80° C. for 1 h then concentrated under reduced pressure. Sat. aq. NaHCO₃(10 mL) was added, and the layers were separated. The aqueous phase was extracted with EtOAc (3×5 mL), and the combined organic layers were washed with sat. aq. NaCl, dried over MgSO₄, filtered and concentrated under reduced pressure. The residue was purified by SiO₂ gel chromatography (0% to 30% EtOAc in hexanes). The undesired 5-bromo-4-chloro-6-(trifluoromethoxy)quinoline isomer was obtained in the earlier-eluting fractions as an off-white solid (80 mg, 38%), followed by the title compound in the later-eluting fractions as an off-white solid (115 mg, 55%). MS (ES⁺) C₁₀H₄BrClF₃NO requires: 325, found: 326 [M+H]⁺.

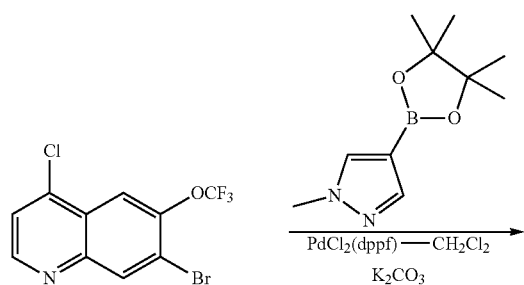

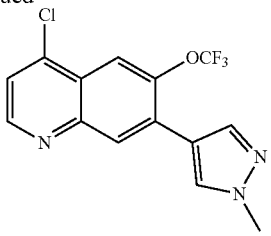

4-Chloro-7-(1-methyl-1H-pyrazol-4-yl)-6-(trifluoromethoxy)quinoline

To a solution of 7-bromo-4-chloro-6-(trifluoromethoxy)quinoline (115 mg, 0.352 mmol) in 1,4-dioxane (3 ml) were added 1-methyl-4-(4,4,5,5-tetramethyl-1,3,2-dioxaborolan-2-yl)-1H-pyrazole (81.0 mg, 0.387 mmol), PdCl₂(dppf)-CH₂Cl₂ adduct (28.8 mg, 0.035 mmol) and 2.0 M aq. K₂CO₃ (0.352 ml, 0.704 mmol), and the resulting mixture was stirred at 100° C. for 2 h. H₂O (10 mL) was added, and the layers were separated. The aqueous phase was extracted with EtOAc (3×10 mL), and the combined organic layers were washed with sat. aq. NaCl, dried over MgSO₄, filtered and concentrated under reduced pressure. The residue was purified by SiO₂ gel chromatography (0% to 5% MeOH in CH₂Cl₂) to give the title compound as an off-white solid (101 mg, 88%). MS (ES⁺) C₁₄H₉ClF₃N₃O requires: 327, found: 328 [M+H]⁺.

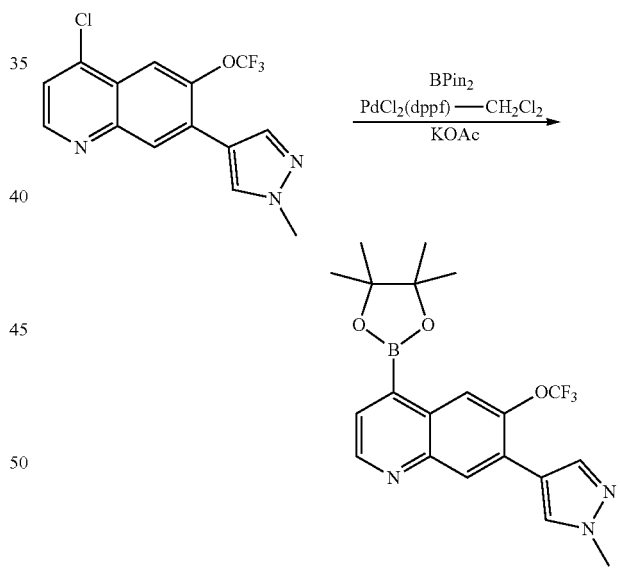

(7-(1-Methyl-1H-pyrazol-4-yl)-6-(trifluoromethoxy)quinolin-4-yl)boronic acid

A degassed solution of 4-chloro-7-(1-methyl-1H-pyrazol-4-yl)-6-(trifluoromethoxy)quinoline (100 mg, 0.305 mmol), BPin₂ (93.0 mg, 0.366 mmol), PdCl₂(dppf)-CH₂Cl₂ adduct (24.92 mg, 0.0310 mmol) and KOAc (90.0 mg, 0.916 mmol) in 1,4-dioxane (2 ml) was stirred at 90° C. for 16 h, then allowed to cool to RT. H₂O (10 mL) was added, and the layers were separated. The aqueous phase was extracted with EtOAc (3×5 mL), and the combined organic layers were washed with sat. aq. NaCl, dried over MgSO$_4$, filtered and concentrated under reduced pressure. The residue was purified by SiO$_2$ gel chromatography (0% to 5% MeOH in CH$_2$Cl$_2$) to give the title compound as a tan solid (48 mg, 47%). MS (ES$^+$) C$_{14}$H$_{11}$BF$_3$N$_3$O$_3$ requires: 337, found: 338 [M+H]$^+$.

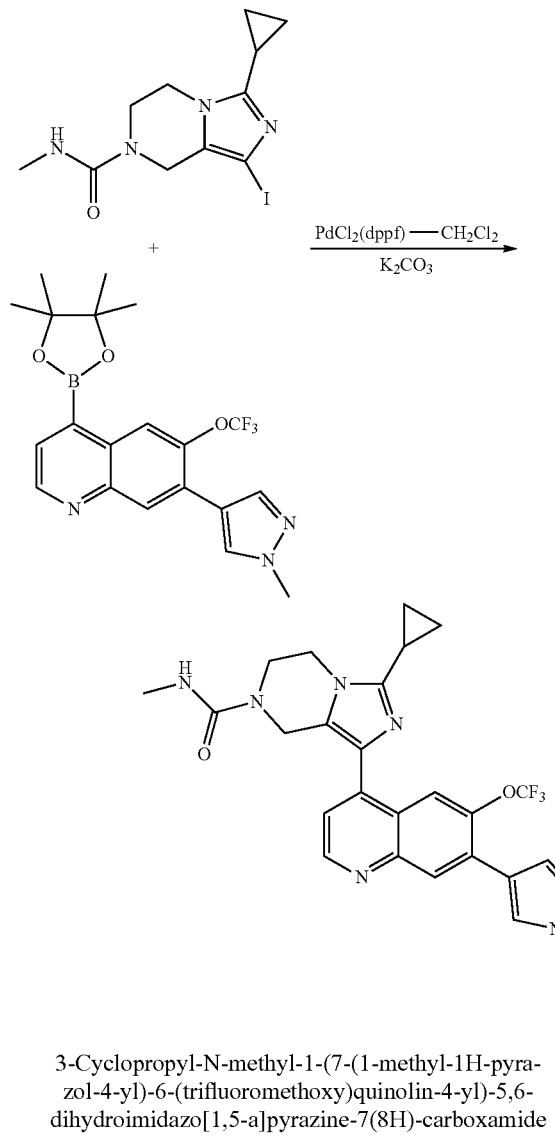

3-Cyclopropyl-N-methyl-1-(7-(1-methyl-1H-pyrazol-4-yl)-6-(trifluoromethoxy)quinolin-4-yl)-5,6-dihydroimidazo[1,5-a]pyrazine-7(8H)-carboxamide A degassed solution of Intermediate "B" (26.7 mg, 0.077 mmol), (7-(1-methyl-1H-pyrazol-4-yl)-6-(trifluoromethoxy)quinolin-4-yl)boronic acid (26 mg, 0.077 mmol), PdCl$_2$(dppf)-CH$_2$Cl$_2$ adduct (6.30 mg, 7.71 µmol) and 2.0 M aq. K$_2$CO$_3$ (0.077 ml, 0.154 mmol) in DMF (0.5 ml) was stirred at 90° C. for 1 h, then concentrated under reduced pressure. The residue was purified by SiO$_2$ gel chromatography (0% to 10% MeOH in CH$_2$Cl$_2$) to give the title compound as a yellow powder (16 mg, 41%). MS (ES$^+$) C$_{25}$H$_{24}$F$_3$N$_7$O$_2$ requires: 511, found: 512 [M+H]$^+$. $^1$H NMR (CD$_3$OD) δ 8.85 (d, 1H, J=4.6 Hz), 8.74 (s, 1H), 8.25 (s, 1H), 8.13 (s, 1H), 7.98 (s, 1H), 7.41 (d, 1H, J=4.6 Hz), 4.77 (s, 2H), 4.23 (t, 2H, J=5.5 Hz), 4.00 (s, 3H), 3.93 (t, 2H, J=5.5 Hz), 2.72 (s, 3H), 2.09-2.02 (m, 1H), 1.09-1.03 (m, 4H).

Example 3

3-cyclopropyl-1-(7-(difluoromethyl)-6-(1-methyl-1H-pyrazol-4-yl)-3,4-dihydroquinolin-1(2H)-yl)-N-methyl-5,6-dihydroimidazo[1,5-a]pyrazine-7(8H)-carboxamide

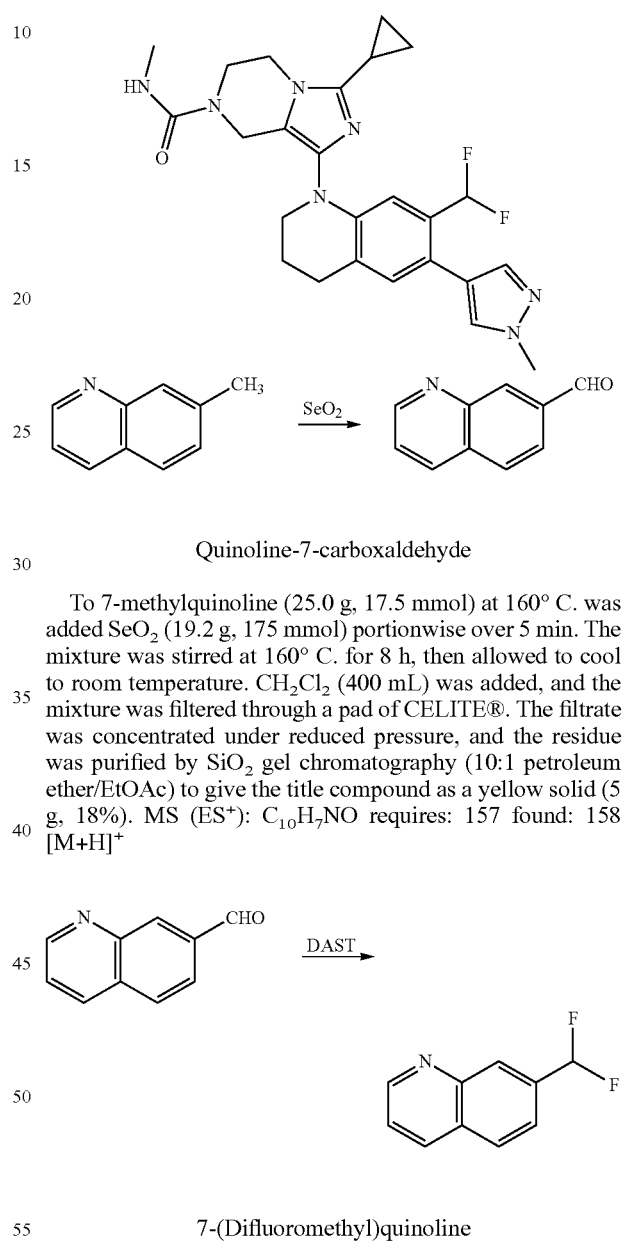

Quinoline-7-carboxaldehyde

To 7-methylquinoline (25.0 g, 17.5 mmol) at 160° C. was added SeO$_2$ (19.2 g, 175 mmol) portionwise over 5 min. The mixture was stirred at 160° C. for 8 h, then allowed to cool to room temperature. CH$_2$Cl$_2$ (400 mL) was added, and the mixture was filtered through a pad of CELITE®. The filtrate was concentrated under reduced pressure, and the residue was purified by SiO$_2$ gel chromatography (10:1 petroleum ether/EtOAc) to give the title compound as a yellow solid (5 g, 18%). MS (ES$^+$): C$_{10}$H$_7$NO requires: 157 found: 158 [M+H]$^+$ 7-(Difluoromethyl)quinoline To a solution of quinoline-7-carboxaldehyde (5.00 g, 31.8 mmol) in CH$_2$Cl$_2$ (50 mL) at 0° C. was added DAST (23.1 g, 159 mmol) dropwise over 20 min. The mixture was stirred at RT for 16 h. The mixture was poured into sat. aq. NaHCO$_3$ (300 mL) at 0° C., and the resulting mixture was extracted with CH$_2$Cl$_2$ (3×50 mL). The combined organic layers were dried over Na$_2$SO$_4$, filtered and concentrated under reduced pressure. The residue was purified by SiO$_2$ gel chromatography (10:1 petroleum ether/EtOAc) to give the title compound as a yellow solid (3.4 g, 61%). MS (ES$^+$): C$_{10}$H$_7$F$_2$N requires: 179, found: 180 [M+H]$^+$.

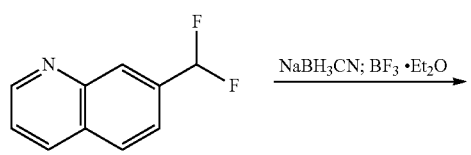 NaBH₃CN; BF₃·Et₂O →

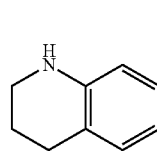

7-(Difluoromethyl)-1,2,3,4-tetrahydroquinoline

To a solution of 7-(difluoromethyl)quinoline (3.4 g, 19 mmol) and NaBH₃CN (6.0 g, 95 mmol) in MeOH (30 mL) at 0° C. was added BF₃·Et₂O (4.7 mL, 38 mmol) dropwise over 20 min. The mixture was stirred at 90° C. for 24 h, then allowed to cool to RT. The mixture was poured into sat. aq. NaHCO₃(400 mL) at 0° C., and the resulting mixture was extracted with CH₂Cl₂ (3×300 mL). The combined organic layers were dried over Na₂SO₄, filtered and concentrated under reduced pressure. The residue was purified by SiO₂ gel chromatography (20:1 petroleum ether/EtOAc) to give the title compound as a brown oil (1.1 g, 31%). MS (ES⁺): $C_{10}H_{11}F_2N$ requires: 183, found: 184 $[M+H]^+$.

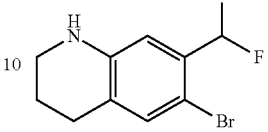 NBS →

6-Bromo-7-(difluoromethyl)-1,2,3,4-tetrahydroquinoline

To a solution of 7-(difluoromethyl)-1,2,3,4-tetrahydroquinoline (1.1 g, 6.0 mmol) in CH₂Cl₂ (20 ml) at 0° C. was added NBS (1.0 g, 5.6 mmol) portionwise over 20 min. The mixture was stirred at room temperature for 16 h. The mixture was poured into water (20 mL) and extracted with CH₂Cl₂ (2×40 mL). The combined organic layers were dried over Na₂SO₄, filtered and concentrated under reduced pressure. The residue was purified by SiO₂ gel chromatography (300:1 petroleum ether/EtOAc) to give the title compound as a yellow oil (1 g, 64%). MS (ES⁺): $C_{10}H_{10}BrF_2N$ requires: 261, found: 262 $[M+H]^+$.

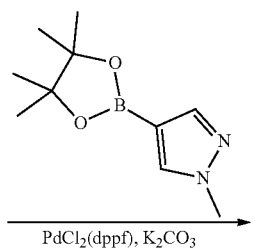 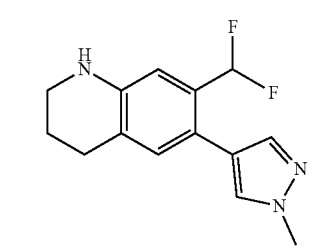

PdCl₂(dppf), K₂CO₃ →

7-(Difluoromethyl)-6-(1-methyl-1H-pyrazol-4-yl)-1,2,3,4-tetrahydroquinoline

To a mixture of 6-bromo-7-(difluoromethyl)-1,2,3,4-tetrahydroquinoline (1.0 g, 3.8 mmol) in 1,4-dioxane (8 mL) and H₂O (2 mL) was added K₂CO₃ (1.1 g, 7.6 mmol), PdCl₂(dppf) (277 mg, 0.38 mmol) and 1-methyl-4-(4,4,5,5-tetramethyl-1,3,2-dioxaborolan-2-yl)-1H-pyrazole (790 mg, 3.8 mmol). The mixture was stirred at 110° C. for 18 h, then allowed to cool to RT and concentrated under reduced pressure. The residue was purified by SiO₂ gel chromatography (40:1 petroleum ether/EtOAc) to give the title compound as a yellow solid (500 mg). MS (ES⁺): $C_{14}H_{15}F_2N_3$ requires: 263, found: 264 $[M+H]^+$.

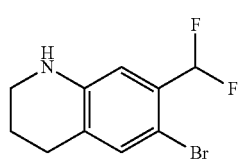

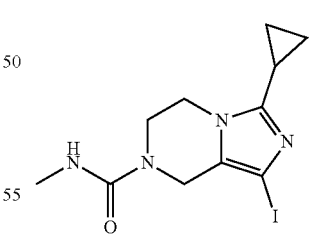

+

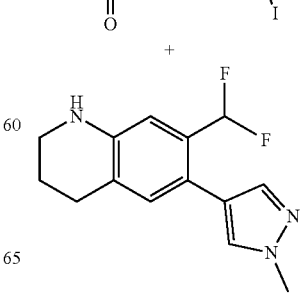

Brettphos, XPhos Pd G2 / NaOtBu →

67

-continued

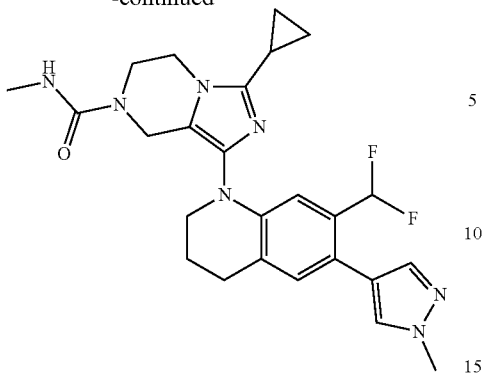

3-Cyclopropyl-1-(7-(difluoromethyl)-6-(1-methyl-1H-pyrazol-4-yl)-3,4-dihydroquinolin-1(2H)-yl)-N-methyl-5,6-dihydroimidazo[1,5-a]pyrazine-7(8H)-carboxamide A degassed solution of Intermediate "B" (10 mg, 0.029 mmol), 7-(difluoromethyl)-6-(1-methyl-1H-pyrazol-4-yl)-1,2,3,4-tetrahydroquinoline (7.61 mg, 0.029 mmol), NaOtBu (5.55 mg, 0.058 mmol), Brettphos (1.55 mg, 2.89 μmol) and XPhos Pd G2 (2.27 mg, 2.89 μmol) in 1,4-dioxane (0.5 ml) was stirred at 120° C. for 16 h, then concentrated under reduced pressure. The residue was purified by mass-triggered preparative HPLC (Mobile phase: A=0.1% TFA/H$_2$O, B=0.1% TFA/MeCN; Gradient: B=10% to 40%; 12 min; Column: C18) to give the title compound as its bis(TFA) salt, as an off-white solid (6 mg, 29%).

MS (ES$^+$) C$_{25}$H$_{29}$F$_2$N$_7$O requires: 481, found: 482 [M+H]$^+$. $^1$H NMR (CD$_3$OD) δ 7.66 (s, 1H), 7.52 (s, 1H), 7.19 (s), 6.77-6.48 (m, 2H), 4.47 (appar br s, 2H), 4.42-4.27 (m, 2H), 4.11-4.03 (m, 2H), 3.92 (s, 3H), 3.63-3.56 (m, 2H), 2.97-2.91 (m, 2H), 2.28-2.20 (m, 3H), 2.13-2.06 (m, 3H), 1.35-1.28 (m, 2H), 1.17-1.11 (m, 2H).

Example 4

2-Fluoro-1-(1-(1-methyl-3-(1-methyl-1H-pyrazol-4-yl)-1H-indazol-5-yl)-3-(tetrahydrofuran-3-yl)-5,6-dihydroimidazo[1,5-a]pyrazin-7(8H)-yl)ethan-1-one

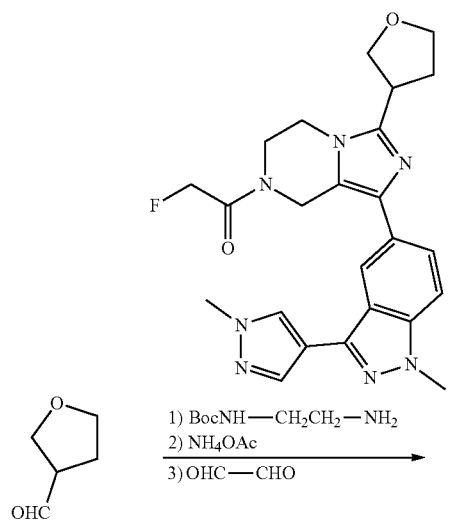

68

-continued

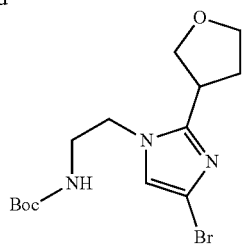

tert-Butyl(2-(2-(tetrahydrofuran-3-yl)-1H-imidazol-1-yl)ethyl)carbamate

Tetrahydrofuran-3-carbaldehyde (2.00 g, 10.0 mmol) was dissolved in MeOH (10 mL) at 25° C. tert-butyl(2-aminoethyl)carbamate (1.60 g, 10.0 mmol) was added dropwise followed by addition of NH$_4$OAc (0.771 g, 10.0 mmol). Glyoxal (1.45 g, 10.0 mmol) was then added dropwise, and the mixture was stirred at 25° C. for 24 h. The mixture was concentrated under reduced pressure. To the residue was added H$_2$O (500 mL) and sat. aq. NaHCO$_3$, the mixture was extracted with EtOAc (3×200 mL), and the combined organic layers were washed with sat. aq. NaCl, dried over MgSO$_4$, filtered and concentrated under reduced pressure to give the crude title compound as a yellow foam (1.01 g, 36%), which was used without further purification. MS (ES$^+$) C$_{14}$H$_{23}$N$_3$O$_3$ requires: 281 found: 282 [M+H]$^+$.

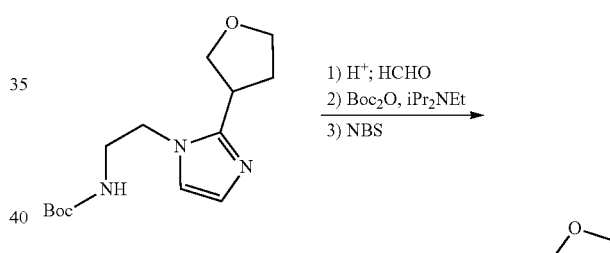

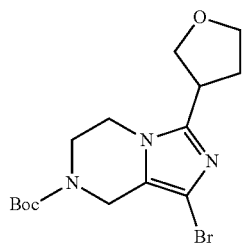

tert-Butyl 1-bromo-3-(tetrahydrofuran-3-yl)-5,6-dihydroimidazo[1,5-a]pyrazine-7(8H)-carboxylate To a solution of HCl in MeOH (pre-made by adding AcCl (2 mL) to MeOH (8 mL)) was added the product from the previous step (400 mg, 1.42 mmol), and the resulting mixture was stirred at 20° C. for 1 h then concentrated under reduced pressure. To the solution of the residue in EtOH (10.00 mL) was added 50% aq. formaldehyde (1.567 mL, 28.4 mmol) and the resulting mixture was stirred at 80° C. for 1 h. The mixture was concentrated under reduced pressure. To a solution of the residue in CH$_2$Cl$_2$ (10.00 mL) were added iPr$_2$NEt (0.745 mL, 4.27 mmol) and Boc$_2$O (931 mg, 4.27 mmol), and the resulting mixture was stirred at 20° C. for 16 h then concentrated under reduced pressure. To a solution of the residue in CH$_2$Cl$_2$ (5 mL) was added NBS (759 mg, 4.27 mmol) and the resulting mixture was stirred at 20° C. for 1 h then concentrated under reduced pressure. The residue was purified by SiO₂ gel chromatography (0% to 5% MeOH in CH₂Cl₂) to give the title compound as a yellow liquid (120 mg, 23%). MS (ES⁺) $C_{15}H_{22}BrN_3O_3$ requires: 371, found: 372 [M+H]⁺.

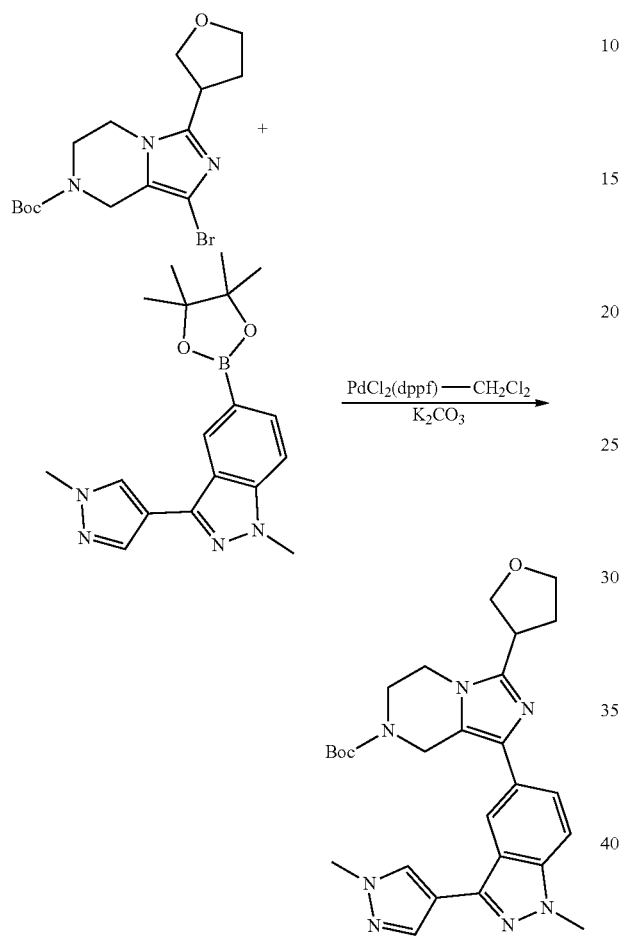

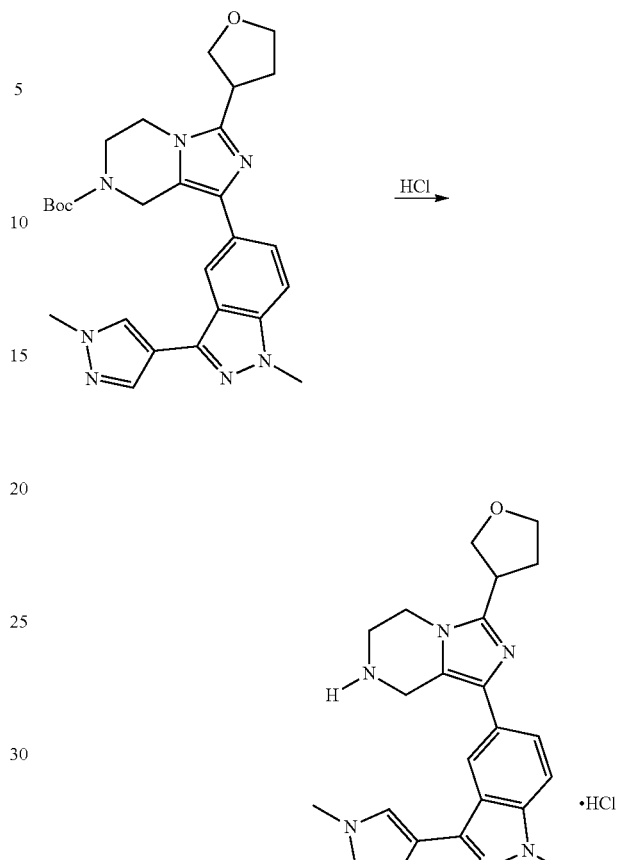

tert-Butyl 1-(1-methyl-3-(1-methyl-1H-pyrazol-4-yl)-1H-indazol-5-yl)-3-(tetrahydrofuran-3-yl)-5,6-dihydroimidazo[1,5-a]pyrazine-7(8H)-carboxylate A degassed solution of the product from the previous step (120 mg, 0.322 mmol), Intermediate "F" (182 mg, 0.322 mmol), PdCl₂(dppf)-CH₂Cl₂ (26.3 mg, 0.032 mmol) and K₂CO₃ (0.322 mL, 0.645 mmol) in DMF (2 mL) was stirred at 90° C. for 1 h, then concentrated under reduced pressure. The residue was purified by mass-triggered preparative HPLC (Mobile layer: A=0.1% TFA/H₂O, B=0.1% TFA/MeCN; Gradient: B=10% to 40%; 12 min; Column: C18) to give the title compound as a TFA salt. To this salt was added sat. aq. NaHCO₃(5 mL) and the mixture was extracted with EtOAc (3×5 mL). The combined organic layers were washed with sat. aq. NaCl, dried over MgSO₄, filtered and concentrated under reduced pressure. The residue was lyophilized to give the title compound as a white powder (44 mg, 27%). MS (ES⁺) $C_{27}H_{33}N_7O_3$ requires: 503, found: 504 [M+H]⁺.

1-(1-Methyl-3-(1-methyl-1H-pyrazol-4-yl)-1H-indazol-5-yl)-3-(tetrahydrofuran-3-yl)-5,6,7,8-tetrahydroimidazo[1,5-a]pyrazine hydrochloride A solution of HCl in MeOH (premade by adding AcCl (0.2 mL) to MeOH (0.8 mL)) was added to the product from the previous step (30 mg, 0.060 mmol), and the resulting mixture was stirred at 20° C. for 2 h. The mixture was concentrated under reduced pressure to give the crude title compound, which was used without further purification. MS (ES⁺) $C_{22}H_{25}N_7O$ requires: 403, found: 404 [M+H]⁺.

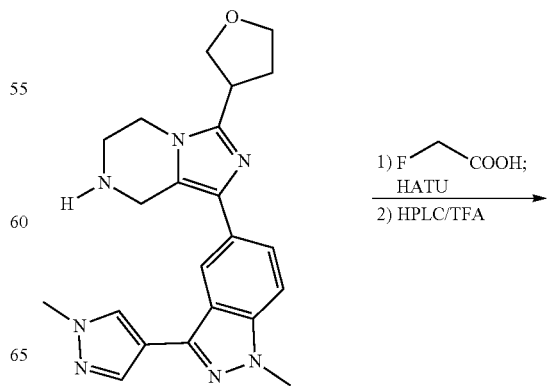

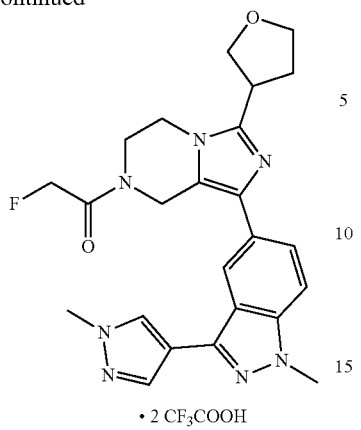

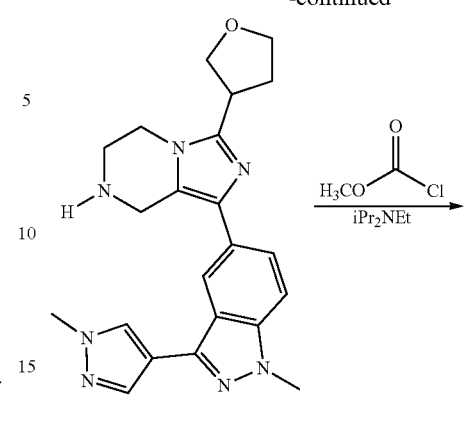

2-Fluoro-1-(1-(1-methyl-3-(1-methyl-1H-pyrazol-4-yl)-1H-indazol-5-yl)-3-(tetrahydrofuran-3-yl)-5,6-dihydroimidazo[1,5-a]pyrazin-7(8H)-yl)ethanone bis(2,2,2-trifluoroacetate)

To a solution of the product from the previous step hydrochloride (5.0 mg, 0.011 mmol) in DMF (0.5 mL) were added 2-fluoroacetic acid (1.064 mg, 0.014 mmol), HATU (5.19 mg, 0.014 mmol) and iPr$_2$NEt (9.92 µl, 0.057 mmol), and the resulting mixture was stirred at 20° C. for 1 h. The mixture was concentrated under reduced pressure. The residue was purified by mass-triggered preparative HPLC (Mobile layer: A=0.1% TFA/H$_2$O, B=0.1% TFA/MeCN; Gradient: B=10% to 40%; 12 min; Column: C18) to give the title compound as an off-white solid (3 mg, 38%).

MS (ES$^+$) C$_{24}$H$_{26}$FN$_7$O$_2$ requires: 463, found: 464 [M+H]$^+$.

$^1$H NMR (CD$_3$OD) (2:1 ratio of rotamers) δ 8.22 (s, 1H), 8.18 (s, 1H), 8.07 (s, 1H), 7.75 (d, J=8.6 Hz, 1H), 7.62 (d, J=8.4 Hz, 1H), 5.35 (s, 0.7H), 5.22 (s, 1H), 5.15 (s, 0.3H), 5.03 (s, 1.3H), 4.96 (s, 0.7H), 4.41 (s, 1.3H), 4.35 (s, 0.7H), 4.24-3.97 (m, 12H), 3.97-3.87 (m, 1H), 2.62-2.54 (m, 1H), 2.31-2.22 (m, 1H).

Example 5

Methyl 1-(1-methyl-3-(1-methyl-1H-pyrazol-4-yl)-1H-indazol-5-yl)-3-(tetrahydrofuran-3-yl)-5,6-dihydroimidazo[1,5-a]pyrazine-7(8H)-carboxylate

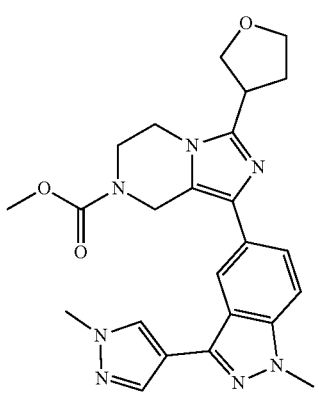

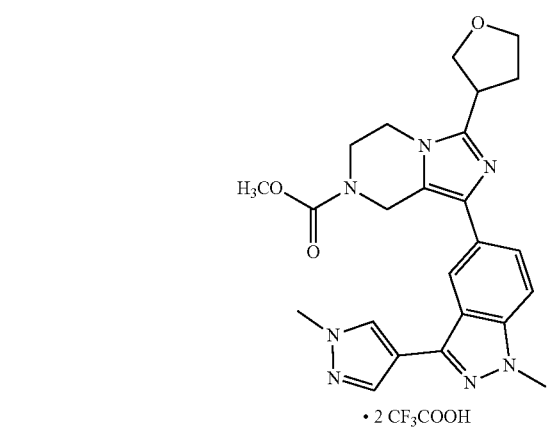

Methyl 1-(1-methyl-3-(1-methyl-1H-pyrazol-4-yl)-1H-indazol-5-yl)-3-(tetrahydrofuran-3-yl)-5,6-dihydroimidazo[1,5-a]pyrazine-7(8H)-carboxylate bis(2,2,2-trifluoroacetate)

To a solution of 1-(1-methyl-3-(1-methyl-1H-pyrazol-4-yl)-1H-indazol-5-yl)-3-(tetrahydrofuran-3-yl)-5,6,7,8-tetrahydroimidazo[1,5-a]pyrazine hydrochloride (5.0 mg, 0.011 mmol) in CH$_2$Cl$_2$ (0.5 mL) were added iPr$_2$NEt (9.92 µl, 0.057 mmol) and methyl chloroformate (1.32 µl, 0.017 mmol), and the resulting mixture was stirred at 20° C. for 1 h then concentrated under reduced pressure. The residue was purified by mass-triggered preparative HPLC (Mobile layer: A=0.1% TFA/H$_2$O, B=0.1% TFA/MeCN; Gradient: B=10% to 40%; 12 min; Column: C18) to give the title compound as an off-white solid (4 mg, 51%).

MS (ES$^+$) C$_{24}$H$_{27}$N$_7$O$_3$ requires: 461, found: 462 [M+H]$^+$.

$^1$H NMR (MeOD) δ 8.22 (s, 1H), 8.18 (s, 1H), 8.08 (s, 1H), 7.76 (d, J=8.7 Hz, 1H), 7.60 (d, J=8.1 Hz, 1H), 4.94 (s, 2H), 4.37-4.29 (m, 2H), 4.20-3.97 (m, 12H), 3.94-3.87 (m, 1H), 3.76 (s, 3H), 2.63-2.55 (m, 1H), 2.31-2.23 (m, 1H).

Example 6

N-Methyl-1-(1-methyl-3-(1-methyl-1H-pyrazol-4-yl)-1H-indazol-5-yl)-3-(tetrahydrofuran-3-yl)-5,6-dihydroimidazo[1,5-a]pyrazine-7(8H)-carboxamide

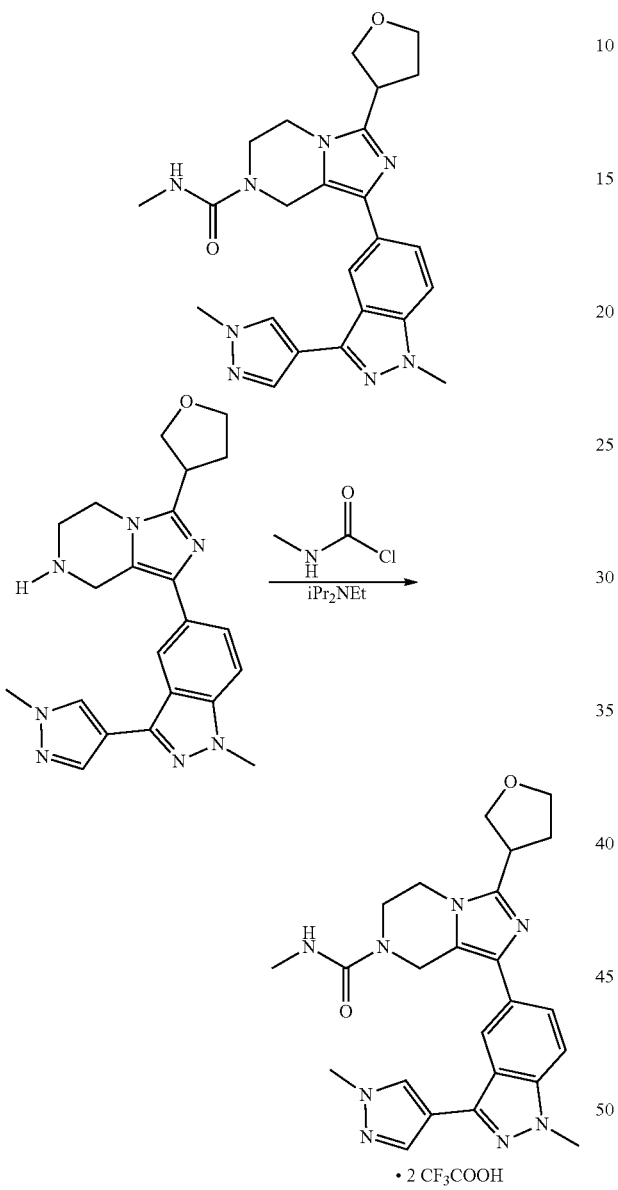

N-Methyl-1-(1-methyl-3-(1-methyl-1H-pyrazol-4-yl)-1H-indazol-5-yl)-3-(tetrahydrofuran-3-yl)-5,6-dihydroimidazo[1,5-a]pyrazine-7(8H)-carboxamide bis(2,2,2-trifluoroacetate)

To a solution of 1-(1-methyl-3-(1-methyl-1H-pyrazol-4-yl)-1H-indazol-5-yl)-3-(tetrahydrofuran-3-yl)-5,6,7,8-tetrahydroimidazo[1,5-a]pyrazine hydrochloride (10 mg, 0.023 mmol) in $CH_2Cl_2$ (0.5 mL) were added $iPr_2NEt$ (0.020 mL, 0.11 mmol) and 4-nitrophenyl chloroformate (5.50 mg, 0.027 mmol), and the resulting mixture was stirred at 20° C. for 1 h then concentrated under reduced pressure. To the residue in THF (0.5 mL) was added $MeNH_2$ (2.0 M in THF, 0.227 mL, 0.455 mmol), and the resulting mixture was stirred at 70° C. for 4 h then concentrated under reduced pressure. The residue was purified by mass-triggered preparative HPLC (Mobile layer: A=0.1% $TFA/H_2O$, B=0.1% TFA/MeCN; Gradient: B=10% to 40%; 12 min; Column: C18) to give the title compound as a white solid (3 mg, 19%).

MS (ES$^+$) $C_{24}H_{28}N_8O_2$ requires: 460, found: 461 [M+H]$^+$.

$^1$H NMR (MeOD) δ 8.21 (s, 1H), 8.17 (s, 1H), 8.09 (s, 1H), 7.75 (d, J=8.4 Hz, 1H), 7.61 (d, J=8.3 Hz, 1H), 4.95 (s, 2H), 4.37-4.30 (m, 2H), 4.22-3.99 (m, 16H), 3.94-3.86 (m, 1H), 2.63-2.55 (m, 1H), 2.31-2.23 (m, 1H).

Example 7

3-Cyclobutyl-N-methyl-1-(1-methyl-3-(1-methyl-1H-pyrazol-4-yl)-1H-indazol-5-yl)-5,6-dihydroimidazo[1,5-a]pyrazine-7(8H)-carboxamide

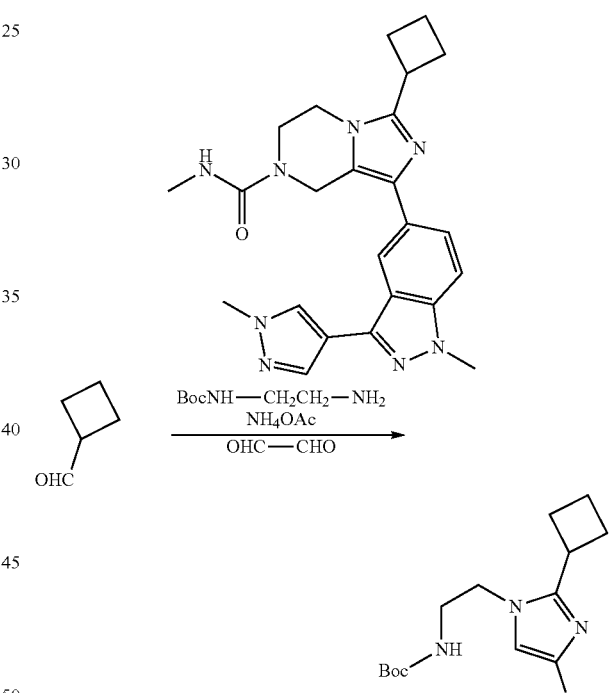

tert-Butyl 2-(2-cyclobutyl-1H-imidazol-1-yl)ethylcarbamate

To a solution of cyclobutanecarbaldehyde (1.68 g, 20 mmol) in MeOH (10 mL) was added tert-butyl 2-aminoethylcarbamate (3.2 g, 20 mmol), $NH_4OAc$ (1.54 g, 20 mmol) and glyoxal (1.08 g, 20 mmol). The mixture was stirred at RT overnight, then poured into water, and the mixture was extracted with EtOAc. The organic layer was washed with sat. aq. NaCl, dried over $Na_2SO_4$, filtered and concentrated under reduced pressure to obtain the crude title compound as a brown oil (5.0 g, 94%), which was used without further purification. MS (ES$^+$): $C_{14}H_{23}N_3O_2$ requires: 265, found: 266 [M+H]$^+$

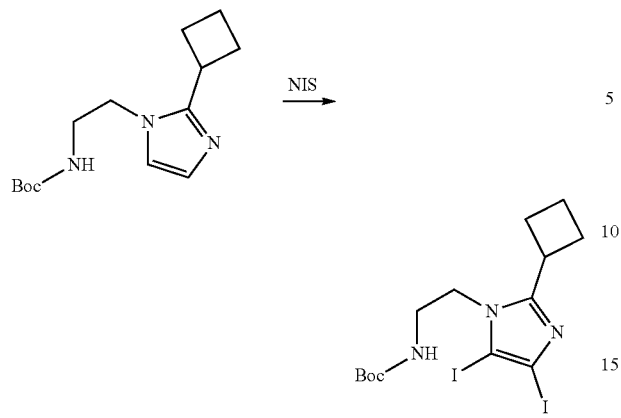

tert-Butyl 2-(2-cyclobutyl-4,5-diiodo-M-imidazol-1-yl)ethylcarbamate

To a solution of the product from the previous step (5.0 g, 19 mmol) in DMF (10 mL) was added NIS (12.6 g, 56.3 mmol). The mixture was stirred at 45° C. for 3 h, then poured into water. The mixture was extracted with EtOAc (30 mL×2), and the combined organic layers were washed with sat. aq. NaCl (20 mL×4), dried over $Na_2SO_4$, filtered and concentrated under reduced pressure. The residue was purified by $SiO_2$ gel chromatography (0% to 40% EtOAc in petroleum ether) to give the title compound as a yellow solid (1.9 g, 20%). MS (ES$^+$): $C_{14}H_{21}I_2N_3O_2$ requires: 517, found: 518 [M+H]$^+$.

3-Cyclobutyl-1-iodo-5,6,7,8-tetrahydroimidazo[1,5-a]pyrazine hydrochloride

A mixture of the product from the previous step (1.3 g, 3.3 mmol) in 2 M HCl/MeOH (5 mL) was stirred at RT for 2 h, then concentrated under reduced pressure. To the residue was added MeOH (10 mL) and paraformaldehyde (1.98 g, 66 mmol), and the resulting mixture was stirred at 80° C. for 16 h. The mixture was filtered through CELITE®, and the filtrate was concentrated under reduced pressure to give the title compound as a white solid (800 mg, 72%). MS (ES$^+$): $C_{10}H_{14}IN_3$ requires: 303, found: 304 [M+H]$^+$.

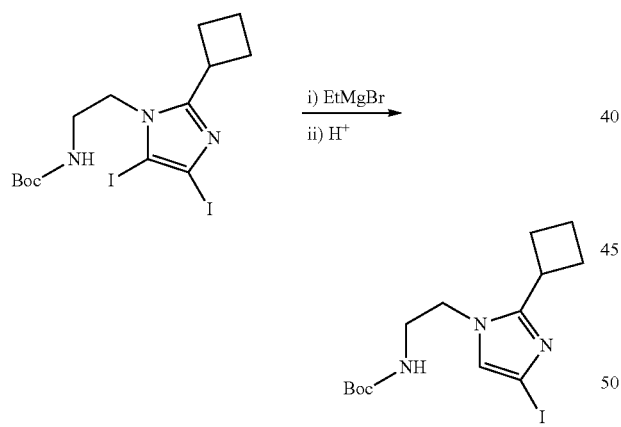

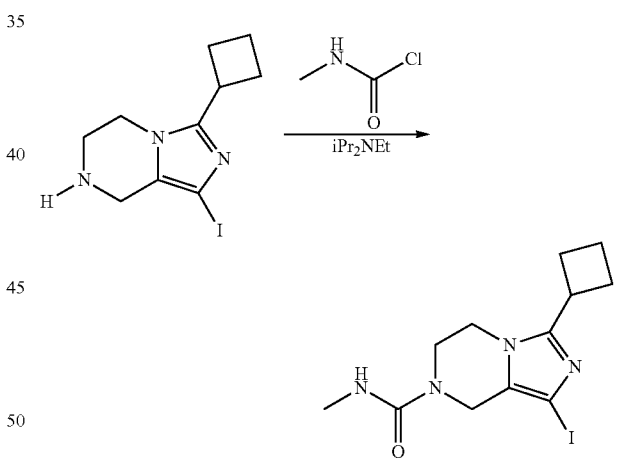

tert-Butyl 2-(2-cyclobutyl-4-iodo-1H-imidazol-1-yl)ethylcarbamate

To a solution of the product from the previous step (1.9 g, 3.6 mmol) in THF (10 mL) at −20° C. was added 3.0 M EtMgBr in Et$_2$O (3.6 mL, 10.8 mmol). The mixture was stirred at −20° C. for 2 h, then treated with sat. aq. NH$_4$Cl and extracted with EtOAc (30 mL×2). The combined organic layers were washed with sat. aq. NaCl (10 mL×1), dried over Na$_2$SO$_4$, filtered and concentrated under reduced pressure to give the title compound as a yellow oil (1.3 g, 93%). MS (ES$^+$): $C_{14}H_{22}IN_3O_2$ requires: 391, found: 392 [M+H]$^+$.

3-Cyclobutyl-1-iodo-N-methyl-5,6-dihydroimidazo[1,5-a]pyrazine-7(8H)carboxamide To a solution of the product from the previous step (100 mg, 0.29 mmol) in CH$_2$Cl$_2$ (3 mL) was added methylcarbamic chloride (30 mg, 0.33 mmol) and iPr$_2$NEt (129 mg, 1.0 mmol). The mixture was stirred for 1 h at RT, then sequentially washed with 1 M aq. HCl, sat. aq. NaHCO$_3$ and sat. aq. NaCl, dried over Na$_2$SO$_4$, filtered and concentrated under reduced pressure to give the crude title compound as a yellow solid (100 mg, 96%). MS (ES$^+$): $C_{12}H_{17}IN_4O$ requires: 360, found: 361 [M+H]$^+$.

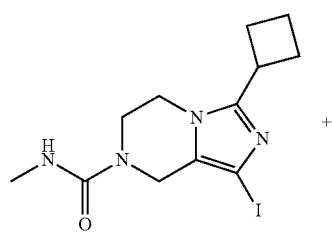

+

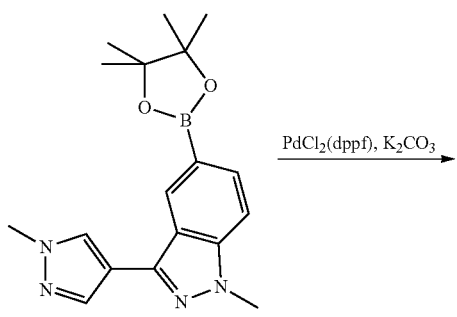

3-Cyclobutyl-N-methyl-1-(1-methyl-3-(1-methyl-1H-pyrazol-4-yl)-1H-indazol-5-yl)-5,6-dihydroimidazo[1,5-a]pyrazine-7(8H)-carboxamide A mixture of the product from the previous step (100 mg, 0.27 mmol), PdCl$_2$(dppf) (19 mg, 0.027 mmol), Intermediate "F" (136 mg, 0.402 mmol) and K$_2$CO$_3$ (111 mg, 0.81 mmol) in DMF (3 mL) was stirred at 90° C. for 1 h then allowed to cool to RT. The mixture was filtered, and the filtrate concentrated under reduced pressure. The residue was purified by reverse phase preparative HPLC (Mobile phase: A=10 mM NH$_4$HCO$_3$/H$_2$O, B=MeCN; Gradient: B=10% to 45% in 18 min; Column: C18) to give the title compound as a yellow solid (33.7 mg, 28%).

MS (ES$^+$): C$_{24}$H$_{28}$N$_8$O requires: 444, found: 445 [M+H]$^+$.

$^1$H NMR (500 MHz, DMSO-d$_6$) δ 8.29 (s, 1H), 7.95 (s, 1H), 7.89 (s, 1H), 7.78 (d, J=8.7 Hz, 1H), 7.64 (d, J=8.8 Hz, 1H), 6.80 (q, J=4.3 Hz, 1H), 4.83 (s, 2H), 4.05 (s, 3H), 3.95 (s, 3H), 3.85 (t, J=5.6 Hz, 2H), 3.75 (t, J=5.6 Hz, 2H), 3.64-3.57 (m, 1H), 2.58 (d, J=4.2 Hz, 3H), 2.43-2.36 (m, 2H), 2.36-2.31 (m, H), 2.04-1.97 (m, 1H), 1.93-1.86 (m, 1H).

Example 8

N-Methyl-1-(1-methyl-3-(1-methyl-1H-pyrazol-4-yl)-1H-indazol-5-yl)-3-(1-methylazetidin-3-yl)-5,6-dihydroimidazo[1,5-a]pyrazine-7(8H)-carboxamide

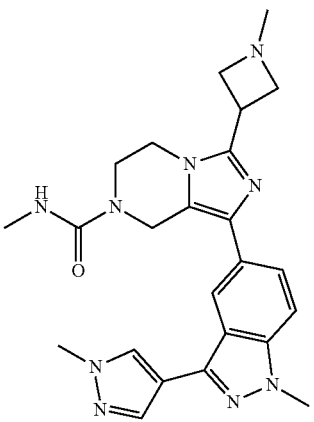

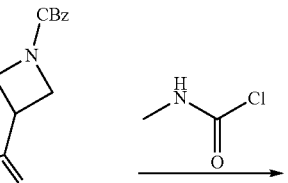

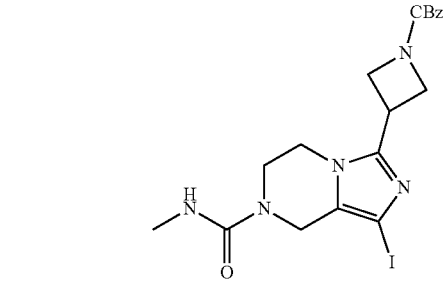

Benzyl 3-(1-iodo-7-(methylcarbamoyl)-5,6,7,8-tetrahydroimidazo[1,5-a]pyrazin-3-yl)azetidine-1-carboxylate To a solution of benzyl 3-(1-iodo-5,6,7,8-tetrahydroimidazo[1,5-a]pyrazin-3-yl)azetidine-1-carboxylate hydrochloride (330 mg, 0.753 mmol) in CH$_2$Cl$_2$ (30 mL) at 0° C. were added Et$_3$N (0.314 mL, 2.26 mmol) and methylcarbamic chloride (105.62 mg, 1.13 mmol). The mixture was stirred for 1 h, then sequentially washed with 1 M aq. HCl, sat. aq. NaHCO$_3$ and sat. aq. NaCl, dried over Na$_2$SO$_4$, filtered and concentrated under reduced pressure. The residue was purified by SiO$_2$ gel chromatography (5% to 25% EtOAc in petroleum ether) to give the title compound as a white solid (274 mg, 73%). MS (ES$^+$): C$_{19}$H$_{22}$IN$_5$O$_3$ requires: 495, found: 496 [M+H]$^+$.

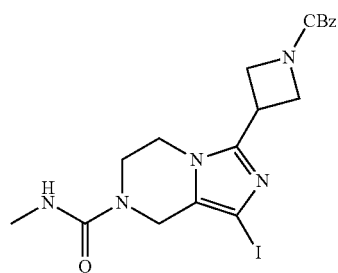

+

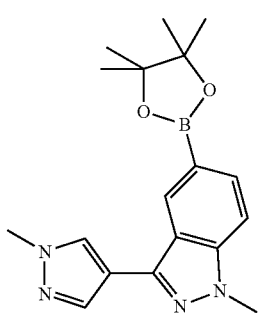

PdCl₂(dppf), K₂CO₃ →

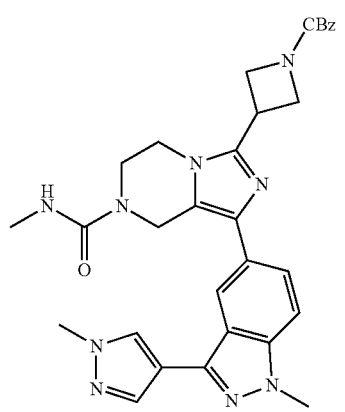

Benzyl 3-(1-(1-methyl-3-(1-methyl-1H-pyrazol-4-yl)-1H-indazol-5-yl)-7-(methylcarbamoyl)-5,6,7,8-tetrahydroimidazo[1,5-a]pyrazin-3-yl)azetidine-1-carboxylate A mixture of the product from the previous step (274 mg, 553 μmol), Intermediate "F" (224.51 mg, 663.81 μmoles), 2.0 M aq. K₂CO₃ (0.830 mL, 1.66 mmol) and PdCl₂(dppf) (69.15 mg, 82.98 μmol) in DMF (5 mL) was degassed and purged with N₂, then stirred at 90° C. for 1 h. The mixture was concentrated under reduced pressure, and the residue was purified by SiO₂ gel chromatography (25% to 100% EtOAc in petroleum ether) to give the title compound as a yellow solid (210 mg, 65%). MS (ES⁺): $C_{31}H_{33}N_9O_3$ requires: 579, found: 580 [M+H]⁺.

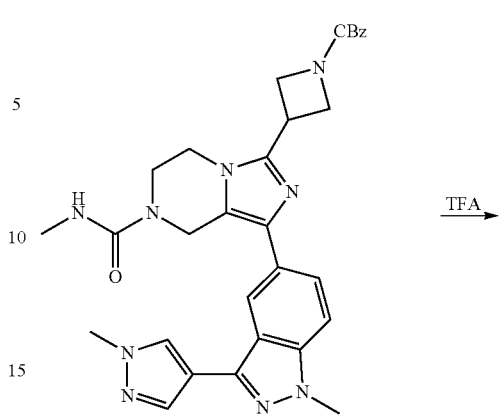

TFA →

3-(Azetidin-3-yl)-N-methyl-1-(1-methyl-3-(1-methyl-1H-pyrazol-4-yl)-1H-indazol-5-yl)-5,6-dihydroimidazo[1,5-a]pyrazine-7(8H)-carboxamide (Intermediate "G")

A mixture of the product from the previous step (210 mg, 362 μmol) in TFA (10 mL) was heated at 65° C. for 1 h, then concentrated under reduced pressure to give the crude title compound as a yellow solid (152 mg, 94%). MS (ES⁺): $C_{23}H_{27}N_9O$ requires: 445, found: 446 [M+H]⁺.

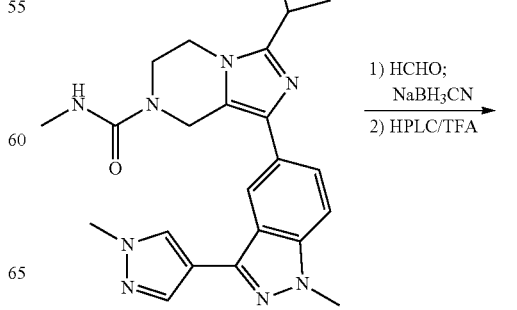

1) HCHO; NaBH₃CN
2) HPLC/TFA →

-continued

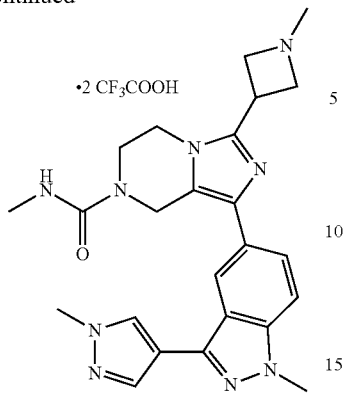

N-Methyl-1-(1-methyl-3-(1-methyl-1H-pyrazol-4-yl)-1H-indazol-5-yl)-3-(1-methylazetidin-3-yl)-5,6-dihydroimidazo[1,5-a]pyrazine-7(8H)-carboxamide bis(2,2,2-trifluoroacetate)

To a mixture of the product from the previous step (50.0 mg, 112 μmol) and 37% aq. formaldehyde (91.07 μL, 1.22 mmol) in MeOH (10 mL) was added NaBH$_3$CN (8.46 mg, 135 μmol). The mixture was stirred at RT for 30 min, then concentrated under reduced pressure. The residue was purified by reverse phase preparative HPLC (Mobile phase: A=0.1% TFA/H$_2$O, B=0.1% TFA/MeCN; Gradient: B=0% to 45% in 18 min; Column: C18) to give the title compound as a white solid (22 mg, 29%).

MS (ES$^+$): C$_{24}$H$_{29}$N$_9$O requires: 459, found: 460 [M+H]$^+$.

$^1$H NMR (500 MHz, CD$_3$OD) δ 8.25 (br s, 1H), 8.10 (br s, 1H), 8.08 (s, 1H), 7.78-7.66 (m, 1H), 7.62-7.58 (m, 1H), 4.86 (br s, 2H), 4.16-4.06 (m, 3H), 4.05-3.96 (m, 5H), 3.95-3.82 (m, 5H), 3.60-2.55 (m, 2H), 2.74 (s, 3H), 2.47 (s, 3H).

Example 9

3-(1-Acetylazetidin-3-yl)-N-methyl-1-(1-methyl-3-(1-methyl-1H-pyrazol-4-yl)-1H-indazol-5-yl)-5,6-dihydroimidazo[1,5-a]pyrazine-7(8H)-carboxamide

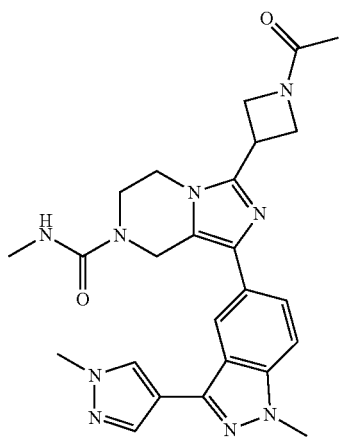

-continued

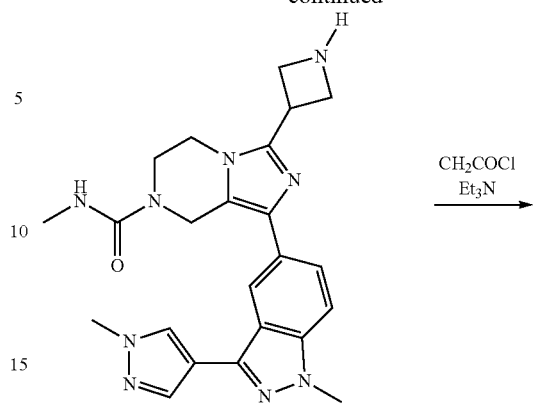

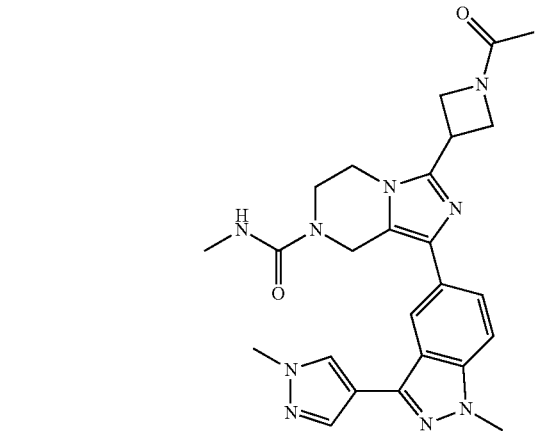

3-(1-Acetylazetidin-3-yl)-N-methyl-1-(1-methyl-3-(1-methyl-1H-pyrazol-4-yl)-1H-indazol-5-yl)-5,6-dihydroimidazo[1,5-a]pyrazine-7(8H)-carboxamide To a solution of Intermediate "G" (50.0 mg, 112 μmol) in CH$_2$Cl$_2$ (10 mL) at 0° C. were added Et$_3$N (46.80 μL, 336.7 μmol) and AcCl (12.01 μL, 168.3 μmol). The mixture was stirred for 30 min, then sequentially washed with 1 M aq. HCl, sat. aq. NaHCO$_3$ and sat. aq. NaCl, dried over Na$_2$SO$_4$, filtered and concentrated under reduced pressure. The residue was purified by SiO$_2$ gel chromatography (5% to 25% EtOAc in petroleum ether) to give the title compound as a yellow solid (12 mg, 22%).

MS (ES$^+$): C$_{25}$H$_{29}$N$_9$O$_2$ requires: 487 found: 488 [M+H]$^+$.

$^1$H NMR (500 MHz, CD$_3$OD) δ 8.27 (s, 1H), 8.12 (s, 1H), 8.09 (s, 1H), 7.74 (d, J=8.8 Hz, 1H), 7.63 (d, J=8.8 Hz, 1H), 4.90 (s, 2H), 4.62 (d, J=8.0 Hz, 2H), 4.42 (t, J=9.3 Hz, 1H), 4.31-4.27 (m, 1H), 4.19-4.09 (m, 4H), 4.07-4.01 (m, 5H), 3.93-3.85 (m, 2H), 2.75 (s, 3H), 1.96 (s, 3H).

Example 10

1-(1-(1-Methyl-3-(1-methyl-1H-pyrazol-4-yl)-1H-indazol-5-yl)-5,6-dihydroimidazo[1,5-a]pyrazin-7(8H)-yl)ethanone

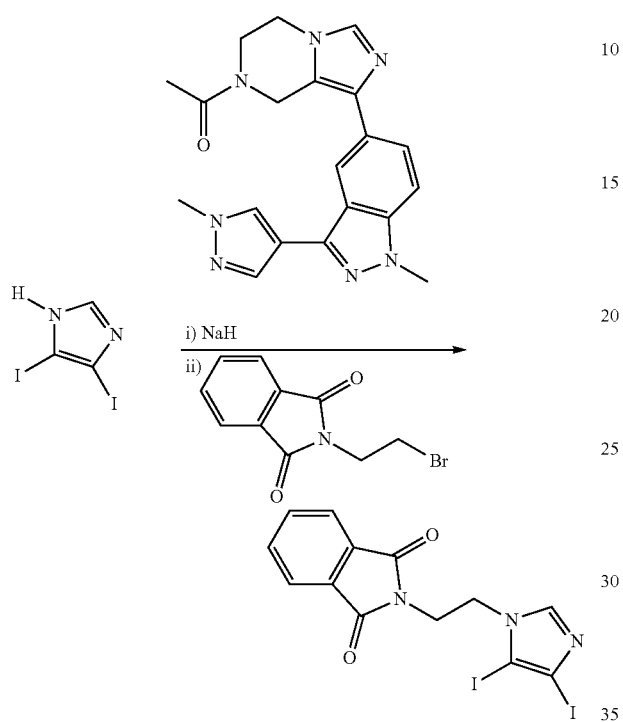

2-(2-(4,5-Diiodo-1H-imidazol-1-yl)ethyl)isoindoline-1,3-dione

To a solution of 4,5-diiodo-1H-imidazole (2.0 g, 5.9 mmol) in DMF (45 mL) was added NaH (60% in mineral oil, 356 mg, 8.91 mmol). The mixture was stirred at RT for 30 min, then treated with 2-(2-bromoethyl)isoindoline-1,3-dione (2.33 g, 8.91 mmol). The mixture was stirred at 60° C. overnight, then allowed to cool to RT and poured into water (30 mL). The precipitated solid was collected and dried to give the title compound as a white solid (1.72 g, 59%). MS (ES+): $C_{13}H_9I_2N_3O_2$ requires: 493, found: 434 [M+H]+.

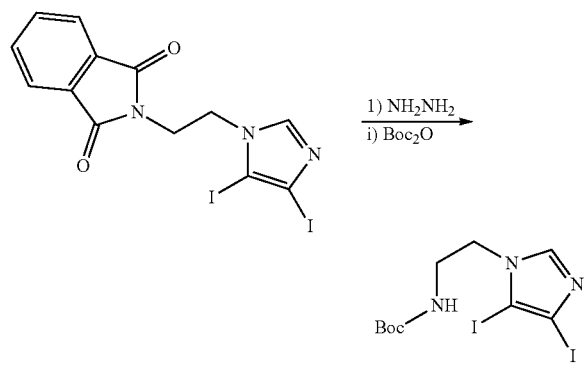

tert-Butyl 2-(4,5-diiodo-1H-imidazol-1-yl)ethylcarbamate

To a solution of the product from the previous step (1.56 g, 3.16 mmol) in EtOH (15 mL) was added hydrazine hydrate (791.97 mg, 15.82 mmol), and the mixture was stirred at reflux for 2 h, allowed to cool to RT and diluted with $CH_2Cl_2$ (150 mL). The mixture was filtered to remove solids, and the filtrate was concentrated under reduced pressure to give a colorless oil. The oil was dissolved in $CH_2Cl_2$ (60 mL), and to the solution was added $Boc_2O$ (966.77 mg, 4.43 mmol). The mixture was stirred at RT overnight, then washed with sat. aq. NaCl, dried over $Na_2SO_4$, filtered and concentrated under reduced pressure. The residue was purified by $SiO_2$ gel chromatography (10% to 60% EtOAc in petroleum ether) to give the title compound as a white solid (1.21 g, 83%). $^1$H NMR (500 MHz, $CDCl_3$) δ 7.80 (s, 1H), 4.18-4.14 (m, 2H), 3.40-3.37 (m, 2H), 1.42 (s, 9H).

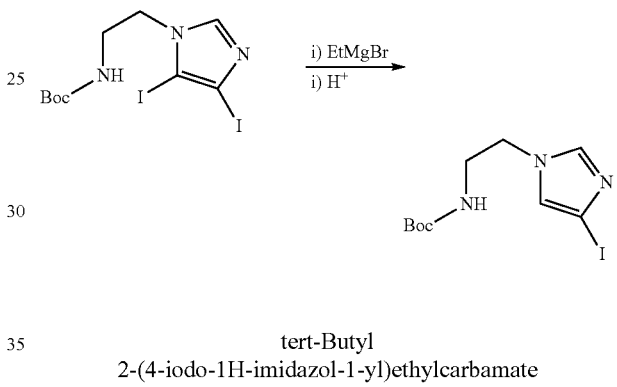

tert-Butyl 2-(4-iodo-1H-imidazol-1-yl)ethylcarbamate

To a solution of the product from the previous step (1.21 g, 2.61 mmol) in THF (20 mL) at −20° C. was added 3.0 M EtMgBr in $Et_2O$ (2.61 mL, 7.84 mmol). The mixture was stirred at −20° C. for 2 h, then treated with sat. aq. $NH_4Cl$ and extracted with EtOAc (45 mL×2). The combined organic layers were washed with sat. aq. NaCl (30 mL), dried over $Na_2SO_4$, filtered and concentrated under reduced pressure to give the title compound as a white solid (0.85 g, 96%). MS (ES+): $C_{10}H_{16}IN_3O_2$ requires: 337, found: 338 [M+H]+.

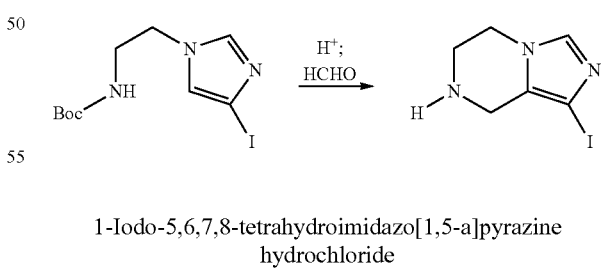

1-Iodo-5,6,7,8-tetrahydroimidazo[1,5-a]pyrazine hydrochloride

A mixture of the title compound (850 mg, 2.52 mmol) and 2 M HCl in MeOH (10 mL) was stirred at RT for 5 h, then concentrated under reduced pressure. The residue was treated with a mixture of paraformaldehyde (1.50 g, 50.1 mmol) in EtOH (15 mL). The resulting mixture was stirred at 80° C. for 2 h, allowed to cool to RT, then partially concentrated under reduced pressure, and the solid was isolated by filtration to give the title compound as a white solid (645 mg, 90%). MS (ES⁺): $C_6H_8IN_3$ requires: 249, found: 250 [M+H]⁺.

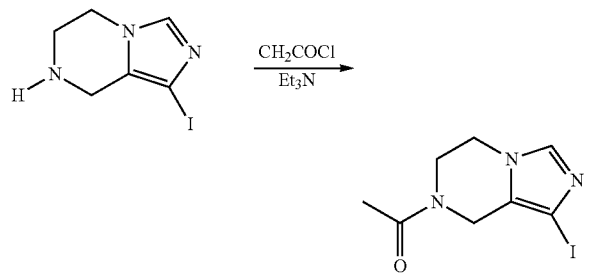

1-(1-Iodo-5,6-dihydroimidazo[1,5-a]pyrazin-7(8H)-yl)ethanone

To a solution of the product from the previous step (325 mg, 1.14 mmol) in $CH_2Cl_2$ (15 mL) at 0° C. was added $Et_3N$ (0.475 mL, 3.41 mmol) and AcCl (0.122 mL, 1.71 mmol). The mixture was stirred for 1 h, then sequentially washed with 1 M aq. HCl, sat. aq. $NaHCO_3$ and sat. aq. NaCl, dried over $Na_2SO_4$, filtered and concentrated under reduced pressure. The residue was purified by $SiO_2$ gel chromatography (5% to 25% EtOAc in petroleum ether) to give the title compound as a yellow solid (320 mg, 97%). MS (ES⁺): $C_8H_{10}IN_3O$ requires: 291, found: 292 [M+H]⁺.

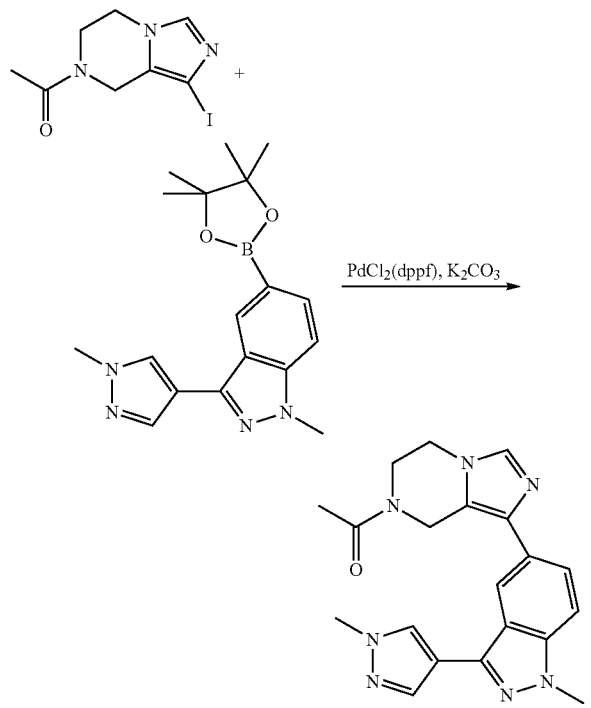

1-(1-(1-Methyl-3-(1-methyl-1H-pyrazol-4-yl)-1H-indazol-5-yl)-5,6-dihydroimidazo[1,5-a]pyrazin-7(8H)-yl)ethanone A mixture of the product from the previous step (90.0 mg; 309 μmol), Intermediate "F" (125.5 mg, 371.0 μmol), 2.0 M aq. $K_2CO_3$ (0.464 mL, 928 μmol) and $PdCl_2$(dppf) (38.65 mg, 46.38 μmol) in DMF (2 mL) was degassed and purged with $N_2$. The mixture was stirred at 90° C. for 1 h, then concentrated under reduced pressure. The residue was purified by $SiO_2$ gel chromatography (25% to 100% EtOAc in petroleum ether) to give the title compound as a white solid (60 mg, 52%).

MS (ES⁺): $C_{20}H_{21}N_7O$ requires: 375, found: 376 [M+H]⁺.

¹H NMR ($CD_3OD$) (2:1 ratio of rotamers) δ 8.23 (s, 1H), 8.13-8.01 (m, 2H), 7.77 (s, 1H), 7.70-7.62 (m, 1H), 7.59-7.46 (m, 1H), 5.04 (s, 0.7H), 5.00 (s, 1.3H), 4.28-4.26 (m, 1.3H), 4.25-4.13 (m, 0.7H), 4.07 (s, 1H), 4.06 (s, 2H), 4.01 (br s, 3H), 4.00-3.93 (m, 2H), 2.24 (s, 2H), 2.23 (s, 1H).

Example 11

N-Methyl-1-(1-methyl-3-(1-methyl-1H-pyrazol-4-yl)-1H-indazol-5-yl)-5,6-dihydroimidazo[1,5-a]pyrazine-7(8H)-carboxamide

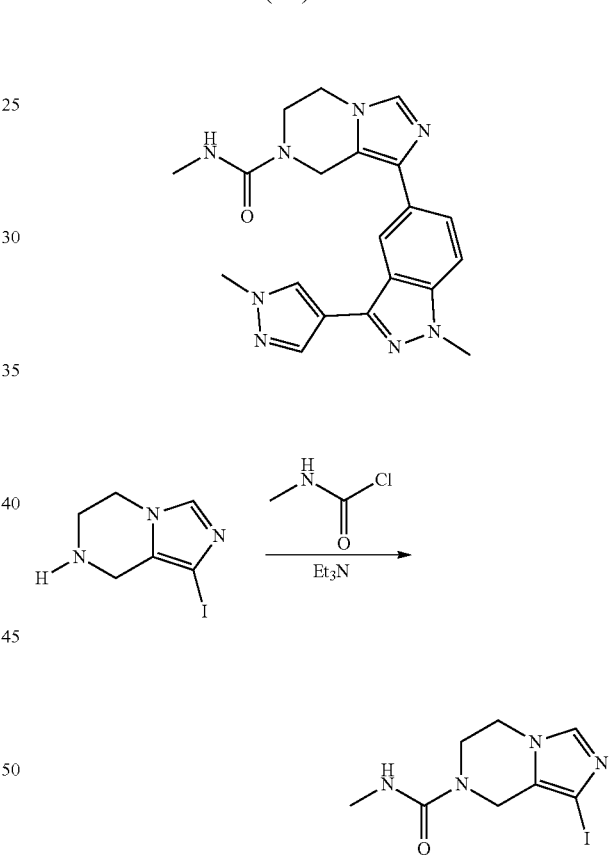

1-Iodo-N-methyl-6,8-dihydro-5H-imidazo[1,5-a]pyrazine-7-carboxamide

To a solution of 1-iodo-5,6,7,8-tetrahydroimidazo[1,5-a]pyrazine hydrochloride (320 mg, 1.12 mmol) in $CH_2Cl_2$ (15 mL) at 0° C. was added $Et_3N$ (0.467 mL, 3.36 mmol) and methylcarbamic chloride (157.2 mg, 1.68 mmol). The mixture was stirred for 1 h, then sequentially washed with 1 M aq. HCl, sat. aq. $NaHCO_3$ and sat. aq. NaCl, dried over $Na_2SO_4$, filtered and concentrated under reduced pressure. The residue was purified by $SiO_2$ gel chromatography (5% to 25% EtOAc in petroleum ether) to give the title compound as a yellow solid (336 mg, 98%). MS (ES⁺): C₈H₁₁IN₄O requires: 306, found: 307 [M+H]⁺.

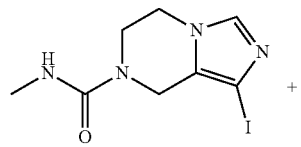

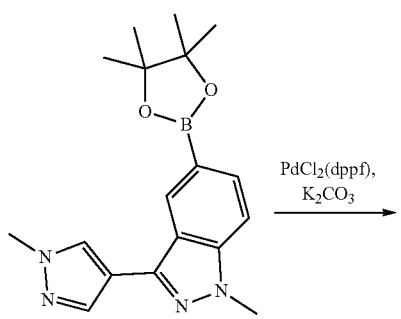

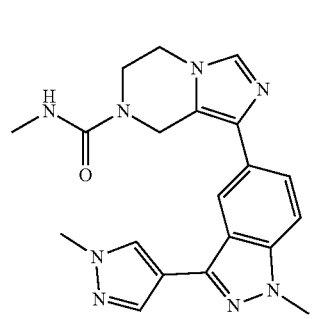

N-Methyl-1-(1-methyl-3-(1-methyl-1H-pyrazol-4-yl)-1H-indazol-5-yl)-5,6-dihydroimidazo[1,5-a]pyrazine-7(8H)-carboxamide A mixture of the product from the previous step (100 mg, 327 μmol), Intermediate "F" (132.59 mg, 392.02 μmol), 2.0 M aq. K₂CO₃ (0.490 mL, 980 μmol) and PdCl₂(dppf) (40.83 mg, 49.00 μmoles) in DMF (2 mL) was degassed and purged with N₂. The mixture was stirred at 90° C. for 1 h, then concentrated under reduced pressure. The residue was purified by SiO₂ gel chromatography (25% to 100% EtOAc in petroleum ether) to give the title compound as a white solid (70 mg, 55%).

MS (ES⁺): C₂₀H₂₂N₈O requires: 390, found: 391 [M+H]⁺.

¹H NMR (CD₃OD) δ 8.28 (s, 1H), 8.17 (s, 1H), 8.09 (s, 1H), 7.77 (s, 1H), 7.71 (d, J=9.0 Hz, 1H), 7.61 (d, J=9.0 Hz, 1H), 4.94 (s, 2H), 4.22 (t, J=5.4 Hz, 2H), 4.11 (s, 3H), 4.04 (s, 3H), 3.88 (t, J=5.5 Hz, 2H), 2.78 (s, 3H).

Example 12

1-(3-(7-Acetyl-1-(1-methyl-3-(1-methyl-1H-pyrazol-4-yl)-1H-indazol-5-yl)-5,6,7,8-tetrahydroimidazo[1,5-a]pyrazin-3-yl)azetidin-1-yl)ethan-1-one

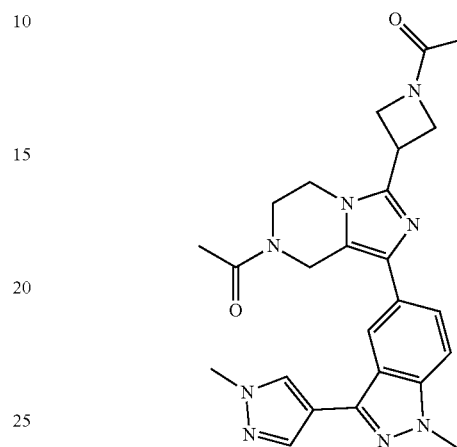

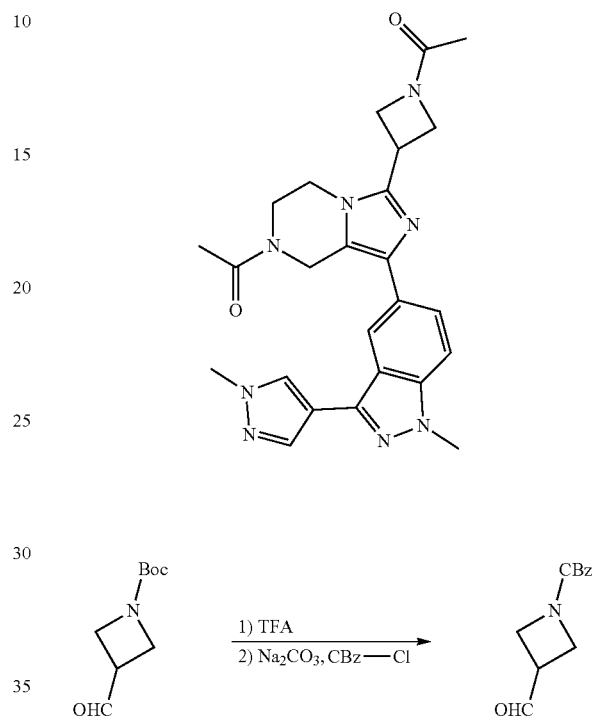

Benzyl 3-formylazetidine-1-carboxylate

To a solution of tert-butyl 3-formylazetidine-1-carboxylate (4.5 g, 24 mmol) in CH₂Cl₂ (60 mL) was added TFA (20 mL). The mixture was stirred at RT for 2 h, then concentrated under reduced pressure to a colorless oil. The oil was taken up in THF (100 mL) and water (100 mL), and the mixture was treated with Na₂CO₃ (10.22 g, 96.42 mmol) then benzyl chloroformate (3.80 mL, 25.3 mmol). The mixture was stirred at RT overnight, then extracted with EtOAc (60 mL×3). The combined organic layers were washed with sat. aq. NaCl (30 mL×2), dried over Na₂SO₄, filtered and concentrated under reduced pressure. The residue was purified by SiO₂ gel chromatography (10% to 60% EtOAc in petroleum ether) to give the title compound as a yellow oil (2.2 g, 42%). ¹H NMR (400 MHz, CDCl₃) δ 9.83 (appar dd, J=2.7, 1.9 Hz, 1H), 7.43-7.28 (m, 5H), 5.10 (s, 2H), 4.29-4.10 (m, 4H), 3.45-3.33 (m, 1H).

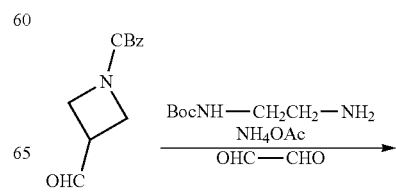

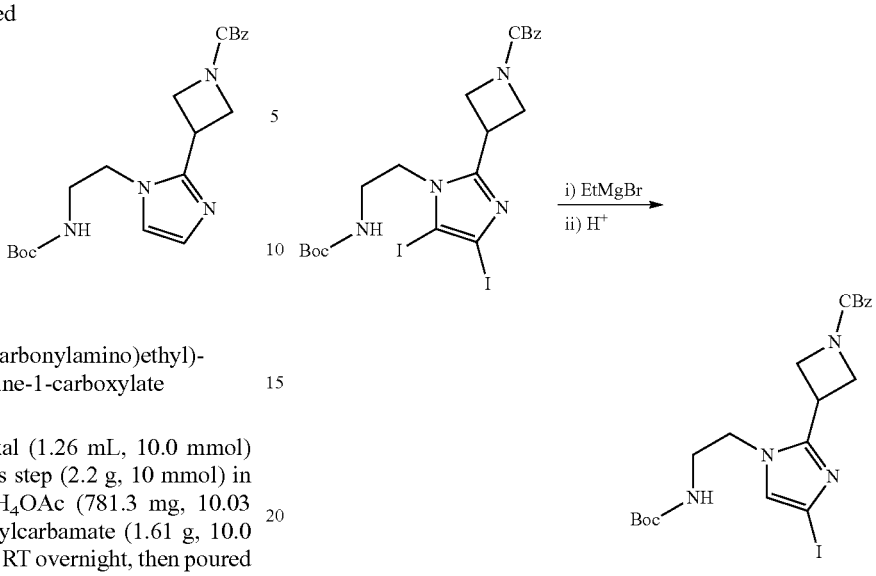

Benzyl 3-(1-(2-(tert-butoxycarbonylamino)ethyl)-1H-imidazol-2-yl)azetidine-1-carboxylate To a stirring solution of glyoxal (1.26 mL, 10.0 mmol) and the product from the previous step (2.2 g, 10 mmol) in MeOH (90 mL) were added NH₄OAc (781.3 mg, 10.03 mmol) and tert-butyl 2-aminoethylcarbamate (1.61 g, 10.0 mmol). The mixture was stirred at RT overnight, then poured into water and extracted with EtOAc. The organic layer was washed with sat. aq. NaCl, dried over Na₂SO₄, filtered and concentrated under reduced pressure. The residue was purified by SiO₂ gel chromatography (0% to 60% EtOAc in petroleum ether) to give the title compound as a yellow oil (3.88 g, 97%). MS (ES⁺): $C_{21}H_{28}N_4O_4$ requires: 400, found: 401 [M+H]⁺.

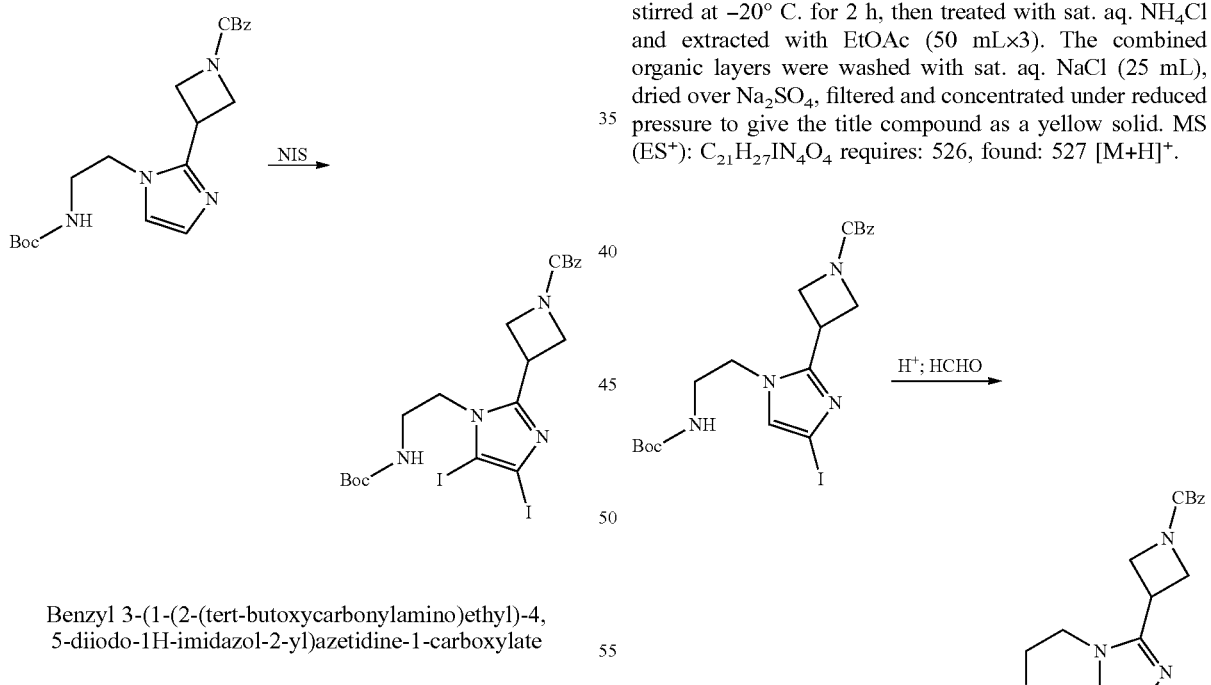

Benzyl 3-(1-(2-(tert-butoxycarbonylamino)ethyl)-4,5-diiodo-1H-imidazol-2-yl)azetidine-1-carboxylate To a solution of the product from the previous step (3.88 g, 9.71 mmol) in DMF (75 mL) was added NIS (6.56 g, 29.1 mmol). The mixture was stirred at 50° C. overnight, then poured into water and the mixture was extracted with EtOAc (60 mL×3). The combined organic layers were washed with sat. aq. NaCl (25 mL×4), dried over Na₂SO₄, filtered and concentrated under reduced pressure. The residue was purified by SiO₂ gel chromatography (0% to 40% EtOAc in petroleum ether) to give the title compound as a yellow solid. MS (ES⁺): $C_{21}H_{26}I_2N_4O_4$ requires: 652, found: 653 [M+H]⁺.

Benzyl 3-[1-[2-(tert-butoxycarbonylamino)ethyl]-4-iodo-imidazol-2-yl]azetidine-1-carboxylate To a solution of the product from the previous step (2.3 g, 3.5 mmol) in THF (50 mL) at −20° C. was added 3.0 M EtMgBr in Et₂O (3.53 mL, 10.6 mmol). The mixture was stirred at −20° C. for 2 h, then treated with sat. aq. NH₄Cl and extracted with EtOAc (50 mL×3). The combined organic layers were washed with sat. aq. NaCl (25 mL), dried over Na₂SO₄, filtered and concentrated under reduced pressure to give the title compound as a yellow solid. MS (ES⁺): $C_{21}H_{27}IN_4O_4$ requires: 526, found: 527 [M+H]⁺.

Benzyl 3-(1-iodo-5,6,7,8-tetrahydroimidazo[1,5-a]pyrazin-3-yl)azetidine-1-carboxylate hydrochloride A mixture of the product from the previous step (1.76 g, 3.34 mmol) in 2 M HCl/MeOH (20 mL) was stirred at RT for 5 h, then concentrated under reduced pressure to give a yellow solid. To the solid was added paraformaldehyde (1.47 g, 49.0 mmol) and EtOH (45 mL). The mixture was heated at 80° C. for 2 h, then partially concentrated under reduced pressure, and the resulting solid was isolated by filtration and washed with $CH_2Cl_2$ (5 mL×3) to give the title compound as a white solid (760 mg, 48%). MS (ES$^+$): $C_{17}H_{19}IN_4O_2$ requires: 438, found: 439 [M+H]$^+$.

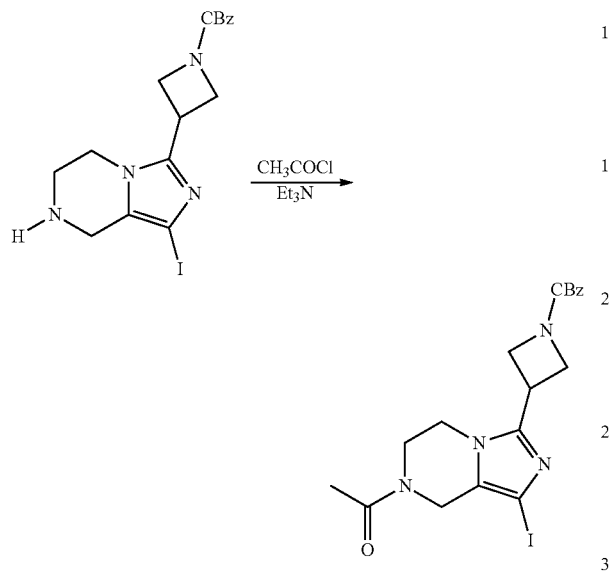

Benzyl 3-(7-acetyl-1-iodo-5,6,7,8-tetrahydroimidazo[1,5-a]pyrazin-3-yl)azetidine-1-carboxylate To a solution of the product from the previous step (340 mg, 717 μmol) in $CH_2Cl_2$ (25 mL) at 0° C. was added $Et_3N$ (0.324 mL, 2.33 mmol) and AcCl (0.083 mL, 1.16 mmol). The reaction was stirred for 1 h, then sequentially washed with sat. aq. $NaHCO_3$ and sat. aq. NaCl, dried over $Na_2SO_4$, filtered and concentrated under reduced pressure to give the title compound as a yellow solid (285 mg, 83%). MS (ES$^+$): $C_{19}H_{21}IN_4O_3$ requires: 480, found: 481 [M+H]$^+$.

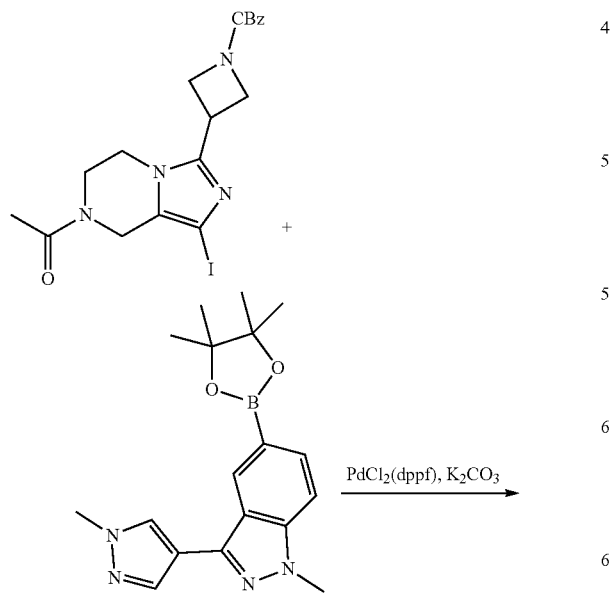

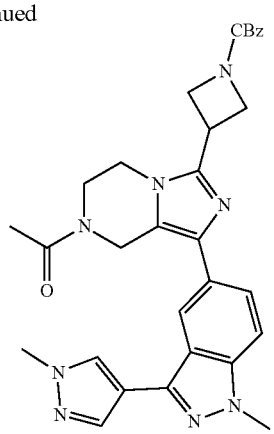

Benzyl 3-(7-acetyl-1-(1-methyl-3-(1-methyl-1-pyrazol-4-yl)-1H-indazol-5-yl)-5,6,7,8-tetrahydroimidazo[1,5-a]pyrazin-3-yl)azetidine-1-carboxylate A mixture of the product from the previous step (285 mg, 593 μmol), Intermediate "F" (240.83 mg, 712.05 μmol), 2.0 M aq. $K_2CO_3$ (0.890 mL, 1.78 mmoles) and $PdCl_2$(dppf) (74.17 mg, 89.01 μmol) in DMF (5 mL) was degassed and purged with $N_2$, then stirred at 90° C. for 1 h. The mixture was concentrated under reduced pressure, and the residue was purified by $SiO_2$ gel chromatography (0% to 10% MeOH in $CH_2Cl_2$) to give the title compound as a yellow solid (225 mg, 67%). MS (ES$^+$): $C_{31}H_{32}N_{18}O_3$ requires: 564, found: 565 [M+H]$^+$.

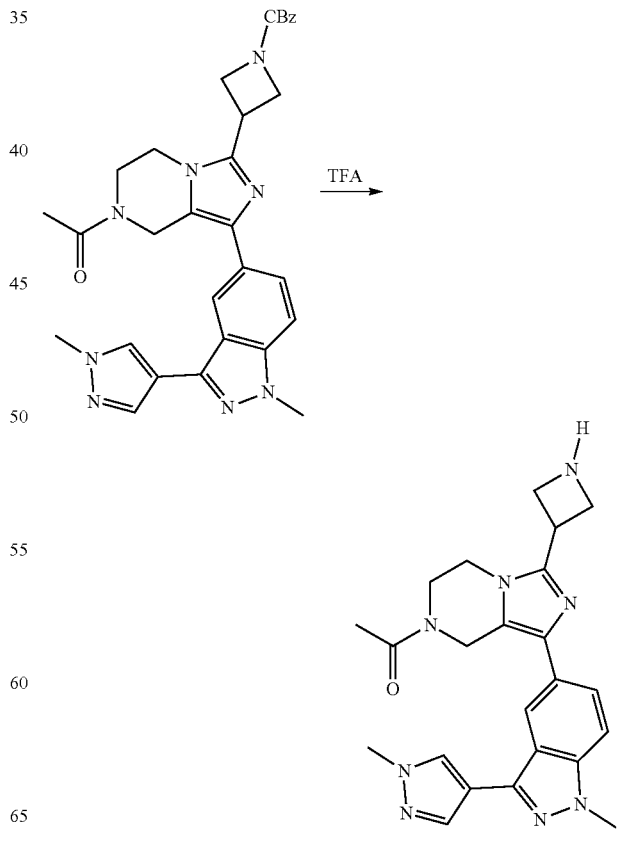

1-(3-(Azetidin-3-yl)-1-(1-methyl-3-(1-methyl-1H-pyrazol-4-yl)-1H-indazol-5-yl)-5,6-dihydroimidazo[1,5-a]pyrazin-7(8H)-yl)ethanone (Intermediate "H")

A mixture of the product from the previous step (220 mg, 390 μmol) and TFA (10 mL) was stirred at 65° C. for 1 h, then concentrated under reduced pressure to give the crude title compound as a yellow solid (165 mg, 98%). MS (ES+): $C_{23}H_{26}N_8O$ requires: 430, found: 431 [M+H]+.

Example 13

1-(1-(1-Methyl-3-(1-methyl-1H-pyrazol-4-yl)-1H-indazol-5-yl)-3-(1-methylazetidin-3-yl)-5,6-dihydro-imidazo[1,5-a]pyrazin-7(8H)-yl)ethanone

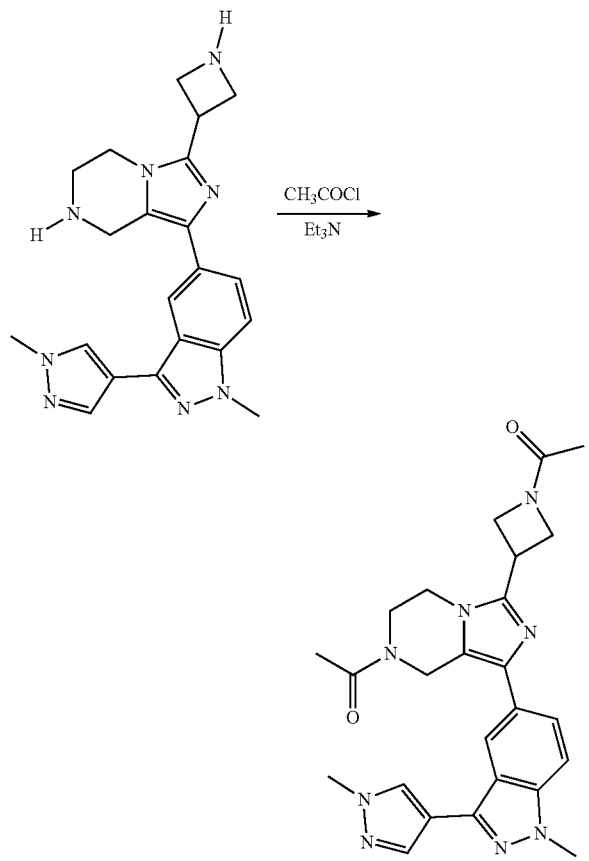

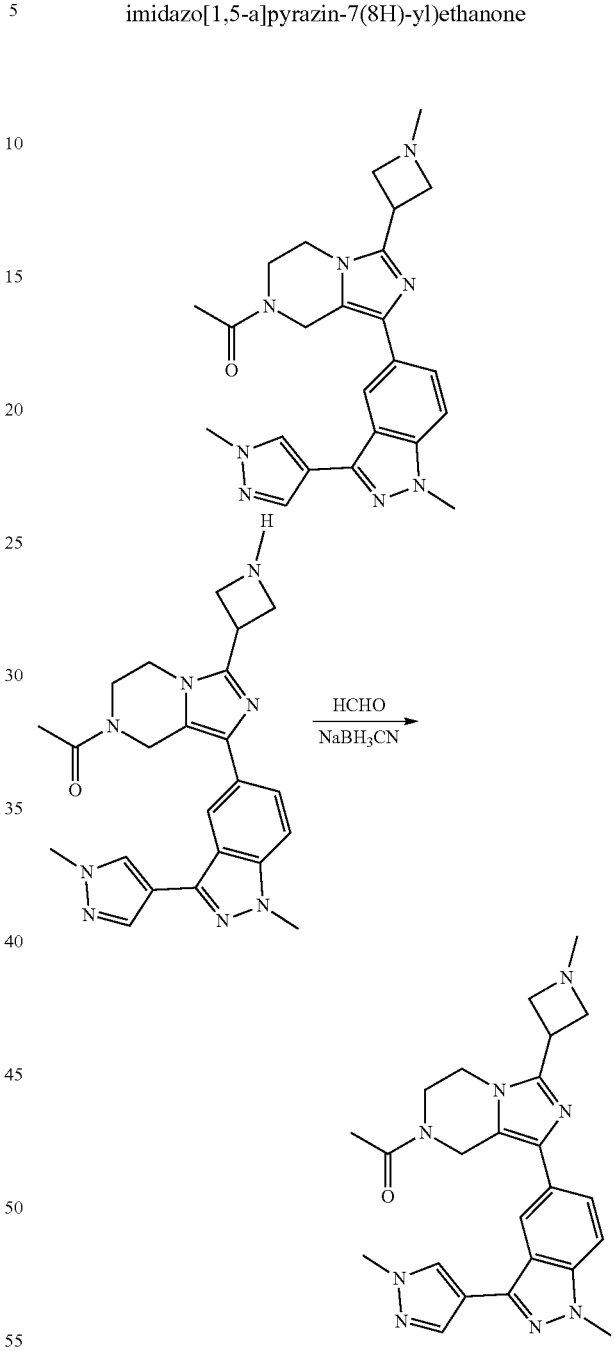

1-(3-(7-Acetyl-1-(1-methyl-3-(1-methyl-1H-pyrazol-4-yl)-1H-indazol-5-yl)-5,6,7,8-tetrahydroimidazo[1,5-a]pyrazin-3-yl)azetidin-1-yl)ethanone To a solution of the product from the previous step (45.0 mg, 105 μmol) in $CH_2Cl_2$ (10 mL) at 0° C. were added $Et_3N$ (0.436 mL, 314 μmol) and AcCl (11.19 μL, 156.8 μmol). The mixture was stirred for 30 min, then sequentially washed with 1 M aq. HCl, sat. aq. $NaHCO_3$ and sat. aq. NaCl, dried over $Na_2SO_4$, filtered and concentrated under reduced pressure. The residue was purified by $SiO_2$ gel chromatography (5% to 25% EtOAc in petroleum ether) to give the title compound as a yellow solid (20 mg, 40%).

MS (ES+): $C_{25}H_{28}N_8O_2$ requires: 472 found: 473 [M+H]+.

$^1$H NMR (CD$_3$OD) (2:1 ratio of rotamers) δ 8.24 (br s, 1H), 8.15-8.00 (m, 2H), 7.73-7.72 (m, 1H), 7.62-7.59 (m, 1H), 5.02 (s, 0.7H), 5.00 (s, 1.3H), 4.63-4.60 (m, 2H), 4.43-4.39 (m, 1H), 4.30-4.26 (m, 1H), 4.17-4.06 (m, 5H), 4.02-3.99 (m, 6H), 2.24 (s, 2H), 2.20 (s, 1H), 1.96 (s, 2H), 1.95 (s, 1H).

To a solution of 37% aq. formaldehyde (90.94 μL, 1.21 mmol) and Intermediate "H" (55.0 mg, 121 μmol) in MeOH (10 mL) was added NaBH$_3$CN (9.15 mg, 146 μmol). The resulting mixture was stirred at RT for 1 h, then concentrated under reduced pressure. The residue was purified by reverse phase preparative HPLC (Mobile phase: A=0.1% NH$_4$HCO$_3$/H$_2$O, B=MeCN; Gradient: B=5% to 95% in 18 min; Column: C18) to give the title compound as a white solid (34 mg, 63%).

MS (ES+): $C_{24}H_{28}N_8O$ requires: 444, found: 445 [M+H]+.

¹H NMR (CD₃OD) (2:1 ratio of rotamers) δ 8.26 (s, 1H), 8.18-8.01 (m, 2H), 7.74-7.72 (m, 1H), 7.67-7.55 (m, 1H), 5.03 (s, 0.7H), 5.00 (s, 1.3H), 4.11 (appar br s, 4H), 4.06-3.96 (m, 6H), 3.96-3.89 (m, 3H), 3.71-3.58 (m, 2H), 2.52 (s, 3H), 2.25 (s, 2H), 2.19 (s, 1H).

Example 14

1-[3-(1,1-Dioxothian-4-yl)-1-[1-methyl-3-(1-methylpyrazol-4-yl)indazol-5-yl]-6,8-dihydro-5H-imidazo[1,5-a]pyrazin-7-yl]ethanone

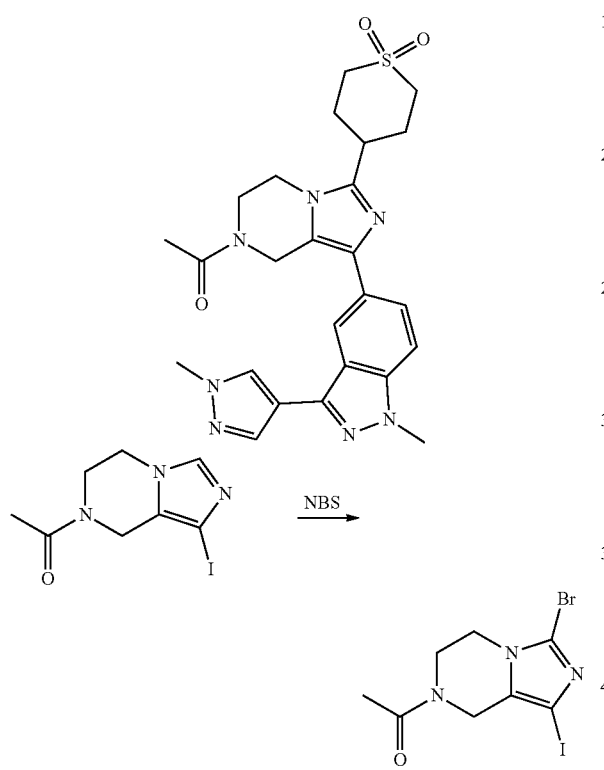

1-(3-Bromo-1-iodo-5,6-dihydroimidazo[1,5-a]pyrazin-7(8H)-yl)ethanone

To a solution of 1-(1-iodo-5,6-dihydroimidazo[1,5-a]pyrazin-7(8H)-yl)ethanone (225 mg, 773 μmol) in MeCN (15 mL) was added NBS (170.19 mg, 927.54 μmol). The mixture was stirred at RT for 3 h, then treated with sat. aq. Na₂SO₃ (1 mL) and EtOAc (45 mL). The mixture was washed with sat. aq. NaHCO₃ (15 mL×2), dried over Na₂SO₄, filtered and concentrated under reduced pressure to give the title compound as a yellow solid (220 mg, 77%). MS (ES⁺): $C_8H_9BrIN_3O$ requires: 369, found: 370 [M+H]⁺.

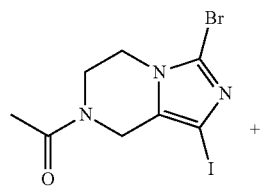

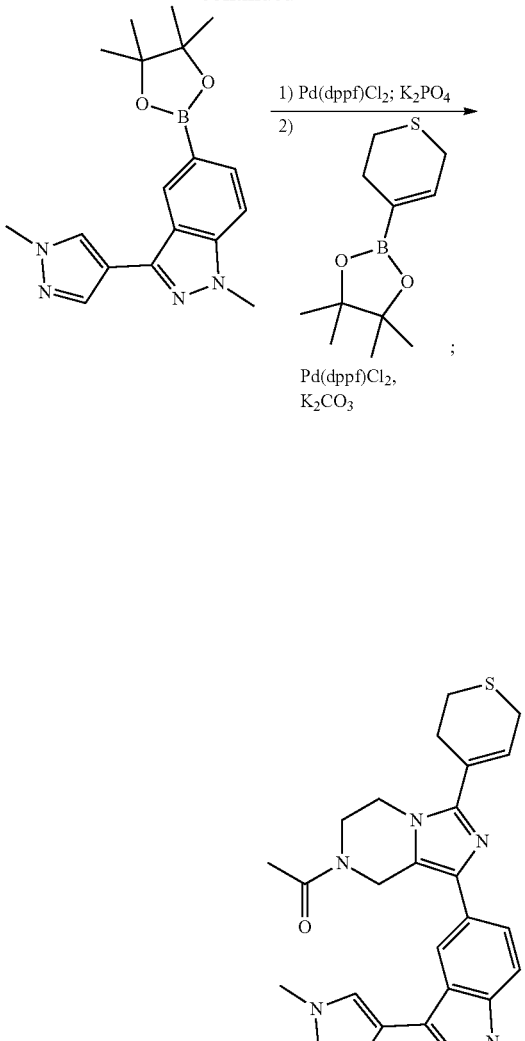

1-(3-(3,6-Dihydro-2H-thiopyran-4-yl)-1-(1-methyl-3-(1-methyl-1H-pyrazol-4-yl)-1H-indazol-5-yl)-5,6-dihydroimidazo[1,5-a]pyrazin-7(8H)-yl)ethanone A mixture of the product from the previous step (200 mg, 541 μmol), Intermediate "F" (182.83 mg, 540.56 μmol), K₃PO₄ (344 mg, 1.62 mmol) and PdCl₂(dppf) (45.05 mg, 54.06 μmol) in 1,4-dioxane/H₂O (3:1, 2 mL) was degassed and purged with N₂. The mixture was stirred at 90° C. for 3 h, then concentrated under reduced pressure. To the residue was added 1,4-dioxane/H₂O (3:1, 2 mL), 2-(3,6-dihydro-2H-thiopyran-4-yl)-4,4,5,5-tetramethyl-1,3,2-dioxaborolane (170.73 mg, 754.96 μmoles), K₂CO₃ (223.6 mg, 1.62 mmol), and PdCl₂(dppf) (44.94 mg, 53.93 μmol). The mixture was degassed and purged with N₂, stirred at 100° C. for 1 h, then concentrated under reduced pressure. The residue was purified by SiO₂ gel chromatography (25% to 100% EtOAc in petroleum ether) to give the title compound as a white solid (105 mg, 41%). MS (ES⁺): $C_{25}H_{27}N_7OS$ requires: 473, found: 474 [M+H]⁺.

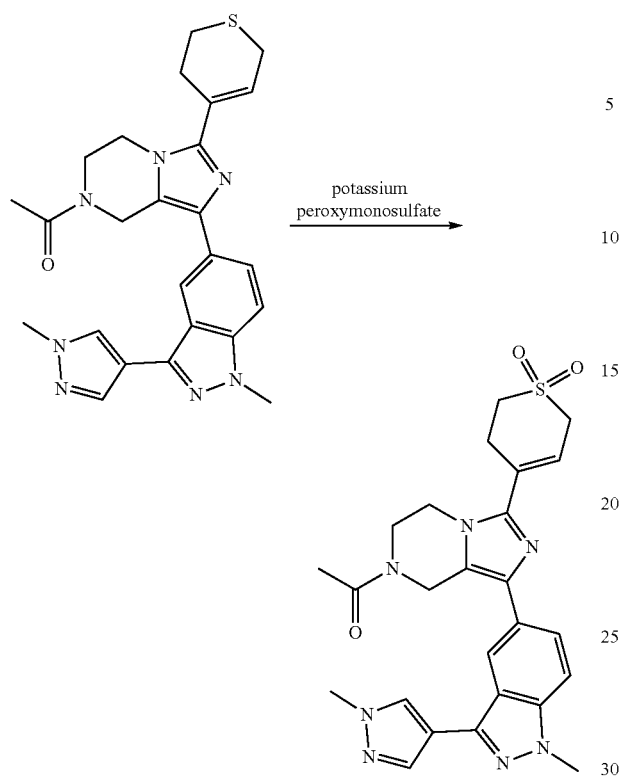

1-[3-(1,1-Dioxo-3,6-dihydro-2H-thiopyran-4-yl)-1-[1-methyl-3-(1-methylpyrazol-4-yl)indazol-5-yl]-6,8-dihydro-5H-imidazo[1,5-a]pyrazin-7-yl]ethanone To a mixture of the product from the previous step (75.0 mg, 0.158 mmol) and MeOH/H₂O (10:1, 10 mL) was added potassium peroxymonosulfate (275 mg, 1.58 mmol). The mixture was stirred at RT for 5 h, filtered, and the filtrate was concentrated under reduced pressure. The residue was diluted with CH₂Cl₂ (25 mL), and the resulting mixture was sequentially washed with sat. aq. Na₂SO₃ (5 mL) and sat. aq. NaCl (10 mL×2), dried over MgSO₄, filtered and concentrated under reduced pressure to give the title compound as a yellow oil (56 mg, 70%). MS (ES⁺): $C_{25}H_{27}N_7O_3S$ requires: 505, found: 506 [M+H]⁺.

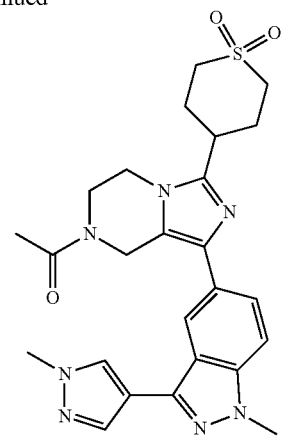

1-[3-(1,1-Dioxothian-4-yl)-1-[1-methyl-3-(1-methylpyrazol-4-yl)indazol-5-yl]-6,8-dihydro-5H-imidazo[1,5-a]pyrazin-7-yl]ethanone A mixture of the product from the previous step (56 mg, 110 μmol) and 20% Pd(OH)₂/C (30 mg) in MeOH (15 mL) was stirred under an atmosphere of H₂ overnight, filtered and concentrated under reduced pressure. The residue was purified by reverse phase preparative HPLC (Mobile phase: A=0.1% NH₄HCO₃/H₂O, B=MeCN; Gradient: B=0% to 45% in 18 min; Column: C18) to give the title compound as a yellow solid (6 mg, 11%).

MS (ES⁺): $C_{25}H_{29}N_7O_3S$ requires: 507, found: 508 [M+H]⁺.

¹H NMR (CD₃OD) (2:1 ratio of rotamers) δ 8.26 (s, 1H), 8.11-8.07 (m, 2H), 7.72-7.70 (m, 1H), 7.64-7.60 (m, 1H), 5.05 (s, 0.7H), 5.02 (s, 1.3H), 4.24 (appar t, J=5.5 Hz, 1H), 4.17-4.09 (m, 4H), 4.08-3.99 (m, 6H), 3.32-3.20 (m, 4H), 2.61-2.47 (m, 2H), 2.42-2.32 (m, 2H), 2.26 (s, 2H), 2.21 (s, 1H).

Example 15

3-(1,1-Dioxothian-4-yl)-N-methyl-1-[1-methyl-3-(1-methylpyrazol-4-yl)indazol-5-yl]-6,8-dihydro-5H-imidazo[1,5-a]pyrazine-7-carboxamide

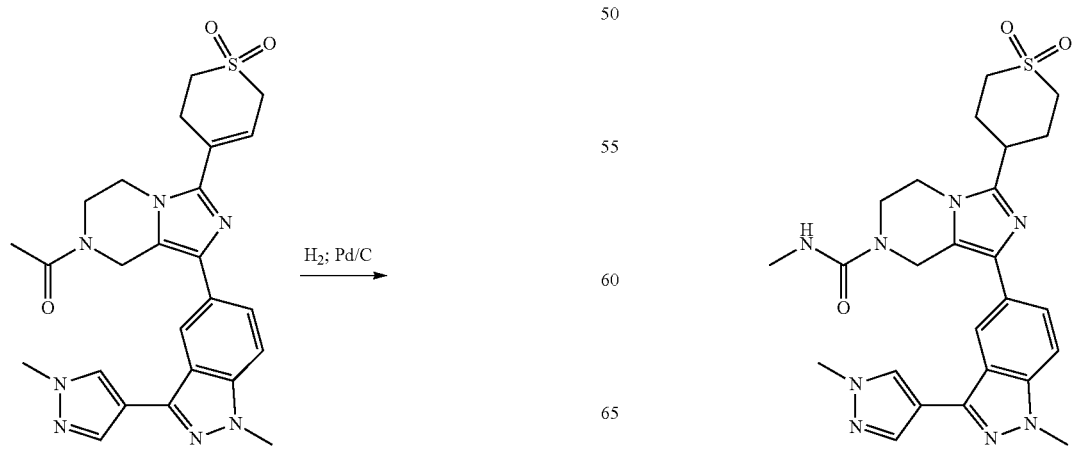

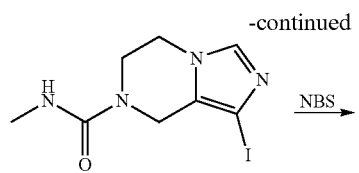
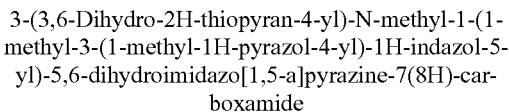
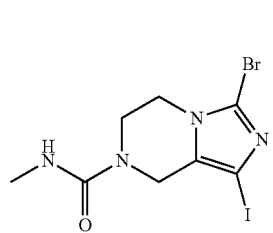

3-Bromo-1-iodo-N-methyl-6,8-dihydro-5H-imidazo[1,5-a]pyrazine-7-carboxamide

To a solution of 1-iodo-N-methyl-6,8-dihydro-5H-imidazo[1,5-a]pyrazine-7-carboxamide (236 mg, 771 μmol) in MeCN (20 mL) was added NBS (169.76 mg, 925.17 μmol). The mixture was stirred at RT for 3 h, then treated with sat. aq. Na$_2$SO$_3$ (1 mL) and EtOAc (45 mL). The mixture was washed with sat. aq. NaHCO$_3$(15 mL×2), dried over Na$_2$SO$_4$, filtered and concentrated under reduced pressure to give the title compound as a yellow solid (251 mg, 85%). MS (ES$^+$): C$_8$H$_{10}$BrIN$_4$O requires: 384, found: 385 [M+H]$^+$.

3-(3,6-Dihydro-2H-thiopyran-4-yl)-N-methyl-1-(1-methyl-3-(1-methyl-1H-pyrazol-4-yl)-1H-indazol-5-yl)-5,6-dihydroimidazo[1,5-a]pyrazine-7(8H)-carboxamide A mixture of the product from the previous step (251 mg, 652 μmol), Intermediate "F" (220.50 mg, 651.94 μmol), K$_3$PO$_4$ (415 mg, 1.96 mmol) and PdCl$_2$(dppf) (54.33 mg, 65.19 μmol) in 1,4-dioxane/H$_2$O (3:1, 10 mL) was degassed and purged with N$_2$. The mixture was stirred at 90° C. for 2 h, then concentrated under reduced pressure. To the residue was added 1,4-dioxane-H$_2$O (3:1, 2 mL), 2-(3,6-dihydro-2H-thiopyran-4-yl)-4,4,5,5-tetramethyl-1,3,2-dioxaborolane (205.75 mg, 909.78 μmol), K$_2$CO$_3$ (269 mg, 1.95 mmol) and PdCl$_2$(dppf) (54.15 mg, 64.98 μmol). The mixture was degassed and purged with N$_2$, and the mixture was heated at 100° C. for 5 h then concentrated under reduced pressure. The residue was purified by SiO$_2$ gel chromatography (0% to 25% MeOH in CH$_2$Cl$_2$) to give the title compound as a brown solid (138 mg, 43%). MS (ES$^+$): C$_{25}$H$_{28}$N$_8$OS requires: 488, found: 489 [M+H]$^+$.

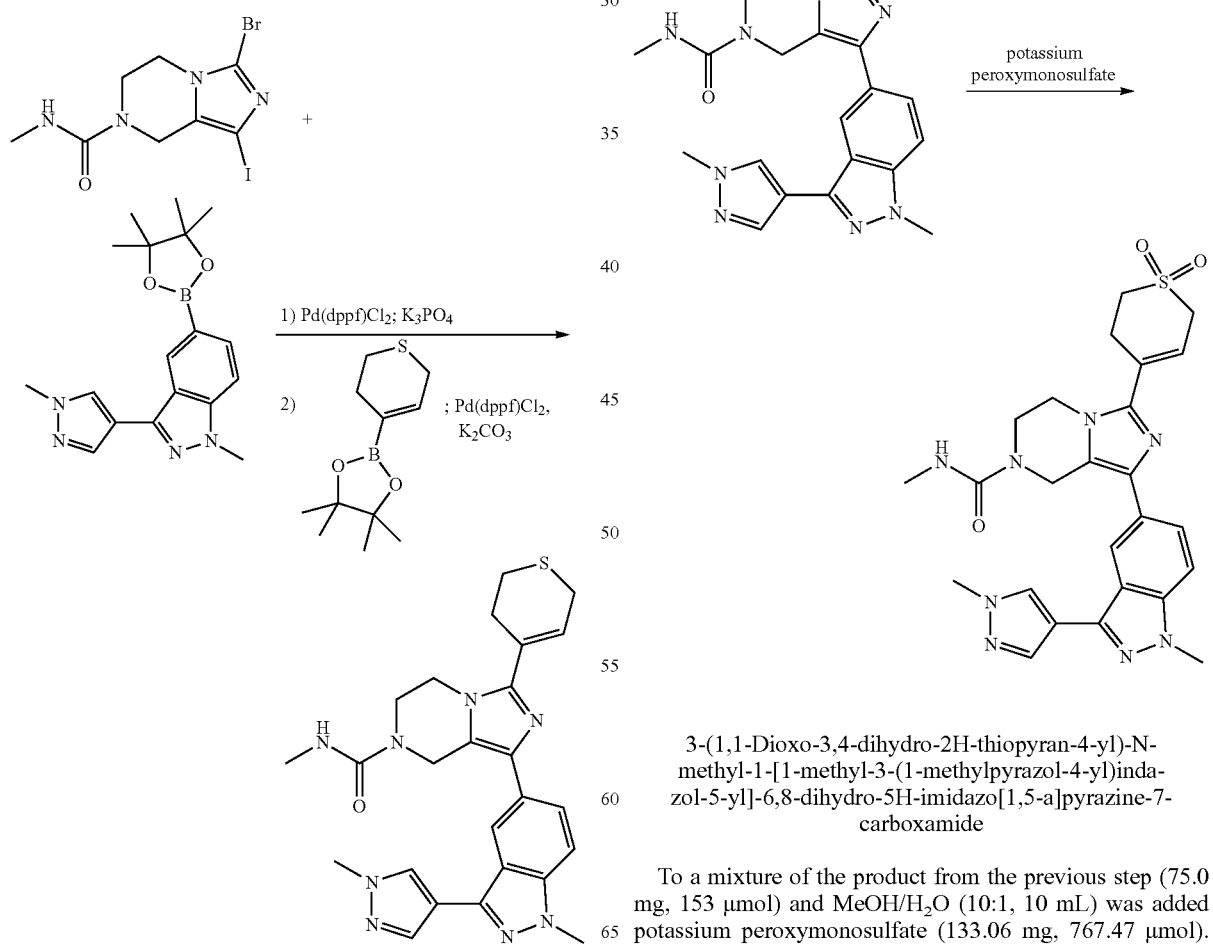

3-(1,1-Dioxo-3,4-dihydro-2H-thiopyran-4-yl)-N-methyl-1-[1-methyl-3-(1-methylpyrazol-4-yl)indazol-5-yl]-6,8-dihydro-5H-imidazo[1,5-a]pyrazine-7-carboxamide To a mixture of the product from the previous step (75.0 mg, 153 μmol) and MeOH/H$_2$O (10:1, 10 mL) was added potassium peroxymonosulfate (133.06 mg, 767.47 μmol). The mixture was stirred at RT overnight, then filtered and concentrated under reduced pressure. The residue was treated with CH$_2$Cl$_2$ (25 mL) and sequentially washed with sat. aq. Na$_2$SO$_3$ (5 mL) and sat. aq. NaCl (10 mL×2), dried over MgSO$_4$, filtered and concentrated under reduced pressure to give the title compound as a yellow oil (42 mg, 53%). MS (ES$^+$): C$_{25}$H$_{28}$N$_8$O$_3$S requires: 520, found: 521 [M+H]$^+$.

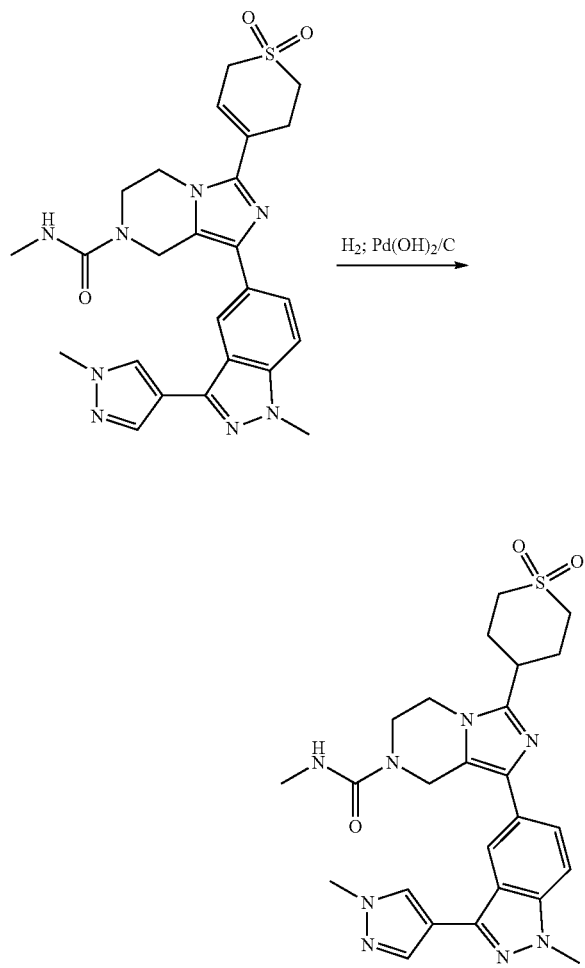

3-(1,1-Dioxothian-4-yl)-N-methyl-1-[1-methyl-3-(1-methylpyrazol-4-yl)indazol-5-yl]-6,8-dihydro-5H-imidazo[1,5-a]pyrazine-7-carboxamide A mixture of the product from the previous step (42 mg, 81 µmol) and 20% Pd(OH)$_2$/C (30 mg) in MeOH (15 mL) was stirred under an atmosphere of H$_2$ overnight, filtered and concentrated under reduced pressure. The residue was purified by reverse phase preparative HPLC (Mobile phase: A=0.1% NH$_4$HCO$_3$/H$_2$O, B=MeCN; Gradient: B=0% to 45% in 18 min; Column: C18) to give the title compound as a yellow solid (3.1 mg, 7%).

MS (ES$^+$): C$_{25}$H$_{30}$N$_8$O$_3$S requires: 522, found: 523 [M+H]$^+$.

$^1$H NMR (CD$_3$OD) δ 8.26 (s, 1H), 8.11 (s, 1H), 8.07 (s, 1H), 7.71 (d, J=8.8 Hz, 1H), 7.60 (d, J=8.7 Hz, 1H), 4.94 (s, 2H), 4.17-4.08 (m, 5H), 4.06-3.95 (m, 4H), 3.90 (t, J=5.4 Hz, 2H), 3.33-3.14 (m, 4H), 2.77 (s, 3H), 2.62-2.45 (m, 2H), 2.42-2.24 (m, 2H).

Example 16

1-(1-(1-Methyl-3-(1-methyl-1H-pyrazol-4-yl)-1H-indazol-5-yl)-3-morpho-lino-5,6-dihydroimidazo[1,5-a]pyrazin-7(8H)-yl)ethanone

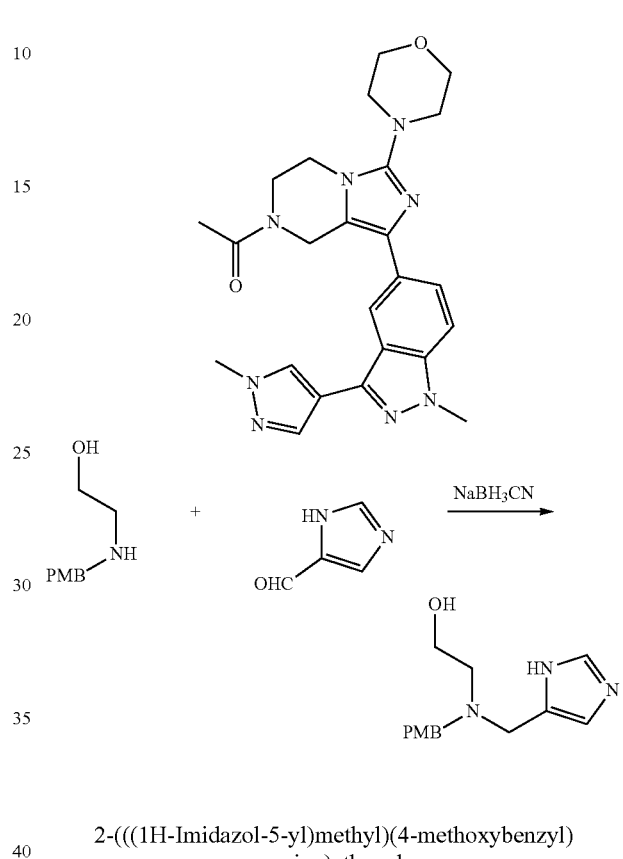

2-(((1H-Imidazol-5-yl)methyl)(4-methoxybenzyl)amino)ethanol

To a solution of 1H-imidazole-4-carbaldehyde (14.85 g, 154.5 mmol) and 2-(4-methoxybenzylamino)ethanol (20.00 g, 110.4 mmol) in MeCN (220 mL) and MeOH (22 mL) was added AcOH (10 mL). The mixture was stirred at RT for 1 h, cooled to 0° C., then treated with NaBH$_3$CN (8.32 g, 132 mmol) portionwise. The resulting mixture was stirred at RT for 3 h, then concentrated under reduced pressure. The residue was partitioned between CH$_2$Cl$_2$ (200 mL) and sat. aq. NaHCO$_3$(200 mL). The aqueous layer was treated with 1 M aq. NaOH to adjust the pH to 14, then extracted with CH$_2$Cl$_2$ (75 mL×4). The combined organic layers were dried over Na$_2$SO$_4$, filtered and concentrated under reduced pressure to give the title compound as a colorless oil (22.30 g, 77%). MS (ES$^+$): C$_{14}$H$_{19}$N$_3$O$_2$ requires: 261, found: 262 [M+H]$^+$.

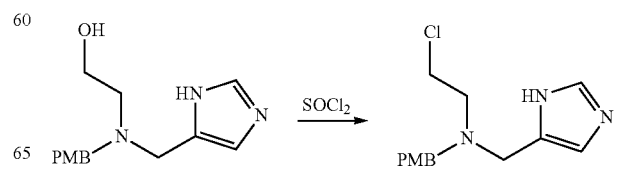

2-Chloro-N-(1H-imidazol-5-ylmethyl)-N-[(4-methoxyphenyl)methyl]ethanamine

To a solution of the product from the previous step (23.00 g, 88.01 mmoles) in 1,4-dioxane (200 mL) was added $SOCl_2$ (25.54 mL, 352 mmol) over 10 min. The mixture was stirred at 60° C. for 3 h, then allowed to cool to RT and concentrated under reduced pressure. The residue was taken up in 1,4-dioxane and toluene, then again concentrated under reduced pressure to give the title compound as a white solid (20.40 g, 83%). MS (ES$^+$): $C_{14}H_{18}ClN_3O$ requires: 279, found: 280 $[M+H]^+$.

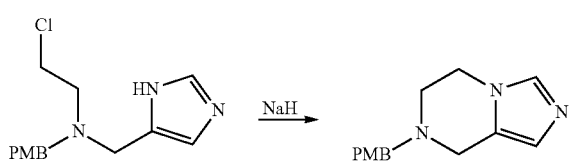

7-[(4-Methoxyphenyl)methyl]-6,8-dihydro-5H-imidazo[1,5-a]pyrazine

To a solution of the product from the previous step (5.00 g, 17.9 mmol) in DMF (45 mL) at 0° C. was added NaH (60% in mineral oil, 2.86 g, 71.5 mmol). The mixture was stirred, allowing to slowly warm to RT, for 2 h, then treated with sat. aq. $NH_4Cl$ and extracted with $CH_2Cl_2$ (60 mL×4). The combined organic layers were dried over $MgSO_4$, filtered and concentrated under reduced pressure. The residue was purified by $SiO_2$ gel chromatography (0% to 5% MeOH in $CH_2Cl_2$) to give the title compound as a yellow oil (1.62 g, 37%). MS (ES$^+$): $C_{14}H_{17}N_3O$ requires: 243, found: 244 $[M+H]^+$.

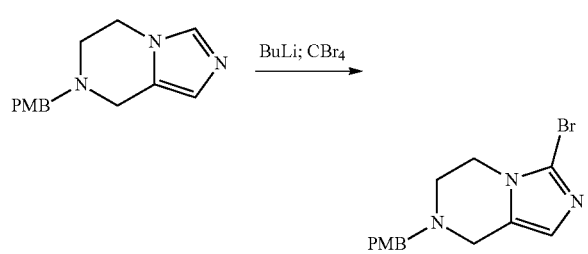

3-Bromo-7-(4-methoxybenzyl)-5,6,7,8-tetrahydroimidazo[1,5-a]pyrazine

To a solution of the product from the previous step (500.0 mg, 2.06 mmol) in THF (20 mL) at −78° C. was added BuLi (2.5 M in hexanes, 1.15 mL, 2.88 mmol). The mixture was stirred at −78° C. for 1 h, then treated with $CBr_4$ (954 mg, 2.88 mmol) in 2 mL of THF. The mixture was stirred at −78° C. for 30 min, then treated with sat. aq. $NH_4Cl$ and allowed to warm to RT. The mixture was extracted with $CH_2Cl_2$ (20 mL×3), and the combined organic layers were washed with sat. aq. NaCl (20 mL), dried over $MgSO_4$, filtered and concentrated under reduced pressure. The residue was purified by $SiO_2$ gel chromatography (0% to 5% MeOH in EtOAc) to give the title compound as a yellow solid (280.0 mg, 42%). MS (ES$^+$): $C_{14}H_{16}BrN_3O$ requires: 321, found: 322 $[M+H]^+$.

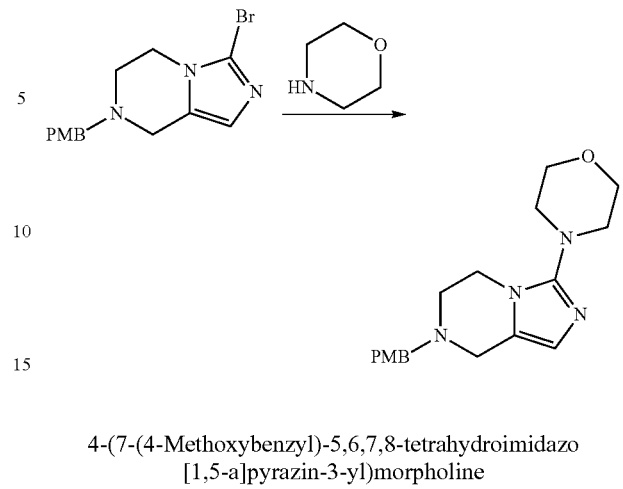

4-(7-(4-Methoxybenzyl)-5,6,7,8-tetrahydroimidazo[1,5-a]pyrazin-3-yl)morpholine A mixture of the product from the previous step (200.0 mg, 620.7 µmol) and morpholine (10 mL) was stirred at 140° C. in a sealed tube for 40 h, then allowed to cool to RT and diluted with $CH_2Cl_2$ (45 mL). The mixture was washed with sat. aq. NaCl (25 mL×3), dried over $MgSO_4$, filtered and concentrated under reduced pressure. The residue was purified by $SiO_2$ gel chromatography (0% to 5% MeOH in EtOAc) to give the title compound as a yellow oil (180.0 mg, 88%). MS (ES$^+$): $C_{18}H_{24}N_4O_2$ requires: 328, found: 329 $[M+H]^+$.

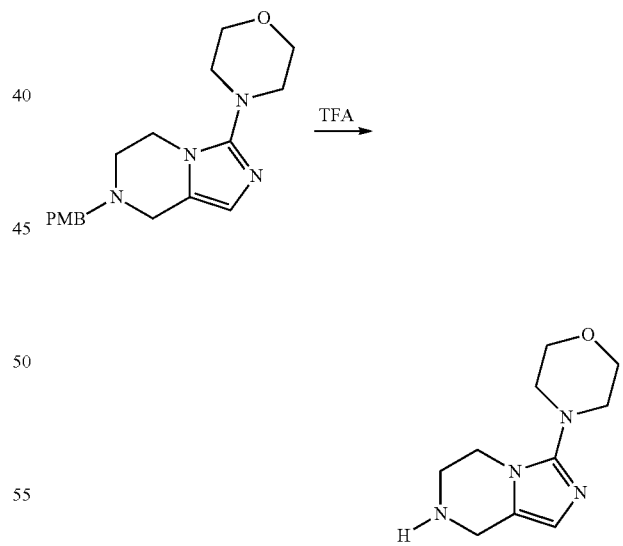

4-(5,6,7,8-Tetrahydroimidazo[1,5-a]pyrazin-3-yl)morpholine

A mixture of the product from the previous step (160.0 mg, 487.2 µmol) in TFA (5 mL) was stirred at 130° C. for 25 min, then concentrated under reduced pressure to give the crude title compound as a yellow solid (100.0 mg, 99%). MS (ES$^+$): $C_{10}H_{16}N_4O$ requires: 208, found: 209 $[M+H]^+$.

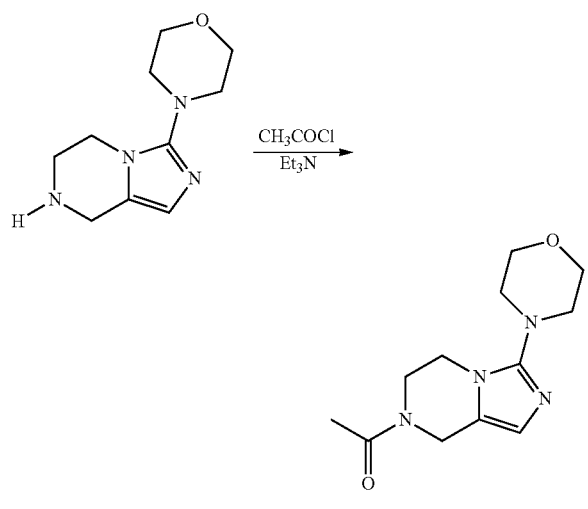

1-(3-Morpholino-5,6-dihydroimidazo[1,5-a]pyrazin-7(8H)-yl)ethanone

To a solution of the product from the previous step (100.0 mg, 480.2 μmol) in CH$_2$Cl$_2$ (15 mL) at 0° C. were added Et$_3$N (0.267 mL, 1.92 mmol) and AcCl (51.40 μL, 720.2 μmol). The mixture was stirred for 2.5 h, then sequentially washed with sat. aq. NaHCO$_3$ and sat. aq. NaCl, dried over Na$_2$SO$_4$, filtered and concentrated under reduced pressure. The residue was purified by SiO$_2$ gel chromatography (5% to 25% EtOAc in petroleum ether) to give the title compound as a brown solid (110.0 mg, 92%). MS (ES$^+$): C$_{12}$H$_{18}$N$_4$O$_2$ requires: 250, found: 251 [M+H]$^+$.

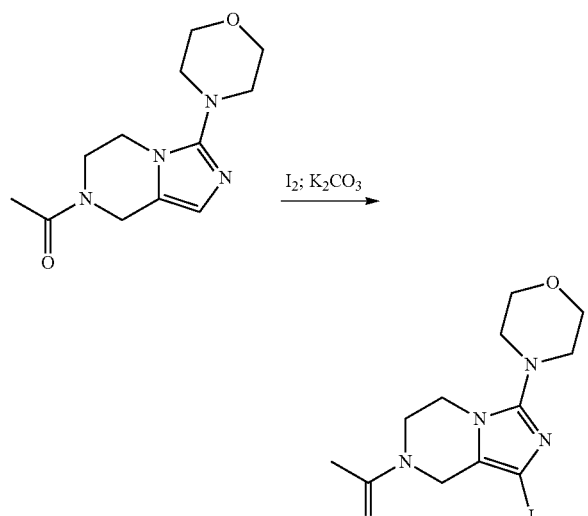

1-(1-Iodo-3-morpholino-5,6-dihydroimidazo[1,5-a]pyrazin-7(8H)-yl)ethanone

To a mixture of the product from the previous step (120.0 mg, 479.4 μmol) and K$_2$CO$_3$ (265 mg, 1.92 mmol) in DMF (5 mL) was added I$_2$ (182.52 mg, 719.13 μmol). The mixture was stirred at RT for 5 h, then treated with sat. aq. Na$_2$SO$_3$ and extracted with CH$_2$Cl$_2$ (15 mL×3). The combined organic layers were washed with sat. aq. NaCl (10 mL×3), dried over MgSO$_4$, filtered and concentrated under reduced pressure to give the title compound as a brown oil (60.0 mg, 33%). MS (ES$^+$): C$_{12}$H$_{17}$IN$_4$O$_2$ requires: 376, found: 377 [M+H]$^+$.

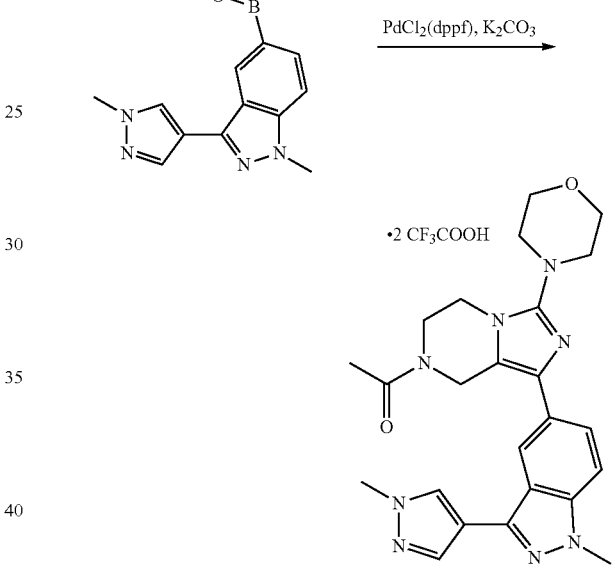

1-(1-(1-Methyl-3-(1-methyl-M-pyrazol-4-yl)-1H-indazol-5-yl)-3-morpho-lino-5,6-dihydroimidazo[1,5-a]pyrazin-7(8H)-yl)ethanone bis(2,2,2-trifluoroacetate)

A mixture of the product from the previous step (60.00 mg, 159.5 μmol), Intermediate "F" (64.73 mg, 191.4 μmol), 2.0 M aq. K$_2$CO$_3$ (0.239 mL, 478 μmol) and PdCl$_2$(dppf) (19.94 mg, 23.92 μmol) in DMF (2 mL) was degassed and purged with N$_2$. The mixture was stirred at 90° C. for 1 h, then concentrated under reduced pressure. The residue was purified by reverse phase preparative HPLC (Mobile phase: A=0.1% TFA/water, B=0.1% TFA/MeCN; Gradient: B=10% to 45% in 18 min; Column: C18) to give the title compound as a white solid (16.0 mg, 15%).

MS (ES$^+$): C$_{24}$H$_{28}$N$_8$O$_2$ requires: 460, found: 461 [M+H]$^+$.

$^1$H NMR (CD$_3$OD) (2:1 ratio of rotamers) δ 8.26 (s, 1H), 8.22-8.14 (m, 1H), 8.12-8.07 (m, 1H), 7.81-7.72 (m, 1H), 7.69-7.52 (m, 1H), 5.06 (s, 0.7H), 4.97 (s, 1.3H), 4.25 (t, J=6.5 Hz, 1.3H) 4.14 (appar br s, 3.7H), 4.06-3.97 (m, 5H), 3.93-3.91 (m, 4H), 3.53-3.42 (m, 4H), 2.27 (s, 2H), 2.22 (s, 1H).

Example 17

3-Cyclopropyl-N-methyl-1-(3-(6-(methylcarbamoyl)pyridin-3-yl)isoquinolin-8-yl)-5,6-dihydroimidazo[1,5-a]pyrazine-7(8H)-carboxamide

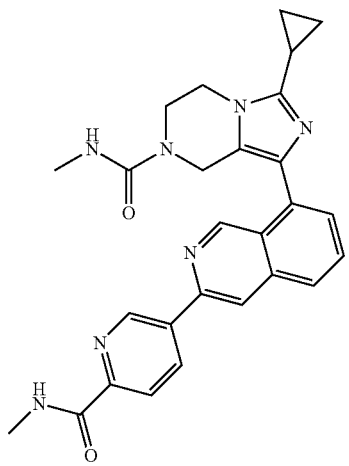

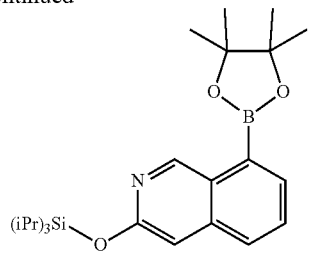

8-(4,4,5,5-Tetramethyl-1,3,2-dioxaborolan-2-yl)-3-(triisopropylsilyloxy) isoquinoline A mixture of the product from the previous step (1.5 g, 4.5 mmol) and XPhos Pd G2 (350 mg, 0.45 mmol), XPhos (210 mg, 167.4 mmol), KOAc (1.30 g, 13.5 mmol) and BPin$_2$ (1.4 g, 5.4 mmol) in 1,4-dioxane (20 mL) was stirred at 110° C. for 2 h in a microwave reactor. The mixture was poured into water (50 mL) and extracted with EtOAc (50 mL×3). The combined organic layers were dried over Na$_2$SO$_4$, filtered and concentrated under reduced pressure. The residue was purified by SiO$_2$ gel chromatography (100% petroleum ether) to afford the title compound as a yellow solid (1.7 g, 88%). MS (ES$^+$): C$_{24}$H$_{38}$BNO$_3$Si requires: 427, found: 428 [M+H]$^+$.

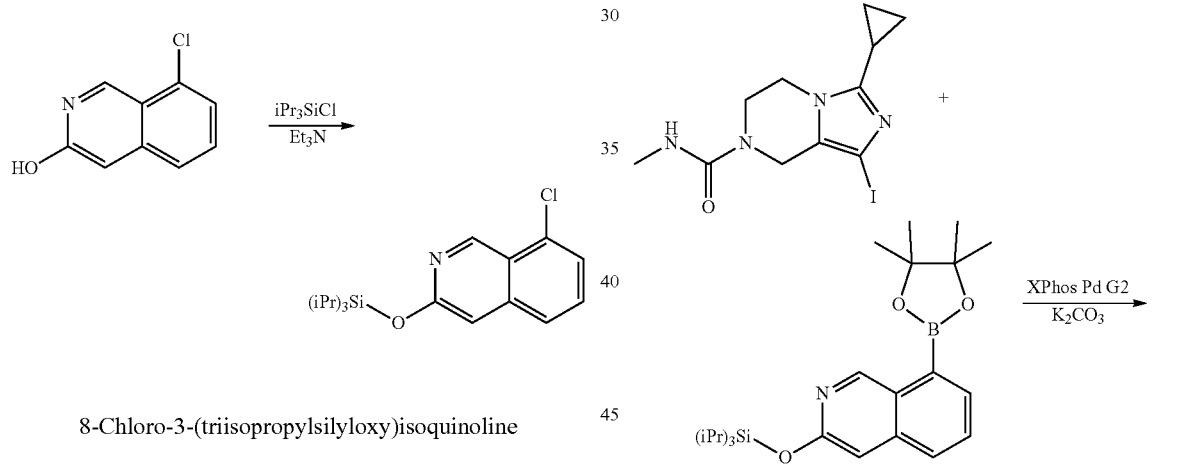

8-Chloro-3-(triisopropylsilyloxy)isoquinoline

To a suspension of 8-chloroisoquinolin-3-ol (10.0 g, 55.8 mmol) and Et$_3$N (16.9 g, 167 mmol) in CH$_2$Cl$_2$ (200 mL) was added iPr$_3$SiCl (16.2 g, 83.7 mmol) and the resulting mixture was stirred at RT for 3 h. The mixture was poured into water (300 mL) and extracted with CH$_2$Cl$_2$ (200 mL×3). The combined organic layers were dried over Na$_2$SO$_4$, filtered and concentrated under reduced pressure. The residue was purified by SiO$_2$ gel chromatography (100% petroleum ether) to give the title compound as a yellow solid (5.5 g, 29%). MS (ES$^+$): C$_{18}$H$_{26}$ClNOSi requires: 335, found: 336 [M+H]$^+$.

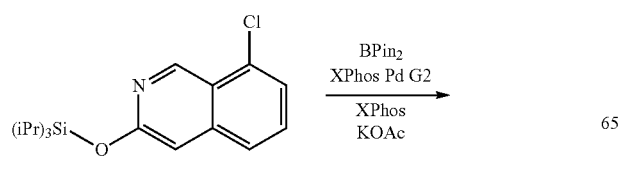

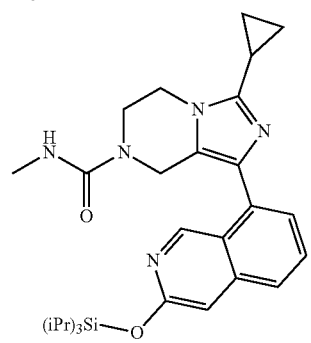

3-Cyclopropyl-N-methyl-1-(3-(triisopropylsilyloxy)isoquinolin-8-yl)-5,6-dihydroimidazo[1,5-a]pyrazine-7(8H)-carboxamide A suspension of Intermediate "B" (400 mg, 1.1 mmol), XPhos Pd G2 (87 mg, 0.11 mmol), K$_2$CO$_3$ (456 mg, 3.3 mmol) and the product from the previous step (700 mg, 1.64 mmol) in 1,4-dioxane (20 mL) and H₂O (4 mL) was stirred at 100° C. for 3 h. The mixture was poured into water (50 mL) and extracted with EtOAc (80 mL×3). The combined organic layers were dried over Na₂SO₄, filtered and concentrated under reduced pressure. The residue was purified by SiO₂ gel chromatography (100% petroleum ether) to give the title compound as a yellow solid (210 mg, 25%). MS (ES⁺): $C_{29}H_{41}N_5O_2Si$ requires: 519, found: 520 [M+H]⁺.

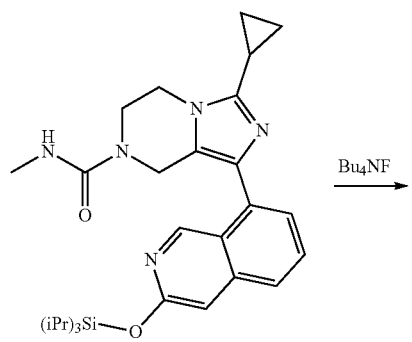

3-Cyclopropyl-1-(3-hydroxyisoquinolin-8-yl)-N-methyl-5,6-dihydroimidazo[1,5-a]pyrazine-7(8H)-carboxamide To a suspension of the product from the previous step (210 mg, 0.404 mmol) in 1,4-dioxane (10 mL) was added Bu₄NF (158 mg, 0.604 mmol), and the resulting mixture was stirred at RT for 2 h. The mixture was poured into water (50 mL) and extracted with EtOAc (80 mL×3). The combined organic layers were dried over Na₂SO₄, filtered and concentrated under reduced pressure to give the crude title compound as a yellow solid (50 mg, 34%), which was used without further purification. MS (ES⁺): $C_{20}H_{21}N_5O_2$ requires: 363, found: 364 [M+H]⁺.

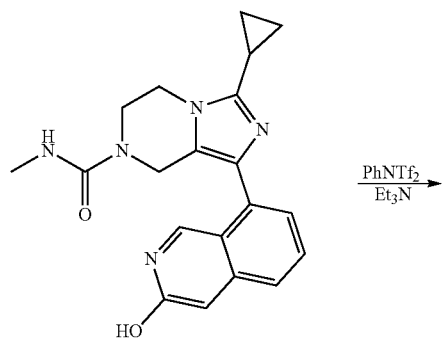

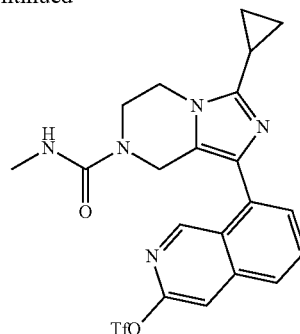

8-(3-Cyclopropyl-7-(methylcarbamoyl)-5,6,7,8-tetrahydroimidazo[1,5-a]pyrazin-1-yl)isoquinolin-3-yl trifluoromethanesulfonate A suspension of the product from the previous step (50 mg, 0.14 mmol), 1,1,1-trifluoro-N-phenyl-N-(trifluoromethylsulfonyl)methanesulfonamide (75 mg, 0.21 mmol), and Et₃N (43 mg, 0.42 mmol) in 1,4-dioxane (3 mL) was stirred at RT for 3 h. The mixture was poured into water (20 mL) and extracted with CH₂Cl₂ (20 mL×3). The combined organic layers were dried over Na₂SO₄, filtered and concentrated under reduced pressure to give the crude title compound as a yellow solid (70 mg, 100%), which was used without further purification. MS (ES⁺): $C_{21}H_{20}F_3N_5O_4S$ requires: 495, found: 496 [M+H]⁺.

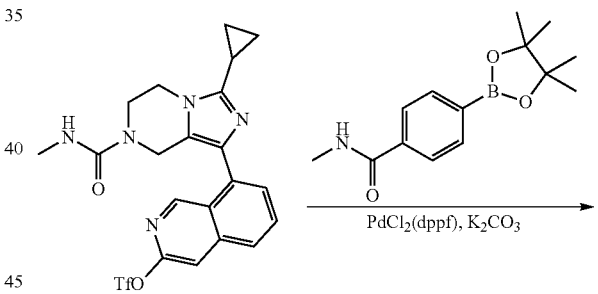

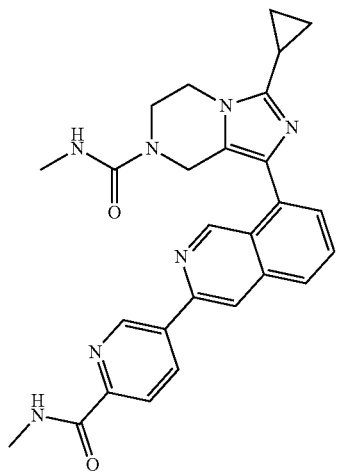

3-Cyclopropyl-N-methyl-1-(3-(6-(methylcarbamoyl)pyridin-3-yl)isoquinolin-8-yl)-5,6-dihydroimidazo[1,5-a]pyrazine-7(8H)-carboxamide A suspension of the product from the previous step (300 mg, 0.61 mmol), N-methyl-5-(4,4,5,5-tetramethyl-1,3,2-dioxaborolan-2-yl)picolinamide (192 mg, 0.73 mmol), PdCl$_2$(dppf) (45 mg, 0.061 mmol), and K$_2$CO$_3$ (253 mg, 1.83 mmol) in 1,4-dioxane (10 mL) and H$_2$O (2 mL) was stirred at 100° C. for 3 h. The mixture was poured into water (50 mL) and extracted with EtOAc (80 mL×3). The combined organic layers were dried over Na$_2$SO$_4$, filtered and concentrated under reduced pressure. The residue was purified by reverse phase preparative HPLC (Mobile phase: A=0.1% NH$_4$HCO$_3$/H$_2$O, B=MeCN; Gradient: B=0% to 45% in 18 min; Column: C18) to give the title compound as a yellow solid (35 mg, 12%).

MS (ES$^+$): C$_{27}$H$_{27}$N$_7$O$_2$ requires: 481, found: 482 [M+H]$^+$.

$^1$H NMR (DMSO-d$_6$) δ 10.04 (s, 1H), 9.46 (appar br s, 1H), 8.88 (q, J=4.9 Hz, 1H), 8.77 (dd, J=8.2, 2.2 Hz, 1H), 8.66 (s, 1H), 8.17 (d, J=8.2 Hz, 1H), 7.98 (d, J=8.2 Hz, 1H), 7.85 (appar t, J=7.6 Hz, 1H), 7.54 (d, J=6.6 Hz, 1H), 6.75 (q, J=4.4 Hz, 1H), 4.69 (s, 2H), 4.14 (t, J=5.4 Hz, 2H), 3.85 (t, J=5.3 Hz, 2H), 2.86 (d, J=4.8 Hz, 3H), 2.56 (d, J=4.3 Hz, 3H), 2.09-2.05 (m, 1H), 1.00-0.93 (m, 4H).

Example 18

3-cyclopropyl-N-methyl-1-(3-morpholinoisoquinolin-8-yl)-5,6-dihydroimidazo[1,5-a]pyrazine-7(8H)-carboxamide

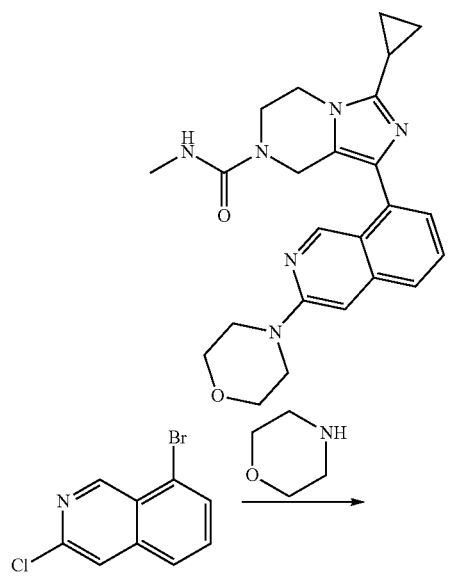

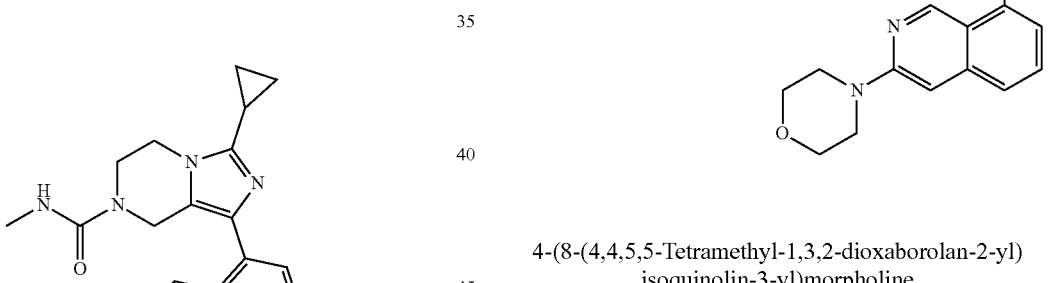

4-(8-Bromoisoquinolin-3-yl)morpholine

A solution of 8-bromo-3-chloroisoquinoline (400 mg, 1.65 mmol) and morpholine (3 mL) in DMSO (5 mL) was stirred at 150° C. for 1 h in a microwave reactor, then allowed to cool to RT. The mixture was diluted with EtOAc (90 mL), washed with sat. aq. NaCl (25 mL×3), dried over Na$_2$SO$_4$, filtered and concentrated under reduced pressure. The residue was purified by SiO$_2$ gel chromatography (0% to 45% EtOAc in petroleum ether) to give the title compound as a yellow solid (325 mg, 67%). MS (ES$^+$): C$_{13}$H$_{13}$BrN$_2$O requires: 292, found: 293 [M+H]$^+$.

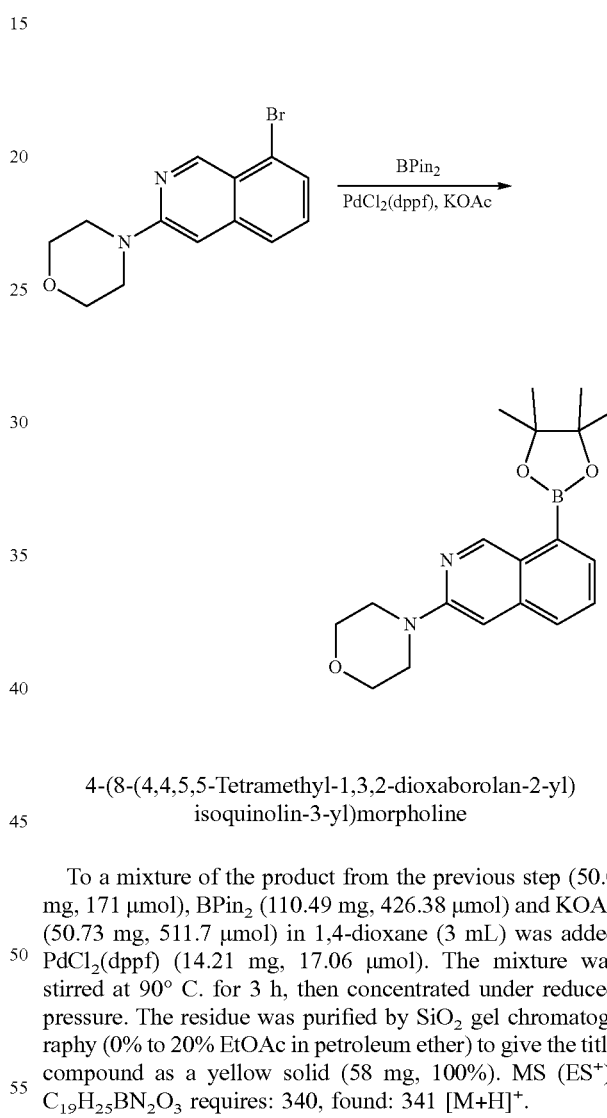

4-(8-(4,4,5,5-Tetramethyl-1,3,2-dioxaborolan-2-yl)isoquinolin-3-yl)morpholine To a mixture of the product from the previous step (50.0 mg, 171 µmol), BPin$_2$ (110.49 mg, 426.38 µmol) and KOAc (50.73 mg, 511.7 µmol) in 1,4-dioxane (3 mL) was added PdCl$_2$(dppf) (14.21 mg, 17.06 µmol). The mixture was stirred at 90° C. for 3 h, then concentrated under reduced pressure. The residue was purified by SiO$_2$ gel chromatography (0% to 20% EtOAc in petroleum ether) to give the title compound as a yellow solid (58 mg, 100%). MS (ES$^+$): C$_{19}$H$_{25}$BN$_2$O$_3$ requires: 340, found: 341 [M+H]$^+$.

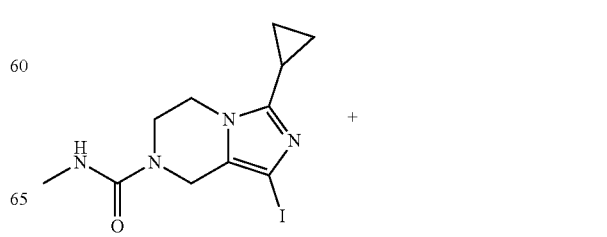

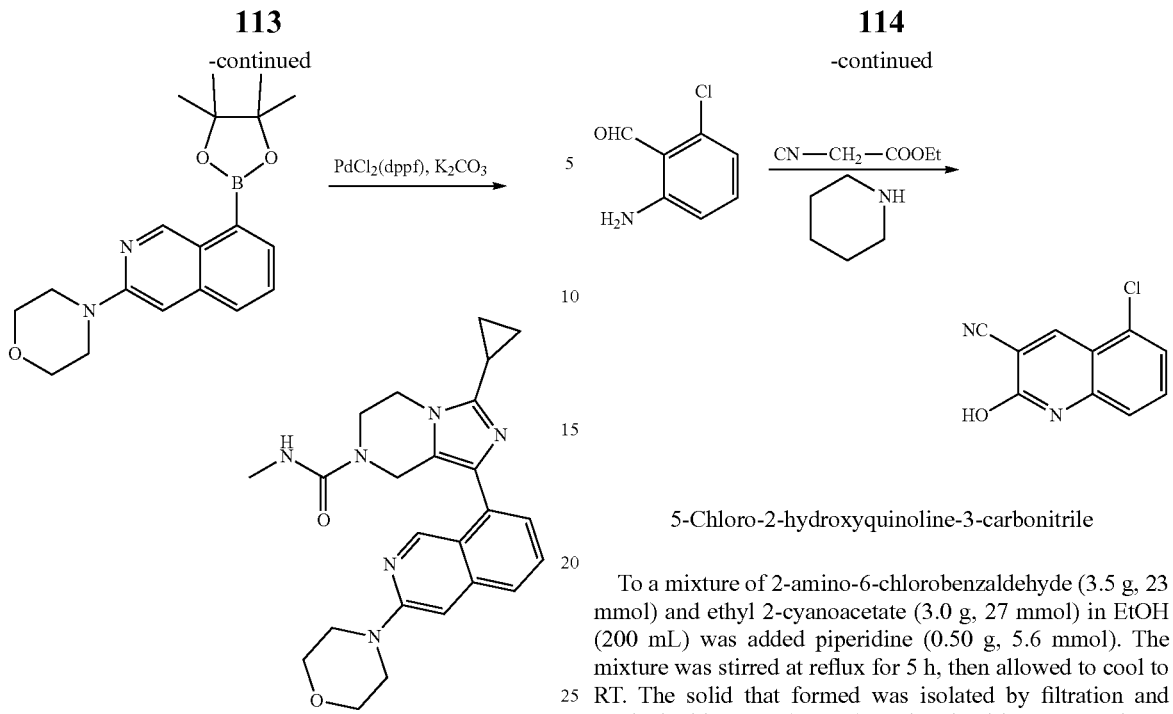

3-Cyclopropyl-N-methyl-1-(3-morpholinoisoquinolin-8-yl)-5,6-dihydroimidazo[1,5-a]pyrazine-7(8H)-carboxamide A mixture of Intermediate "B" (60.0 mg, 0.173 mmol), the product from the previous step (70.8 mg, 0.208 mmol), 2.0 M aq. $K_2CO_3$ (0.260 mL, 0.520 mmol), and $PdCl_2$(dppf) (14.4 mg, 0.017 mmol) in 1,4-dioxane (3 mL) was degassed and purged with $N_2$. The mixture was stirred at 100° C. for 5 h, then concentrated under reduced pressure. The residue was purified by $SiO_2$ gel chromatography (25% to 100% EtOAc in petroleum ether) to give the title compound as a brown solid (40 mg, 53%).

MS (ES$^+$): $C_{24}H_{28}N_6O_2$ requires: 432, found: 433 [M+H]$^+$.

$^1$H NMR (CD$_3$OD) δ 9.13 (s, 1H), 7.70 (d, J=8.5 Hz, 1H), 7.60 (dd, J=8.3, 7.0 Hz, 1H), 7.26 (d, J=7.0 Hz, 1H), 7.02 (s, 1H), 4.61 (s, 2H), 4.24 (t, J=5.5 Hz, 2H), 3.94 (t, J=5.5 Hz, 2H), 3.91-3.84 (m, 4H), 3.58-3.50 (m, 4H), 2.71 (s, 3H), 2.09-2.01 (m, 1H), 1.10-1.01 (m, 4H).

Example 19

1-(3-Cyano-2-(1-methyl-1H-pyrazol-4-yl)quinolin-5-yl)-3-cyclopropyl-N-methyl-5,6-dihydroimidazo[1,5-a]pyrazine-7(8H)-carboxamide

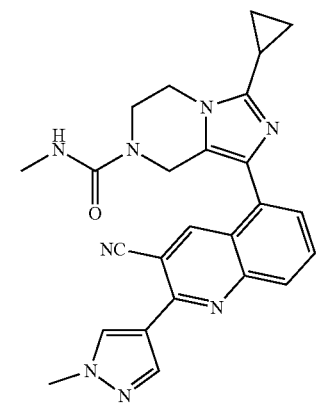

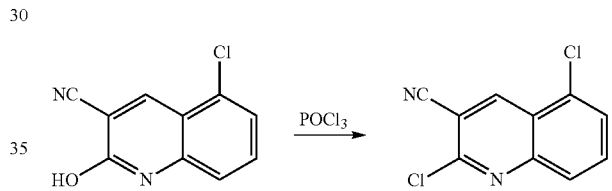

5-Chloro-2-hydroxyquinoline-3-carbonitrile

To a mixture of 2-amino-6-chlorobenzaldehyde (3.5 g, 23 mmol) and ethyl 2-cyanoacetate (3.0 g, 27 mmol) in EtOH (200 mL) was added piperidine (0.50 g, 5.6 mmol). The mixture was stirred at reflux for 5 h, then allowed to cool to RT. The solid that formed was isolated by filtration and washed with EtOH (20 mL) to give the title compound as a white solid (4.1 g, 88%). MS (ES$^+$): $C_{10}H_5ClN_2O$ requires: 204, found: 205 [M+H]$^+$.

2,5-Dichloroquinoline-3-carbonitrile

A mixture of the product from the previous step (4.1 g, 20 mmol) in POCl$_3$ (100 mL) was stirred at 100° C. for 3 h, then allowed to cool to RT. The mixture was concentrated under reduced pressure, then treated with sat. aq. NaHCO$_3$ until the pH of the mixture was >8. The mixture was extracted with EtOAc (50 mL×4), the combined organic layers were concentrated under reduced pressure, and the residue was purified by SiO$_2$ gel chromatography (0% to 30% EtOAc in petroleum ether) to give the title compound as a light yellow solid (4.0 g, 90%). MS (ES$^+$): $C_{10}H_4Cl_2N_2$ requires: 222, found: 223 [M+H]$^+$.

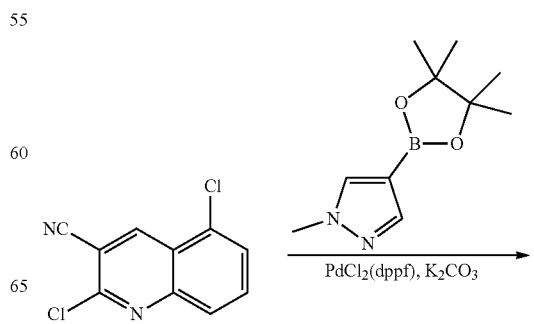

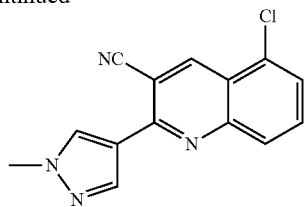

5-Chloro-2-(1-methyl-M-pyrazol-4-yl)quinoline-3-carbonitrile

A mixture of the product from the previous step (1.1 g, 4.9 mmol), 1-methyl-4-(4,4,5,5-tetramethyl-1,3,2-dioxaborolan-2-yl)-1H-pyrazole (1.1 g, 5.4 mmol), K$_2$CO$_3$ (2.0 g, 15 mmol) and PdCl$_2$(dppf) (400 mg, 0.49 mmol) in 1,4-dioxane/H$_2$O (20 mL/4 mL) was degassed and purged with N$_2$, then stirred at 100° C. for 2 h. The mixture was concentrated under reduced pressure, and the residue was purified by SiO$_2$ gel chromatography (0% to 50% EtOAc in petroleum ether) to give the title compound as a tan solid (680 mg, 51%). MS (ES$^+$): C$_{14}$H$_9$ClN$_4$ requires: 268, found: 269 [M+H]$^+$.

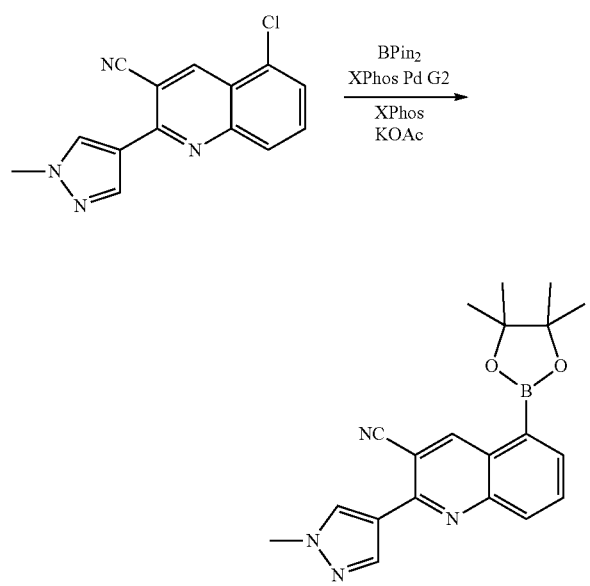

2-(1-methyl-1H-pyrazol-4-yl)-5-(4,4,5,5-tetramethyl-1,3,2-dioxaborolan-2-yl)quinoline-3-carbonitrile A mixture of the product from the previous step (100 mg, 0.37 mmol), BPin$_2$ (114 mg, 0.45 mmol), KOAc (108 mg, 1.1 mmol), XPhos Pd G2 (29 mg, 0.04 mmol) and XPhos (35 mg, 0.07 mmol) in dry 1,4-dioxane (3 mL) was degassed and purged with Ar, then stirred at 100° C. for 4 h. The reaction was repeated four times, and the combined mixtures were concentrated under reduced pressure. The residue was purified by SiO$_2$ gel chromatography (0% to 50% EtOAc in petroleum ether) to give the crude title compound, which was further washed with DMF (5 mL) to give the title compound as a white solid (375 mg, 69%). MS (ES$^+$): C$_{20}$H$_{21}$BN$_4$O$_2$ requires: 360, found: 361 [M+H]$^+$.

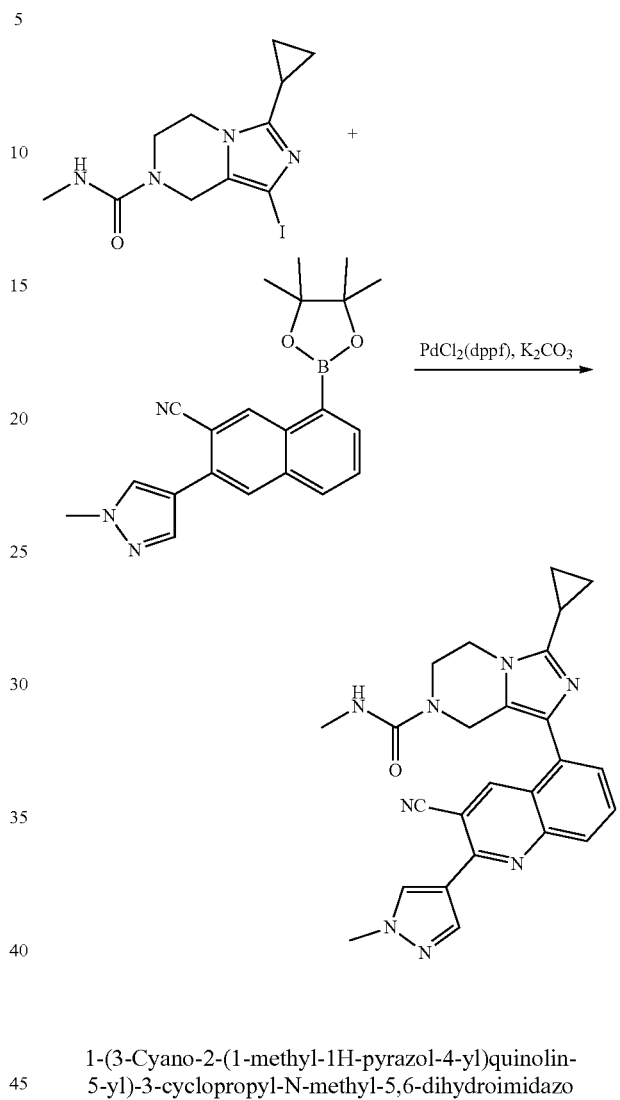

1-(3-Cyano-2-(1-methyl-1H-pyrazol-4-yl)quinolin-5-yl)-3-cyclopropyl-N-methyl-5,6-dihydroimidazo[1,5-a]pyrazine-7(8H)-carboxamide A mixture of Intermediate "B" (66 mg, 0.19 mmol), the product from the previous step (82 mg, 0.23 mmol), K$_2$CO$_3$ (78 mg, 0.57 mmol) and PdCl$_2$(dppf) (16 mg, 0.02 mmol) in 1,4-dioxane/H$_2$O (2 mL/0.4 mL) was degassed and purged with N$_2$, then stirred at 100° C. for 2 h. The mixture was concentrated under reduced pressure, and the residue was purified by reverse phase preparative HPLC (Mobile phase: A=10 mM NH$_4$HCO$_3$/H$_2$O, B=MeCN; Gradient: B=10% to 45% in 18 min; Column: C18) to give the title compound as a white solid (50 mg, 58%).

MS (ES$^+$): C$_{25}$H$_{24}$N$_8$O requires: 452, found: 453 [M+H]$^+$.

$^1$H NMR (500 MHz, DMSO-d$_6$) δ 9.66 (s, 1H), 8.56 (s, 1H), 8.26 (s, 1H), 8.02-7.81 (m, 2H), 7.50 (dd, J=6.3, 2.0 Hz, 1H), 6.75 (q, J=4.0 Hz, 1H), 4.68 (s, 2H), 4.13 (t, J=5.5 Hz, 2H), 3.99 (s, 3H), 3.83 (t, J=5.4 Hz, 2H), 2.56 (d, J=4.0 Hz, 3H), 2.13-2.01 (m, 1H), 1.07-0.82 (m, 4H).

Example 20

3-(3,3-Difluorocyclobutyl)-N-methyl-1-(2-(1-methyl-1H-pyrazol-4-yl)-3-(trifluoromethyl)quinolin-5-yl)-5,6-dihydroimidazo[1,5-a]pyrazine-7(8H)-carboxamide

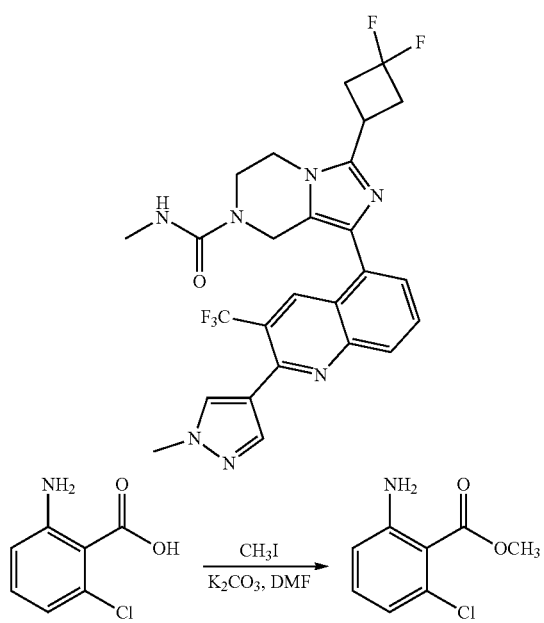

Methyl 2-amino-6-chlorobenzoate

To a solution of 2-amino-6-chlorobenzoic acid (1.0 g, 5.8 mmol) in DMF (10 mL) were added CH₃I (99.5 mg, 7.01 mmol) and K₂CO₃ (967 mg, 7.01 mmol). The mixture was stirred at RT overnight, then treated with H₂O (50 mL) and extracted with EtOAc (50 mL×3). The combined organic layers were sequentially washed with water and sat. aq. NaCl, dried over Na₂SO₄, filtered and concentrated under reduced pressure. The residue was purified by SiO₂ gel chromatography (0% to 15% EtOAc in hexanes) to give the title compound as a yellow oil (800 mg, 93%). MS (ES⁺) C₈H₈ClNO₂ requires: 185, found: 186 [M+H]⁺.

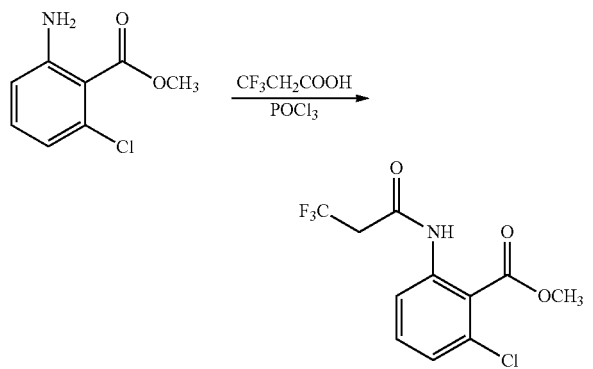

Methyl 2-chloro-6-(3,3,3-trifluoropropanamido)benzoate

To a solution of the product from the previous step (800 mg, 4.32 mmol) in pyridine (8 mL) were added 3,3,3-trifluoropropionic acid (664 mg, 5.8 mmol) and POCl₃ (793 mg, 5.8 mmol). The resulting mixture was stirred at RT for 3 h, then treated with sat. aq. NaHCO₃(10 mL). The layers were separated, and the aqueous phase was extracted with EtOAc (3×10 mL). The combined organic layers were washed with sat. aq. NaCl, dried over Na₂SO₄, filtered and concentrated under reduced pressure. The residue was purified by SiO₂ gel chromatography (0% to 15% EtOAc in hexane) to give the title compound as an off-white solid (500 mg, 39%). MS (ES⁺) C₁₁H₉ClF₃NO₃ requires: 295, found: 296 [M+H]⁺.

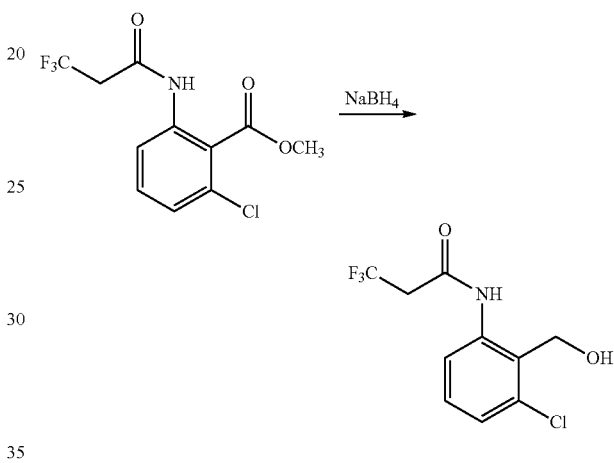

N-(3-Chloro-2-(hydroxymethyl)phenyl)-3,3,3-trifluoropropanamide

To a degassed solution of the product from the previous step (2000 mg, 6.76 mmol) in THF (20 mL) was added NaBH₄ (256.88 mg, 6.76 mmol). The resulting mixture was stirred at RT for 2 h, then concentrated under reduced pressure. The residue was purified by SiO₂ gel chromatography (0% to 50% EtOAc in petroleum ether) to give the title compound as an off-white solid (300 mg, 17%). MS (ES⁺) C₁₀H₉ClF₃NO₂ requires: 267, found: 268 [M+H]⁺.

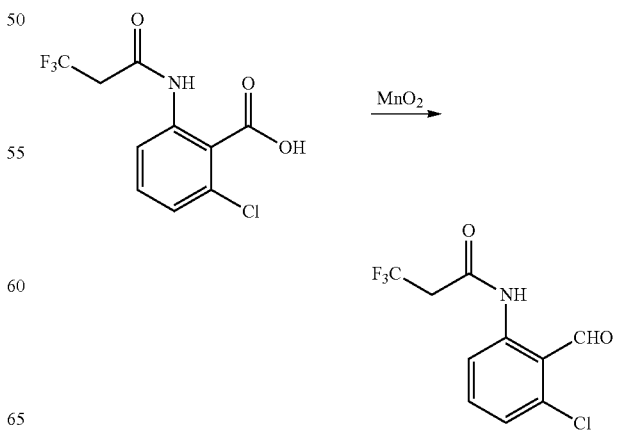

N-(3-Chloro-2-formylphenyl)-3,3,3-trifluoropropanamide

To a degassed solution of the product from the previous step (300 mg, 1.12 mmol) in CH$_2$Cl$_2$ (10 mL) was added MnO$_2$ (195 mg, 2.24 mmol). The resulting mixture was stirred at RT for 2 h, then filtered and the filtrate concentrated under reduced pressure. The residue was purified by SiO$_2$ gel chromatography (0% to 50% EtOAc in petroleum ether) to give the title compound as an off-white solid (250 mg, 84%). MS (ES$^+$) C$_{10}$H$_7$ClF$_3$NO$_2$ requires: 265, found: 266 [M+H]$^+$.

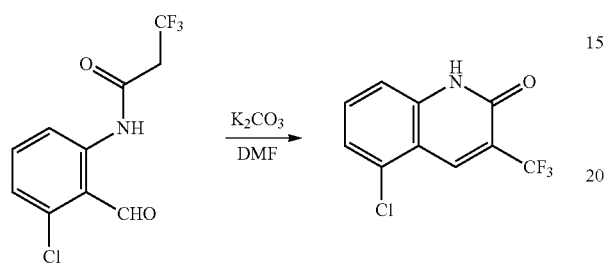

5-Chloro-3-(trifluoromethyl)quinolin-2(1H)-one

To a degassed solution of the product from the previous step (250 mg, 0.943 mmol) in DMF (5 mL) was added K$_2$CO$_3$ (260 mg, 1.89 mmol) and the resulting mixture was stirred at RT for 2 h, then treated with H$_2$O (10 mL) and extracted with EtOAc (3×10 mL). The combined organic layers were washed with sat. aq. NaCl, dried over Na$_2$SO$_4$, filtered and concentrated under reduced pressure. The residue was purified by SiO$_2$ gel chromatography (0% to 30% EtOAc in petroleum ether) to give the title compound as an off-white solid (200 mg, 86%). MS (ES$^+$) C$_{10}$H$_5$ClF$_3$NO requires: 247, found: 248 [M+H]$^+$.

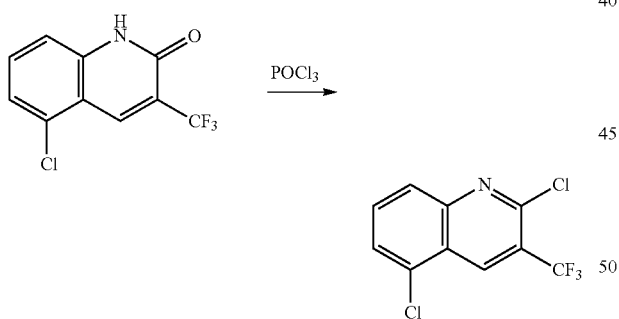

2,5-Dichloro-3-(trifluoromethyl)quinoline

A degassed solution of the product from the previous step (200 mg, 0.810 mmol) in POCl$_3$ (5 mL) was stirred at 100° C. for 3 h. To the mixture was added sat. aq. NaHCO$_3$ (10 mL), and layers were separated. The aqueous phase was extracted with EtOAc (3×10 mL), and the combined organic layers were washed with sat. aq. NaCl, dried over Na$_2$SO$_4$, filtered and concentrated under reduced pressure. The residue was purified by SiO$_2$ gel chromatography (0% to 20% EtOAc in hexane) to give the title compound as an off-white solid (100 mg, 46%). MS (ES$^+$) C$_{10}$H$_4$Cl$_2$F$_3$N requires: 265, found: 266 [M+H]$^+$.

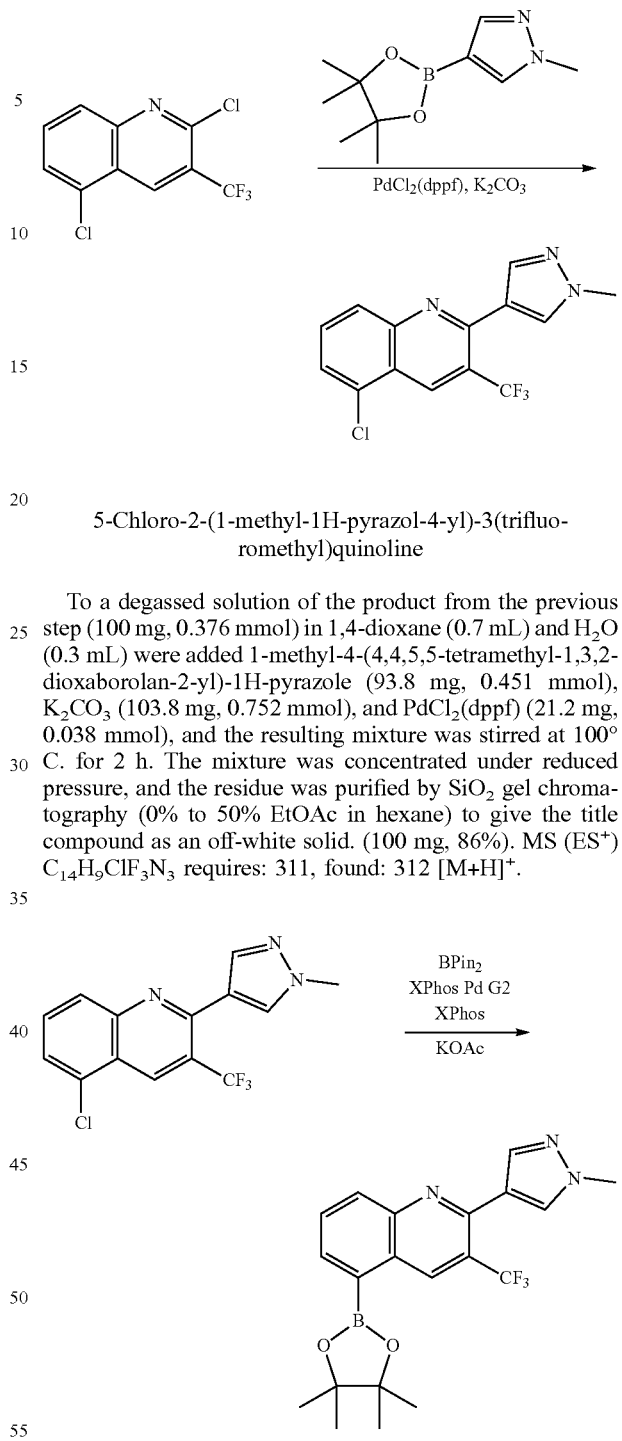

5-Chloro-2-(1-methyl-1H-pyrazol-4-yl)-3(trifluoromethyl)quinoline

To a degassed solution of the product from the previous step (100 mg, 0.376 mmol) in 1,4-dioxane (0.7 mL) and H$_2$O (0.3 mL) were added 1-methyl-4-(4,4,5,5-tetramethyl-1,3,2-dioxaborolan-2-yl)-1H-pyrazole (93.8 mg, 0.451 mmol), K$_2$CO$_3$ (103.8 mg, 0.752 mmol), and PdCl$_2$(dppf) (21.2 mg, 0.038 mmol), and the resulting mixture was stirred at 100° C. for 2 h. The mixture was concentrated under reduced pressure, and the residue was purified by SiO$_2$ gel chromatography (0% to 50% EtOAc in hexane) to give the title compound as an off-white solid. (100 mg, 86%). MS (ES$^+$) C$_{14}$H$_9$ClF$_3$N$_3$ requires: 311, found: 312 [M+H]$^+$.

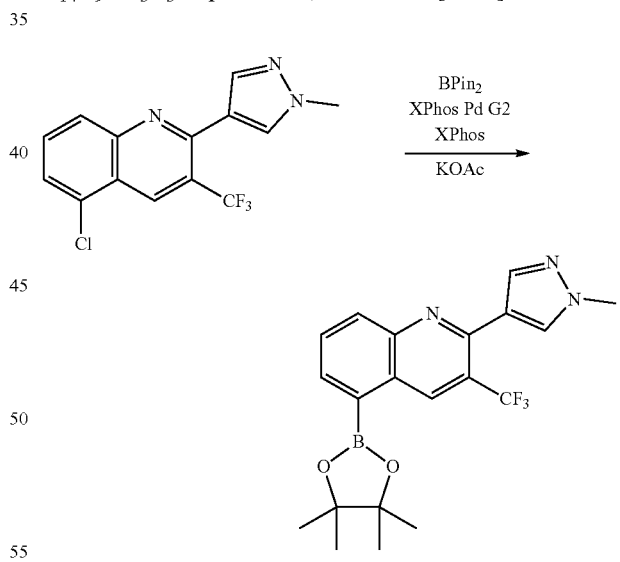

2-(1-Methyl-1H-pyrazol-4-yl)-5-(4,4,5,5-tetramethyl-1,3,2-dioxaborolan-2-yl)-3-(trifluoromethyl)quinoline To a solution of the product from the previous step (100 mg, 0.332 mmol) in 1,4-dioxane (2.0 mL) were added BPin$_2$ (168.7 mg, 0.664 mmol), KOAc (63.3 mg, 0.664 mmol), Xphos Pd G2 (30.2 mg, 0.033 mmol), and XPhos (13.6 mg, 0.033 mmol), and the resulting mixture was stirred at 100° C. for 2 h. The mixture was concentrated under reduced pressure, and the residue was purified by SiO₂ gel chromatography (0% to 50% EtOAc in petroleum ether) to give the title compound as an off-white solid (90 mg, 67%). MS (ES⁺) C₂₀H₂₁BF₃N₃O₂ requires: 403, found: 404 [M+H]⁺.

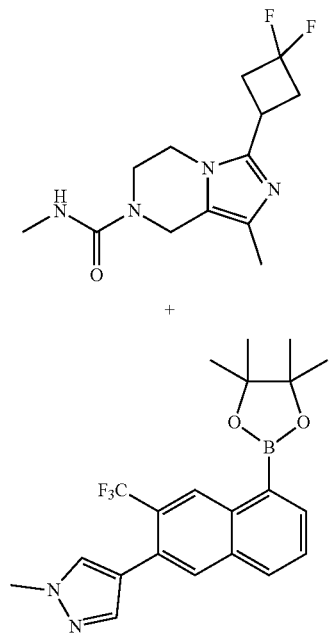

3-(3,3-Difluorocyclobutyl)-N-methyl-1-(2-(1-methyl-1H-pyrazol-4-yl)-3-(trifluoromethyl)quinolin-5-yl)-5,6-dihydroimidazo[1,5-a]pyrazine-7(8H)-carboxamide To a degassed solution of the product from the previous step (50 mg, 0.12 mmol) in 1,4-dioxane (0.7 mL) and H₂O (0.3 mL) were added Intermediate "E" (49.1 mg, 0.124 mmol), K₂CO₃ (34.2 mg, 0.248 mmol), and PdCl₂(dppf) (11.0 mg, 0.012 mmol), and the resulting mixture was stirred at 100° C. for 2 h. The mixture was concentrated under reduced pressure, and the residue was purified by reverse phase preparative HPLC (Mobile phase: A=10 mM NH₄HCO₃/H₂O, B=MeCN; Gradient: B=10% to 45% in 18 min; Column: C18) to give the title compound as an off-white solid (32 mg, 59%).

MS (ES⁺) C₂₆H₂₄F₅N₇O requires: 545, found: 546 [M+H]⁺.

¹H NMR (500 MHz, DMSO-d₆) δ 9.95 (s, 1H), 8.27 (s, 1H), 8.04-7.90 (m, 3H), 7.59-7.51 (m, 1H), 6.83-6.72 (m, 1H), 4.76 (s, 2H), 4.00 (t, J=5.5 Hz, 2H), 3.96 (s, 3H), 3.81 (t, J=5.4 Hz, 2H), 3.69-3.57 (m, 1H), 3.13-2.96 (m, 4H), 2.57 (d, J=4.3 Hz, 3H).

Example 21

3-Cyclopropyl-N-methyl-1-(3-(tetrahydro-2H-pyran-4-yl)isoquinolin-8-yl)-5,6-dihydroimidazo[1,5-a]pyrazine-7(8H)-carboxamide

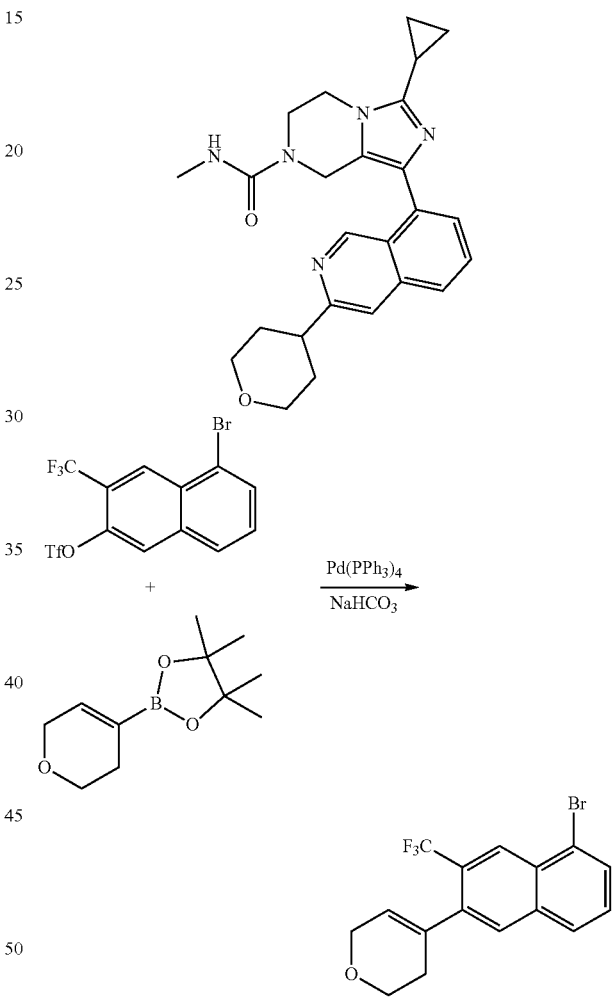

8-Bromo-3-(3,6-dihydro-2H-pyran-4-yl)isoquinoline

A mixture of 8-bromoisoquinolin-3-yl trifluoromethanesulfonate (3.0 g, 8.4 mmol), 2-(3,6-dihydro-2H-pyran-4-yl)-4,4,5,5-tetramethyl-1,3,2-dioxaborolane (1.77 g, 8.45 mmol), NaHCO₃ (2.1 g, 25 mmol) and Pd(PPh₃)₄ (920 mg, 0.80 mmol) in 1,4-dioxane/H₂O (20 mL/4 mL) was degassed and purged with N₂. The mixture was stirred at 50° C. overnight, then concentrated under reduced pressure. The residue was purified by SiO₂ gel chromatography (0% to 50% EtOAc in petroleum ether) to give the title compound as a yellow solid (1.4 g, 57%). MS (ES⁺): C₁₄H₁₂BrNO requires: 289, found: 290 [M+H]⁺.

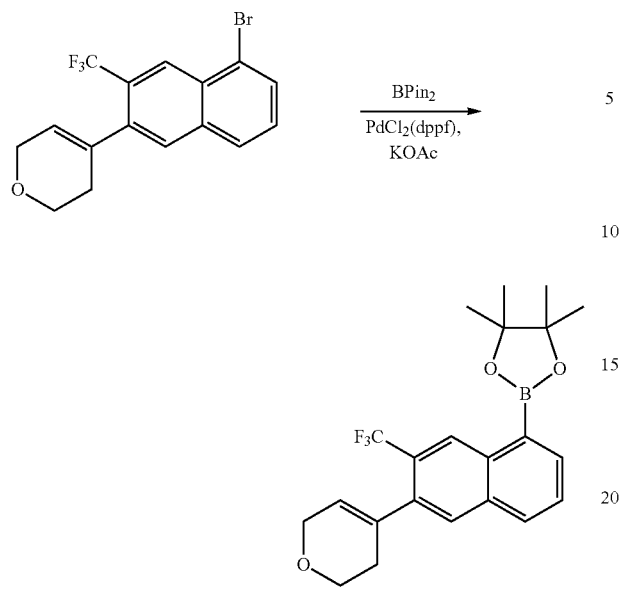

3-(3,6-Dihydro-2H-pyran-4-yl)-8-(4,4,5,5-tetramethyl-1,3,2-dioxaborolan-2-yl)isoquinoline To a mixture of the product from the previous step (1.4 g, 4.8 mmol), BPin$_2$ (1.5 g, 5.8 mmol) and KOAc (1.40 g, 14.4 mmol) in 1,4-dioxane (20 mL) was added PdCl$_2$(dppf) (400 mg, 0.5 mmol). The resulting mixture was purged with N$_2$ for 5 min, then sealed and heated at 100° C. for 5 h. The mixture was concentrated under reduced pressure, and the residue was purified by SiO$_2$ gel chromatography (0% to 60% EtOAc in petroleum ether) to give the title compound as a yellow solid (1.0 g, 62%). MS (ES$^+$): C$_{20}$H$_{24}$BNO$_3$ requires: 337, found: 338 [M+H]$^+$.

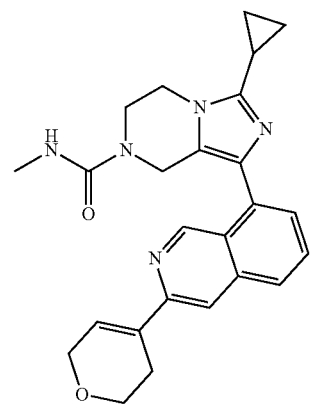

3-Cyclopropyl-1-(3-(3,6-dihydro-2H-pyran-4-yl)isoquinolin-8-yl)-N-methyl-5,6-dihydroimidazo[1,5-a]pyrazine-7(8H)-carboxamide A mixture of Intermediate "B" (150 mg, 0.43 mmol), the product from the previous step (175 mg, 0.52 mmol), K$_2$CO$_3$ (178 mg, 1.29 mmol) and PdCl$_2$(dppf) (33 mg, 0.04 mmol) in 1,4-dioxane/H$_2$O (5 mL/1 mL) was degassed and purged with N$_2$. The mixture was stirred at 100° C. for 2 h, then concentrated under reduced pressure. The residue was purified by SiO$_2$ gel chromatography (0% to 10% MeOH in EtOAc) to give the title compound as a yellow solid (100 mg, 54%). MS (ES$^+$): C$_{25}$H$_{27}$N$_5$O$_2$ requires: 429, found: 430 [M+H]$^+$.

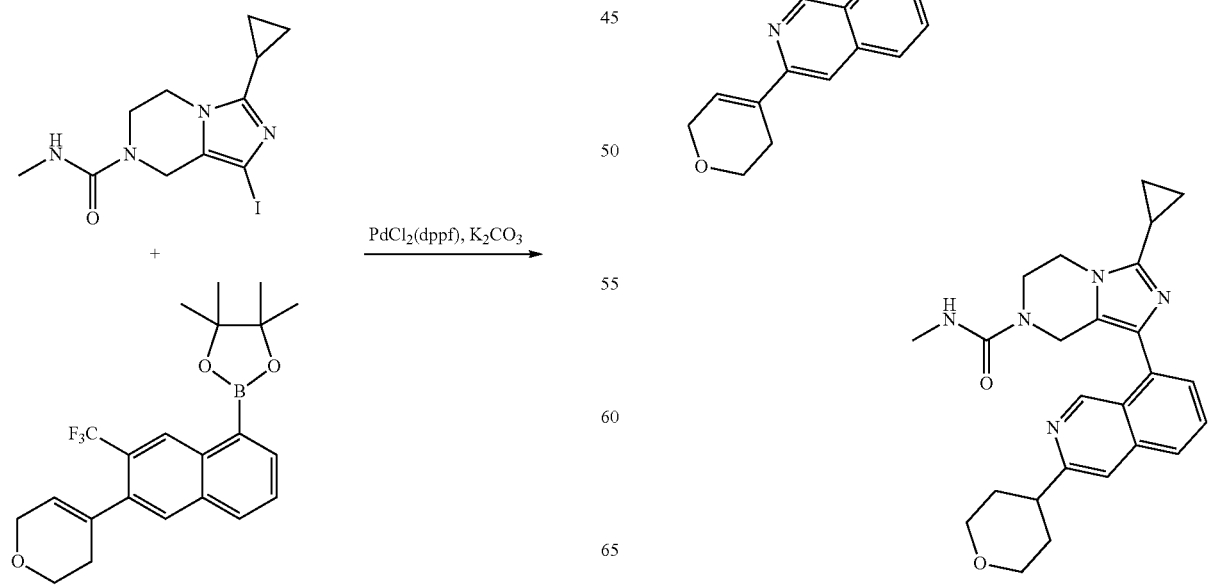

3-Cyclopropyl-N-methyl-1-(3-(tetrahydro-2H-pyran-4-yl)isoquinolin-8-yl)-5,6-dihydroimidazo[1,5-a]pyrazine-7(8H)-carboxamide A mixture of the product from the previous step (100 mg, 0.23 mmol) and 10% Pd/C (20 mg) in EtOH (10 mL) was degassed and purged with $H_2$, then stirred at RT under an atmosphere of $H_2$ overnight. The mixture was filtered, and the filtrate concentrated under reduced pressure. The residue was purified by reverse phase preparative HPLC (Mobile phase: A=10 mM $NH_4HCO_3/H_2O$, B=MeCN; Gradient: B=10% to 45% in 18 min; Column: C18) to give the title compound as a white solid (50 mg, 50%).

MS (ES$^+$): $C_{25}H_{29}N_5O_2$ requires: 431, found: 432 [M+H]$^+$.

$^1$H NMR (500 MHz, DMSO-d$_6$) δ 9.79 (s, 1H), 7.82 (d, J=8.2 Hz, 1H), 7.78-7.69 (m, 1H), 7.65 (s, 1H), 7.41 (d, J=6.3 Hz, 1H), 6.73 (q, J=4.3 Hz, 1H), 4.63 (s, 2H), 4.12 (t, J=5.5 Hz, 2H), 4.00-3.98 (m, 2H), 3.82 (t, J=5.5 Hz, 2H), 3.52-3.47 (m, 2H), 3.06-3.02 (m, 1H), 2.55 (d, J=4.3 Hz, 3H), 2.14-1.97 (m, 1H), 1.92-1.76 (m, 4H), 1.07-0.80 (m, 4H).

Example 22

3-Cyclopropyl-1-(7-fluoro-3-(2-methylthiazol-5-yl)isoquinolin-8-yl)-N-methyl-5,6-dihydroimidazo[1,5-a]pyrazine-7(8H)-carboxamide

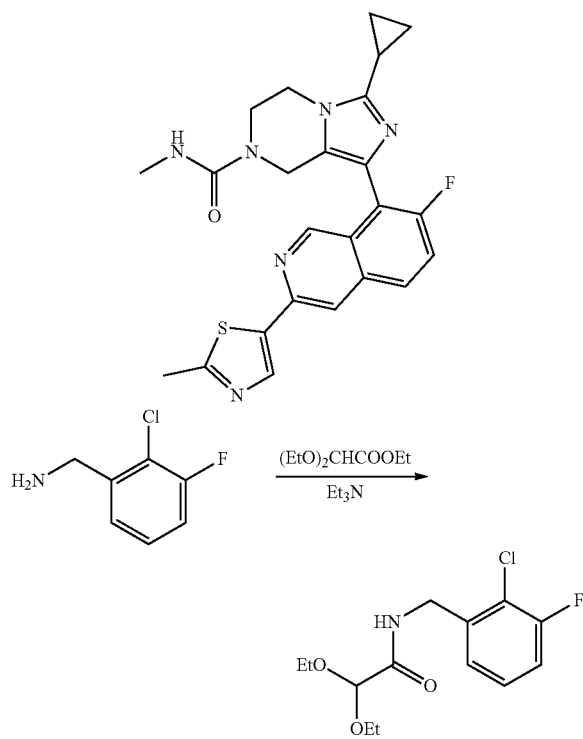

N-(2-Chloro-3-fluorobenzyl)-2,2-diethoxyacetamide

To a mixture of (2-chloro-3-fluorophenyl)methanamine (12 g, 75 mmol) and ethyl 2,2-diethoxyacetate (19.93 g, 113.2 mmol) in MeOH (120 mL) was added Et$_3$N (22.87 g, 226.4 mmol), and the mixture was stirred at 80° C. overnight then concentrated under reduced pressure. The residual oil was poured into water (150 mL) and the mixture was extracted with Et$_2$O (150 mL×3). The combined organic layers were dried over Na$_2$SO$_4$, filtered and concentrated under reduced pressure. The residue was purified by SiO$_2$ gel chromatography (40% to 60% EtOAc in petroleum ether) to give the title compound as a yellow solid (17.3 g, 79%). MS (ES$^+$) $C_{13}H_{17}ClFNO_3$ requires: 289, found: 290 [M+H]$^+$.

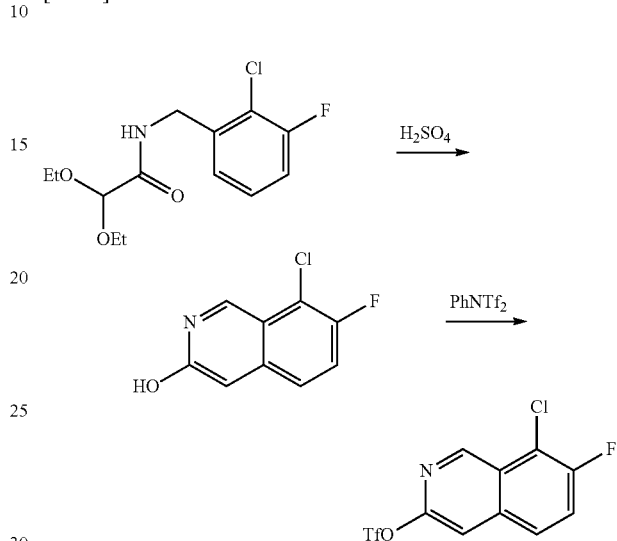

8-Chloro-7-fluoroisoquinolin-3-yl trifluoromethanesulfonate

The product from the previous step (17.3 g, 59.9 mmol) was dissolved in conc. aq. H$_2$SO$_4$ (200 ml), and the mixture was stirred at RT overnight. The mixture was poured into ice water (400 mL), the pH was adjusted to 7, and the mixture was extracted with Et$_2$O (400 mL×3). The combined organic layers were dried over Na$_2$SO$_4$, filtered and concentrated under reduced pressure to give crude 8-chloro-7-fluoroisoquinolin-3-ol as a yellow solid (15.8 g). A mixture of 8-chloro-7-fluoroisoquinolin-3-ol (15.8 g, 80.2 mmol), 1,1,1-trifluoro-N-phenyl-N-(trifluoromethylsulfonyl)methanesulfonamide (34.36 g, 96.24 mmol), and Et$_3$N (24.3 g, 241 mmol) in CH$_2$Cl$_2$ (500 ml) was stirred at RT for 3 h, then poured into water (500 mL) and extracted with CH$_2$Cl$_2$ (500 mL×3). The combined organic layers were dried over Na$_2$SO$_4$, filtered and concentrated under reduced pressure. The residue was purified by SiO$_2$ gel chromatography (3% to 5% EtOAc in petroleum ether) to give the title compound as a yellow solid (14.7 g, 75%). MS (ES$^+$) $C_{10}H_4ClF_4NO_3S$ requires: 329, found: 330 [M+H]$^+$.

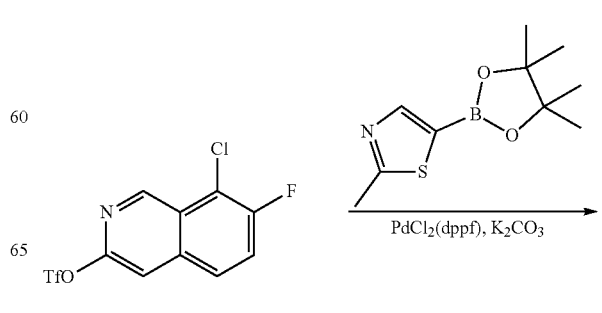

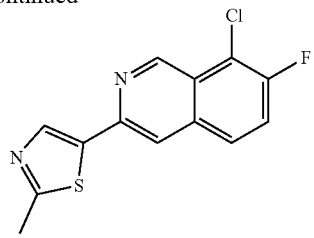

5-(8-Chloro-7-fluoroisoquinolin-3-yl)-2-methylthiazole

A mixture of the product from the previous step (500 mg, 1.52 mmol), 2-methyl-5-(4,4,5,5-tetramethyl-1,3,2-dioxaborolan-2-yl)thiazole (412 mg, 1.83 mmol), PdCl$_2$(dppf) (110 mg, 0.15 mmol), and K$_2$CO$_3$ (630 mg, 4.56 mmol) in 1,4-dioxane (15 mL) and H$_2$O (3 mL) was stirred at 80° C. for 2 h. The mixture was poured into water (40 mL) and extracted with EtOAc (40 mL×3). The combined organic layers were dried over Na$_2$SO$_4$, filtered and concentrated under reduced pressure. The residue was purified by SiO$_2$ gel chromatography (70% to 100% EtOAc in petroleum ether) to give the title compound as a gray solid (460 mg, 100%). MS (ES$^+$) C$_{13}$H$_8$ClFN$_2$S requires: 278, found: 279 [M+H]$^+$.

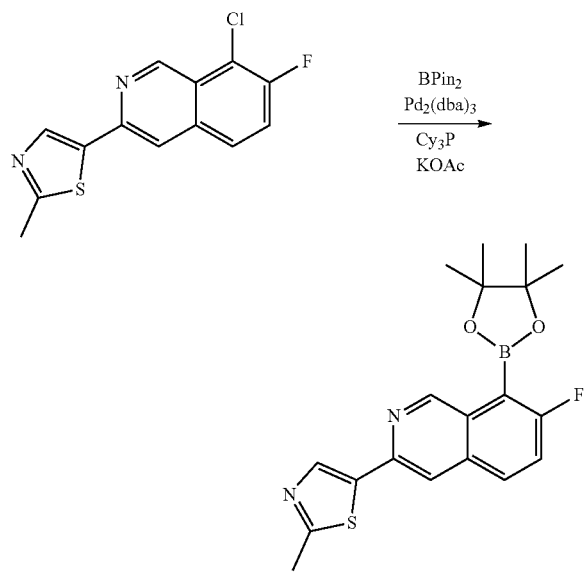

5-(7-Fluoro-8-(4,4,5,5-tetramethyl-1,3,2-dioxaborolan-2-yl)isoquinolin-3-yl)-2-methylthiazole A mixture of the product from the previous step (70 mg, 0.25 mmol) and Pd$_2$(dba)$_3$ (28 mg, 0.03 mmol), Cy$_3$P (23 mg, 0.08 mmol), KOAc (106 mg, 1.08 mmol) and BPin$_2$ (97 mg, 0.38 mmol) in 1,4-dioxane (3 mL) was stirred at 120° C. overnight. The mixture was allowed to cool to RT, filtered, and the filtrate concentrated to give the crude title compound (63 mg, 68%), which was used without further purification. MS (ES$^+$) C$_{19}$H$_{20}$BFN$_2$O$_2$S requires: 370, found: 371 [M+H]$^+$.

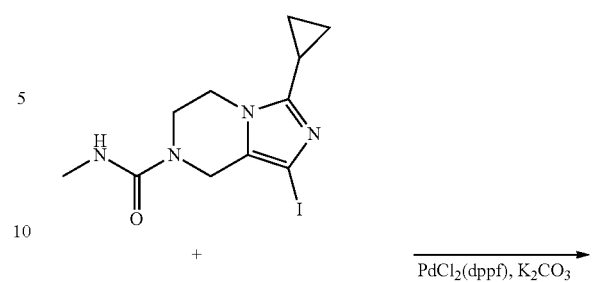

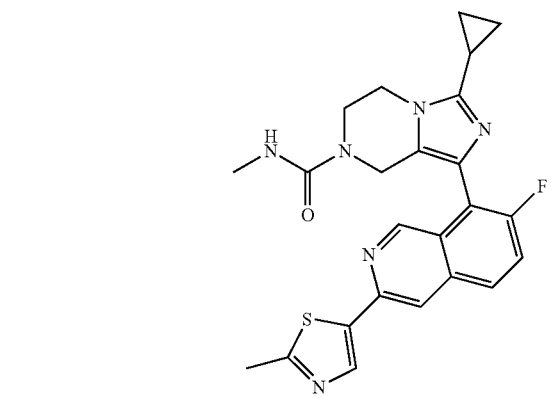

3-Cyclopropyl-1-(7-fluoro-3-(2-methylthiazol-5-yl)isoquinolin-8-yl)-N-methyl-5,6-dihydroimidazo[1,5-a]pyrazine-7(8H)-carboxamide A mixture of the product from the previous step (63 mg, 0.17 mmol), Intermediate "B" (59 mg, 0.17 mmol), PdCl$_2$(dppf) (15 mg, 0.02 mmol), and 2.0 M aq. K$_2$CO$_3$ (0.270 mL, 0.54 mmol) in 1,4-dioxane (3 mL) was degassed and purged with N$_2$, then stirred at 90° C. for 1.5 h. The mixture was concentrated under reduced pressure, and the residue was purified by reverse phase preparative HPLC (Mobile phase: A=10 mM NH$_4$HCO$_3$/H$_2$O, B=MeCN; Gradient: B=10% to 45% in 18 min; Column: C18) to give the title compound as a light yellow solid (16 mg, 20%).

MS (ES$^+$) C$_{24}$H$_{23}$FN$_6$OS requires: 462, found: 463 [M+H]$^+$.

$^1$H NMR (500 MHz, DMSO-d$_6$) δ 9.46 (s, 1H), 8.42 (s, 1H), 8.34 (s, 1H), 8.04-8.01 (m, 1H), 7.80 (t, J=9.5 Hz, 1H), 6.68 (q, J=4.0 Hz, 1H), 4.43 (s, 2H), 4.14 (t, J=5.3 Hz, 2H), 3.83 (t, J=5.5 Hz, 2H), 2.70 (s, 3H), 2.52 (d, J=4.0 Hz, 3H), 2.07-2.06 (m, 1H), 0.98-0.95 (m, 2H), 0.93-0.91 (m, 2H).

Example 23

3-Cyclopropyl-N-methyl-1-(3-(2-methylthiazol-5-yl)
isoquinolin-8-yl)-5,6-dihydroimidazo[1,5-a]pyrazine-7(8H)-carboxamide

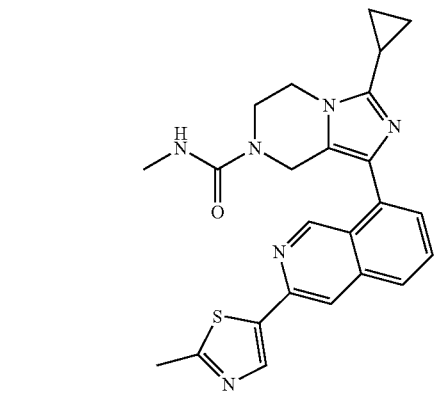

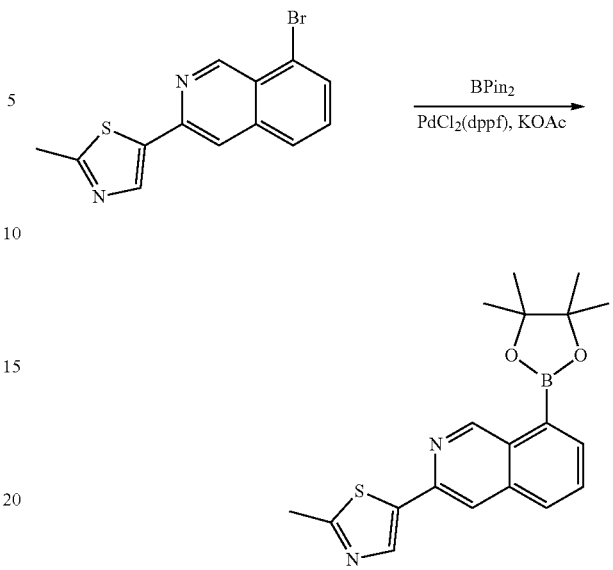

2-Methyl-5-(8-(4,4,5,5-tetramethyl-1,3,2-dioxaborolan-2-yl)isoquinolin-3-yl)thiazole To a mixture of the product from the previous step (450 mg, 1.48 mmol), BPin$_2$ (450 mg, 1.78 mmol) and KOAc (435 mg, 4.44 mmol) in 1,4-dioxane (20 mL) was added PdCl$_2$(dppf) (120 mg, 0.15 mmol). The resulting mixture was purged with N$_2$ for 5 min, then sealed and stirred at 100° C. overnight. The mixture was concentrated under reduced pressure, and the residue was purified by SiO$_2$ gel chromatography (0% to 100% EtOAc in petroleum ether) to give the title compound as a yellow solid (400 mg, 76%). MS (ES$^+$): C$_{19}$H$_{21}$BN$_2$O$_2$S requires: 352, found: 353 [M+H]$^+$.

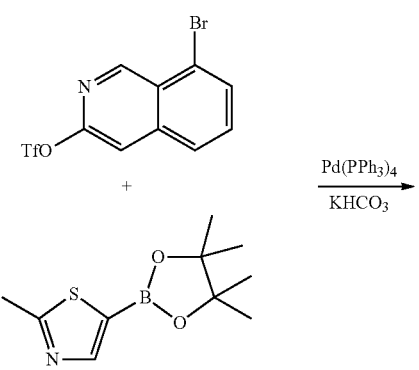

5-(8-Bromoisoquinolin-3-yl)-2-methylthiazole

A mixture of 8-bromoisoquinolin-3-yl trifluoromethanesulfonate (0.90 g, 2.5 mmol), 2-methyl-5-(4,4,5,5-tetramethyl-1,3,2-dioxaborolan-2-yl)thiazole (0.57 g, 2.5 mmol), sodium hydrogen carbonate (0.63 g, 7.5 mmol) and Pd(PPh$_3$)$_4$ (280 mg, 0.25 mmol) in THF/H$_2$O (20 mL/4 mL) was degassed and purged with N$_2$, then stirred at 50° C. overnight. The mixture was concentrated under reduced pressure, and the residue was purified by SiO$_2$ gel chromatography (0% to 50% EtOAc in petroleum ether) to give the title compound as a yellow solid (450 mg, 60%). MS (ES$^+$): C$_{13}$H$_9$BrN$_2$S requires: 304, found: 305 [M+H]$^+$.

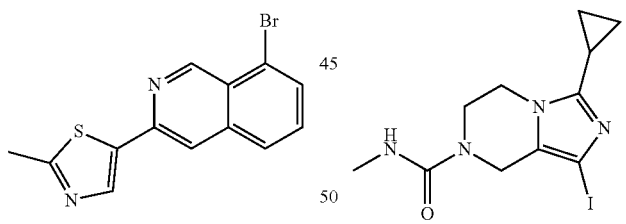

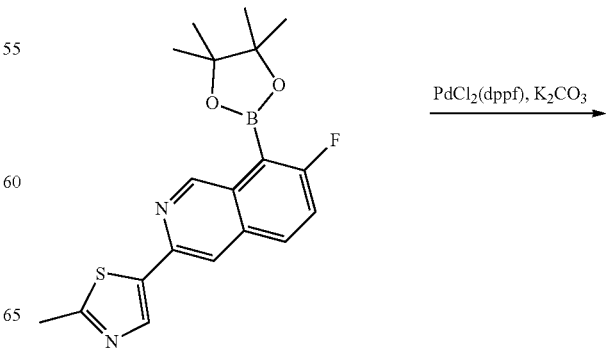

131

-continued

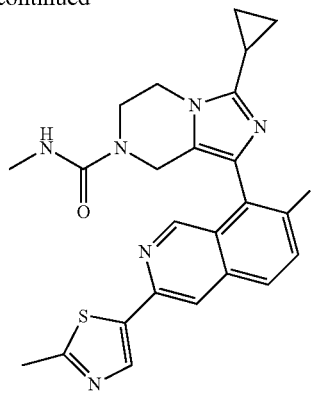

3-Cyclopropyl-N-methyl-1-(3-(2-methylthiazol-5-yl)isoquinolin-8-yl)-5,6-dihydroimidazo[1,5-a]pyrazine-7(8H)-carboxamide A mixture of Intermediate "B" (50 mg, 0.14 mmol), the product from the previous step (61 mg, 0.17 mmol), $K_2CO_3$ (58 mg, 0.42 mmol) and $PdCl_2(dppf)$ (11 mg, 0.014 mmol) in 1,4-dioxane/$H_2O$ (2 mL/0.4 mL) was degassed and purged with $N_2$, then stirred at 100° C. for 2 h. The mixture was concentrated under reduced pressure, and the residue was purified by reverse phase preparative HPLC (Mobile phase: A=10 mM $NH_4HCO_3/H_2O$, B=MeCN; Gradient: B=10% to 45% in 18 min; Column: C18) to give the title compound as a white solid (30 mg, 48%).

MS (ES$^+$): $C_{24}H_{24}N_6OS$ requires: 444, found: 445 [M+H]$^+$.

$^1$H NMR (500 MHz, DMSO-d$_6$) δ 9.85 (s, 1H), 8.36 (appar s, 2H), 7.87 (d, J=8.3 Hz, 1H), 7.80 (appar t, J=7.8 Hz, 1H), 7.46 (d, J=7.1 Hz, 1H), 6.74 (q, J=4.3 Hz, 1H), 4.65 (s, 2H), 4.13 (t, J=5.5 Hz, 2H), 3.83 (t, J=5.5 Hz, 2H), 2.70 (s, 3H), 2.57 (d, J=4.4 Hz, 3H), 2.07-2.04 (m, 1H), 1.05-0.83 (m, 4H).

Example 24

1-(3-Cyano-2-morpholinoquinoline-5-yl)-3-cyclopropyl-N-methyl-5,6-dihydroimidazo[1,5-a]pyrazine-7(8H)-carboxamide

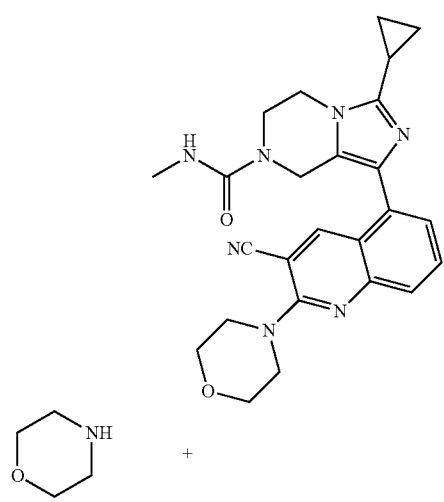

132

-continued

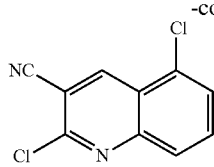

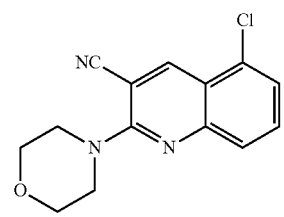

5-Chloro-2-morpholinoquinoline-3-carbonitrile

A mixture of 2,5-dichloroquinoline-3-carbonitrile (100 mg, 0.45 mmol), morpholine (0.088 g, 0.90 mmol), $Pd_2(dba)_3$ (46 mg, 0.05 mmol), Xantphos (29 mg, 0.05 mmol) and $iPr_2NEt$ (116 mg, 0.90 mmol) in 1,4-dioxane (3 mL) was stirred at 85° C. overnight, then concentrated under reduced pressure. The residue was purified by $SiO_2$ gel chromatography (80% to 100% EtOAc in petroleum ether) to give the title compound as a yellow solid (102 mg, 83%). MS (ES$^+$): $C_{14}H_{12}ClN_3O$ requires: 273, found: 274 [M+H]$^+$.

2)

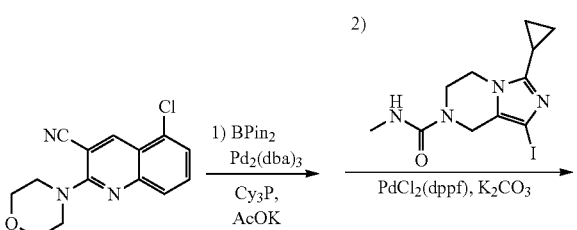

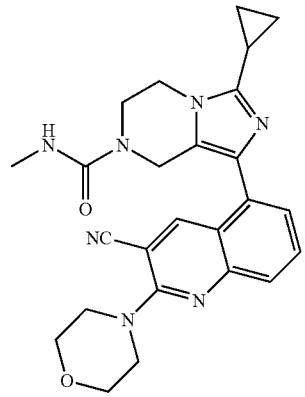

1-(3-Cyano-2-morpholinoquinolin-5-yl)-3-cyclopropyl-N-methyl-5,6-dihydroimidazo[1,5-a]pyrazine-7(8H)-carboxamide A mixture of the product from the previous step (50.0 mg, 0.183 mmol), $Pd_2(dba)_3$ (19 mg, 0.02 mmol), $Cy_3P$ (23 mg, 0.08 mmol), AcOK (54.0 mg, 0.549 mmol) and $BPin_2$ (72 mg, 0.28 mmol) in 1,4-dioxane (3 mL) was stirred at 120° C. overnight, then allowed to cool to RT, filtered, and concentrated under reduced pressure. To the residue was added 1,4-dioxane (3 mL), Intermediate "B" (61.0 mg, 0.175 mmol), PdCl₂(dppf) (15 mg, 0.02 mmol), and 2.0 M aq. K₂CO₃ (0.180 mL, 0.36 mmol). The mixture was degassed and purged with N₂, stirred at 90° C. for 1.5 h, then concentrated under reduced pressure. The residue was purified by reverse phase preparative HPLC (Mobile phase: A=10 mM NH₄HCO₃/H₂O, B=MeCN; Gradient: B=10% to 45% in 18 min; Column: C18) to give the title compound as a yellow solid (29 mg, 36%).

MS (ES⁺): C₂₅H₂₇N₇O₂ requires: 457, found: 458 [M+H]⁺.

¹H NMR (DMSO-d₆) δ 9.43 (s, 1H), 7.81-7.78 (m, 1H), 7.64 (d, J=9.0 Hz, 1H), 7.30 (d, J=7.5 Hz, 1H), 6.75 (q, J=4.0 Hz, 1H), 4.65 (s, 2H), 4.11 (t, J=5.8 Hz, 2H), 3.82-3.78 (m, 6H), 3.62-3.61 (m, 4H), 2.56 (d, J=4.0 Hz, 3H), 2.07-2.03 (m, 1H), 01.01-0.98 (m, 2H), 0.91-0.88 (m, 2H).

Example 25

1-(3-cyclopropyl-1-(4-fluoro-1-methyl-3-(1-methyl-1H-pyrazol-4-yl)-1H-indazol-5-yl)-5,6-dihydroimidazo[1,5-a]pyrazin-7(8H)-yl)ethan-1-one

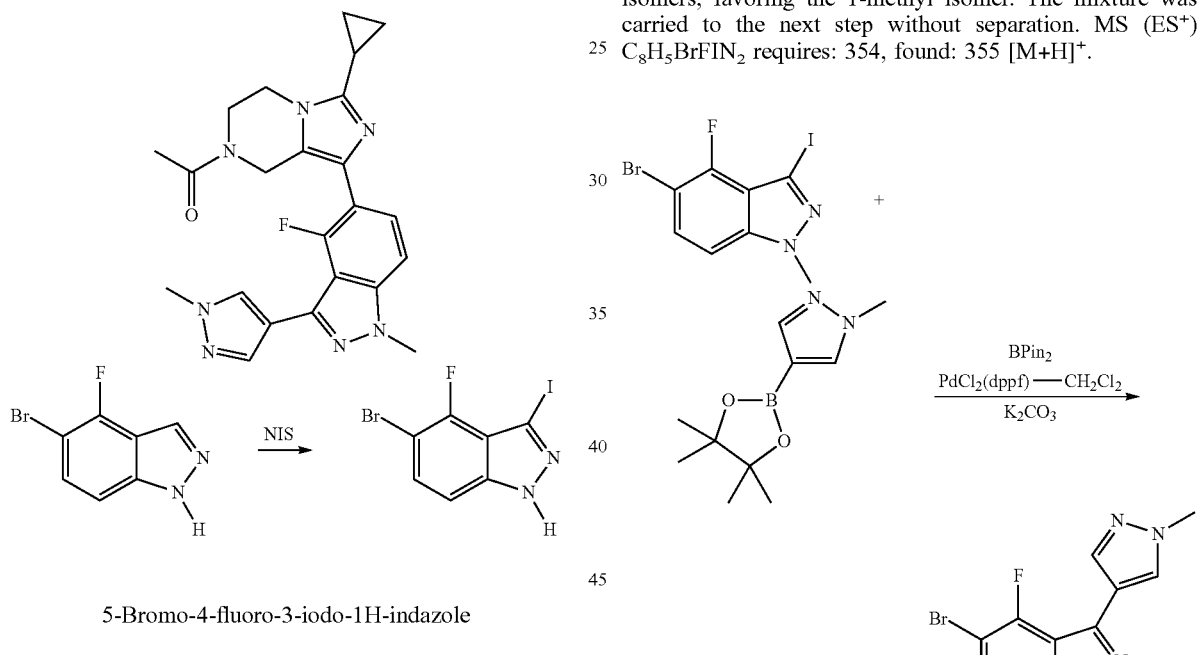

5-Bromo-4-fluoro-3-iodo-1H-indazole

To a solution of 5-bromo-4-fluoro-1H-indazole (400 mg, 1.86 mmol) in DMSO (4 mL) was added NIS (419 mg, 1.86 mmol) and the resulting mixture was stirred at 90° C. for 2 h. H₂O (20 mL) was added, and the mixture was extracted with EtOAc (3×10 mL). The combined organic layers were washed with sat. aq. NaCl, dried over MgSO₄, filtered and concentrated under reduced pressure to give the crude title compound as a tan solid (564 mg, 89%), which was used without further purification. MS (ES⁺) C₇H₃BrFIN₂ requires: 340, found: 341 [M+H]⁺.

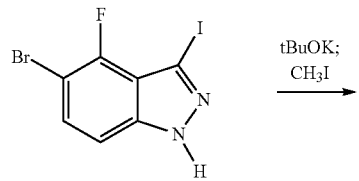

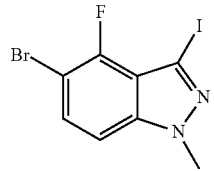

5-Bromo-4-fluoro-3-iodo-1-methyl-1H-indazole

To a solution of the product from the previous step (560 mg, 1.64 mmol) in THF (10 mL) were added t-BuOK (369 mg, 3.29 mmol) and CH₃I (0.308 mL, 4.93 mmol), and the resulting mixture was stirred at 70° C. for 2 h. The reaction mixture was allowed to cool to RT, filtered through a Büchner funnel, and the filtrate was concentrated under reduced pressure. The residue was purified by SiO₂ gel chromatography (0% to 30% EtOAc in hexanes) to give the title compound as an off-white solid (522 mg, 90%). The product is a 3:1 mixture of indazole 1-methyl and 2-methyl isomers, favoring the 1-methyl isomer. The mixture was carried to the next step without separation. MS (ES⁺) C₈H₅BrFIN₂ requires: 354, found: 355 [M+H]⁺.

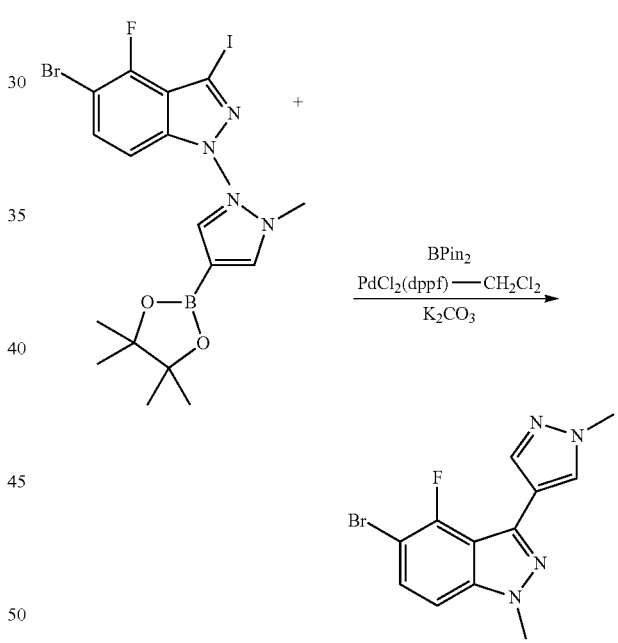

5-Bromo-4-fluoro-1-methyl-3-(1-methyl-1H-pyrazol-4-yl)-1H-indazole

To a solution of the product from the previous step (522 mg, 1.47 mmol, contaminated with 2-methyl isomer) in DMF (5 mL) was added 1-methyl-4-(4,4,5,5-tetramethyl-1,3,2-dioxaborolan-2-yl)-1H-pyrazole (337 mg, 1.62 mmol), PdCl₂(dppf)-CH₂Cl₂ (120 mg, 0.147 mmol) and 2.0 M aq. K₂CO₃ (1.47 mL, 2.94 mmol), and the resulting mixture was stirred at 90° C. for 1 h then concentrated under reduced pressure. The residue was purified by mass-triggered preparative HPLC (Mobile layer: A=0.1% TFA/H₂O, B=0.1% TFA/MeCN; Gradient: B=30% to 70%; 12 min; Column: C18). Two indazole isomers (1-methyl and 2-methyl) were isolated as TFA salts. Both TFA salts were treated with sat. aq. NaHCO₃ and the resulting mixtures extracted with EtOAc. The organic layers were concentrated under reduced pressure to give the title compound as a tan solid (252 mg, 55%) and 5-bromo-4-fluoro-2-methyl-3-(1-methyl-1H-pyrazol-4-yl)-2H-indazole (61 mg, 13%) as a tan solid. For both compounds, MS (ES⁺) $C_{12}H_{10}BrFN_4$ requires: 308, found: 309 [M+H]⁺.

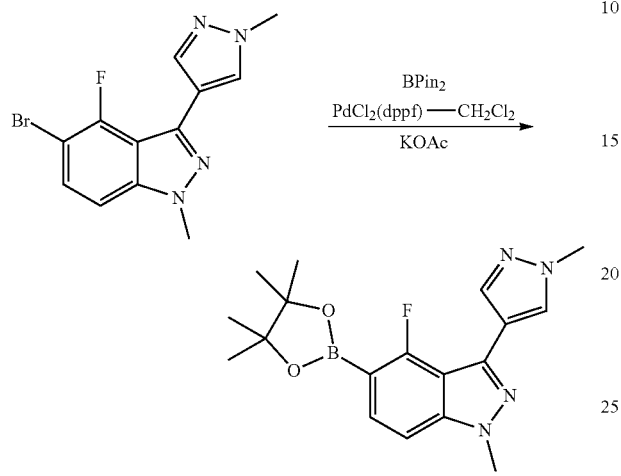

4-Fluoro-1-methyl-3-(1-methyl-1H-pyrazol-4-yl)-5-(4,4,5,5-tetramethyl-1,3,2-dioxaborolan-2-yl)-1H-indazole A degassed solution of the product from the previous step (250 mg, 0.809 mmol), BPin₂ (246 mg, 0.970 mmol), PdCl₂(dppf)-CH₂Cl₂ (66 mg, 0.081 mmol) and KOAc (238 mg, 2.43 mmol) in 1,4-dioxane (5 mL) was stirred at 90° C. for 16 h. The reaction mixture was allowed to cool to RT, then washed with H₂O (20 mL). The aqueous layer was extracted with EtOAc (3×10 mL), and the four combined organic layers were washed with sat. aq. NaCl, dried over MgSO₄, filtered and concentrated under reduced pressure. The residue was purified by SiO₂ gel chromatography (0% to 5% MeOH in CH₂Cl₂) to give the title compound as a tan solid (288 mg, 100%). MS (ES⁺) $C_{18}H_{22}BFN_4O_2$ requires: 356, found: 357 [M+H]⁺.

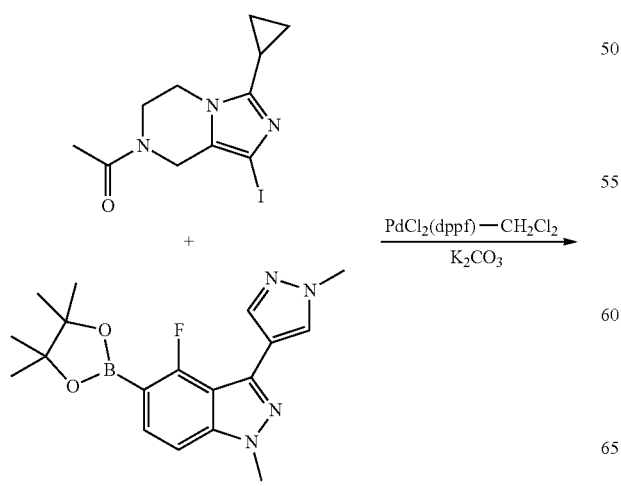

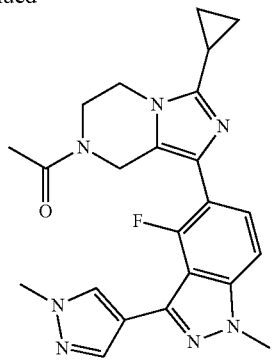

1-(3-Cyclopropyl-1-(4-fluoro-1-methyl-3-(1-methyl-1H-pyrazol-4-yl)-1H-indazol-5-yl)-5,6-dihydroimidazo[1,5-a]pyrazin-7(8H)-yl)ethan-1-one A degassed solution of 1-(3-cyclopropyl-1-iodo-5,6-dihydroimidazo[1,5-a]pyrazin-7(8H)-yl)ethanone (25 mg, 0.075 mmol), the product from the previous step (26.9 mg, 0.075 mmol), PdCl₂(dppf)-CH₂Cl₂ (6.17 mg, 7.55 μmol) and K₂CO₃ (0.075 mL, 0.15 mmol) in DMF (0.5 mL) was stirred at 90° C. for 1 h. The residue was purified by mass-triggered preparative HPLC (Mobile layer: A=0.1% TFA/H₂O, B=0.1% TFA/MeCN; Gradient: B=10% to 40%; 12 min; Column: C18) to give the TFA salt of the title compound. To this salt was added sat. aq. NaHCO₃(5 mL) and the resulting mixture was extracted with EtOAc (3×5 mL). The combined organic layers were washed with sat. aq. NaCl, dried over MgSO₄, filtered and concentrated under reduced pressure. The product was lyophilized to give the title compound as a white powder (15 mg, 48%).

MS (ES⁺) $C_{23}H_{24}FN_7O$ requires: 433, found: 434 [M+H]⁺.

¹H NMR (CDCl₃) (2:1 ratio of rotamers) δ 8.11 (s, 1H), 7.99 (s, 1H), 7.58-7.46 (m, 2H), 4.88-4.83 (m, 2H), 4.45 (t, J=5.5 Hz, 1.3H), 4.36 (t, J=5.8 Hz, 0.7H), 4.16-4.10 (m, 5H), 3.97 (s, 3H), 2.31-2.26 (m, 1H), 2.25 (s, 2H), 2.22 (s, 1H), 1.40-1.33 (m, 2H), 1.25-1.18 (m, 2H).

Example 26

1-(3-cyclopropyl-1-(1-methyl-3-(1-methyl-1H-pyrazol-4-yl)-1H-pyrazolo[3,4-b]pyridin-5-yl)-5,6-dihydroimidazo[1,5-a]pyrazin-7(8H)-yl)ethan-1-one

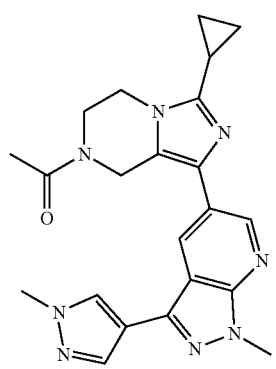

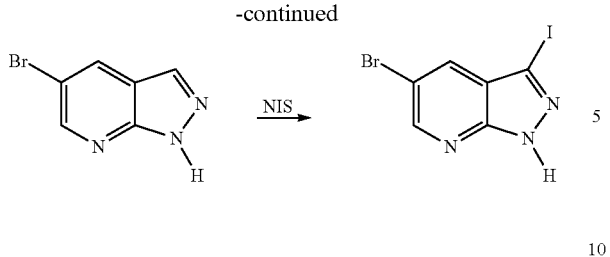

5-Bromo-3-iodo-1H-pyrazolo[3,4-b]pyridine

To a solution of 5-bromo-1H-pyrazolo[3,4-b]pyridine (200 mg, 1.01 mmol) in DMSO (5 mL) was added NIS (341 mg, 1.52 mmol), and the resulting mixture was stirred at 90° C. for 2 h. H$_2$O (10 mL) and sat. aq. Na$_2$S$_2$O$_3$ (1 mL) were added, the mixture was extracted with EtOAc (3×10 mL), and the combined organic layers were washed with sat. aq. NaCl, dried over MgSO$_4$, filtered and concentrated under reduced pressure. The residue was purified by SiO$_2$ gel chromatography (0% to 30% EtOAc in hexanes) to give the title compound as a tan solid (215 mg, 66%). MS (ES$^+$) C$_6$H$_3$BrIN$_3$ requires: 323, found: 324 [M+H]$^+$.

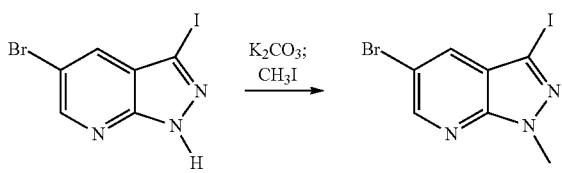

5-Bromo-3-iodo-1-methyl-1H-pyrazolo[3,4-b]pyridine

To a solution of product from the previous step (215 mg, 0.664 mmol) in DMF (2 mL) were added K$_2$CO$_3$ (275 mg, 1.99 mmol) and MeI (0.083 mL, 1.3 mmol), and the resulting mixture was stirred at 60° C. for 1 h. H$_2$O (10 mL) was added, the mixture was extracted with EtOAc (3×10 mL), and the combined organic layers were washed with sat. aq. NaCl, dried over MgSO$_4$, filtered and concentrated under reduced pressure. The residue was purified by SiO$_2$ gel chromatography (0% to 30% EtOAc in hexanes) to give the title compound as a tan solid (224 mg, 100%). MS (ES$^+$) C$_7$H$_5$BrIN$_3$ requires: 337, found: 338 [M+H]$^+$.

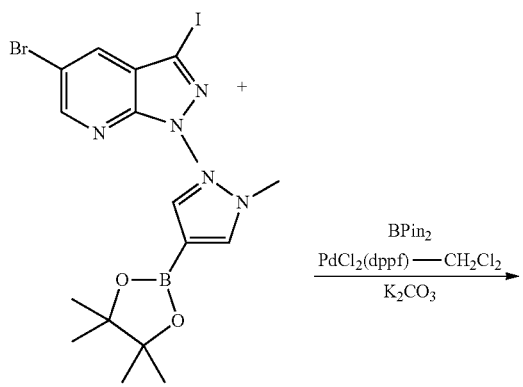

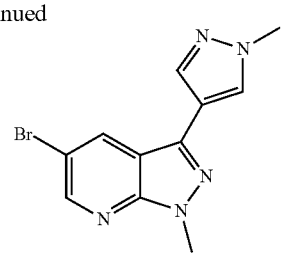

5-Bromo-1-methyl-3-(1-methyl-1H-pyrazol-4-yl)-1H-pyrazolo[3,4-b]pyridine

To a solution of the product from the previous step (224 mg, 0.663 mmol) in DMF (3 mL) were added 1-methyl-4-(4,4,5,5-tetramethyl-1,3,2-dioxaborolan-2-yl)-1H-pyrazole (152 mg, 0.729 mmol), PdCl$_2$(dppf)-CH$_2$Cl$_2$ (54.1 mg, 0.066 mmol) and 2.0 M aq. K$_2$CO$_3$ (0.663 mL, 1.33 mmol) and the resulting mixture was stirred at 90° C. for 1 h. H$_2$O (10 mL) was added, the mixture was extracted with EtOAc (3×10 mL), and the combined organic layers were washed with sat. aq. NaCl, dried over MgSO$_4$, filtered and concentrated under reduced pressure. The residue was purified by SiO$_2$ gel chromatography (0% to 5% MeOH in CH$_2$Cl$_2$) to give the title compound as an off-white solid (188 mg, 97%). MS (ES$^+$) C$_{11}$H$_{10}$BrN$_5$ requires: 291, found: 292 [M+H]$^+$.

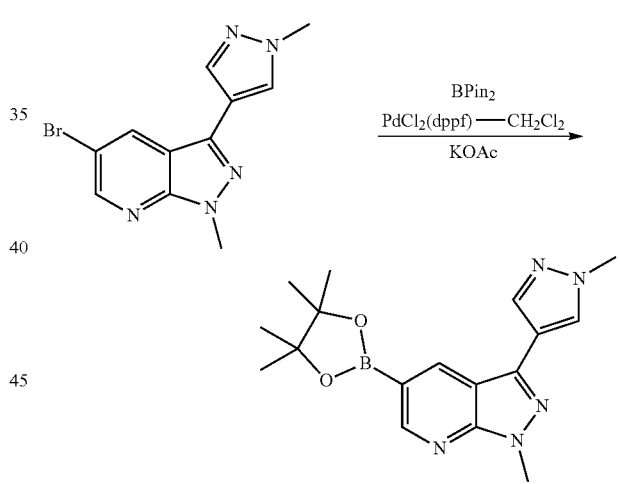

1-Methyl-3-(1-methyl-1H-pyrazol-4-yl)-5-(4,4,5,5-tetramethyl-1,3,2-dioxaborolan-2-yl)-1H-pyrazolo[3,4-b]pyridine A degassed mixture of the product from the previous step (188 mg, 0.644 mmol), BPin$_2$ (196 mg, 0.772 mmol), PdCl$_2$(dppf)-CH$_2$Cl$_2$ (52.6 mg, 0.064 mmol) and KOAc (189 mg, 1.93 mmol) in 1,4-dioxane (5 mL) was stirred at 90° C. for 16 h then allowed to cool to RT. H$_2$O (20 mL) was added, the mixture was extracted with EtOAc (3×10 mL), and the combined organic layers were washed with sat. aq. NaCl, dried over MgSO$_4$, filtered and concentrated under reduced pressure. The residue was purified by SiO$_2$ gel chromatography (0% to 5% MeOH in CH$_2$Cl$_2$) to give the title compound as a tan solid (95 mg, 44%). MS (ES$^+$) C$_{17}$H$_{22}$BN$_5$O$_2$ requires: 339, found: 340 [M+H]$^+$.

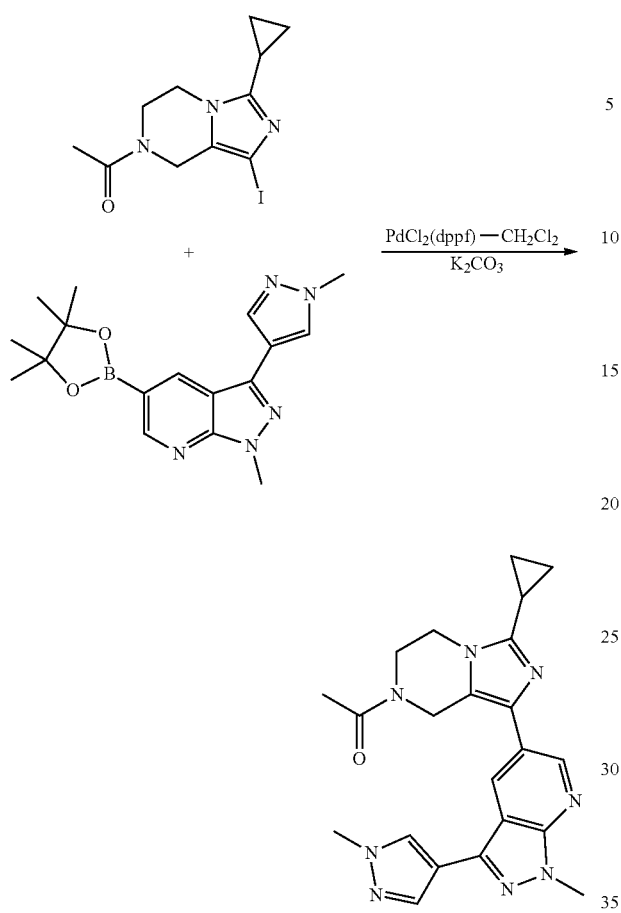

1-(3-Cyclopropyl-1-(1-methyl-3-(1-methyl-1H-pyrazol-4-yl)-1H-pyrazolo[3,4-b]pyridin-5-yl)-5,6-dihydroimidazo[1,5-a]pyrazin-7(8H)-yl)ethan-1-one A degassed mixture of 1-(3-cyclopropyl-1-iodo-5,6-dihydroimidazo[1,5-a]pyrazin-7(8H)-yl)ethanone (25 mg, 0.075 mmol), the product from the previous step (25.6 mg, 0.075 mmol), PdCl$_2$(dppf)-CH$_2$Cl$_2$ (6.17 mg, 7.55 µmol) and 2.0 M aq. K$_2$CO$_3$ (0.075 mL, 0.15 mmol) in DMF (0.5 mL) was stirred at 90° C. for 1 h. The residue was purified by mass-triggered preparative HPLC (Mobile layer: A=0.1% TFA/H$_2$O, B=0.1% TFA/MeCN; Gradient: B=10% to 40%; 12 min; Column: C18) to give the title compound as a TFA salt. To this salt was added sat. aq. NaHCO$_3$(5 mL) and the mixture was extracted with EtOAc (3×5 mL). The combined organic layers were washed with sat. aq. NaCl, dried over MgSO$_4$, filtered and concentrated under reduced pressure. The residue was lyophilized to give the title compound as a white powder (9 mg, 19%).

MS (ES$^+$) C$_{22}$H$_{24}$N$_8$O requires: 416, found: 417 [M+H]$^+$.

$^1$H NMR (CD$_3$OD) (2:1 ratio of rotamers) δ 8.73-8.70 (m, 1H), 8.62 (s, 0.3H), 8.60 (s, 0.7H), 8.26 (s, 1H), 8.10 (s, 1H), 5.05 (s, 0.7H), 5.01 (s, 1.3H) 4.47-4.44 (t, J=5.6 Hz, 1.3H), 4.37-4.34 (t, J=5.3 Hz, 0.7H) 4.18-4.11 (m, 5H), 4.01 (s, 3H), 2.32-2.27 (m, 1H), 2.26 (s, 2H), 2.17 (s, 1H), 1.40-1.35 (m, 2H), 1.28-1.22 (m, 2H).

Example 27

1-(3-Cyclopropyl-1-(4-fluoro-2-methyl-3-(1-methyl-1H-pyrazol-4-yl)-2H-indazol-5-yl)-5,6-dihydroimidazo[1,5-a]pyrazin-7(8H)-yl)ethan-1-one

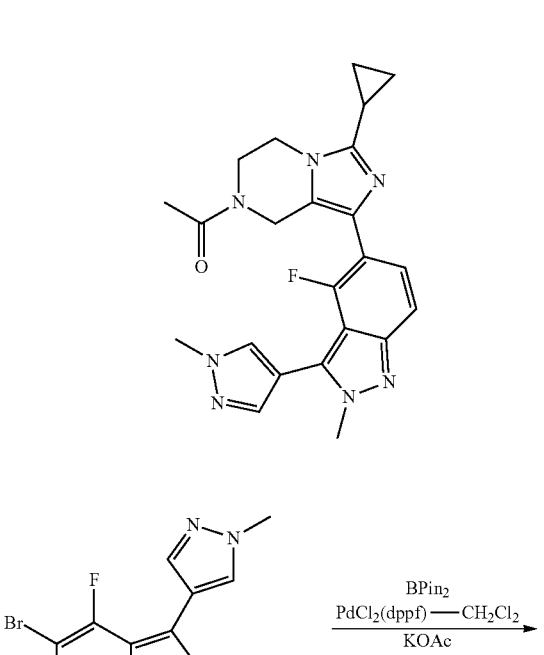

4-Fluoro-2-methyl-3-(1-methyl-1H-pyrazol-4-yl)-5-(4,4,5,5-tetramethyl-1,3,2-dioxaborolan-2-yl)-2H-indazole A degassed solution of 5-bromo-4-fluoro-2-methyl-3-(1-methyl-1H-pyrazol-4-yl)-2H-indazole (60 mg, 0.19 mmol) (side-product from the preparation of 5-bromo-4-fluoro-1-methyl-3-(1-methyl-1H-pyrazol-4-yl)-1H-indazole), BPin$_2$ (59.1 mg, 0.233 mmol), PdCl$_2$(dppf)-CH$_2$Cl$_2$ (15.85 mg, 0.019 mmol) and KOAc (57.1 mg, 0.582 mmol) in 1,4-dioxane (2 mL) was stirred at 90° C. for 16 h, then allowed to cool to RT. H$_2$O (20 mL) was added, the mixture was extracted with EtOAc (3×10 mL), and the combined organic layers were washed with sat. aq. NaCl, dried over MgSO$_4$, filtered and concentrated under reduced pressure. The residue was purified by SiO$_2$ gel chromatography (0% to 5% MeOH in CH$_2$Cl$_2$) to give the title compound as a tan solid (62 mg, 90%). MS (ES$^+$) C$_{18}$H$_{22}$BFN$_4$O$_2$ requires: 356, found: 357 [M+H]$^+$.

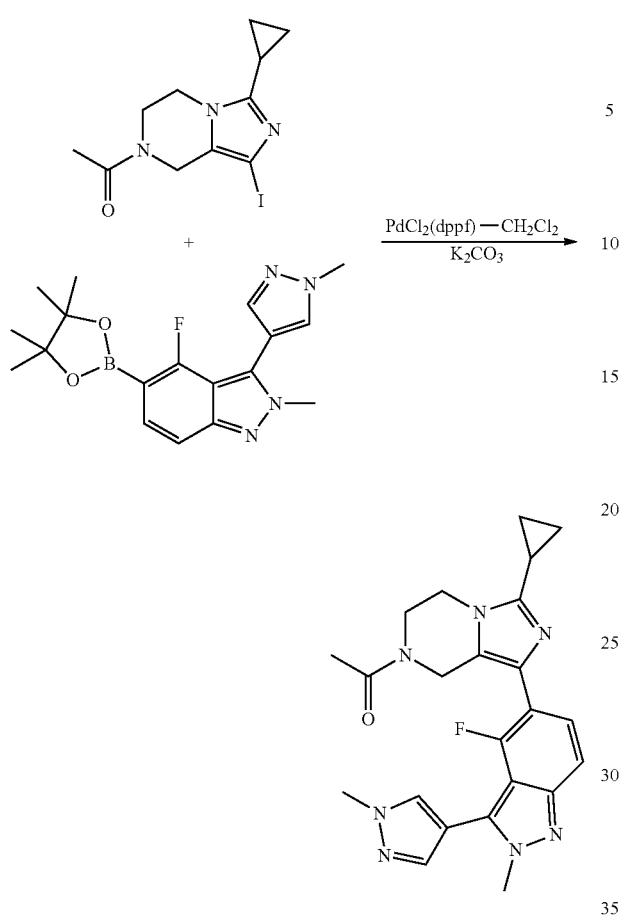

1-(3-Cyclopropyl-1-(4-fluoro-2-methyl-3-(1-methyl-1H-pyrazol-4-yl)-2H-indazol-5-yl)-5,6-dihydroimidazo[1,5-a]pyrazin-7(8H)-yl)ethan-1-one A degassed solution of 1-(3-cyclopropyl-1-iodo-5,6-dihydroimidazo[1,5-a]pyrazin-7(8H)-yl)ethanone (20 mg, 0.060 mmol), the product from the previous step (21.51 mg, 0.060 mmol), PdCl₂(dppf)-CH₂Cl₂ (4.93 mg, 6.04 μmol) and K₂CO₃ (0.060 mL, 0.12 mmol) in DMF (0.5 mL) was stirred at 90° C. for 1 h, then concentrated under reduced pressure. The residue was purified by mass-triggered preparative HPLC (Mobile layer: A=0.1% TFA/H₂O, B=0.1% TFA/MeCN; Gradient: B=10% to 40%; 12 min; Column: C18) to give the title compound as a TFA salt. To this salt was added sat. aq. NaHCO₃(5 mL), the mixture was extracted with EtOAc (3×5 mL), and the combined organic layers were washed with sat. aq. NaCl, dried over MgSO₄, filtered and concentrated under reduced pressure. The residue was lyophilized to give the title compound as a white powder (6 mg, 15%).

MS (ES⁺) C₂₃H₂₄FN₇O requires: 433, found: 434 [M+H]⁺.

¹H NMR (CD₃OD) (2:1 ratio of rotamers) δ 8.12 (s, 1H), 7.90-7.85 (m, 1H), 7.59-7.54 (m, 1H), 7.38-7.31 (m, 1H), 4.84-4.78 (m, 2H), 4.44-4.42 (m, 1.3H), 4.32-4.30 (m, 0.7H), 4.21 (s, 3H), 4.15-4.07 (m, 2H), 4.02 (s, 3H), 2.28-2.24 (m, 3H), 2.14 (s, 1H), 1.37-1.31 (m, 2H), 1.24-1.18 (m, 2H).

Example 28

1-(3-Cyclopropyl-1-(6-fluoro-1-methyl-3-(1-methyl-1H-pyrazol-4-yl)-1H-indazol-5-yl)-5,6-dihydroimidazo[1,5-a]pyrazin-7(8H)-yl)ethan-1-one 5-Bromo-6-fluoro-3-iodo-1-methyl-1H-indazole To a solution of 5-bromo-6-fluoro-1-methyl-1H-indazole (500 mg, 2.18 mmol) in DMSO (5 mL) was added NIS (982 mg, 4.37 mmol) and the resulting mixture was stirred at 90° C. for 16 h. H₂O (30 mL) and sat. aq. Na₂S₂O₃ (3 mL) were added, the mixture was extracted with EtOAc (3×20 mL), and the combined organic layers were washed with sat. aq. NaCl, dried over MgSO₄, filtered and concentrated under reduced pressure. The residue was purified by SiO₂ gel chromatography (0% to 15% EtOAc in hexanes) to give the title compound as a white solid (688 mg, 89%). MS (ES⁺) C₈H₅BrFIN₂ requires: 354, found: 355 [M+H]⁺.

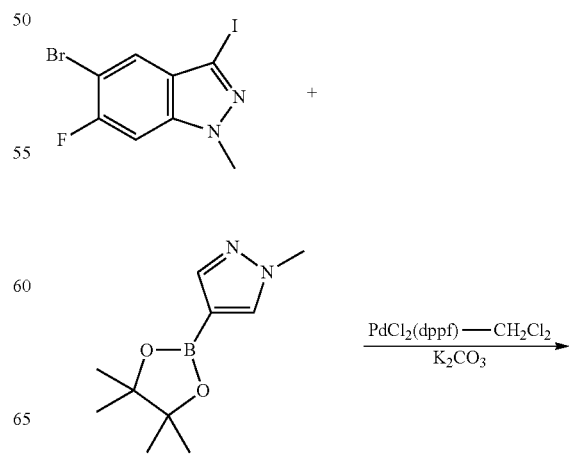

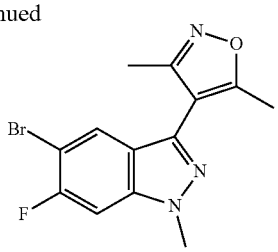

5-Bromo-6-fluoro-1-methyl-3-(1-methyl-1H-pyrazol-4-yl)-1H-indazole

To a solution of the product from the previous step (674 mg, 1.90 mmol) in 1,4-dioxane (10 mL) were added 1-methyl-4-(4,4,5,5-tetramethyl-1,3,2-dioxaborolan-2-yl)-1H-pyrazole (435 mg, 2.09 mmol), PdCl$_2$(dppf)-CH$_2$Cl$_2$ (155 mg, 0.190 mmol) and 2.0 M aq. K$_2$CO$_3$ (1.899 mL, 3.80 mmol), and the resulting mixture was stirred at 100° C. for 6 h. H$_2$O (30 mL) was added, and the layers were separated. The aqueous layer was extracted with EtOAc (3×20 mL), and the combined organic layers were washed with sat. aq. NaCl, dried over MgSO$_4$, filtered and concentrated under reduced pressure. The residue was purified by SiO$_2$ gel chromatography (20% to 100% EtOAc in hexanes) to give the title compound as a tan solid (360 mg, 61%). MS (ES$^+$) C$_{12}$H$_{10}$BrFN$_4$ requires: 308, found: 309 [M+H]$^+$.

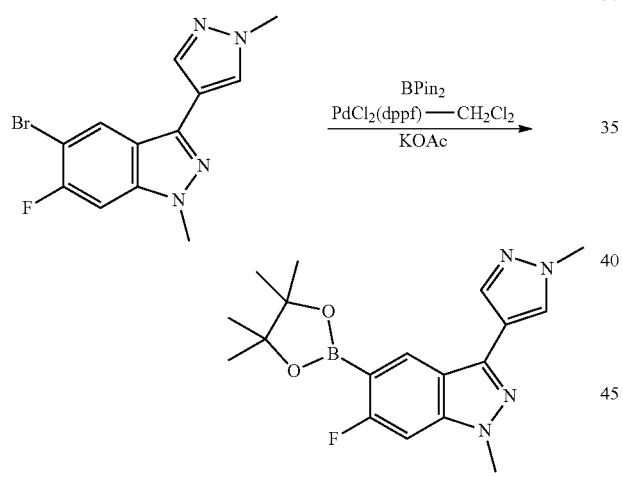

6-Fluoro-1-methyl-3-(1-methyl-1H-pyrazol-4-yl)-5-(4,4,5,5-tetramethyl-1,3,2-dioxaborolan-2-yl)-1H-indazole A degassed mixture of the product from the previous step (360 mg, 1.16 mmol), BPin$_2$ (355 mg, 1.40 mmol), PdCl$_2$(dppf)-CH$_2$Cl$_2$ (95 mg, 0.12 mmol) and KOAc (343 mg, 3.49 mmol) in 1,4-dioxane (10 mL) was stirred at 100° C. for 4 h, then allowed to cool to RT. H$_2$O (20 mL) was added, and the layers were separated. The aqueous layer was extracted with EtOAc (3×10 mL), and the combined organic layers were washed with sat. aq. NaCl, dried over MgSO$_4$, filtered and concentrated under reduced pressure. The residue was purified by SiO$_2$ gel chromatography (0% to 5% MeOH in CH$_2$Cl$_2$) to give the title compound as a tan solid (288 mg, 69%). MS (ES$^+$) C$_{18}$H$_{22}$BFN$_4$O$_2$ requires: 356, found: 357 [M+H]$^+$.

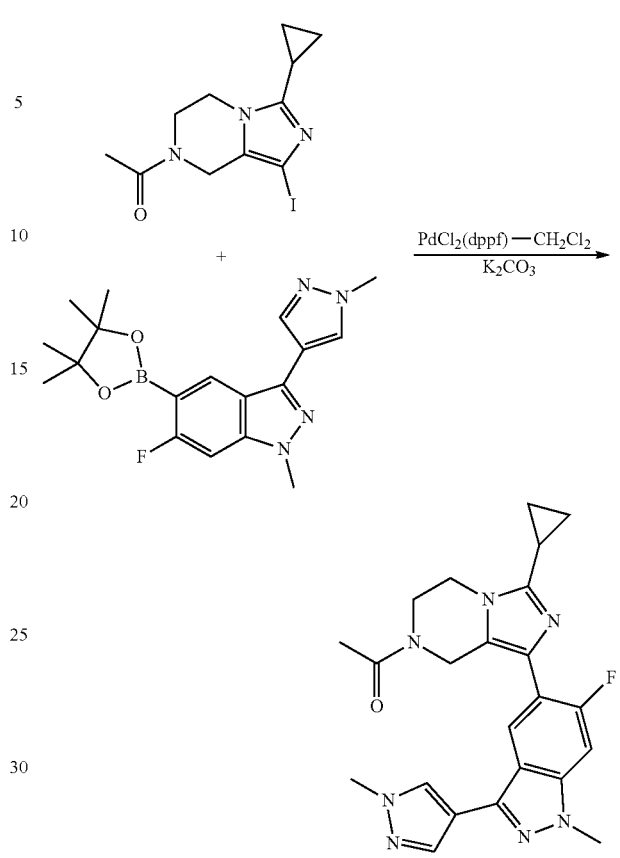

1-(3-Cyclopropyl-1-(6-fluoro-1-methyl-1H-pyrazol-4-yl)-1H-indazol-5-yl)-5,6-dihydroimidazo[1,5-a]pyrazin-7(8H)-yl)ethan-1-one A degassed solution of 1-(3-cyclopropyl-1-iodo-5,6-dihydroimidazo[1,5-a]pyrazin-7(8H)-yl)ethanone (15 mg, 0.045 mmol), the product from the previous step (16.13 mg, 0.045 mmol), PdCl$_2$(dppf)-CH$_2$Cl$_2$ (3.70 mg, 4.53 µmol) and 2.0 M aq. K$_2$CO$_3$ (0.045 mL, 0.090 mmol) in DMF (0.5 mL) was stirred at 90° C. for 1 h, then concentrated under reduced pressure. The residue was purified by mass-triggered preparative HPLC (Mobile layer: A=0.1% TFA/H$_2$O, B=0.1% TFA/MeCN; Gradient: B=10% to 40%; 12 min; Column: C18) to give the title compound as a TFA salt. To this salt was added sat. aq. NaHCO$_3$ (5 mL), the mixture was extracted with EtOAc (3×5 mL), and the combined organic layers were washed with sat. aq. NaCl, dried over MgSO$_4$, filtered and concentrated under reduced pressure. The residue was lyophilized to give the title compound as a white powder (15 mg, 50%).

MS (ES$^+$) C$_{23}$H$_{24}$FN$_7$O requires: 433, found: 434 [M+H]$^+$.

$^1$H NMR (CD$_3$OD) (2:1 ratio of rotamers) δ 8.20 (s, 1H), 8.16 (d, J=6.5 Hz, 0.3H), 8.13 (d, J=6.7 Hz, 0.7H), 8.06 (s, 0.3H), 8.05 (s, 0.7H), 7.60-7.56 (m, 1H), 4.93-4.87 (m, 2H), 4.46 (t, J=5.6 Hz, 1.3H), 4.36 (t, J=5.6 Hz, 0.7H), 4.16-4.11 (m, 2H), 4.08 (s, 3H), 4.00 (s, 3H), 2.32-2.26 (m, 1H), 2.25 (s, 2H), 2.15 (s, 1H), 1.39-1.34 (m, 2H), 1.25-1.21 (m, 2H).

Example 29

1-(3-Cyclopropyl-1-(1-methyl-2-(1-methyl-1H-pyrazol-4-yl)-1H-pyrrolo[2,3-b]pyridin-4-yl)-5,6-dihydroimidazo[1,5-a]pyrazin-7(8H)-yl)ethan-1-one

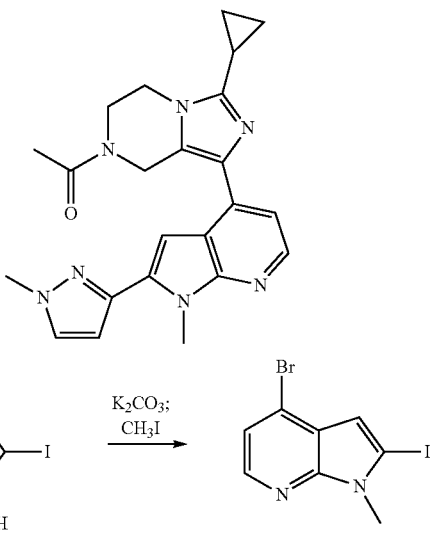

4-Bromo-2-iodo-1-methyl-1H-pyrrolo[2,3-b]pyridine

To a solution of 4-bromo-2-iodo-1H-pyrrolo[2,3-b]pyridine (215 mg, 0.666 mmol) in DMF (2 mL) were added $K_2CO_3$ (276 mg, 2.00 mmol) and MeI (0.083 mL, 1.3 mmol), and the resulting mixture was stirred at 60° C. for 1 h. $H_2O$ (10 mL) was added, the mixture was extracted with EtOAc (3×10 mL), and the combined organic layers were washed with sat. aq. NaCl, dried over $MgSO_4$, filtered and concentrated under reduced pressure. The residue was purified by $SiO_2$ gel chromatography (0% to 5% MeOH in $CH_2Cl_2$) to give the title compound as a white solid (101 mg, 45%). MS (ES$^+$) $C_8H_6BrIN_2$ requires: 336, found: 337 [M+H]$^+$.

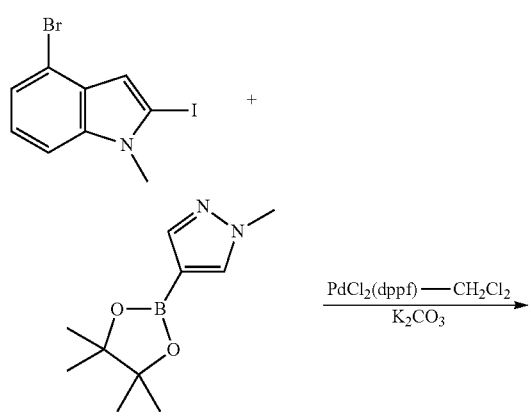

4-Bromo-1-methyl-2-(1-methyl-1H-pyrazol-4-yl)-1H-pyrrolo[2,3-hi]pyridine

To a solution of the product from the previous step (90 mg, 0.27 mmol) in 1,4-dioxane (3 mL) were added 1-methyl-4-(4,4,5,5-tetramethyl-1,3,2-dioxaborolan-2-yl)-1H-pyrazole (61.1 mg, 0.294 mmol), $PdCl_2(dppf)\text{-}CH_2Cl_2$ (21.81 mg, 0.027 mmol) and 2.0 M aq. $K_2CO_3$ (0.267 mL, 0.534 mmol), and the resulting mixture was stirred at 90° C. for 1 h. $H_2O$ (10 mL) was added, and the layers were separated. The aqueous layer was extracted with EtOAc (3×10 mL), and the combined organic layers were washed with sat. aq. NaCl, dried over $MgSO_4$, filtered and concentrated under reduced pressure. The residue was purified by $SiO_2$ gel chromatography (0% to 5% MeOH in $CH_2Cl_2$) to give the title compound as an off-white solid (71 mg, 91%). MS (ES$^+$) $C_{11}H_{10}BrN_5$ requires: 291, found: 292 [M+H]$^+$.

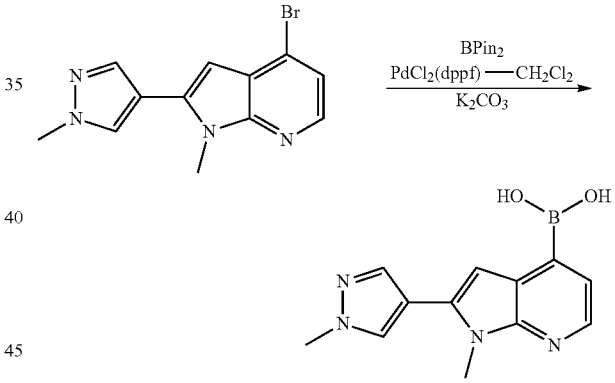

(1-Methyl-2-(1-methyl-1H-pyrazol-4-yl)-1H-pyrrolo[2,3-b]pyridin-4-yl)boronic acid A degassed solution of the product from the previous step (70 mg, 0.24 mmol), BPin$_2$ (73.3 mg, 0.289 mmol), PdCl$_2$(dppf)-CH$_2$Cl$_2$ (19.63 mg, 0.024 mmol) and KOAc (70.8 mg, 0.721 mmol) in 1,4-dioxane (2 mL) was stirred at 90° C. for 16 h, then allowed to cool to RT. $H_2O$ (10 mL) was added, and the layers were separated. The aqueous layer was extracted with EtOAc (3×5 mL), and the combined organic layers were washed with sat. aq. NaCl, dried over $MgSO_4$, filtered and concentrated under reduced pressure. The residue was purified by $SiO_2$ gel chromatography (0% to 5% MeOH in $CH_2Cl_2$) to give the title compound as a tan solid (58 mg, 94%). MS (ES$^+$) $C_{12}H_{13}BN_4O_2$ requires: 256, found: 257 [M+H]$^+$.

147

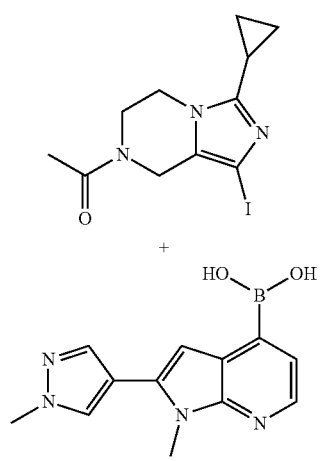

+

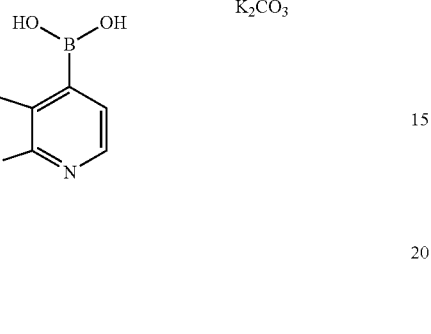

$\xrightarrow{\text{PdCl}_2(\text{dppf}) - \text{CH}_2\text{Cl}_2}{\text{K}_2\text{CO}_3}$

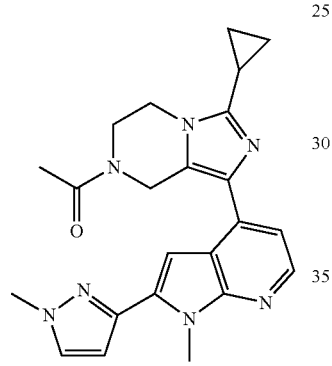

1-(3-Cyclopropyl-1-(1-methyl-2-(1-methyl-1H-pyrazol-4-yl)-1H-pyrrolo[2,3-b]pyridin-4-yl)-5,6-dihydroimidazo[1,5-a]pyrazin-7(8H)-yl)ethan-1-one A degassed solution of 1-(3-cyclopropyl-1-iodo-5,6-dihydroimidazo[1,5-a]pyrazin-7(8H)-yl)ethanone (15 mg, 0.045 mmol), (1-methyl-2-(1-methyl-1H-pyrazol-4-yl)-1H-pyrrolo[2,3-b]pyridin-4-yl)boronic acid (21.89 mg, 0.065 mmol), PdCl$_2$(dppf)-CH$_2$Cl$_2$ (5.28 mg, 6.47 μmol) and 2.0 M aq. K$_2$CO$_3$ (0.065 mL, 0.130 mmol) in DMF (0.5 mL) was stirred at 90° C. for 1 h, then concentrated under reduced pressure. The residue was purified by mass-triggered preparative HPLC (Mobile layer: A=0.1% TFA/H$_2$O, B=0.1% TFA/MeCN; Gradient: B=0% to 30%; 12 min; Column: C18) to give the title compound as a yellow solid (5 mg, 12%).

MS (ES$^+$) C$_{23}$H$_{25}$N$_7$O requires: 415, found: 416 [M+H]$^+$.

$^1$H NMR (CD$_3$OD) (2:1 ratio of rotamers) δ 8.38-8.33 (m, 1H), 8.14 (s, 0.7H), 8.13 (s, 0.3H), 7.94 (s, 0.7H), 7.91 (s, 0.3H), 7.24-7.20 (m, 1H), 6.69 (s, 0.7H), 6.67 (s, 0.3H), 4.90 (s, 2H), 4.47 (t, J=5.6 Hz, 1.3H), 4.37 (t, J=5.6 Hz, 0.7H), 4.16 (t, J=5.6 Hz, 2H), 4.00 (s, 6H), 2.32-2.27 (m, 1H), 2.26 (s, 2H), 2.11 (s, 1H), 1.39-1.34 (m, 2H), 1.29-1.24 (m, 2H).

148

Example 30

1-(3-Cyclopropyl-1-(3-(3,5-dimethylisoxazol-4-yl)-1-methyl-1H-indazol-5-yl)-5,6-dihydroimidazo[1,5-a]pyrazin-7(8H)-yl)ethan-1-one

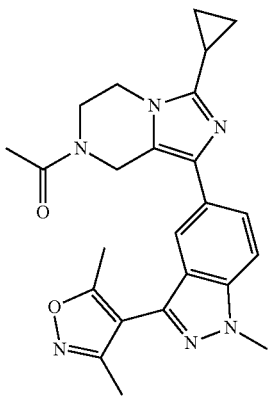

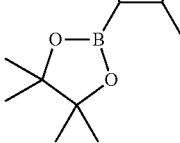

+

$\xrightarrow{\text{PdCl}_2(\text{dppf}) - \text{CH}_2\text{Cl}_2}{\text{K}_2\text{CO}_3}$

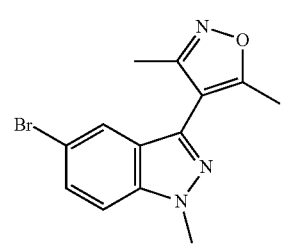

4-(5-Bromo-1-methyl-1H-indazol-3-yl)-3,5-dimethylisoxazole

To a solution of 5-bromo-3-iodo-1-methyl-1H-indazole (100 mg, 0.297 mmol) in 1,4-dioxane (3 mL) were added 3,5-dimethyl-4-(4,4,5,5-tetramethyl-1,3,2-dioxaborolan-2-yl)isoxazole (72.8 mg, 0.326 mmol), PdCl$_2$(dppf)-CH$_2$Cl$_2$ (24.24 mg, 0.030 mmol) and 2.0 M aq. K$_2$CO$_3$ (0.297 mL, 0.594 mmol), and the resulting mixture was stirred at 100° C. for 6 h. H$_2$O (10 mL) was added, and the layers were separated. The aqueous layer was extracted with EtOAc (3×10 mL), and the combined organic layers were washed with sat. aq. NaCl, dried over MgSO$_4$, filtered and concentrated under reduced pressure. The residue was purified by SiO$_2$ gel chromatography (20% to 100% EtOAc in hexanes) to give the title compound as a tan solid (64 mg, 70%). MS (ES$^+$) C$_{13}$H$_{12}$BrN$_3$O requires: 305, found: 306 [M+H]$^+$.

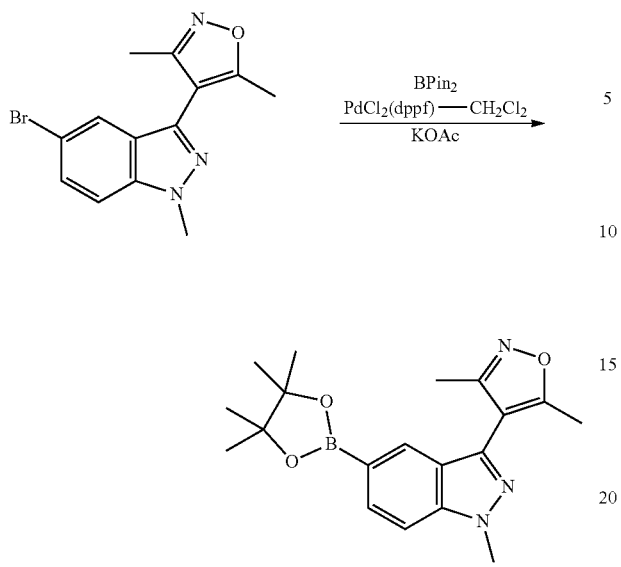

3,5-Dimethyl-4-(1-methyl-5-(4,4,5,5-tetramethyl-1,3,2-dioxaborolan-2-yl)-1H-indazol-3-yl)isoxazole A degassed solution of the product from the previous step (60 mg, 0.20 mmol), BPin$_2$ (59.7 mg, 0.235 mmol), PdCl$_2$(dppf)-CH$_2$Cl$_2$ (16.00 mg, 0.020 mmol) and KOAc (57.7 mg, 0.588 mmol) in 1,4-dioxane (2 mL) was stirred at 90° C. for 16 h, then allowed to cool to RT. H$_2$O (10 mL) was added, and the layers were separated. The aqueous layer was extracted with EtOAc (3×10 mL), and the combined organic layers were washed with sat. aq. NaCl, dried over MgSO$_4$, filtered and concentrated under reduced pressure. The residue was purified by SiO$_2$ gel chromatography (0% to 5% MeOH in CH$_2$Cl$_2$) to give the title compound as a tan solid (44 mg, 64%). MS (ES$^+$) C$_{19}$H$_{24}$BN$_3$O$_3$ requires: 353, found: 354 [M+H]$^+$.

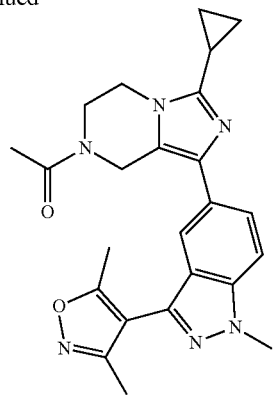

1-(3-Cyclopropyl-1-(3-(3,5-dimethylisoxazol-4-yl)-1-methyl-1H-indazol-5-yl)-5,6-dihydroimidazo[1,5-a]pyrazin-7(8H)-yl)ethan-1-one A degassed solution of 1-(3-cyclopropyl-1-iodo-5,6-dihydroimidazo[1,5-a]pyrazin-7(8H)-yl)ethanone (12 mg, 0.036 mmol), the product from the previous step (15.36 mg, 0.043 mmol), PdCl$_2$(dppf)-CH$_2$Cl$_2$ (2.96 mg, 3.62 µmol) and 2.0 M aq. K$_2$CO$_3$ (0.036 mL, 0.072 mmol) in DMF (0.5 mL) was stirred at 90° C. for 1 h, then concentrated under reduced pressure. The residue was purified by mass-triggered preparative HPLC (Mobile layer: A=0.1% TFA/H$_2$O, B=0.1% TFA/MeCN; Gradient: B=10% to 40%; 12 min; Column: C18) to give the title compound as a TFA salt. To this salt was added sat. aq. NaHCO$_3$(5 mL), the mixture was extracted with EtOAc (3×5 mL), and the combined organic layers were washed with sat. aq. NaCl, dried over MgSO$_4$, filtered and concentrated under reduced pressure. The residue was lyophilized to give the title compound as a white powder (12 mg, 50%).

MS (ES$^+$) C$_{24}$H$_{26}$N$_6$O$_2$ requires: 430, found: 431 [M+H]$^+$.

$^1$H NMR (CD$_3$OD) (2:1 ratio of rotamers) δ 7.85-7.82 (m, 1H), 7.81 (s, 0.3H), 7.79 (s, 0.7H), 7.64 (d, J=8.8 Hz, 1H), 4.99 (s, 0.7H), 4.96 (s, 1.3H), 4.42 (t, J=5.5 Hz, 1.3H), 4.32 (t, J=5.6 Hz, 0.7H), 4.19 (s, 3H), 4.14-4.09 (m, 2H), 2.49 (s, 3H), 2.30 (s, 3H), 2.27-2.12 (m, 3H), 2.14 (s, 1H) 1.37-1.32 (m, 2H), 1.25-1.20 (m, 2H).

Example 31

7-Acetyl-N-methyl-1-(1-methyl-3-(1-methyl-1H-pyrazol-4-yl)-1H-indazol-5-yl)-5,6,7,8-tetrahydroimidazo[1,5-a]pyrazine-3-carboxamide

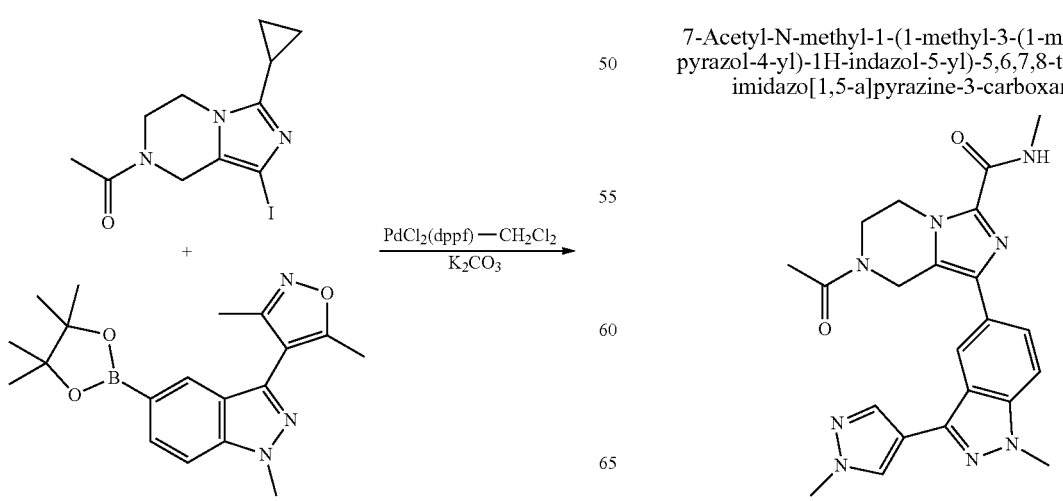

151

-continued

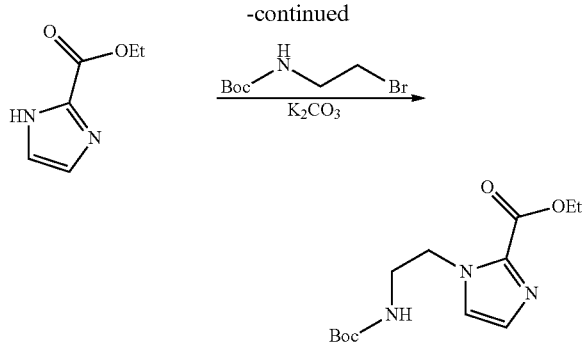

Ethyl 1-(2-((tert-butoxycarbonyl)amino)ethyl)-1H-imidazole-2-carboxylate

To a solution of ethyl 1H-imidazole-2-carboxylate (500 mg, 3.57 mmol) in DMF (10 mL) were added tert-butyl(2-bromoethyl)carbamate (800 mg, 3.57 mmol) and $K_2CO_3$ (986 mg, 7.14 mmol), and the resulting white suspension was stirred at 60° C. for 16 h, allowed to cool to RT, then concentrated under reduced pressure. The residue was purified by $SiO_2$ gel chromatography (20% to 100% EtOAc in hexanes) to give the title compound as a white solid (751 mg, 74%). MS (ES$^+$) $C_{13}H_{21}N_3O_4$ requires: 283, found: 284 [M+H]$^+$.

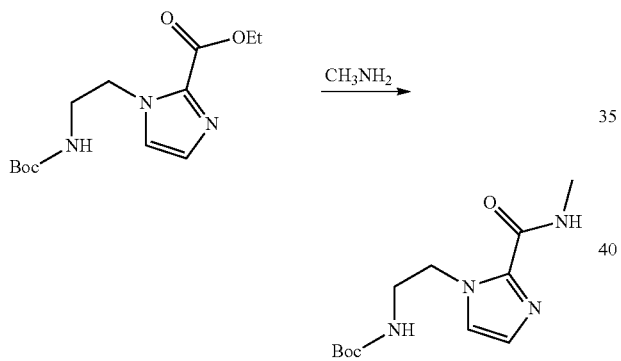

tert-Butyl(2-(2-(methylcarbamoyl)-1H-imidazol-1-yl)ethyl)carbamate

To the product from the previous step (400 mg, 1.41 mmol) was added 2.0 M MeNH$_2$ in THF (3530 μl, 7.06 mmol). The resulting mixture was stirred at 80° C. for 16 h, then concentrated under reduced pressure. The residue was purified by $SiO_2$ gel chromatography (0% to 5% MeOH in $CH_2Cl_2$) to give the title compound as a white solid (366 mg, 97%). MS (ES$^+$) $C_{12}H_{20}N_4O_3$ requires: 268, found: 269 [M+H]$^+$.

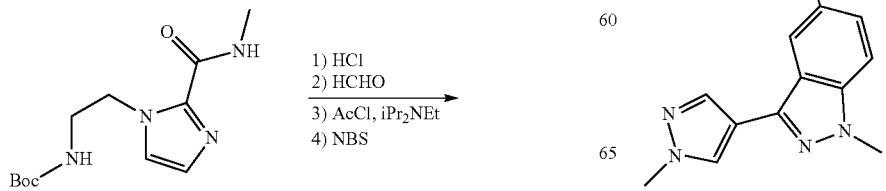

152

-continued

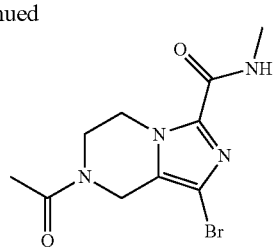

7-Acetyl-1-bromo-N-methyl-5,6,7,8-tetrahydroimidazo[1,5-a]pyrazine-3-carboxamide To a solution of HCl in MeOH (pre-made by adding AcCl (2 mL) to MeOH (8 mL)) was added the product from the previous step (366 mg, 1.36 mmol), and the resulting mixture was stirred at 20° C. for 1 h then concentrated under reduced pressure. To a solution of the residue in EtOH (10.00 mL) was added 50% aq. formaldehyde (1.503 mL, 27.3 mmol), and the resulting mixture was stirred at 80° C. for 1 h then concentrated under reduced pressure. To a solution of the residue in $CH_2Cl_2$ (10.00 mL) were added iPr$_2$NEt (1.191 mL, 6.82 mmol) and AcCl (0.291 mL, 4.09 mmol) and the resulting mixture was stirred at 20° C. for 1 h then concentrated under reduced pressure. To a solution of the residue in DMF (5 mL) was added NBS (728 mg, 4.09 mmol) and the resulting mixture was stirred at 20° C. for 1 h then concentrated under reduced pressure. The residue was purified via $SiO_2$ gel chromatography (0% to 5% MeOH in $CH_2Cl_2$) to give the title compound as a yellow liquid (125 mg, 30%). MS (ES$^+$) $C_{10}H_{13}BrN_4O_2$ requires: 301, found: 302 [M+H]$^+$.

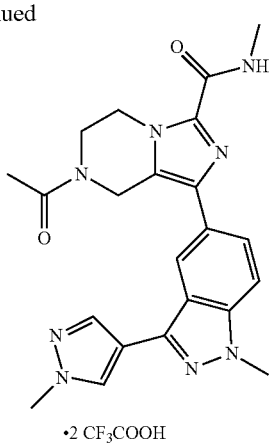

·2 CF₃COOH

7-Acetyl-N-methyl-1-(1-methyl-3-(1-methyl-1H-pyrazol-4-yl)-1H-indazol-5-yl)-5,6,7,8-tetrahydroimidazo[1,5-a]pyrazine-3-carboxamide bis(2,2,2-trifluoroacetate)

A degassed solution of the product from the previous step (12 mg, 0.040 mmol), Intermediate "F" (27.0 mg, 0.040 mmol), PdCl₂(dppf)-CH₂Cl₂ (3.25 mg, 3.98 μmol) and 2.0 M aq. K₂CO₃ (0.040 mL, 0.080 mmol) in DMF (0.5 mL) was stirred at 90° C. for 1 h, then concentrated under reduced pressure. The residue was purified by mass-triggered preparative HPLC (Mobile layer: A=0.1% TFA/H₂O, B=0.1% TFA/MeCN; Gradient: B=10% to 40%; 12 min; Column: C18) to give the title compound as a white solid (6 mg, 23%). MS (ES⁺) $C_{22}H_{24}N_8O_2$ requires: 432, found: 433 [M+H]⁺. ¹H NMR (CD₃OD) (2:1 ratio of rotamers) δ 8.16 (s, 1H), 8.12 (s, 1H), 8.07 (s, 0.3H), 8.06 (s, 0.7H), 7.77-7.72 (m, 1H), 7.61-7.55 (m, 1H), 5.07 (s, 2H), 4.70 (t, J=5.5 Hz, 1.3H), 4.61 (t, J=5.6 Hz, 0.7H), 4.11 (s, 3H), 4.06-3.96 (m, 5H), 2.98 (s, 3H), 2.25 (s, 2H), 2.21 (s, 1H).

Example 32

1-(3-Chloro-1-(1-methyl-3-(1-methyl-1H-pyrazol-4-yl)-1H-indazol-5-yl)-5,6-dihydroimidazo[1,5-a]pyrazin-7(8H)-yl)ethan-1-one

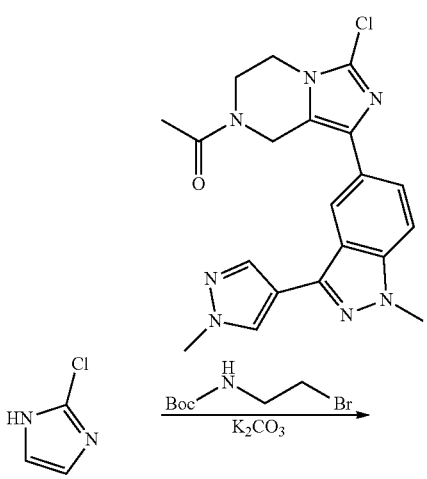

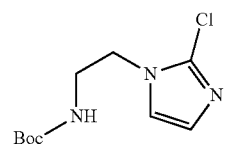

tert-Butyl(2-(2-chloro-1H-imidazol-1-yl)ethyl)carbamate

To a solution of 2-chloro-1H-imidazole (250 mg, 2.44 mmol) in DMF (5 mL) were added K₂CO₃ (1011 mg, 7.32 mmol) and tert-butyl(2-bromoethyl)carbamate (601 mg, 2.68 mmol), and the resulting mixture was stirred at 80° C. for 16 h then concentrated under reduced pressure. H₂O (20 mL) was added, the mixture was extracted with EtOAc (3×10 mL), and the combined organic layers were washed with sat. aq. NaCl, dried over MgSO₄, filtered and concentrated under reduced pressure. The residue was purified by SiO₂ gel chromatography (0% to 5% MeOH in CH₂Cl₂) to give the title compound as a white solid (394 mg, 66%). MS (ES⁺) $C_{10}H_{16}ClN_3O_2$ requires: 245, found: 246 [M+H]⁺.

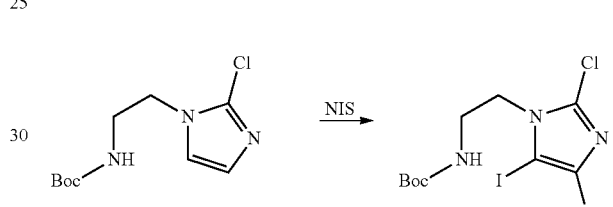

tert-Butyl(2-(2-chloro-4,5-diiodo-1H-imidazol-1-yl)ethyl)carbamate

To a solution of the product from the previous step (380 mg, 1.55 mmol) in THF (10 mL) was added NIS (1044 mg, 4.64 mmol) and the resulting mixture was stirred at 80° C. for 2 h then allowed to cool to RT. H₂O (20 mL) and sat. aq. Na₂S₂O₃ (5 mL) were added, and the layers were separated. The aqueous layer was extracted with EtOAc (3×10 mL), and the combined organic layers were washed with sat. aq. NaCl, dried over MgSO₄, filtered and concentrated under reduced pressure. The residue was purified by SiO₂ gel chromatography (0% to 50% EtOAc in hexanes) to give the title compound as a yellow solid (366 mg, 48%). MS (ES⁺) $C_{10}H_{15}ClI_2N_3O_2$ requires: 497, found: 498 [M+H]⁺.

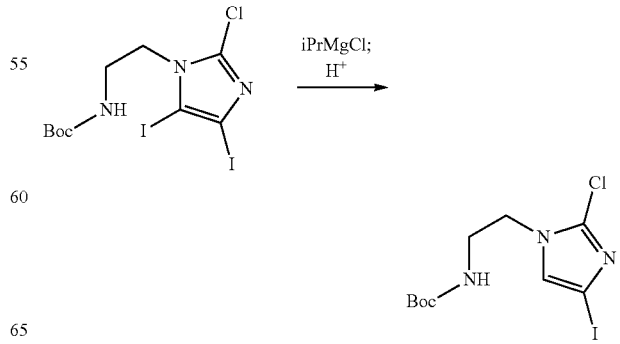

tert-Butyl(2-(2-chloro-4-iodo-1H-imidazol-1-yl)ethyl)carbamate

To a solution of the product from the previous step (366 mg, 0.734 mmol) in THF (10 mL) at −78° C. was added iPrMgCl (1.160 mL, 2.320 mmol) and the resulting mixture was stirred at −78° C. for 0.5 h. The mixture was treated with sat. aq. NH$_4$Cl (20 mL), and the layers were separated. The aqueous layer was extracted with EtOAc (3×10 mL), and the combined organic layers were washed with sat. aq. NaCl, dried over MgSO$_4$, filtered and concentrated under reduced pressure. The residue was purified by SiO$_2$ gel chromatography (0% to 60% EtOAc in hexanes) to give the title compound as an off-white solid (285 mg, 50%). MS (ES$^+$) C$_{10}$H$_{15}$ClIN$_3$O$_2$ requires: 371, found: 372 [M+H]$^+$.

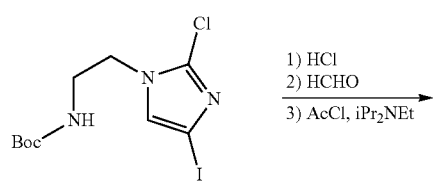

1-(3-Chloro-1-iodo-5,6-dihydroimidazo[1,5-a]pyrazin-7(8H)-yl)ethanone

A solution of the product from the previous step (200 mg, 0.538 mmol) in HCl/MeOH (pre-made by dripping AcCl (2 mL) into MeOH (10 mL)) was stirred at 20° C. for 1 h, then concentrated under reduced pressure. To a mixture of the residue in EtOH (5 mL) was added 50% aq. formaldehyde (0.297 mL, 10.8 mmol) and the resulting mixture was stirred at 100° C. for 3 h, then concentrated under reduced pressure. To a mixture of the residue in CH$_2$Cl$_2$ (5.00 mL) at 0° C. were added iPr$_2$NEt (0.470 mL, 2.69 mmol) and AcCl (0.057 mL, 0.81 mmol), and the resulting mixture was stirred at 20° C. for 0.5 h, then concentrated under reduced pressure. The residue was purified by SiO$_2$ gel chromatography (0% to 5% MeOH in CH$_2$Cl$_2$) to give the title compound as an off-white solid (98 mg, 56%). MS (ES$^+$) C$_8$H$_9$ClIN$_3$O requires: 325, found: 326 [M+H]$^+$.

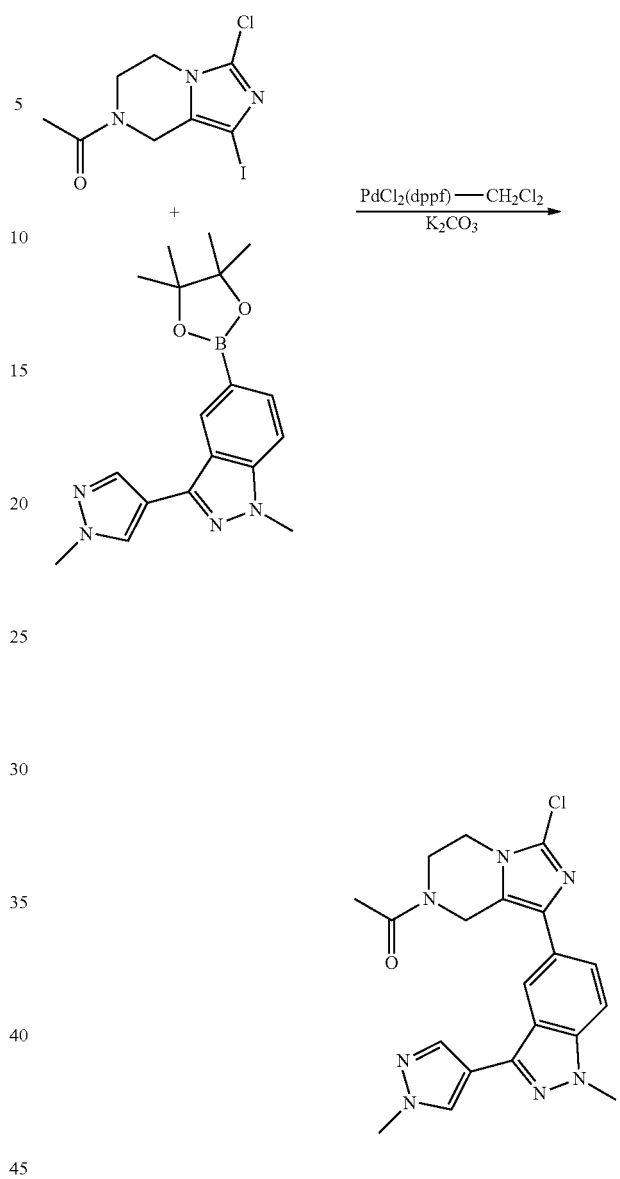

1-(3-Chloro-1-(1-methyl-3-(1-methyl-1H-pyrazol-4-yl)-1H-indazol-5-yl)-5,6-dihydroimidazo[1,5-a]pyrazin-7(8H)-yl)ethan-1-one A degassed mixture of the product from the previous step (20 mg, 0.061 mmol), Intermediate "F" (20.78 mg, 0.061 mmol), PdCl$_2$(dppf)-CH$_2$Cl$_2$ (5.02 mg, 6.14 µmol) and 2.0 M aq. K$_2$CO$_3$ (0.061 mL, 0.12 mmol) in DMF (0.5 mL) was stirred at 90° C. for 1 h, then concentrated under reduced pressure. The residue was purified by SiO$_2$ gel chromatography (0% to 5% MeOH in CH$_2$Cl$_2$) to give the title compound as a pale yellow solid (10 mg, 40%).

MS (ES$^+$) C$_{20}$H$_{20}$ClN$_7$O requires: 409, found: 410 [M+H]$^+$.

$^1$H NMR (CD$_3$OD) (2:1 ratio of rotamers) δ 8.26 (s, 1H), 8.12 (s, 1H), 8.07 (0.3H), 8.06 (0.7H), 7.67-7.57 (m, 2H), 5.05 (s, 0.7H), 5.03 (s, 1.3H), 4.17-3.99 (m, 10H), 2.24 (s, 2H), 2.21 (s, 1H).

Example 33

3-Cyclopropyl-N-methyl-1-(6-(1-methyl-1H-pyrazol-4-yl)-7-(trifluoromethyl)-3,4-dihydro-1,5-naphthyridin-1(2H)-yl)-5,6-dihydroimidazo[1,5-a]pyrazine-7(8H)-carboxamide

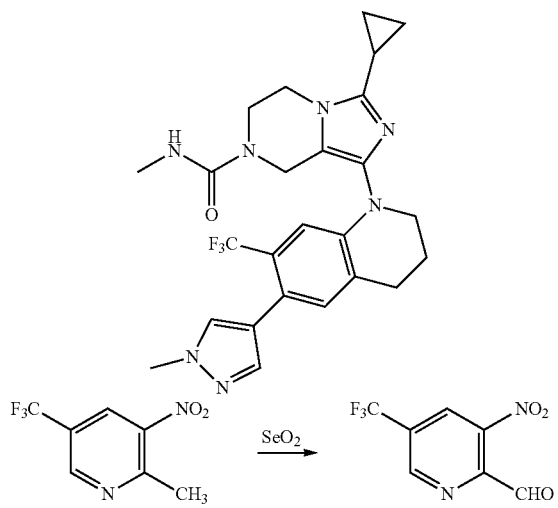

3-Nitro-5-(trifluoromethyl)picolinaldehyde

To a solution of 2-methyl-3-nitro-5-(trifluoromethyl)pyridine (1.00 g, 4.85 mmol) in 1,4-dioxane (20 mL) was added SeO$_2$ (1.077 g, 9.70 mmol) and the resulting mixture was stirred at 100° C. for 6 h, then allowed to cool to RT. The mixture was filtered through CELITE®, and the filtrate was concentrated under reduced pressure. The residue was purified by SiO$_2$ gel chromatography (0% to 60% EtOAc in hexanes) to give the title compound as a yellow solid (912 mg, 85%). MS (ES$^+$) C$_7$H$_3$F$_3$N$_2$O$_3$ requires: 220, found: 221 [M+H]$^+$.

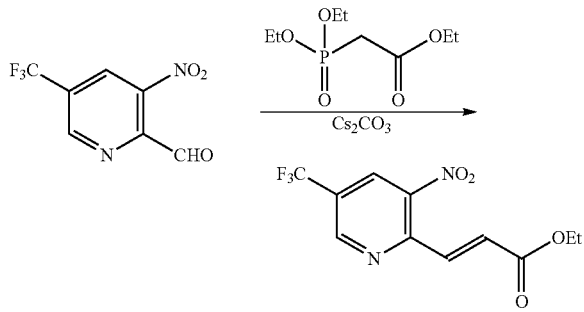

(E)-Ethyl 3-(3-nitro-5-(trifluoromethyl)pyridin-2-yl)acrylate

To a solution of the product form the previous step (725 mg, 3.29 mmol) in THF (30 mL) was added ethyl 2-(diethoxyphosphoryl)acetate (886 mg, 3.95 mmol) and Cs$_2$CO$_3$ (1288 mg, 3.95 mmol) and the resulting mixture was stirred at 20° C. for 0.5 h. The reaction mixture was filtered through CELITE®, and the filtrate was concentrated under reduced pressure. The residue was purified by SiO$_2$ gel chromatography (0% to 15% EtOAc in hexanes) to give the title compound as a colorless liquid (624 mg, 65%). MS (ES$^+$) C$_{11}$H$_9$F$_3$N$_2$O$_4$ requires: 290, found: 291 [M+H]$^+$.

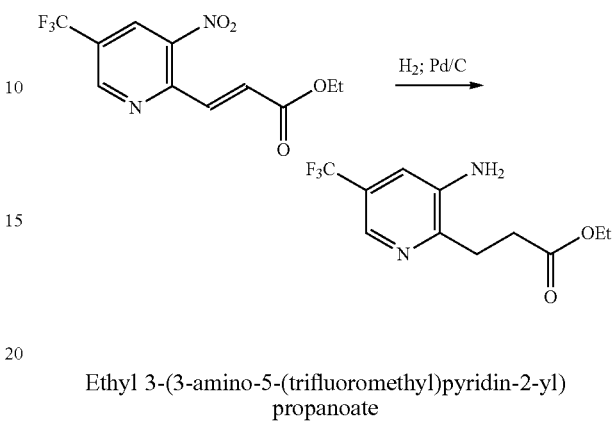

Ethyl 3-(3-amino-5-(trifluoromethyl)pyridin-2-yl)propanoate

A reaction vessel was charged with the product from the previous step (620 mg, 2.14 mmol), 10% Pd/C (227 mg) and EtOH (10 mL) under an N$_2$ atmosphere. The suspension was degassed by bubbling N$_2$ through for 2 min, then purged with H$_2$ for 2 min. The reaction mixture was stirred under an atmosphere of H$_2$ at 1 atm for 1 h. The reaction mixture was then purged with N$_2$, filtered through CELITE® and concentrated under reduced pressure to give the title compound as a colorless liquid (502 mg, 90%), which was used without further purification. MS (ES$^+$) C$_{11}$H$_{11}$F$_3$N$_2$O$_4$ requires: 262, found: 263 [M+H]$^+$.

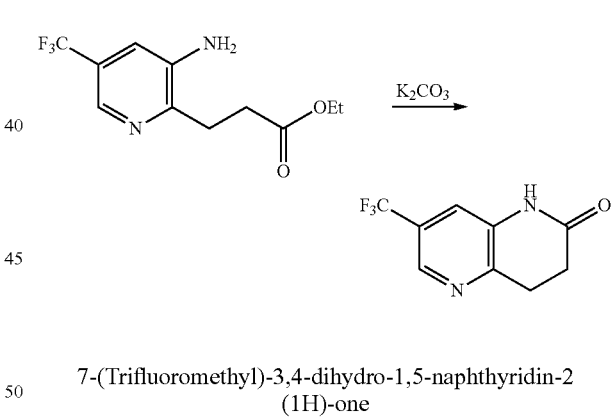

7-(Trifluoromethyl)-3,4-dihydro-1,5-naphthyridin-2(1H)-one

To a solution of the product from the previous step (500 mg, 1.91 mmol) in DMF (10 mL) was added K$_2$CO$_3$ (791 mg, 5.72 mmol), and the resulting mixture was stirred at 80° C. for 4 h, allowed to cool to RT, then concentrated under reduced pressure. The residue was purified by SiO$_2$ gel chromatography (0% to 5% MeOH in CH$_2$Cl$_2$) to give the title compound as a white solid (388 mg, 94%). MS (ES$^+$) C$_9$H$_7$F$_3$N$_2$O requires: 216, found: 217 [M+H]$^+$.

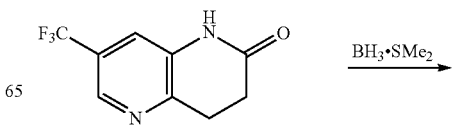

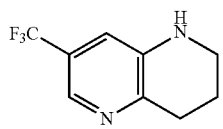

7-(Trifluoromethyl)-1,2,3,4-tetrahydro-1,5-naphthyridine

To a solution of the product from the previous step (385 mg, 1.78 mmol) in THF (10 mL) was added BH$_3$·SMe$_2$ (0.169 mL, 1.78 mmol), and the resulting mixture was stirred at 60° C. for 2 h then allowed to cool to RT. MeOH (10 mL) was added dropwise and the resulting mixture was stirred at 60° C. for 1 h then concentrated under reduced pressure. The residue was purified by SiO$_2$ gel chromatography (0% to 5% MeOH in CH$_2$Cl$_2$) to give the title compound as a white solid (325 mg, 90%). MS (ES$^+$) C$_9$H$_9$F$_3$N$_2$ requires: 202, found: 203 [M+H]$^+$.

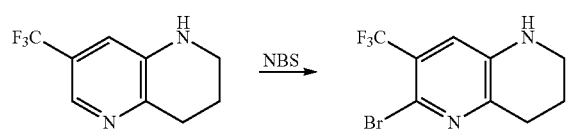

6-Bromo-7-(trifluoromethyl)-1,2,3,4-tetrahydro-1,5-naphthyridine

To a solution of the product from the previous step (300 mg, 1.48 mmol) in THF (10 mL) was added NBS (291 mg, 1.63 mmol), and the resulting mixture was stirred at 20° C. for 1 h. H$_2$O (20 mL) was added, and the layers were separated. The aqueous layer was extracted with EtOAc (3×10 mL), and the combined organic layers were washed with sat. aq. NaCl, dried over MgSO$_4$, filtered and concentrated under reduced pressure. The residue was purified by SiO$_2$ gel chromatography (0% to 40% EtOAc in hexanes) to give the title compound as a white solid (344 mg, 82%). MS (ES$^+$) C$_9$H$_8$BrF$_3$N$_2$ requires: 280, found: 281 [M+H]$^+$.

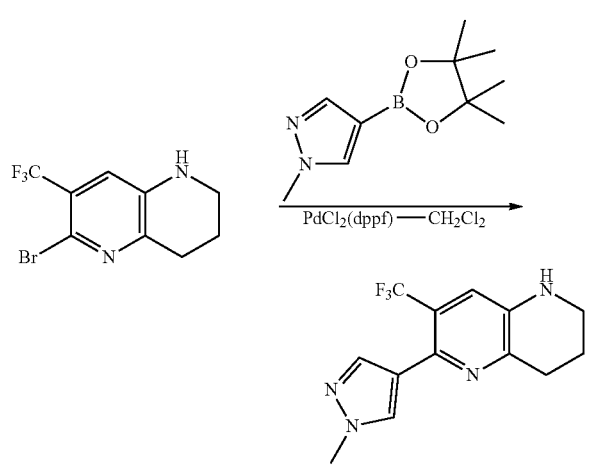

6-(1-Methyl-1H-pyrazol-4-yl)-7-(trifluoromethyl)-1,2,3,4-tetrahydro-1,5-naphthyridine A degassed solution of the product from the previous step (250 mg, 0.889 mmol), 1-methyl-4-(4,4,5,5-tetramethyl-1,3,2-dioxaborolan-2-yl)-1H-pyrazole (222 mg, 1.07 mmol), PdCl$_2$(dppf)-CH$_2$Cl$_2$ (72.6 mg, 0.089 mmol) and K$_2$CO$_3$ (0.889 mL, 1.78 mmol) in DMF (5 mL) was stirred at 90° C. for 1 h, then concentrated under reduced pressure. The residue was purified by SiO$_2$ gel chromatography (0% to 5% MeOH in CH$_2$Cl$_2$) to give the title compound as an off-white solid (186 mg, 74%). MS (ES$^+$) C$_{13}$H$_{13}$F$_3$N$_4$ requires: 282, found: 283 [M+H]$^+$.

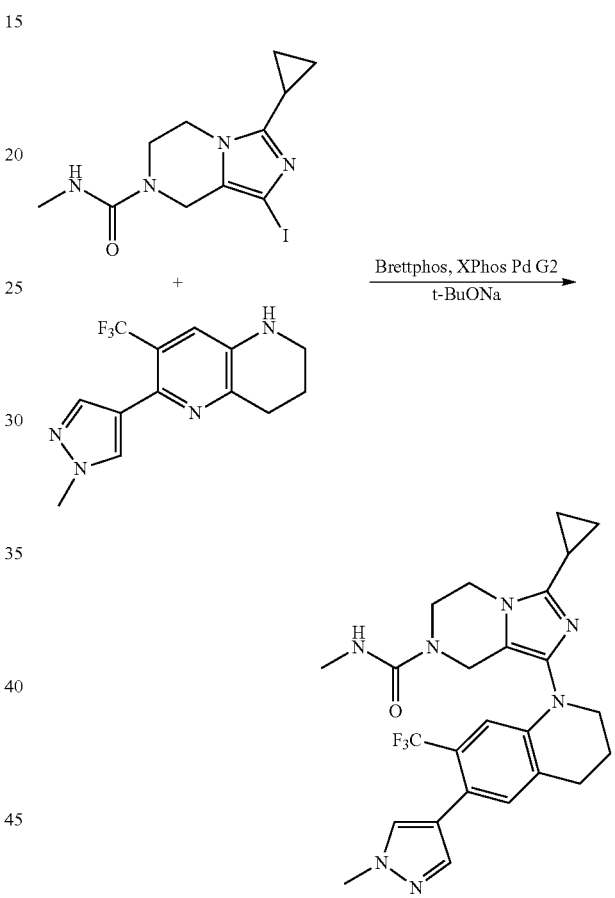

3-Cyclopropyl-N-methyl-1-(6-(1-methyl-1H-pyrazol-4-yl)-7-(trifluoromethyl)-3,4-dihydro-1,5-naphthyridin-1(2H)-yl)-5,6-dihydroimidazo[1,5-a]pyrazine-7(8H)-carboxamide A degassed solution of Intermediate "B" (10 mg, 0.029 mmol), the product form the previous step (8.15 mg, 0.029 mmol), t-BuONa (5.55 mg, 0.058 mmol), Brettphos (1.551 mg, 2.89 µmol) and XPhos Pd G2 (2.273 mg, 2.89 µmol) in 1,4-dioxane (0.5 mL) was stirred at 120° C. for 16 h, then concentrated under reduced pressure. The residue was purified by mass-triggered preparative HPLC (Mobile layer: A=0.1% TFA/H$_2$O, B=0.1% TFA/MeCN; Gradient: B=10% to 40%; 12 min; Column: C18) to give the title compound as an off-white solid (6 mg, 42%).

MS (ES$^+$) C$_{24}$H$_{27}$F$_3$N$_8$O requires: 500, found: 501 [M+H]$^+$.

¹H NMR (CD₃OD) δ 7.81 (s, 1H), 7.66 (s, 1H), 6.87 (s, 1H), 4.40 (s, 2H), 4.15 (t, J=5.2 Hz, 2H), 3.93 (s, 3H), 3.85 (t, J=5.3 Hz, 2H), 3.57 (t, J=5.3 Hz, 2H), 3.03 (t, J=5.3 Hz, 2H), 2.72 (s, 3H), 2.21-2.14 (m, 2H), 1.99-1.92 (m, 1H), 1.02-0.97 (m, 2H), 0.92-0.88 (m, 2H).

Example 34

3-Cyclopropyl-1-(3-(difluoromethyl)-2-(1-methyl-1H-pyrazol-4-yl)quinolin-5-yl)-N-methyl-5,6-dihydroimidazo[1,5-a]pyrazine-7(8H)-carboxamide

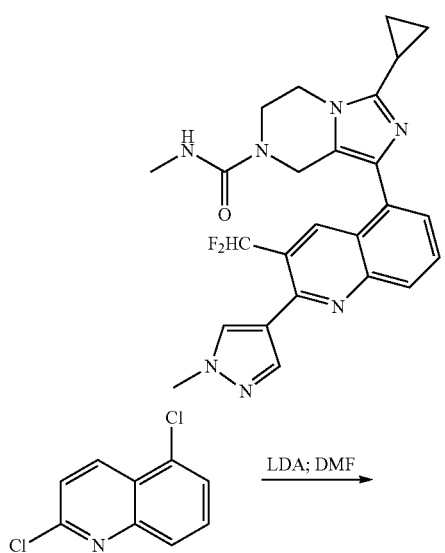

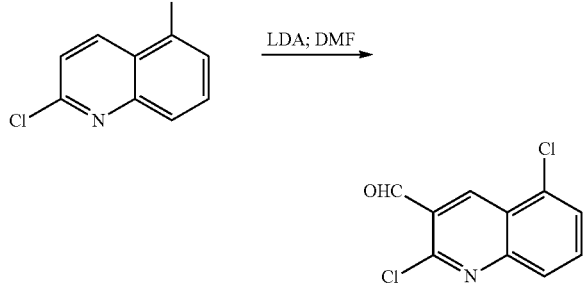

2,5-Dichloroquinoline-3-carbaldehyde

To a solution of iPr₂NH₂ (0.157 mL, 1.10 mmol) in THF (5 mL) at −20° C. was added dropwise a solution of 1.6 M BuLi in hexane (0.687 mL, 1.10 mmol). The resulting solution was stirred at 0° C. for 30 min, then cooled to −78° C. To the solution was added dropwise a solution of 2,5-dichloroquinoline (198 mg, 1.00 mmol) in THF (5 mL). The mixture was stirred for 30 min at −78° C., then treated dropwise with DMF (0.116 mL, 1.50 mmol). The mixture was stirred at −78° C. for 30 min, then treated with sat. aq. NH₄Cl, allowed to warm to RT, and partitioned between EtOAc (20 mL) and water (10 mL). The organic layer was sequentially washed with water and sat. aq. NaCl, dried over MgSO₄, filtered, and concentrated under reduced pressure. The residue was purified by SiO₂ gel chromatography (0% to 15% EtOAc in hexanes) to give the title compound as a white solid (108 mg, 48%). MS (ES⁺) C₁₀H₅Cl₂NO requires: 225, found: 226 [M+H]⁺.

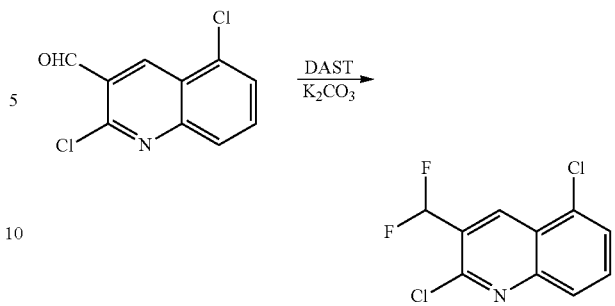

2,5-Dichloro-3-(difluoromethyl)quinoline

To a solution of the product from the previous step (100 mg, 0.442 mmol) in CH₂Cl₂ (3 mL) were added DAST (0.175 mL, 1.33 mmol), and the resulting mixture was stirred at 20° C. for 2 h then treated with sat. aq. NaHCO₃ (10 mL). The layers were separated, and the aqueous layer was extracted with CH₂Cl₂ (3×5 mL). The combined organic layers were washed with sat. aq. NaCl, dried over MgSO₄, filtered and concentrated under reduced pressure. The residue was purified by SiO₂ gel chromatography (0% to 15% EtOAc in hexanes) to give the title compound as an off-white solid (98 mg, 89%). MS (ES⁺) C₁₀H₅Cl₂F₂N requires: 247, found: 248 [M+H]⁺.

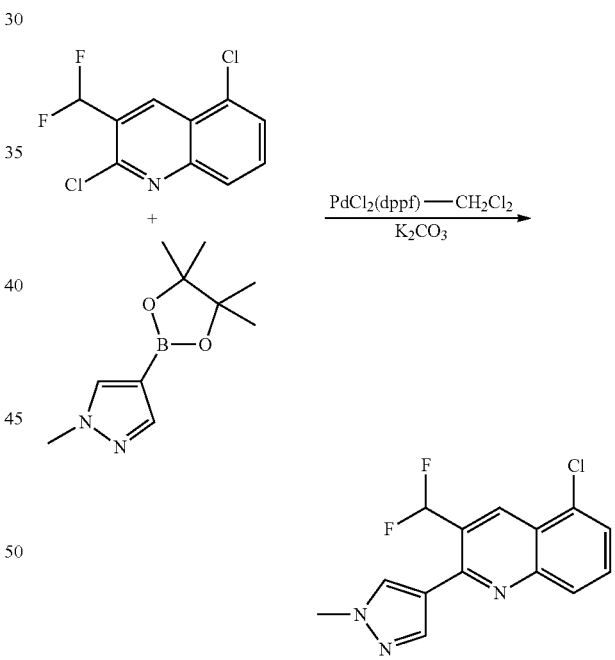

5-Chloro-3-(difluoromethyl)-2-(1-methyl-1H-pyrazol-4-yl)quinoline

A degassed solution of the product from the previous step (112 mg, 0.421 mmol), 1-methyl-4-(4,4,5,5-tetramethyl-1,3,2-dioxaborolan-2-yl)-1H-pyrazole (88 mg, 0.42 mmol), PdCl₂(dppf)-CH₂Cl₂ (17.19 mg, 0.021 mmol) and 2.0 M aq. K₂CO₃ (0.421 mL, 0.842 mmol) in 1,4-dioxane (4 mL) was stirred at 90° C. for 2 h. H₂O (10 mL) was added, and the layers were separated. The aqueous layer was extracted with EtOAc (3×5 mL), and the combined organic layers were washed with sat. aq. NaCl, dried over MgSO$_4$, filtered and concentrated under reduced pressure. The residue was purified by SiO$_2$ gel chromatography (0% to 5% MeOH in CH$_2$Cl$_2$) to give the title compound as an off-white solid (83 mg, 63%). MS (ES$^+$) C$_{14}$H$_9$ClF$_2$N$_3$ requires: 292, found: 293 [M+H]$^+$.

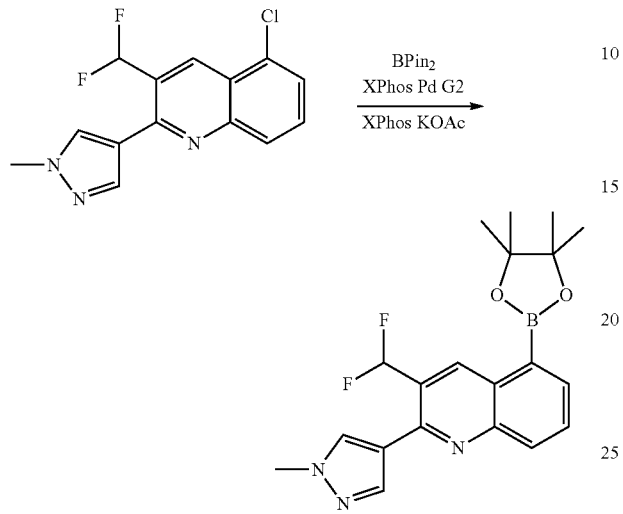

3-(Difluoromethyl)-2-(1-methyl-1H-pyrazol-4-yl)-5-(4,4,5,5-tetramethyl-1,3,2-dioxaborolan-2-yl)quinoline To a degassed solution of the product form the previous step (75 mg, 0.26 mmol) in 1,4-dioxane (2 mL) were added BPin$_2$ (78 mg, 0.31 mmol), KOAc (75 mg, 0.77 mmol), XPhos Pd G2 (20.09 mg, 0.026 mmol), and XPhos (12.17 mg, 0.026 mmol), and the resulting mixture was stirred at 100° C. for 4 h then concentrated under reduced pressure. The residue was purified by SiO$_2$ gel chromatography (0% to 5% MeOH in CH$_2$Cl$_2$) to give the title compound as an off-white solid (96 mg, 98%). MS (ES$^+$) C$_{20}$H$_{22}$BF$_2$N$_3$O$_2$ requires: 385, found: 386 [M+H]$^+$.

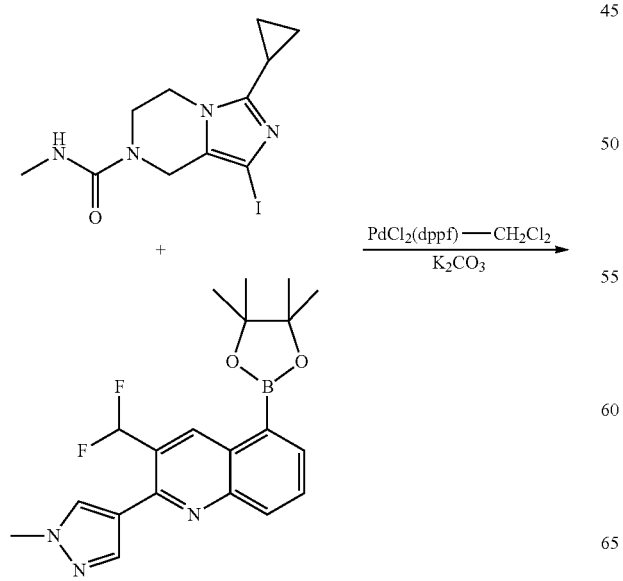

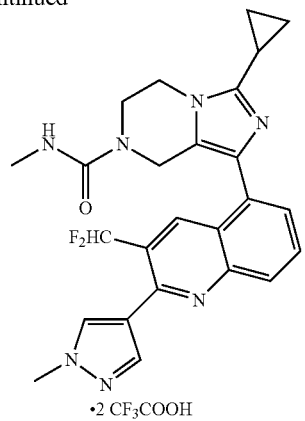

3-Cyclopropyl-1-(3-(difluoromethyl)-2-(1-methyl-1H-pyrazol-4-yl)quinolin-5-yl)-N-methyl-5,6-dihydroimidazo[1,5-a]pyrazine-7(8H)-carboxamide bis (2,2,2-trifluoroacetate)

A degassed solution of Intermediate "B" (15 mg, 0.043 mmol), the product from the previous step (16.69 mg, 0.043 mmol), PdCl$_2$(dppf)-CH$_2$Cl$_2$ (3.54 mg, 4.33 μmol) and K$_2$CO$_3$ (0.043 mL, 0.087 mmol) in DMF (0.5 mL) was stirred at 90° C. for 1 h, then concentrated under reduced pressure. The residue was purified by mass-triggered preparative HPLC (Mobile layer: A=0.1% TFA/H$_2$O, B=0.1% TFA/MeCN; Gradient: B=10% to 40%; 12 min; Column: C18) to give the title compound as a yellow solid (19 mg, 62%).

MS (ES$^+$) C$_{25}$H$_{25}$F$_2$N$_7$O requires: 477, found: 478 [M+H]$^+$.

$^1$H NMR (CD$_3$OD) δ 8.49 (s, 1H), 8.27 (d, J=8.7 Hz, 1H), 8.22 (s, 1H), 8.08 (s, 1H), 7.99 (t, J=7.8 Hz, 1H), 7.76 (d, J=6.9 Hz, 1H), 7.16 (t, J=54 Hz, 1H), 4.59 (s, 2H), 4.41 (t, J=5.3 Hz, 2H), 4.04-4.00 (m, 5H), 2.69 (s, 3H), 2.36-2.30 (m, 1H), 1.41-1.35 (m, 2H), 1.24-1.19 (m, 2H).

Example 35

4-(1-(7-Acetyl-3-cyclopropyl-5,6,7,8-tetrahydroimidazo[1,5-a]pyrazin-1-yl)-1,2,3,4-tetrahydroquinolin-6-yl)benzamide

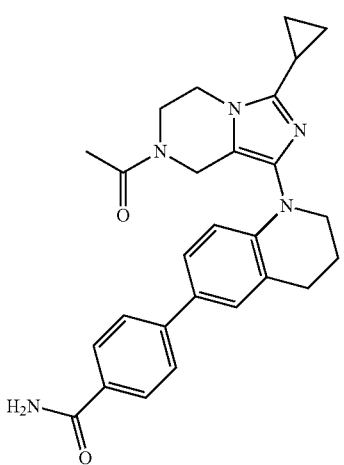

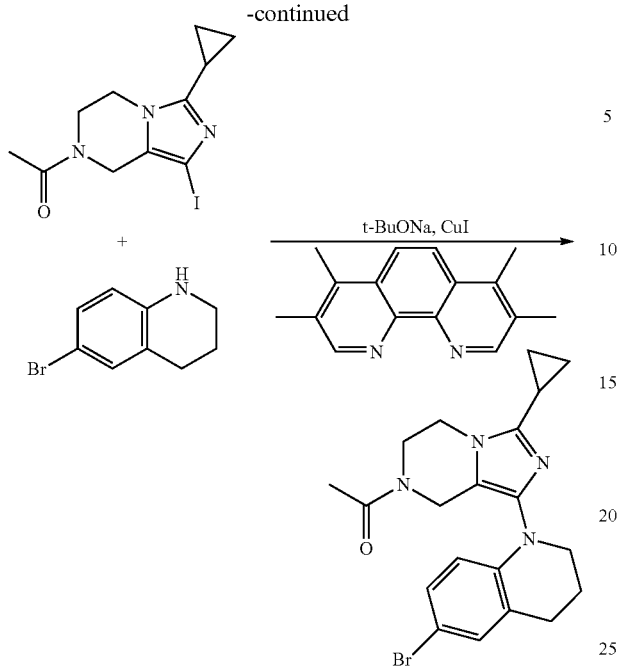

1-(1-(6-Bromo-3,4-dihydroquinolin-1(2H)-yl)-3-cyclopropyl-5,6-dihydroimidazo[1,5-a]pyrazin-7(8H)-yl)ethan-1-one A mixture of Intermediate "A" (800 mg, 2.4 mmol), 6-bromo-1,2,3,4-tetrahydroquinoline (616 mg, 2.9 mmol), CuI (46 mg, 0.24 mmol), 3,4,7,8-tetramethyl-1,10-phenanthroline (118 mg, 0.48 mmol) and t-BuONa (116 mg, 0.12 mmol) were suspended in 1,4-dioxane (5 mL) and the reaction mixture was degassed by bubbling with $N_2$. The mixture was stirred at 100° C. for 16 h, then concentrated under reduced pressure. The residue was purified by $SiO_2$ gel chromatography (0% to 15% isopropanol in $CH_2Cl_2$) to give the title compound as a light brown oil (496 mg, 49%). MS (ES$^+$) $C_{20}H_{23}BrN_4O$ requires: 414, found: 415 [M+H]$^+$.

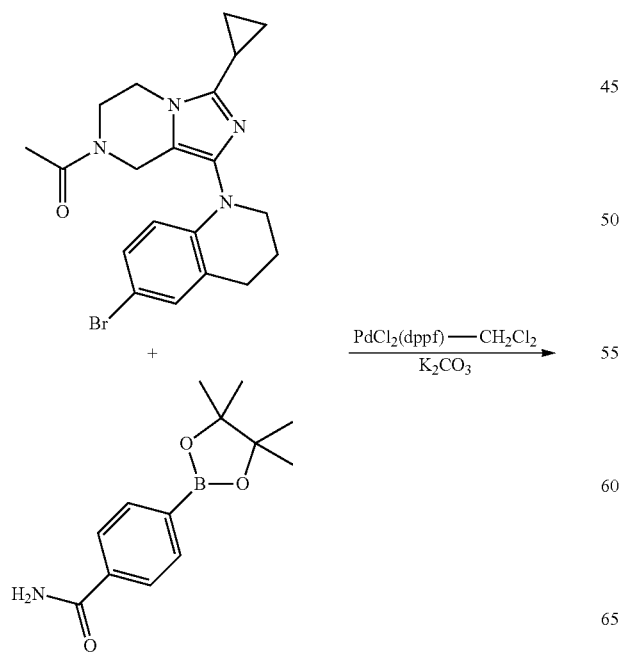

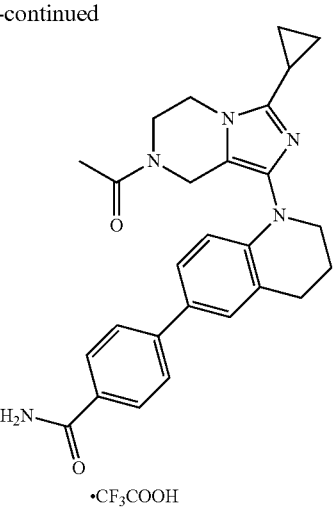

4-(1-(7-Acetyl-3-cyclopropyl-5,6,7,8-tetrahydroimidazo[1,5-a]pyrazin-1-yl)-1,2,3,4-tetrahydroquinolin-6-yl)benzamide 2,2,2-trifluoroacetate To a solution of the product from the previous step (20 mg, 0.048 mmol) in 1,4-dioxane/water (5:1, 2.4 mL) were added 4-(4,4,5,5-tetramethyl-1,3,2-dioxaborolan-2-yl)benzamide (15 mg, 0.058 mmol), $K_2CO_3$ (14 mg, 0.096 mmol) and PdCl$_2$(dppf)-CH$_2$Cl$_2$ (4 mg, 0.005 mmol), and the resulting mixture was stirred at 110° C. for 12 h then concentrated under reduced pressure. The residue was purified by mass-triggered preparative HPLC (Mobile layer: A=0.1% TFA/H$_2$O, B=0.1% TFA/MeCN; Gradient: B=10% to 50%; 12 min; Column: C18) to give the title compound as an off-white powder (9 mg, 33%).

MS (ES$^+$) $C_{27}H_{29}N_5O_2$ requires: 455, found: 456 [M+H]$^+$.

$^1$H NMR (CD$_3$OD) (1.2:0.8 ratio of rotamers) δ 7.96 (d, J=8.3 Hz, 2H), 7.71 (d, J=8.3 Hz, 2H), 7.60-7.39 (m, 1H), 7.47-7.39 (m, 1H), 6.64 (d, J=8.7 Hz, 0.4H), 6.59 (d, J=8.3 Hz, 0.6H), 4.46 (s, 0.8H), 4.45 (s, 1.2H), 4.45 (t, J=5.5 Hz, 1.2H), 4.35 (t, J=5.7 Hz, 0.8H), 4.20-4.11 (m, 2H), 3.72-3.62 (m, 2H), 3.09-2.97 (m, 2H), 2.36-2.23 (m, 3H), 2.23-2.13 (m, 3H), 1.29-1.15 (m, 2H), 1.45-1.32 (m, 2H).

Example 36

3-Cyclopropyl-1-(6-(difluoromethyl)-7-(1-methyl-1H-pyrazol-4-yl)-1,8-naphthyridin-4-yl)-N-methyl-5,6-dihydroimidazo[1,5-a]pyrazine-7(8H)-carboxamide

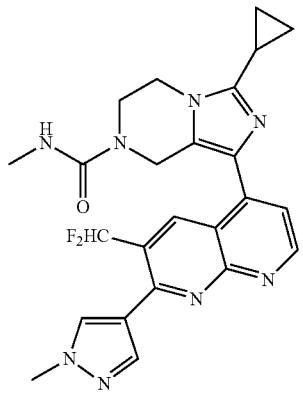

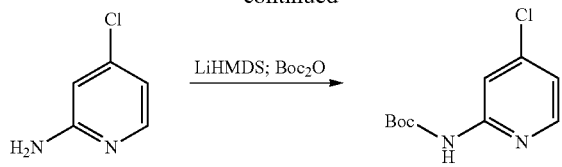

tert-Butyl(4-chloropyridin-2-yl)carbamate

To a solution of 4-chloropyridin-2-amine (643 mg, 5.00 mmol) in THF (20 mL) at 0° C. was added LiHMDS (1.0 M in THF, 10.00 mL, 10.00 mmol) and then Boc$_2$O (1310 mg, 6.00 mmol) in THF (10 mL), and the resulting mixture was stirred at 20° C. for 1 h. The mixture was treated with sat. aq. NH$_4$Cl (10 mL), and the layers were separated. The aqueous layer was extracted with EtOAc (3×20 mL), and the combined organic layers were washed with sat. aq. NaCl, dried over MgSO$_4$, filtered and concentrated under reduced pressure. The residue was purified by SiO$_2$ gel chromatography (0% to 15% EtOAc in hexanes) to give the title compound as a white solid (577 mg, 50%). MS (ES$^+$) C$_{10}$H$_{13}$ClN$_2$O$_2$ requires: 228, found: 229 [M+H]$^+$.

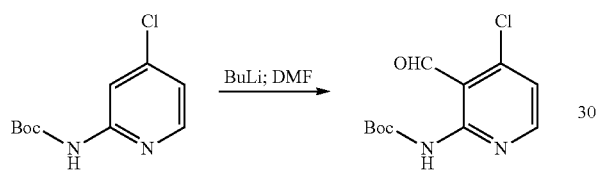

tert-Butyl(4-chloro-3-formylpyridin-2-yl)carbamate

To a solution of the product from the previous step (500 mg, 2.19 mmol) in THF (10 mL) at −78° C. was added BuLi (1.6 M in hexane, 3.42 mL, 5.47 mmol) and the resulting mixture was stirred at −78° C. for 30 min. The mixture was treated dropwise with DMF (0.847 mL, 10.9 mmol), and the resulting mixture was stirred at −78° C. for 30 min. The mixture was treated with sat. aq. NH$_4$Cl (10 mL) and the resulting mixture was allowed to warm to RT, then partitioned between EtOAc (30 mL) and H$_2$O (20 mL). The aqueous layer was extracted with EtOAc (3×10 mL), and the combined organic layers were washed with sat. aq. NaCl, dried over MgSO$_4$, filtered and concentrated under reduced pressure. The residue was purified by SiO$_2$ gel chromatography (0% to 15% EtOAc in hexanes) to give the title compound as a yellow solid (455 mg, 81%). MS (ES$^+$) C$_{11}$H$_{13}$ClN$_2$O$_3$ requires: 256, found: 257 [M+H]$^+$.

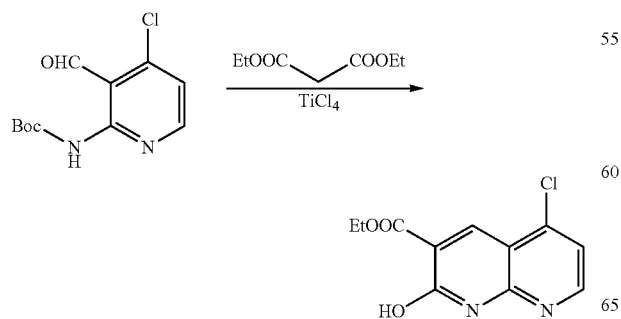

Ethyl 5-chloro-2-hydroxy-1,8-naphthyridine-3-carboxylate

To a solution of the product from the previous step (450 mg, 1.75 mmol) and diethyl malonate (562 mg, 3.51 mmol) in THF (10 mL) at 0° C. was added TiCl$_4$ (0.193 mL, 1.75 mmol) in CH$_2$Cl$_2$ (1.75 mL), and the resulting mixture was stirred at 20° C. for 5 h then treated with MeOH (2 mL). The mixture was concentrated under reduced pressure, treated with sat. aq. NaHCO$_3$ (20 mL), and extracted with EtOAc (3×10 mL). The combined organic layers were washed with sat. aq. NaCl, dried over MgSO$_4$, filtered and concentrated under reduced pressure. The resulting solid was triturated with Et$_2$O and isolated by filtration to give the title compound as a white solid (305 mg, 69%). MS (ES$^+$) C$_{11}$H$_9$ClN$_2$O$_3$ requires: 252, found: 253 [M+H]$^+$.

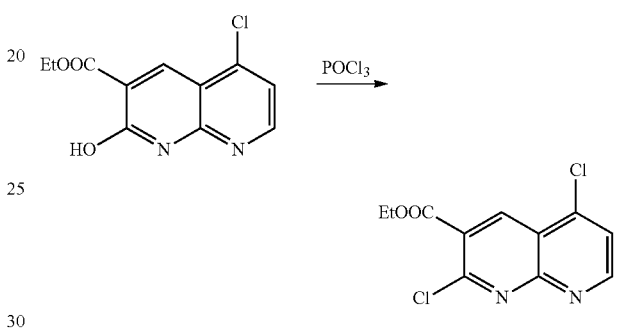

Ethyl 2,5-dichloro-1,8-naphthyridine-3-carboxylate

To a solution of the product from the previous step (300 mg, 1.19 mmol) in MeCN (10 mL) was added POCl$_3$ (0.332 mL, 3.56 mmol), and the resulting mixture was stirred at 90° C. for 3 h then concentrated under reduced pressure. The residue was treated with sat. aq. NaHCO$_3$ (20 mL), the mixture was extracted with EtOAc (3×10 mL), and the combined organic layers were washed with sat. aq. NaCl, dried over MgSO$_4$, filtered and concentrated under reduced pressure. The residue was purified by SiO$_2$ gel chromatography (0% to 5% MeOH in CH$_2$Cl$_2$) to give the title compound as a yellow solid (302 mg, 94%). MS (ES$^+$) C$_{11}$H$_8$Cl$_2$N$_2$O$_2$ requires: 270, found: 271 [M+H]$^+$.

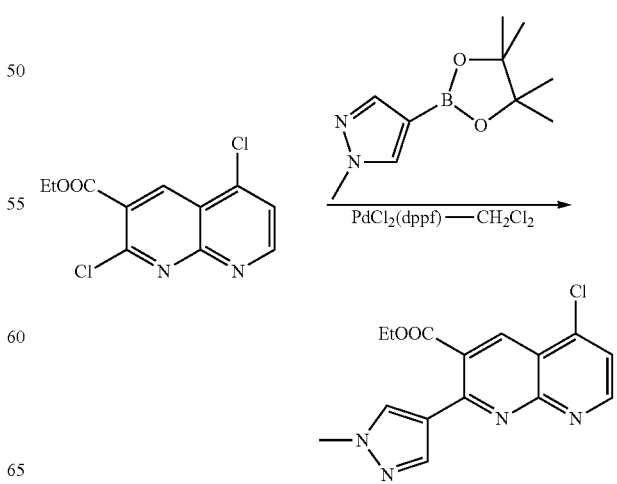

Ethyl 5-chloro-2-(1-methyl-1H-pyrazol-4-yl)-1,8-naphthyridine-3-carboxylate

To a solution of the product from the previous step (600 mg, 2.21 mmol) in 1,4-dioxane (10 mL) were added 1-methyl-4-(4,4,5,5-tetramethyl-1,3,2-dioxaborolan-2-yl)-1H-pyrazole (507 mg, 2.44 mmol), PdCl$_2$(dppf)-CH$_2$Cl$_2$ (90 mg, 0.11 mmol) and 2.0 M aq. K$_2$CO$_3$ (2.213 mL, 4.43 mmol), and the resulting mixture was stirred at 90° C. for 16 h then concentrated under reduced pressure. The residue was purified by mass-triggered preparative HPLC (Mobile layer: A=0.1% TFA/H$_2$O, B=0.1% TFA/MeCN; Gradient: B=20% to 60%; 12 min; Column: C18) to give the title compound as a yellow solid (298 mg, 43%). MS (ES$^+$) C$_{15}$H$_{13}$ClN$_4$O$_2$ requires: 316, found: 317 [M+H]$^+$. Ethyl 2-chloro-5-(1-methyl-1H-pyrazol-4-yl)-1,8-naphthyridine-3-carboxylate was also isolated (86 mg, 12%).

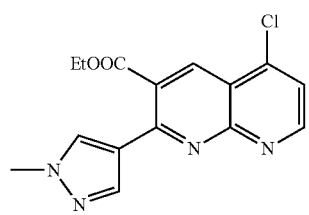

DIBAL-H

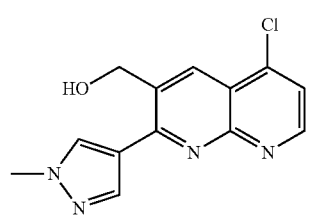

(5-Chloro-2-(1-methyl-1H-pyrazol-4-yl)-1,2-dihydro-1,8-naphthyridin-3-yl)methanol To a solution of the product from the previous step (298 mg, 0.941 mmol) in CH$_2$Cl$_2$ (10 mL) at −78° C. was added DIBAL-H (1.0 M in toluene, 4.70 mL, 4.70 mmol), and the resulting mixture was stirred at −78° C. for 0.5 h. The mixture was treated with H$_2$O (30 mL) and 15% aq. NaOH (5 mL), and the layers were separated. The aqueous layer was extracted with CH$_2$Cl$_2$ (3×20 mL), and the combined organic layers were washed with sat. aq. NaCl, dried over MgSO$_4$, filtered and concentrated under reduced pressure. The residue was purified by SiO$_2$ gel chromatography (0% to 5% MeOH in CH$_2$Cl$_2$) to give the title compound as an off-white solid (215 mg, 83%). MS (ES$^+$) C$_{13}$H$_{13}$ClN$_4$O requires: 276, found: 277 [M+H]$^+$.

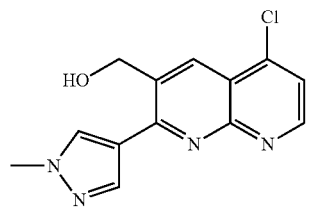

Dess-Martin

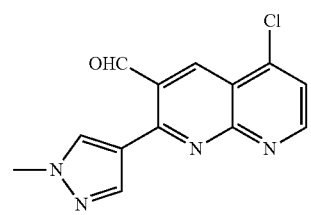

5-Chloro-2-(1-methyl-1H-pyrazol-4-yl)-1,8-naphthyridine-3-carbaldehyde

To a solution of the product from the previous step (210 mg, 0.759 mmol) in CH$_2$Cl$_2$ (10 mL) at 0° C. was added Dess-Martin Periodinane (966 mg, 2.28 mmol), and the resulting mixture was stirred at 20° C. for 10 min. The mixture was treated with sat. aq. Na$_2$S$_2$O$_3$ (10 mL), and the layers were separated. The aqueous layer was extracted with CH$_2$Cl$_2$ (3×10 mL), and the combined organic layers were sequentially washed with sat. aq. NaHCO$_3$ and sat. aq. NaCl, dried over MgSO$_4$, filtered and concentrated under reduced pressure. The residue was purified by SiO$_2$ gel chromatography (0% to 5% MeOH in CH$_2$Cl$_2$) to give the title compound as an off-white solid (188 mg, 91%). MS (ES$^+$) C$_{13}$H$_9$ClN$_4$O requires: 272, found: 273 [M+H]$^+$.

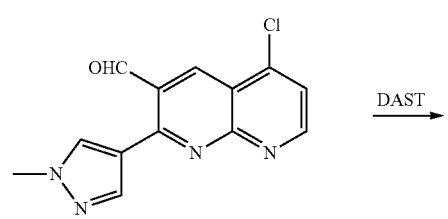

DAST

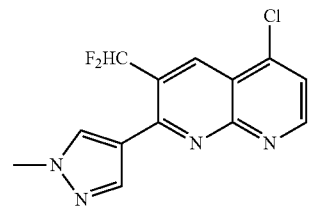

5-Chloro-3-(difluoromethyl)-2-(1-methyl-1H-pyrazol-4-yl)-1,8-naphthyridine

To a solution of the product from the previous step (185 mg, 0.678 mmol) in CH$_2$Cl$_2$ (10 mL) was added DAST (0.090 mL, 0.678 mmol), and the resulting mixture was stirred at 20° C. for 2 h. The mixture was treated with sat. aq. NaHCO$_3$(10 mL), and the layers were separated. The aqueous layer was extracted with CH$_2$Cl$_2$ (3×10 mL), and the combined organic layers were washed with sat. aq. NaCl, dried over MgSO$_4$, filtered and concentrated under reduced pressure. The residue was purified by SiO$_2$ gel chromatography (0% to 5% MeOH in CH$_2$Cl$_2$) to give the title compound as a white solid (127 mg, 64%). MS (ES$^+$) C$_{13}$H$_9$ClF$_2$N$_4$ requires: 294, found: 295 [M+H]$^+$.

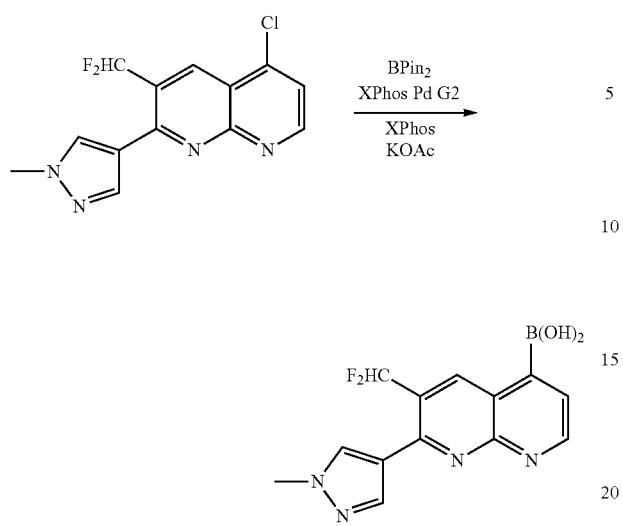

(6-(Difluoromethyl)-7-(1-methyl-1H-pyrazol-4-yl)-
1,8-naphthyridin-4-yl)boronic acid To a degassed solution of the product from the previous step (60 mg, 0.20 mmol) in 1,4-dioxane (2 mL) were added BPin$_2$ (62.0 mg, 0.244 mmol), KOAc (59.9 mg, 0.611 mmol), XPhos Pd G2 (16.02 mg, 0.020 mmol), and XPhos (9.71 mg, 0.020 mmol), and the resulting mixture was stirred at 100° C. for 4 h then concentrated under reduced pressure. The residue was purified by mass-triggered preparative HPLC (Mobile layer: A=0.1% TFA/H$_2$O, B=0.1% TFA/MeCN; Gradient: B=0% to 30%; 12 min; Column: C18) to give the title compound as a pale yellow solid (13 mg, 21%). MS (ES$^+$) C$_{13}$H$_{11}$BF$_2$N$_4$O$_2$ requires: 304, found: 305 [M+H]$^+$.

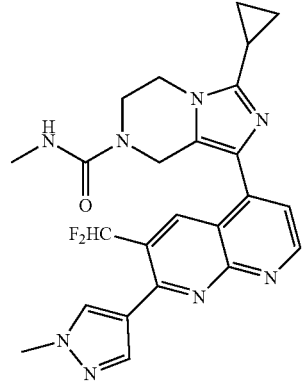

3-Cyclopropyl-1-(6-(difluoromethyl)-7-(1-methyl-1H-pyrazol-4-yl)-1,8-naphthyridin-4-yl)-N-methyl-5,6-dihydroimidazo[1,5-a]pyrazine-7(8H)-carboxamide A degassed solution of Intermediate "B" (12 mg, 0.035 mmol), the product from the previous step (10.54 mg, 0.035 mmol), PdCl$_2$(dppf)-CH$_2$Cl$_2$ (2.83 mg, 3.47 µmol) and 2.0 M aq. K$_2$CO$_3$ (0.035 mL, 0.070 mmol) in DMF (0.5 mL) was stirred at 90° C. for 1 h, then concentrated under reduced pressure. The residue was purified by SiO$_2$ gel chromatography (0% to 5% MeOH in CH$_2$Cl$_2$) to give the title compound as a yellow solid (6 mg, 36%).

MS (ES$^+$) C$_{24}$H$_{24}$F$_2$N$_8$O requires: 478, found: 479 [M+H]$^+$.

$^1$H NMR (CD$_3$OD) δ 9.48 (s, 1H), 9.06 (d, J=4.6 Hz, 1H), 8.27 (s, 1H), 8.14 (s, 1H), 7.51 (d, J=4.7 Hz, 1H), 7.19 (t, J=54 Hz, 1H), 4.80 (s, 2H), 4.24 (t, J=5.5 Hz, 2H), 4.02 (s, 3H), 3.94 (t, J=5.5 Hz, 2H), 2.72 (s, 3H), 2.09-2.03 (m, 1H), 1.12-1.04 (m, 4H).

Example 37

3-Cyclopropyl-N-methyl-1-(2-(1-methyl-1H-pyrazol-4-yl)quinazolin-5-yl)-5,6-dihydroimidazo[1,5-a]pyrazine-7(8H)-carboxamide

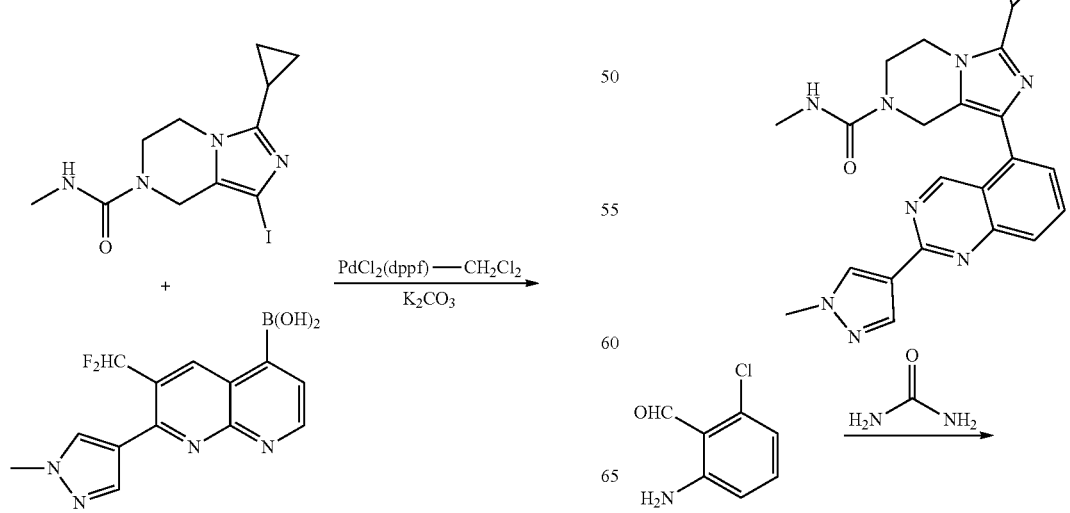

5-Chloroquinazolin-2(1H)-one

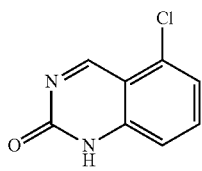

A mixture of 2-amino-6-chlorobenzaldehyde (300 mg, 1.93 mmol) and urea (1158 mg, 19.28 mmol) was stirred at 180° C. for 2 h, then allowed to cool to RT. The mixture was treated with water (20 mL), sonicated, and filtered to give the crude title compound as an off-white solid (315 mg, 90%), which was used without further purification. MS (ES$^+$) C$_8$H$_5$ClN$_2$O requires: 180; found: 181 [M+H]$^+$.

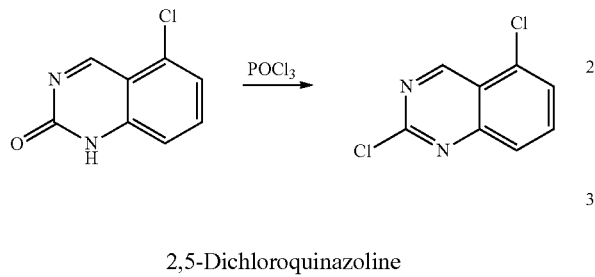

2,5-Dichloroquinazoline

A mixture of the product from the previous step (310 mg, 1.72 mmol) and POCl$_3$ (3200 µl, 34.3 mmol) was stirred at 110° C. for 3 h, then concentrated under reduced pressure. The mixture was treated with ice, and the mixture was neutralized with 10% NaOH solution to pH 7. Solid was isolated by filtration to give the title compound as a pale yellow solid (298 mg, 87%), which was used without further purification. MS (ES$^+$) C$_8$H$_4$Cl$_2$N$_2$ requires: 198, found: 199 [M+H]$^+$.

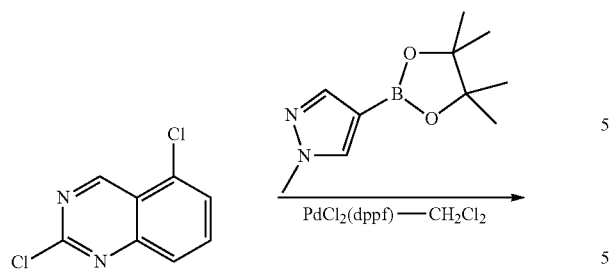

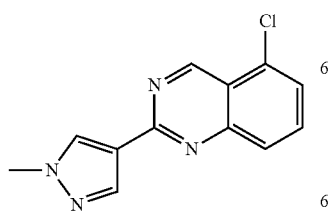

5-Chloro-2-(1-methyl-1H-pyrazol-4-yl)quinazoline

A degassed solution of the product from the previous step (295 mg, 1.48 mmol), 1-methyl-4-(4,4,5,5-tetramethyl-1,3,2-dioxaborolan-2-yl)-1H-pyrazole (308 mg, 1.48 mmol), PdCl$_2$(dppf)-CH$_2$Cl$_2$ (60.5 mg, 0.074 mmol), and K$_2$CO$_3$ (1.482 mL, 2.96 mmol) in DMF (5 mL) was stirred at 90° C. for 1 h, then concentrated under reduced pressure. The residue was treated with H$_2$O (30 mL) and the mixture was extracted with EtOAc (3×20 mL). The combined organic layers were washed with sat. aq. NaCl, dried over MgSO$_4$, filtered and concentrated under reduced pressure. The residue was purified by SiO$_2$ gel chromatography (0% to 5% MeOH in CH$_2$Cl$_2$) to give the title compound as an off-white solid (186 mg, 51%). MS (ES$^+$) C$_{12}$H$_9$ClN$_4$ requires: 244, found: 245 [M+H]$^+$.

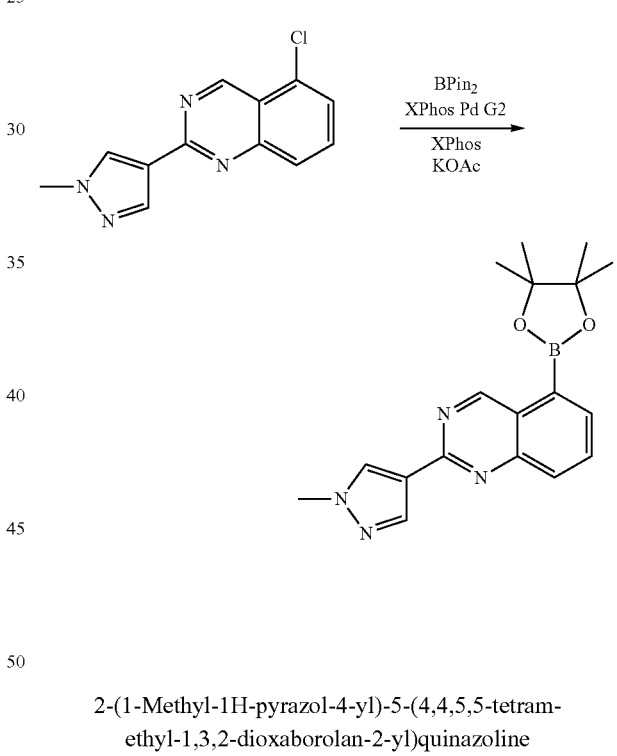

2-(1-Methyl-1H-pyrazol-4-yl)-5-(4,4,5,5-tetramethyl-1,3,2-dioxaborolan-2-yl)quinazoline To a degassed solution of the product from the previous step (180 mg, 0.736 mmol) in 1,4-dioxane (5 mL) were added BPin$_2$ (224 mg, 0.883 mmol), KOAc (217 mg, 2.21 mmol), Xphos Pd G2 (57.9 mg, 0.074 mmol), and XPhos (35.1 mg, 0.074 mmol), and the resulting mixture was stirred at 100° C. for 4 h then concentrated under reduced pressure. The residue was purified by SiO$_2$ gel chromatography (0% to 5% MeOH in CH$_2$Cl$_2$) to give the title compound as an off-white solid (96 mg, 39%). MS (ES$^+$) C$_{18}$H$_{21}$BN$_4$O$_2$ requires: 336, found: 337 [M+H]$^+$.

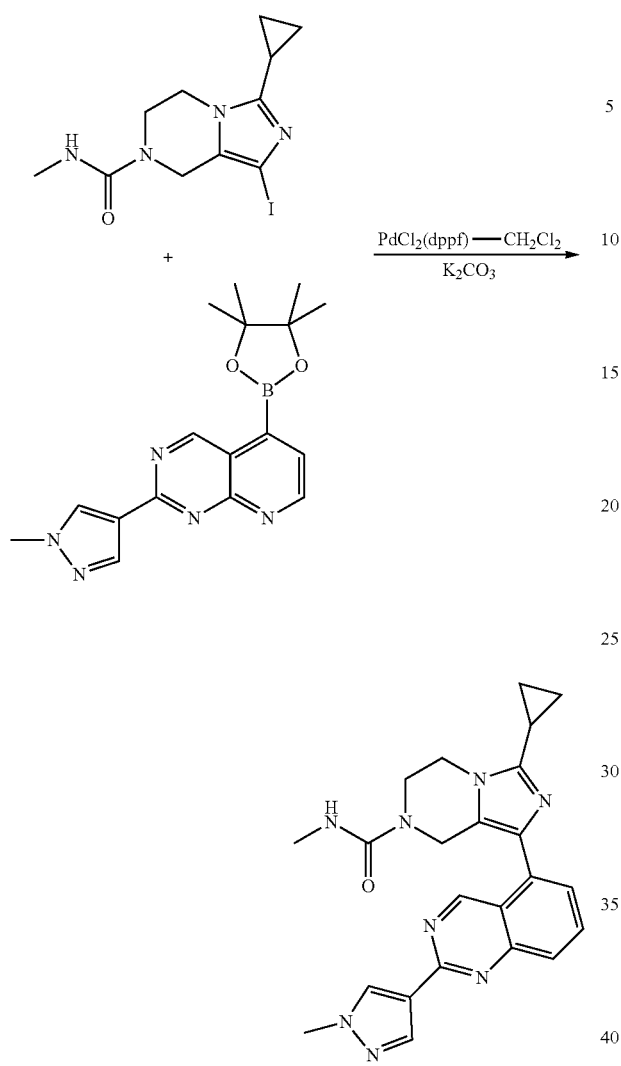

3-Cyclopropyl-N-methyl-1-(2-(1-methyl-1H-pyrazol-4-yl)quinazolin-5-yl)-5,6-dihydroimidazo[1,5-a]pyrazine-7(8H)-carboxamide A degassed solution of Intermediate "B" (30 mg, 0.087 mmol), the product from the previous step (29.1 mg, 0.087 mmol), PdCl$_2$(dppf)-CH$_2$Cl$_2$ (7.08 mg, 8.67 µmol) and 2.0 M aq. K$_2$CO$_3$ (0.087 mL, 0.174 mmol) in DMF (0.5 mL) was stirred at 90° C. for 1 h, then concentrated under reduced pressure. The residue was purified by SiO$_2$ gel chromatography (0% to 5% MeOH in CH$_2$Cl$_2$) to give the title compound as a yellow solid (17 mg, 46%). MS (ES$^+$) C$_{23}$H$_{24}$N$_8$O requires: 428, found: 429 [M+H]$^+$. $^1$H NMR (CD$_3$OD) δ 9.74 (s, 1H), 8.39 (s, 1H), 8.25 (s, 1H), 7.96 (appar t, J=8.4 Hz, 1H), 7.90 (d, J=8.4 Hz, 1H), 7.54 (d, J=7.0 Hz, 1H), 4.68 (s, 2H), 4.23 (t, J=5.5 Hz, 2H), 4.00 (s, 3H), 3.93 (t, J=5.5 Hz, 2H), 2.70 (s, 3H), 2.07-2.01 (m, 1H), 1.08-1.01 (m, 4H).

Example 38

3-Cyclopropyl-N-methyl-1-(6-(1-methyl-1H-pyrazol-4-yl)-1H-pyrrolo[3,2-c]pyridin-3-yl)-5,6-dihydroimidazo[1,5-a]pyrazine-7(8H)-carboxamide

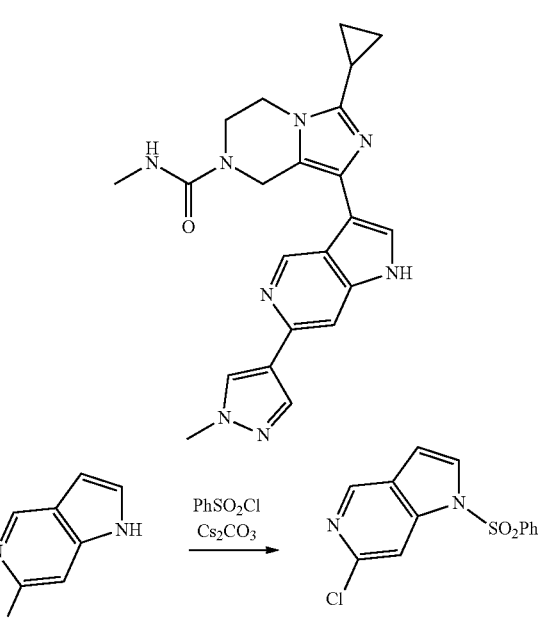

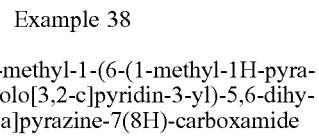

6-Chloro-1-(phenylsulfonyl)-1H-pyrrolo[3,2-c]pyridine

To a solution of 6-chloro-1H-pyrrolo[3,2-c]pyridine (153 mg, 1.00 mmol) in DMF (5 mL) were added PhSO$_2$Cl (195 mg, 1.10 mmol) and Cs$_2$CO$_3$ (653 mg, 2.01 mmol), and the resulting mixture was stirred at 60° C. for 3 h then concentrated under reduced pressure. The residue was treated with H$_2$O (20 mL), and the mixture was extracted with EtOAc (3×10 mL). The combined organic layers were washed with sat. aq. NaCl, dried over MgSO$_4$, filtered and concentrated under reduced pressure to give the crude title compound as a yellow solid (290 g, 99%), which was used without further purification. MS (ES$^+$) C$_{13}$H$_9$ClN$_2$O$_2$S requires: 292, found: 293 [M+H]$^+$.

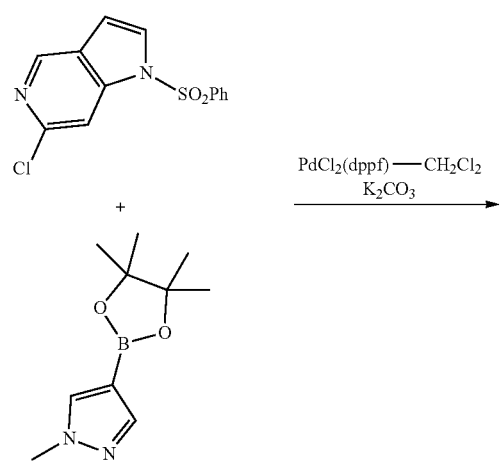

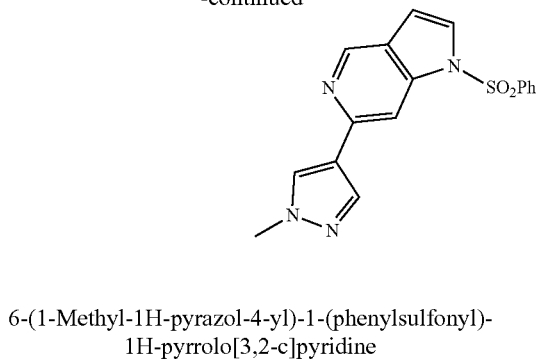

6-(1-Methyl-1H-pyrazol-4-yl)-1-(phenylsulfonyl)-1H-pyrrolo[3,2-c]pyridine

A degassed mixture of the product from the previous step (290 mg, 0.991 mmol), 1-methyl-4-(4,4,5,5-tetramethyl-1,3,2-dioxaborolan-2-yl)-1H-pyrazole (247 mg, 1.19 mmol), PdCl$_2$(dppf)-CH$_2$Cl$_2$ (40.5 mg, 0.050 mmol) and 2.0 M aq. K$_2$CO$_3$ (0.991 mL, 1.98 mmol) in 1,4-dioxane (5 mL) was stirred at 80° C. for 16 h, then concentrated under reduced pressure. The residue was treated with H$_2$O (20 mL), and the mixture was extracted with EtOAc (3×10 mL). The combined organic layers were washed with sat. aq. NaCl, dried over MgSO$_4$, filtered and concentrated under reduced pressure. The residue was purified by SiO$_2$ gel chromatography (0% to 5% MeOH in CH$_2$Cl$_2$) to give the title compound as a yellow liquid (285 mg, 85%). MS (ES$^+$) C$_{17}$H$_{14}$N$_4$O$_2$S requires: 338, found: 339 [M+H]$^+$.

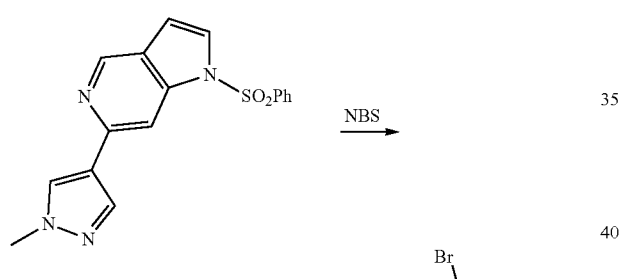

3-Bromo-6-(1-methyl-1H-pyrazol-4-yl)-1-(phenylsulfonyl)-1H-pyrrolo[3,2-c]pyridine To a solution of the product from the previous step (285 mg, 0.842 mmol) in DMF (5 mL) was added NBS (165 mg, 0.926 mmol), and the resulting mixture was stirred at 20° C. for 3 h. The mixture was treated with H$_2$O (20 mL) and extracted with EtOAc (3×10 mL). The combined organic layers were washed with sat. aq. NaCl, dried over MgSO$_4$, filtered and concentrated under reduced pressure. The residue was purified by SiO$_2$ gel chromatography (0% to 5% MeOH in CH$_2$Cl$_2$) to give the title compound as a yellow solid (198 mg, 56%). MS (ES$^+$) C$_{17}$H$_{13}$BrN$_4$O$_2$S requires: 416, found: 417 [M+H]$^+$.

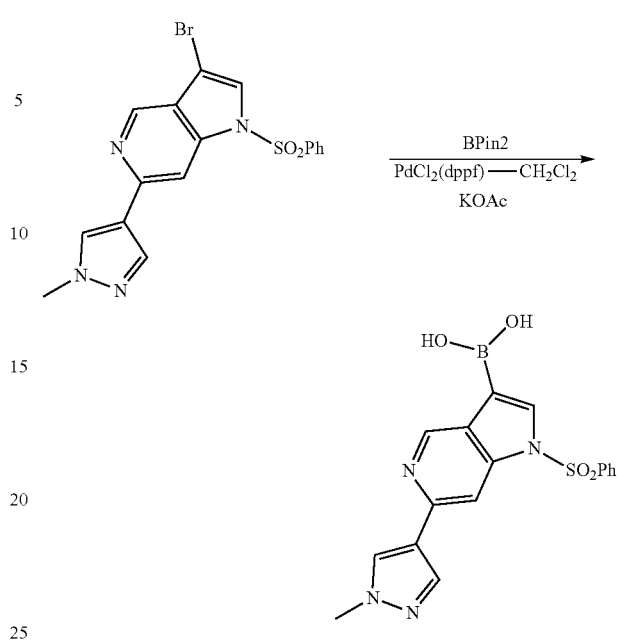

(6-(1-Methyl-1H-pyrazol-4-yl)-1-(phenylsulfonyl)-1H-pyrrolo[3,2-c]pyridin-3-yl)boronic acid To a degassed solution of the product from the previous step (198 mg, 0.475 mmol) in 1,4-dioxane (5 mL) were added BPin$_2$ (145 mg, 0.569 mmol), KOAc (140 mg, 1.42 mmol) and PdCl$_2$(dppf)-CH$_2$Cl$_2$ (38.7 mg, 0.047 mmol), and the resulting mixture was stirred at 100° C. for 5 h then concentrated under reduced pressure. The residue was purified by SiO$_2$ gel chromatography (0% to 5% MeOH in CH$_2$Cl$_2$) to give the title compound as an off-white solid (133 mg, 73%). MS (ES$^+$) C$_{17}$H$_{15}$BN$_4$O$_4$S requires: 382, found: 383 [M+H]$^+$.

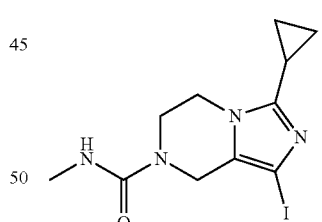

+

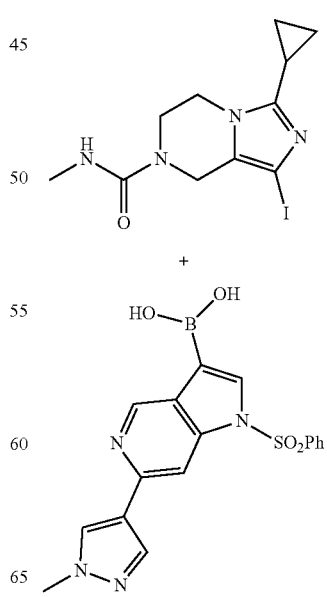

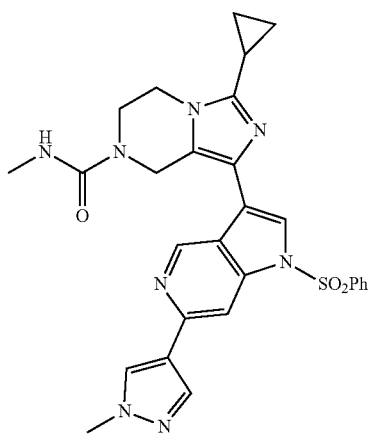

3-Cyclopropyl-N-methyl-1-(6-(1-methyl-1H-pyra-zol-4-yl)-1-(phenylsulfonyl)-1H-pyrrolo[3,2-c]pyri-din-3-yl)-5,6-dihydroimidazo[1,5-a]pyrazine-7(8H)-carboxamide A degassed mixture of Intermediate "B" (20 mg, 0.058 mmol), the product from the previous step (22.08 mg, 0.058 mmol), PdCl₂(dppf)-CH₂Cl₂ (4.72 mg, 5.78 μmol) and 2.0 M aq. K₂CO₃ (0.058 mL, 0.116 mmol) in DMF (0.5 mL) was stirred at 90° C. for 1 h, then concentrated under reduced pressure. The residue was purified by SiO₂ gel chromatography (0% to 5% MeOH in CH₂Cl₂) to give the title compound as a yellow solid (17 mg, 53%). MS (ES⁺) C₂₈H₂₈N₈O₃S requires: 556, found: 557 [M+H]⁺.

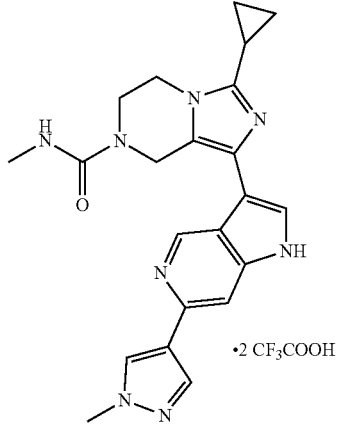

3-Cyclopropyl-N-methyl-1-(6-(1-methyl-1H-pyra-zol-4-yl)-1H-pyrrolo[3,2-c]pyridin-3-yl)-5,6-dihy-droimidazo[1,5-a]pyrazine-7(8H)-carboxamide bis (2,2,2-trifluoroacetate)

To a solution of the product from the previous step (17 mg, 0.031 mmol) in THF (0.5 mL) and H₂O (0.5 mL) was added NaOH (12.22 mg, 0.305 mmol), and the resulting mixture was stirred at 60° C. for 2 h then concentrated under reduced pressure. The residue was purified by reverse layer preparative HPLC (Mobile layer: A=0.1% TFA/H₂O, B=0.1% TFA/MeCN; Gradient: B=0% to 30%; 12 min; Column: C18) to give the title compound as a pale yellow solid (6 mg, 31%).

MS (ES⁺) C₂₂H₂₄N₈O requires: 416, found: 417 [M+H]⁺.

¹H NMR (CD₃OD) δ 9.14 (s, 1H), 8.41 (s, 1H), 8.16 (s, 1H), 8.15 (s, 1H), 8.11 (s, 1H), 4.74 (s, 2H), 4.37 (t, J=5.5 Hz, 2H), 4.03 (s, 3H), 4.01 (t, J=5.5 Hz, 2H), 2.74 (s, 3H), 2.32-2.27 (m, 1H), 1.38-1.34 (m, 2H), 1.27-1.23 (m, 2H).

Example 39

3-Cyclopropyl-N-methyl-1-(6-(1-methyl-1H-pyra-zol-4-yl)thieno[3,2-c]pyridin-3-yl)-5,6-dihydroimi-dazo[1,5-a]pyrazine-7(8H)-carboxamide

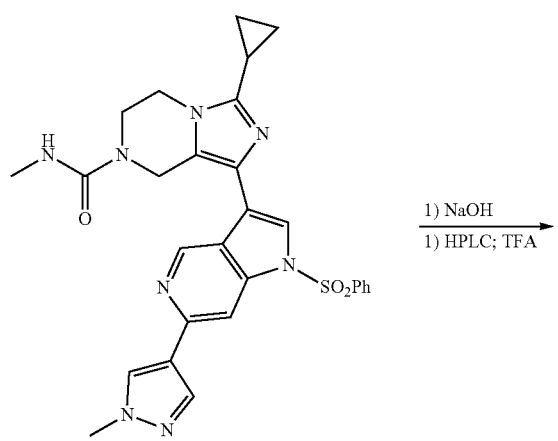 1) NaOH
1) HPLC; TFA

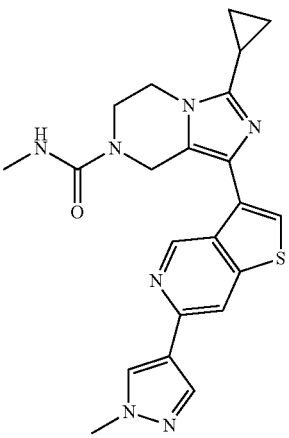

-continued

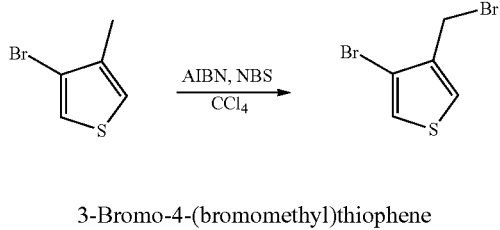

3-Bromo-4-(bromomethyl)thiophene

To a solution of 3-bromo-4-methylthiophene (1000 mg, 5.65 mmol) in CCl₄ (15 mL) were added NBS (1005 mg, 5.65 mmol) and AIBN (46.4 mg, 0.282 mmol), and the resulting mixture was stirred at 80° C. for 2 h then allowed to cool to RT. The mixture was filtered, and the filtrate was concentrated under reduced pressure. The residue was purified by SiO₂ gel chromatography (100% hexanes) to give the title compound as a colorless liquid (922 mg, 64%).

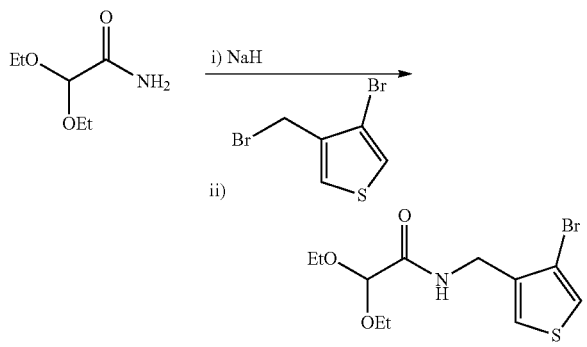

N-((4-Bromothiophen-3-yl)methyl)-2,2-diethoxyacetamide

To a suspension of NaH (60% in mineral oil, 173 mg, 4.31 mmol) in THF (15 mL) was added 2,2-diethoxyacetamide (635 mg, 4.31 mmol) and the mixture was stirred at 20° C. for 5 min. The mixture was then treated with the product from the previous step (920 mg, 3.59 mmol) and NaI (539 mg, 3.59 mmol), and stirred at 70° C. for 2 h then concentrated under reduced pressure. The residue was treated with H₂O (30 mL) and the layers were separated. The aqueous layer was extracted with EtOAc (3×10 mL), and the combined organic layers were washed with sat. aq. NaCl, dried over MgSO₄, filtered and concentrated under reduced pressure. The residue was purified by SiO₂ gel chromatography (0% to 60% EtOAc in hexanes) to give the title compound as a colorless liquid (418 mg, 36%). MS (ES⁺) $C_{11}H_{16}BrNO_3S$ requires: 321, found: 344 [M+Na]⁺.

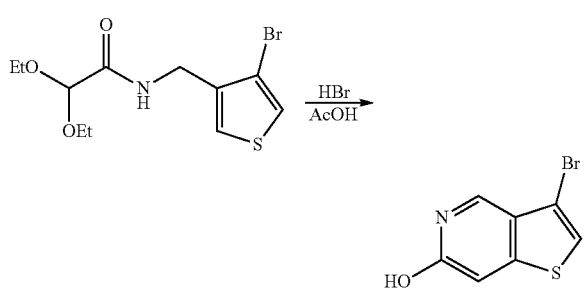

3-Bromothieno[3,2-c]pyridin-6-ol

To a suspension of the product from the previous step (415 mg, 1.29 mmol) in AcOH (3 mL) was added 33% HBr in AcOH (1 mL), and the resulting mixture was stirred at 80° C. for 1 h then allowed to cool to RT. Solid was isolated by Büchner filtration to give the title compound as an off-white solid (115 mg, 39%). MS (ES⁺) $C_7H_4BrNOS$ requires: 229, found: 230 [M+H]⁺.

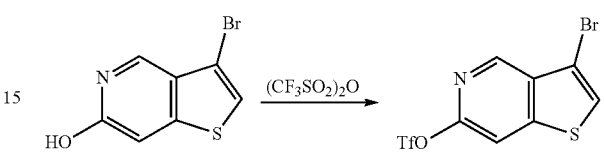

3-Bromothieno[3,2-c]pyridin-6-yl trifluoromethanesulfonate

To a solution of the product from the previous step (115 mg, 0.500 mmol) in CH₂Cl₂ (3 mL) and pyridine (1 mL) at 0° C. was added (CF₃SO₂)₂O (0.127 mL, 0.750 mmol), and the resulting mixture was stirred at 20° C. for 1 h then concentrated under reduced pressure. The residue was treated with H₂O (10 mL), the mixture was extracted with EtOAc (3×5 mL), and the combined organic layers were washed with sat. aq. NaCl, dried over MgSO₄, filtered and concentrated under reduced pressure. The residue was purified by SiO₂ gel chromatography (0% to 10% EtOAc in hexanes) to give the title compound as a colorless liquid (62 mg, 34%). MS (ES⁺) $C_8H_3BrF_3NO_3S_2$ requires: 361, found: 362 [M+H]⁺.

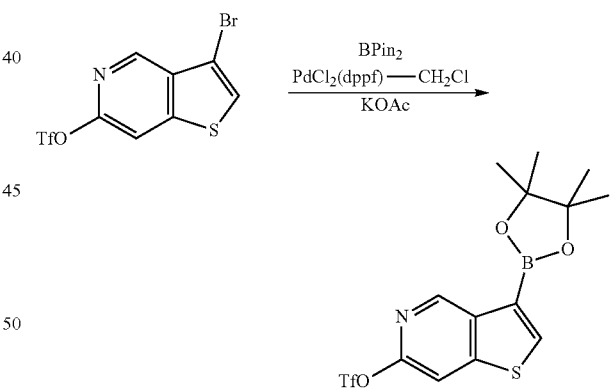

3-(4,4,5,5-Tetramethyl-1,3,2-dioxaborolan-2-yl) thieno[3,2-c]pyridin-6-yl trifluoromethanesulfonate To a degassed solution of the product from the previous step (60 mg, 0.17 mmol) in 1,4-dioxane (1 mL) were added BPin₂ (50.5 mg, 0.199 mmol), KOAc (48.8 mg, 0.497 mmol) and PdCl₂(dppf)-CH₂Cl₂ (13.53 mg, 0.017 mmol), and the mixture was stirred at 100° C. for 2 h, filtered, and concentrated under reduced pressure to give the crude title compound (50 mg, 85%), which was used in the next step without further purification. MS (ES⁺) $C_{14}H_{15}BF_3NO_5S_2$ requires: 409, found: 410 [M+H]⁺.

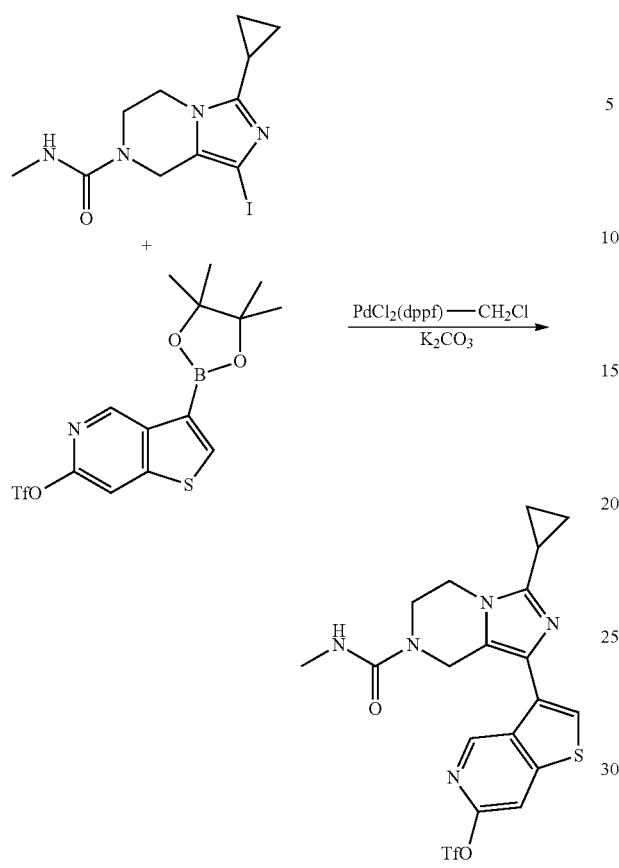

3-(3-Cyclopropyl-7-(methylcarbamoyl)-5,6,7,8-tetrahydroimidazo[1,5-a]pyrazin-1-yl)thieno[3,2-c]pyridin-6-yl trifluoromethanesulfonate A degassed mixture of Intermediate "B" (50 mg, 0.14 mmol), the product from the previous step (59.1 mg, 0.144 mmol), PdCl$_2$(dppf)-CH$_2$Cl$_2$ (11.80 mg, 0.014 mmol) and 2.0 M aq. K$_2$CO$_3$ (0.144 mL, 0.288 mmol) in DMF (0.5 mL) was stirred at 90° C. for 1 h, then concentrated under reduced pressure. The residue was purified by SiO$_2$ gel chromatography (0% to 5% MeOH in CH$_2$Cl$_2$) to give the title compound as a yellow solid (11 mg, 15%). MS (ES$^+$) C$_{19}$H$_{18}$F$_3$N$_5$O$_4$S$_2$ requires: 501, found: 502 [M+H]$^+$.

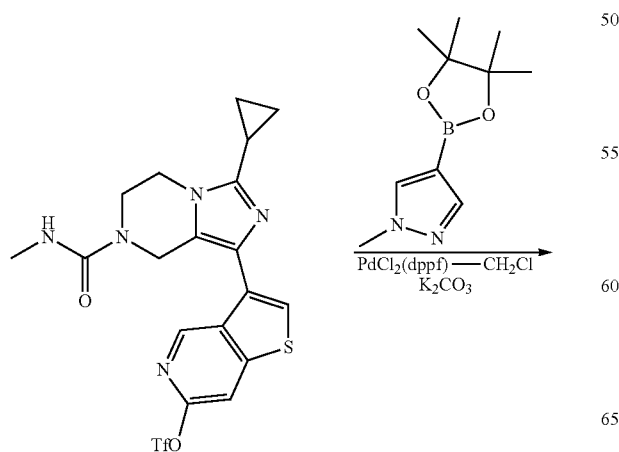

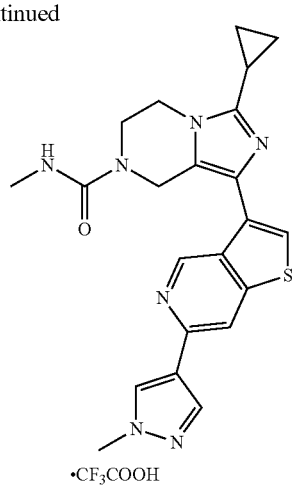

3-Cyclopropyl-N-methyl-1-(6-(1-methyl-1H-pyrazol-4-yl)thieno[3,2-c]pyridin-3-yl)-5,6-dihydroimidazo[1,5-a]pyrazine-7(8H)-carboxamide 2,2,2-trifluoroacetate A degassed mixture of the product from the previous step (5 mg, 10 mol), 1-methyl-4-(4,4,5,5-tetramethyl-1,3,2-dioxaborolan-2-yl)-1H-pyrazole (2.489 mg, 0.012 mmol), PdCl$_2$(dppf)-CH$_2$Cl$_2$ (0.814 mg, 0.997 μmol) and 2.0 M aq. K$_2$CO$_3$ (9.97 μl, 0.020 mmol) in DMF (0.5 mL) was stirred at 90° C. for 1 h, then concentrated under reduced pressure. The residue was purified by mass-triggered preparative HPLC (Mobile layer: A=0.1% TFA/H$_2$O, B=0.1% TFA/MeCN; Gradient: B=10% to 40%; 12 min; Column: C18) to give the title compound as a white solid (1 mg, 18%).

MS (ES$^+$) C$_{22}$H$_{23}$N$_7$OS requires: 433, found: 434 [M+H]$^+$.

$^1$H NMR (CD$_3$OD) δ 9.44 (s, 1H), 8.21 (s, 1H), 8.17 (s, 1H), 8.06 (s, 1H), 7.49 (s, 1H), 4.74 (s, 2H), 4.19 (t, J=5.5 Hz, 2H), 3.96 (s, 3H), 3.91 (t, J=5.5 Hz, 2H), 2.74 (s, 3H), 2.04-1.97 (m, 1H), 1.07-1.01 (m, 4H).

Example 40

3-Cyclopropyl-1-(6-(difluoromethyl)-7-(1-methyl-1H-pyrazol-4-yl)isoquinolin-4-yl)-N-methyl-5,6-dihydroimidazo[1,5-a]pyrazine-7(8H)-carboxamide

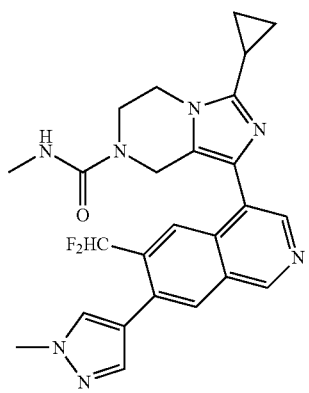

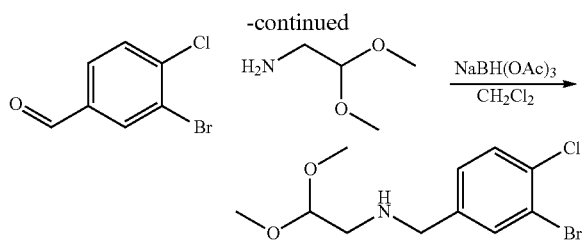

N-(3-Bromo-4-chlorobenzyl)-2,2-dimethoxyethan-1-amine

To a solution of 3-bromo-4-chlorobenzaldehyde (1.2 g, 5.5 mmol) in CH$_2$Cl$_2$ (10 ml) were added 2,2-dimethoxyethan-1-amine (1.725 g, 16.40 mmol) and NaBH(OAc)$_3$ (3.48 g, 16.4 mmol), and the resulting mixture was stirred at 20° C. for 16 h. The mixture was washed with sat. aq. NaHCO$_3$ (20 mL) and the aqueous layer was extracted with CH$_2$Cl$_2$ (3×20 mL). The combined organic layers were washed with sat. aq. NaCl, dried over MgSO$_4$, filtered and concentrated under reduced pressure. The residue was purified by SiO$_2$ gel chromatography (0% to 5% MeOH in CH$_2$Cl$_2$) to give the title compound as a colorless liquid (1.44 g, 85%). MS (ES$^+$) C$_{11}$H$_{15}$BrClNO$_2$ requires: 307, found: 308 [M+H]$^+$.

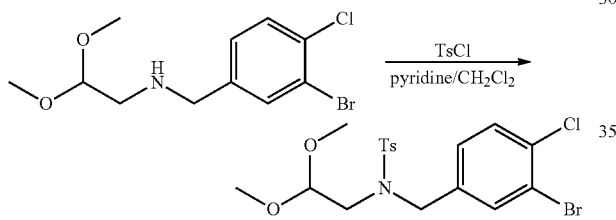

N-(3-Bromo-4-chlorobenzyl)-N-(2,2-dimethoxyethyl)-4-methylbenzenesulfonamide To a solution of the product from the previous step (1.44 g, 4.67 mmol) in CH$_2$Cl$_2$ (20 mL) and pyridine (10 mL) was added TsCl (1.334 g, 7.00 mmol), and the resulting mixture was stirred at 20° C. for 4 h, then concentrated under reduced pressure. The residue was treated with H$_2$O (50 mL), and the mixture was extracted with CH$_2$Cl$_2$ (3×30 mL). The combined organic layers were washed with sat. aq. NaCl, dried over MgSO$_4$, filtered and concentrated under reduced pressure. The residue was purified by SiO$_2$ gel chromatography (0% to 15% EtOAc in hexanes) to give the title compound as a white solid (2.09 g, 97%). MS (ES$^+$) C$_{18}$H$_{21}$BrClNO$_4$S requires: 461, found: 484 [M+Na]$^+$.

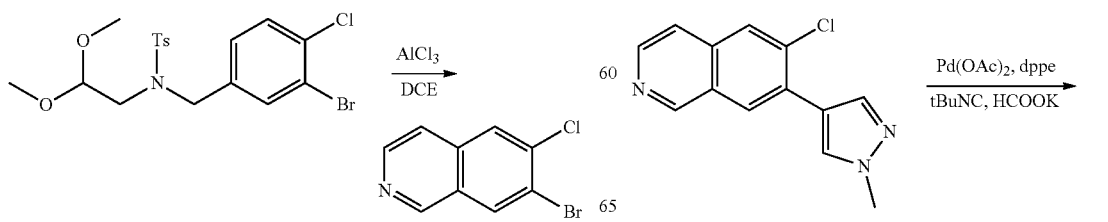

7-Bromo-6-chloroisoquinoline

To a suspension of AlCl$_3$ (2.88 g, 21.6 mmol) in 1,2-dichloroethane (10 mL) at 0° C. was added the product from the previous step (2.00 g, 4.32 mmol) in 1,2-dichloroethane (10 mL), and the resulting mixture was stirred at 20° C. for 16 h. The mixture was poured into ice water and the layers were separated. The aqueous layer was extracted with CH$_2$Cl$_2$ (3×30 mL), and the combined organic layers were washed with sat. aq. NaCl, dried over MgSO$_4$, filtered and concentrated under reduced pressure. The residue was purified by SiO$_2$ gel chromatography (0% to 5% MeOH in hexanes) to give the title compound as a pale yellow solid (745 mg, 71%). MS (ES$^+$) C$_9$H$_5$BrClN requires: 241, found: 242 [M+H]$^+$.

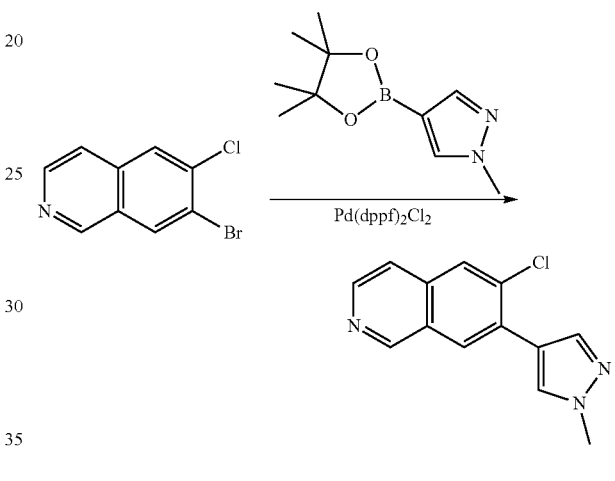

6-Chloro-7-(1-methyl-1-pyrazol-4-yl)isoquinoline

A degassed solution of the product from the previous step (744 mg, 3.07 mmol), 1-methyl-4-(4,4,5,5-tetramethyl-1,3,2-dioxaborolan-2-yl)-1H-pyrazole (670 mg, 3.22 mmol), PdCl$_2$(dppf)-CH$_2$Cl$_2$ (125 mg, 0.153 mmol) and 2.0 M aq. K$_2$CO$_3$ (3.07 ml, 6.14 mmol) in 1,4-dioxane (10 mL) was heated to 90° C. and stirred for 2 h, then concentrated under reduced pressure. The residue was treated with H$_2$O (50 mL), and the mixture was extracted with EtOAc (3×30 mL). The combined organic layers were washed with sat aq. NaCl, dried over MgSO$_4$, filtered and concentrated under reduced pressure. The residue was purified by SiO$_2$ gel chromatography (0% to 5% MeOH in CH$_2$Cl$_2$) to give the title compound as a brown liquid (675 mg, 90%). MS (ES$^+$) C$_{13}$H$_{10}$ClN$_3$ requires: 243, found: 244 [M+H]$^+$.

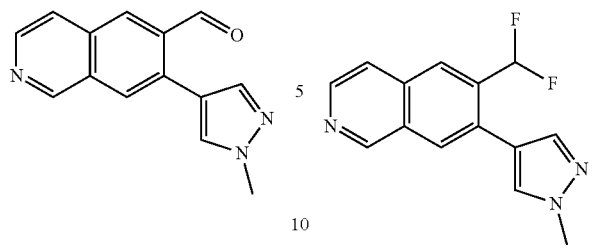

7-(1-Methyl-1H-pyrazol-4-yl)isoquinoline-6-carbaldehyde

To a solution of the product from the previous step (700 mg, 2.87 mmol) in DMSO (5 mL) were Pd(OAc)$_2$ (32.2 mg, 0.144 mmol), dppe (114 mg, 0.287 mmol), 2-isocyano-2-methylpropane (0.357 ml, 3.16 mmol) and potassium formate (483 mg, 5.74 mmol), and the resulting mixture was stirred at 120° C. for 5 h. The mixture was treated with sat. aq. NaHCO$_3$ (30 mL), and the layers were separated. The aqueous layer was extracted with CH$_2$Cl$_2$ (3×20 mL), and the combined organic layers were washed with sat. aq. NaCl, dried over MgSO$_4$, filtered and concentrated under reduced pressure. The residue was purified by SiO$_2$ gel chromatography (0% to 5% MeOH in CH$_2$Cl$_2$) to give the title compound as a yellow solid (552 mg, 81%). MS (ES$^+$) C$_{14}$H$_{11}$N$_3$O requires: 237, found: 238 [M+H]$^+$.

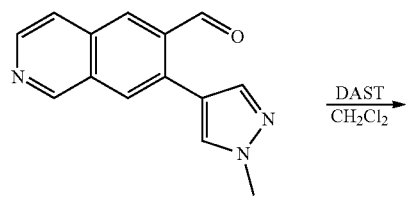

6-(Difluoromethyl)-7-(1-methyl-1H-pyrazol-4-yl)isoquinoline

To a solution of the product from the previous step (550 mg, 2.32 mmol) in CH$_2$Cl$_2$ (10 ml) at 0° C. was added DAST (0.919 ml, 6.95 mmol), and the resulting mixture was stirred at 20° C. for 16 h. The mixture was treated with sat. aq. NaHCO$_3$(30 mL), and the layers were separated. The aqueous layer was extracted with CH$_2$Cl$_2$ (3×20 mL), and the combined organic layers were washed with sat. aq. NaCl, dried over MgSO$_4$, filtered and concentrated under reduced pressure. The residue was purified by SiO$_2$ gel chromatography (0% to 5% MeOH in CH$_2$Cl$_2$) to give the title compound as a yellow liquid (144 mg, 24%). MS (ES$^+$) C$_{14}$H$_{11}$F$_2$N$_3$ requires: 259, found: 260 [M+H]$^+$.

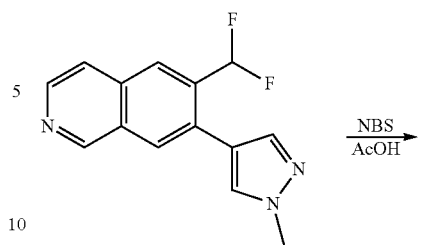

4-Bromo-6-(difluoromethyl)-7-(1-methyl-1H-pyrazol-4-yl)isoquinoline

To a solution of the product from the previous step (140 mg, 0.540 mmol) in AcOH (5 ml) was added NBS (144 mg, 0.810 mmol), and the resulting mixture was stirred at 90° C. for 2 h then concentrated under reduced pressure. The residue was treated with sat. aq. NaHCO$_3$(20 mL) and extracted with CH$_2$Cl$_2$ (3×10 mL). The combined organic layers were washed with sat. aq. NaCl, dried over MgSO$_4$, filtered and concentrated under reduced pressure. The residue was purified by SiO$_2$ gel chromatography (0% to 3% MeOH in CH$_2$Cl$_2$) to give the title compound as a yellow liquid (60 mg, 33%). MS (ES$^+$) C$_{14}$H$_{10}$BrF$_2$N$_3$ requires: 337, found: 338 [M+H]$^+$.

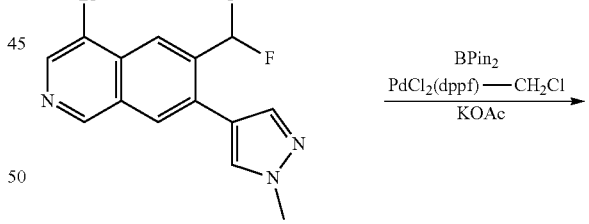

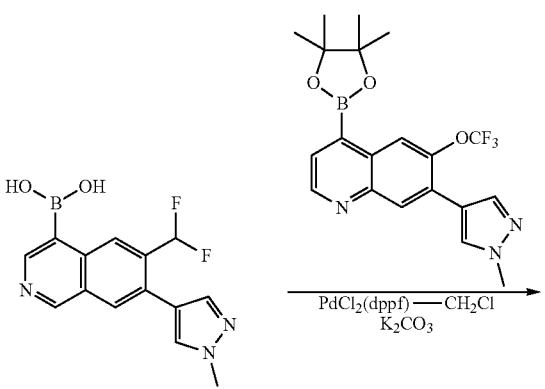

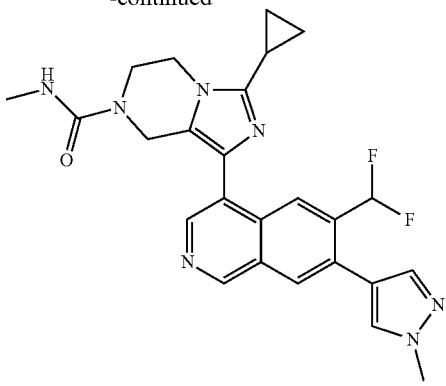

3-Cyclopropyl-1-(6-(difluoromethyl)-7-(1-methyl-1H-pyrazol-4-yl)isoquinolin-4-yl)-N-methyl-5,6-dihydroimidazo[1,5-a]pyrazine-7(8H)-carboxamide bis(2,2,2-trifluoroacetate)

To a degassed solution of the product from the previous step (16 mg, 0.047 mmol) in 1,4-dioxane (5 mL) were added BPin$_2$ (14.42 mg, 0.057 mmol), KOAc (13.93 mg, 0.142 mmol) and PdCl$_2$(dppf)-CH$_2$Cl$_2$ (3.86 mg, 4.73 mol). The mixture was stirred at 90° C. for 1 h, then filtered through CELITE® and the filtrate was concentrated under reduced pressure. To the residue was added Intermediate "B" (10 mg, 0.029 mmol), PdCl$_2$(dppf)-CH$_2$Cl$_2$ (2.359 mg, 2.89 mol), 2.0 M aq. K$_2$CO$_3$ (0.029 ml, 0.058 mmol) and DMF (0.5 ml). The mixture was degassed, stirred at 90° C. for 1 h, and concentrated under reduced pressure. The residue was purified by mass-triggered preparative HPLC (Mobile phase: A=0.1% TFA/H$_2$O, B=0.1% TFA/MeCN; Gradient: B=10% to 40%; 12 min; Column: C18) to give the title compound as a yellow solid (2 mg, 10%).

MS (ES$^+$) C$_{25}$H$_{25}$F$_2$N$_7$O requires: 477, found: 478 [M+H]$^+$.

$^1$H NMR (CD$_3$OD) δ 9.54 (s, 1H), 8.64 (s, 1H), 8.42 (s, 1H), 8.20 (s, 1H), 7.97 (s, 1H), 7.81 (s, 1H), 7.04 (t, 1H, J=54 Hz), 4.63 (s, 2H), 4.42 (t, 2H, J=5.5 Hz), 4.05-3.99 (m, 5H), 2.70 (s, 3H), 2.38-2.31 (m, 1H), 1.42-1.35 (m, 2H), 1.26-1.20 (m, 2H).

TABLE 1

Example compounds 41 to 126

| Ex | Structure | IUPAC Name | MWt/ [M + H] | Ex. Method |
|---|---|---|---|---|
| 41 | 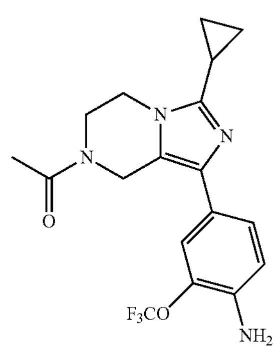 [SMILES: CC(=O)N1CCn2c(C3CC3)nc(-c3ccc(N)c(OC(F)(F)F)c3)c2C1] | 1-(1-(6-amino-5-(trifluoromethoxy)pyridin-3-yl)-3-cyclopropyl-5,6-dihydroimidazo[1,5-a]pyrazin-7(8H)-yl)ethan-1-one | 381/382 | 4 |
| 42 | 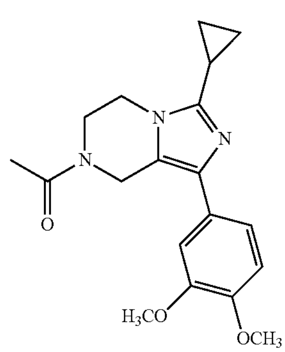 [SMILES: COc1ccc(-c2nc(C3CC3)n3c2CN(C(C)=O)CC3)cc1OC] | 1-(3-cyclopropyl-1-(3,4-dimethoxyphenyl)-5,6-dihydroimidazo[1,5-a]pyrazin-7(8H)-yl)ethan-1-one | 341/342 | 5 |

TABLE 1-continued
Example compounds 41 to 126
| Ex | Structure | IUPAC Name | MWt/ [M + H] | Ex. Method |
|---|---|---|---|---|
| 43 | 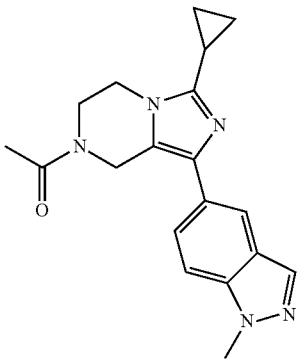 [SMILES: CC(=O)N1CCn2c(C3CC3)nc(-c3ccc4c(cnn4C)c3)c2C1] | 1-(3-cyclopropyl-1-(1-methyl-1H-indazol-5-yl)-5,6-dihydroimidazol[1,5-a]pyrazin-7(8H)-yl)ethan-1-one | 335/336 | 6 |
| 44 | 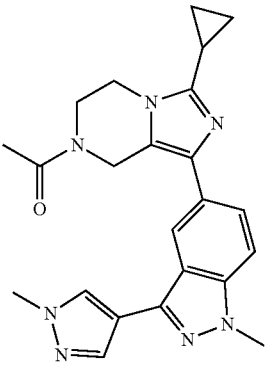 [SMILES: CC(=O)N1CCn2c(C3CC3)nc(-c3ccc4c(c3)c(-c3cnn(C)c3)nn4C)c2C1] | 1-(3-cyclopropyl-1-(1-methyl-3-(1-methyl-1H-pyrazol-4-yl)-1H-indazol-5-yl)-5,6-dihydroimidazo[1,5-a]pyrazin-7(8H)-yl)ethan-1-one | 415/416 | 7 |
| 45 | 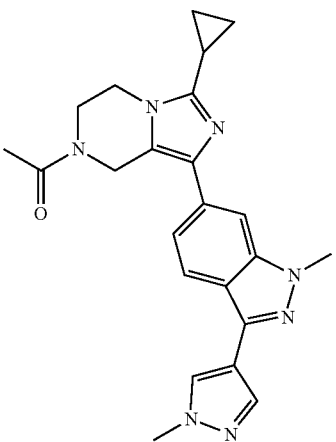 [SMILES: CC(=O)N1CCn2c(C3CC3)nc(-c3ccc4c(-c5cnn(C)c5)nn(C)c4c3)c2C1] | 1-(1-(1-methyl-3-(1-methyl-1H-pyrazol-4-yl)-1H-indazol-5-yl)-3-(tetrahydrofuran-3-yl)-5,6-dihydroimidazo[1,5-a]pyrazin-7(8H)-yl)ethan-1-one | 445/446 | 8 |

TABLE 1-continued

Example compounds 41 to 126

| Ex | Structure | IUPAC Name | MWt/ [M + H] | Ex. Method |
|---|---|---|---|---|
| 46 | 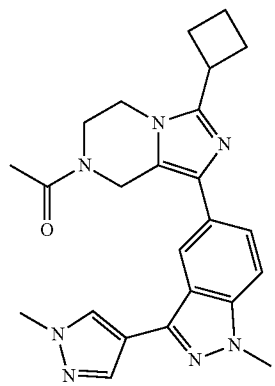 [SMILES: CC(=O)N1CCn2c(C3CCC3)nc(-c3ccc4c(c3)c(-c3cnn(C)c3)nn4C)c2C1] | 1-(3-cyclobutyl-1-(1-methyl-3-(1-methyl-1H-pyrazol-4-yl)-1H-indazol-5-yl)-5,6-dihydroimidazo[1,5-a]pyrazin-7(8H)-yl)ethan-1-one | 429/430 | 9 |
| 47 | 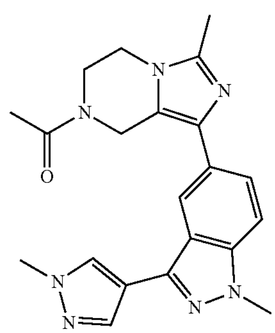 [SMILES: CC(=O)N1CCn2c(C)nc(-c3ccc4c(c3)c(-c3cnn(C)c3)nn4C)c2C1] | 1-(3-methyl-1-(1-methyl-3-(1-methyl-1H-pyrazol-4-yl)-1H-indazol-5-yl)-5,6-dihydroimidazo[1,5-a]pyrazin-7(8H)-yl)ethan-1-one | 389/390 | 10 |
| 48 | 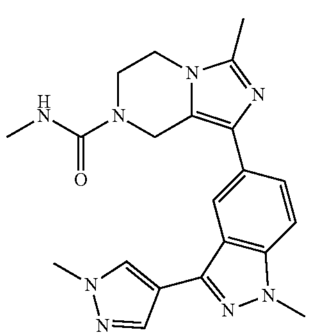 | N,3-dimethyl-1-(1-methyl-3-(1-methyl-1H-pyrazol-4-yl)-1H-indazol-5-yl)-5,6-dihydroimidazo[1,5-a]pyrazine-7(8H)-carboxamide | 404/405 | 11 |
| 49 | 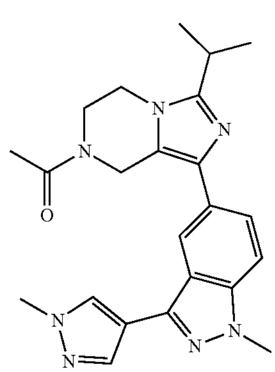 [SMILES: CC(=O)N1CCn2c(C(C)C)nc(-c3ccc4c(c3)c(-c3cnn(C)c3)nn4C)c2C1] | 1-(3-isopropyl-1-(1-methyl-3-(1-methyl-1H-pyrazol-4-yl)-1H-indazol-5-yl)-5,6-dihydroimidazo[1,5-a]pyrazin-7(8H)-yl)ethan-1-one | 417/418 | 12 |

TABLE 1-continued

Example compounds 41 to 126

| Ex | Structure | IUPAC Name | MWt/ [M + H] | Ex. Method |
|---|---|---|---|---|
| 50 | 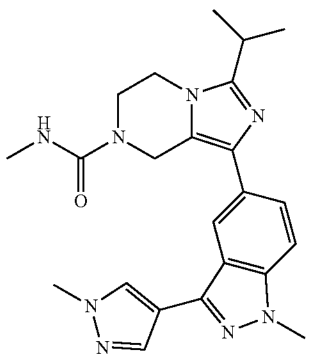 | 3-isopropyl-N-methyl-1-(1-methyl-3-(1-methyl-1H-pyrazol-4-yl)-1H-indazol-5-yl)-5,6-dihydroimidazo[1,5-a]pyrazine-7(8H)-carboxamide | 432/433 | 13 |
| 51 | 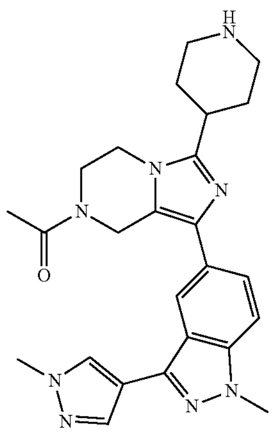 [SMILES: CC(=O)N1CCn2c(C3CCNCC3)nc(-c3ccc4c(c3)c(-c3cnn(C)c3)nn4C)c2C1] | 1-(1-(1-methyl-3-(1-methyl-1H-pyrazol-4-yl)-1H-indazol-5-yl)-3-(piperidin-4-yl)-5,6-dihydroimidazo[1,5-a]pyrazin-7(8H)-yl)ethan-1-one | 458/459 | 14 |
| 52 | 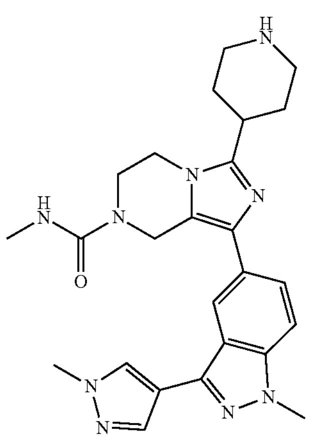 | N-methyl-1-(1-methyl-3-(1-methyl-1H-pyrazol-4-yl)-1H-indazol-5-yl)-3-(piperidin-4-yl)-5,6-dihydroimidazo[1,5-a]pyrazine-7(8H)-carboxamide | 473/474 | 15 |

TABLE 1-continued

Example compounds 41 to 126

| Ex | Structure | IUPAC Name | MWt/ [M + H] | Ex. Method |
|---|---|---|---|---|
| 53 | 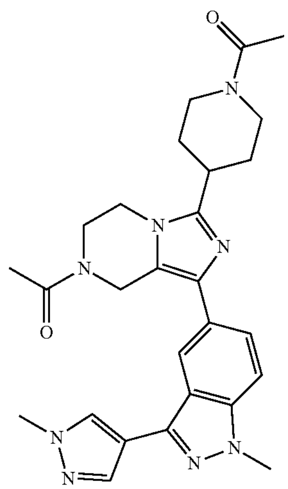 [SMILES: CC(=O)N1CCC(c2nc(-c3ccc4c(c3)c(-c3cnn(C)c3)nn4C)c3n2CCN(C(C)=O)C3)CC1] | 1-(4-(7-acetyl-1-(1-methyl-3-(1-methyl-1H-pyrazol-4-yl)-1H-indazol-5-yl)-5,6,7,8-tetrahydroimidazo[1,5-a]pyrazin-3-yl)piperidin-1-yl)ethan-1-one | 500/501 | 16 |
| 54 | 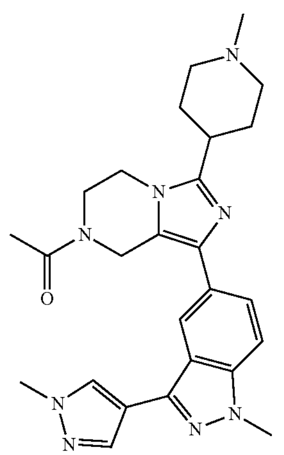 [SMILES: CC(=O)N1CCn2c(C3CCN(C)CC3)nc(-c3ccc4c(c3)c(-c3cnn(C)c3)nn4C)c2C1] | 1-(1-(1-methyl-3-(1-methyl-1H-pyrazol-4-yl)-1H-indazol-5-yl)-3-(1-methylpiperidin-4-yl)-5,6-dihydroimidazo[1,5-a]pyrazin-7(8H)-yl)ethan-1-one | 472/473 | 17 |
| 55 | 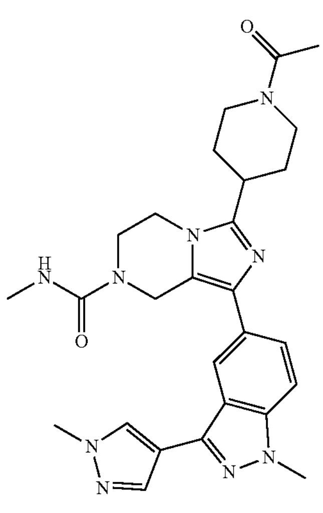 [SMILES: CNC(=O)N1CCn2c(C3CCN(C(C)=O)CC3)nc(-c3ccc4c(c3)c(-c3cnn(C)c3)nn4C)c2C1] | 3-(1-acetylpiperidin-4-yl)-N-methyl-1-(1-methyl-3-(1-methyl-1H-pyrazol-4-yl)-1H-indazol-5-yl)-5,6-dihydroimidazo[1,5-a]pyrazine-7(8H)-carboxamide | 515/516 | 18 |

TABLE 1-continued

Example compounds 41 to 126

| Ex | Structure | IUPAC Name | MWt/ [M + H] | Ex. Method |
|----|-----------|------------|--------------|------------|
| 56 | 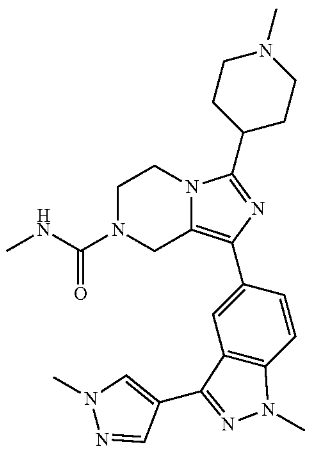 | N-methyl-1-(1-methyl-3-(1-methyl-1H-pyrazol-4-yl)-1H-indazol-5-yl)-3-(1-methylpiperidin-4-yl)-5,6-dihydroimidazo[1,5-a]pyrazine-7(8H)-carboxamide | 487/488 | 19 |
| 57 | 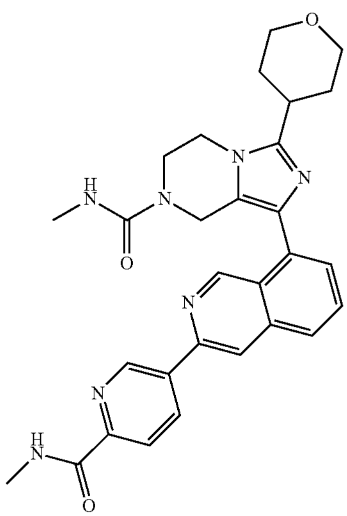 [SMILES: CNC(=O)c1ccc(-c2cc3cccc(-c4nc(C5CCOCC5)n5c4CN(C(=O)NC)CC5)c3cn2)cn1] | N-methyl-1-(3-(6-(methylcarbamoyl)pyridin-3-yl)isoquinolin-8-yl)-3-(tetrahydro-2H-pyran-4-yl)-5,6-dihydroimidazo[1,5-a]pyrazine-7(8H)-carboxamide | 525/526 | 20 |
| 58 | 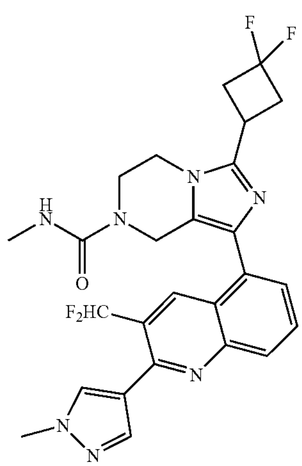 [SMILES: CNC(=O)N1CCn2c(C3CC(F)(F)C3)nc(-c3cccc4nc(-c5cnn(C)c5)c(C(F)F)cc34)c2C1] | 3-(3,3-difluorocyclobutyl)-1-(3-(difluoromethyl)-2-(1-methyl-1H-pyrazol-4-yl)quinolin-5-yl)-N-methyl-5,6-dihydroimidazo[1,5-a]pyrazine-7(8H)-carboxamide | 527/528 | 21 |

TABLE 1-continued

Example compounds 41 to 126

| Ex | Structure | IUPAC Name | MWt/ [M + H] | Ex. Method |
|---|---|---|---|---|
| 59 | 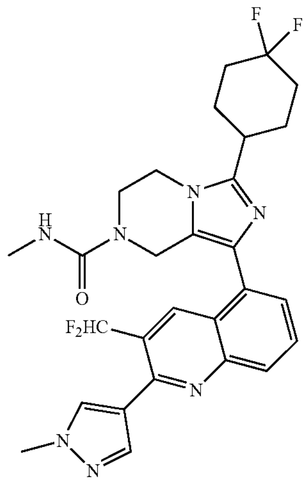 [SMILES: CNC(=O)N1CCn2c(C3CCC(F)(F)CC3)nc(-c3cccc4nc(-c5cnn(C)c5)c(C(F)F)cc34)c2C1] | 3-(4,4-difluorocyclohexyl)-1-(3-(difluoromethyl)-2-(1-methyl-1H-pyrazol-4-yl)quinolin-5-yl)-N-methyl-5,6-dihydroimidazo[1,5-a]pyrazine-7(8H)-carboxamide | 555/556 | 22 |
| 60 | 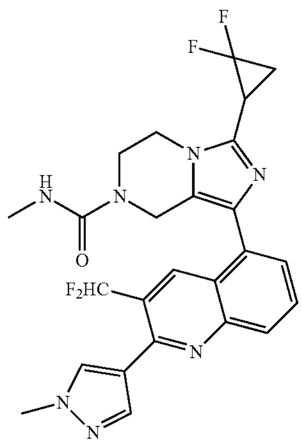 [SMILES: CNC(=O)N1CCn2c(C3CC3(F)F)nc(-c3cccc4nc(-c5cnn(C)c5)c(C(F)F)cc34)c2C1] | 3-(2,2-difluorocyclopropyl)-1-(3-(difluoromethyl)-2-(1-methyl-1H-pyrazol-4-yl)quinolin-5-yl)-N-methyl-5,6-dihydroimidazo[1,5-a]pyrazine-7(8H)-carboxamide | 513/514 | 23 |
| 61 | 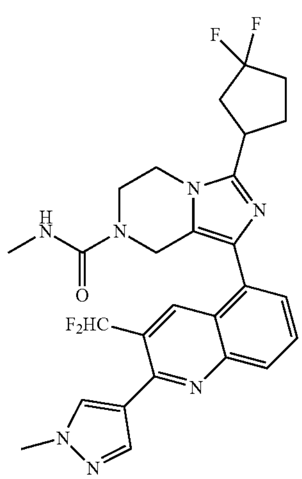 [SMILES: CNC(=O)N1CCn2c(C3CCC(F)(F)C3)nc(-c3cccc4nc(-c5cnn(C)c5)c(C(F)F)cc34)c2C1] | 3-(3,3-difluorocyclopentyl)-1-(3-(difluoromethyl)-2-(1-methyl-1H-pyrazol-4-yl)quinolin-5-yl)-N-methyl-5,6-dihydroimidazo[1,5-a]pyrazine-7(8H)-carboxamide | 541/542 | 24 |

TABLE 1-continued

Example compounds 41 to 126

| Ex | Structure | IUPAC Name | MWt/ [M + H] | Ex. Method |
|---|---|---|---|---|
| 62 | 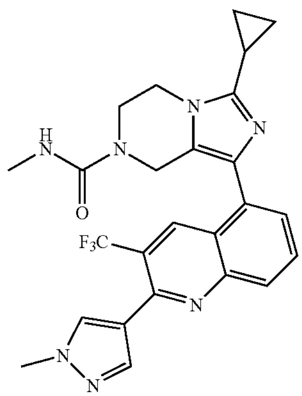 [SMILES: CNC(=O)N1CCn2c(C3CC3)nc(-c3cccc4nc(-c5cnn(C)c5)c(C(F)(F)F)cc34)c2C1] | 3-cyclopropyl-N-methyl-1-(2-(1-methyl-1H-pyrazol-4-yl)-3-(trifluoromethyl)quinolin-5-yl)-5,6-dihydroimidazo[1,5-a]pyrazine-7(8H)-carboxamide | 495/496 | 25 |
| 63 | 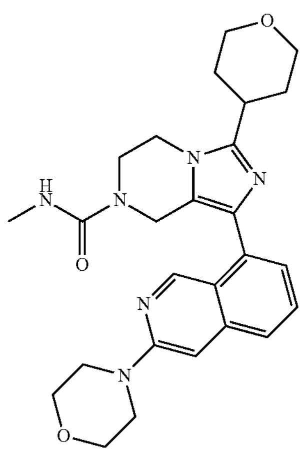 | N-methyl-1-(3-morpholinoisoquinolin-8-yl)-3-(tetrahydro-2H-pyran-4-yl)-5,6-dihydroimidazo[1,5-a]pyrazine-7(8H)-carboxamide | 476/477 | 26 |
| 64 | 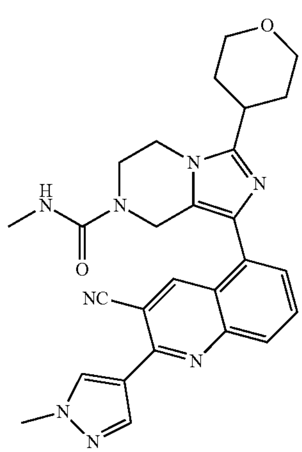 [SMILES: CNC(=O)N1CCn2c(C3CCOCC3)nc(-c3cccc4nc(-c5cnn(C)c5)c(C#N)cc34)c2C1] | 1-(3-cyano-2-(1-methyl-1H-pyrazol-4-yl)quinolin-5-yl)-N-methyl-3-(tetrahydro-2H-pyran-4-yl)-5,6-dihydroimidazo[1,5-a]pyrazine-7(8H)-carboxamide | 496/497 | 27 |

TABLE 1-continued

Example compounds 41 to 126

| Ex | Structure | IUPAC Name | MWt/ [M + H] | Ex. Method |
|---|---|---|---|---|
| 65 | 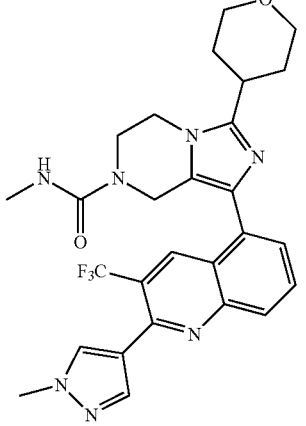 | N-methyl-1-(2-(1-methyl-1H-pyrazol-4-yl)-3-(trifluoromethyl)quinolin-5-yl)-3-(tetrahydro-2H-pyran-4-yl)-5,6-dihydroimidazo[1,5-a]pyrazine-7(8H)-carboxamide | 539/540 | 28 |
| 66 | 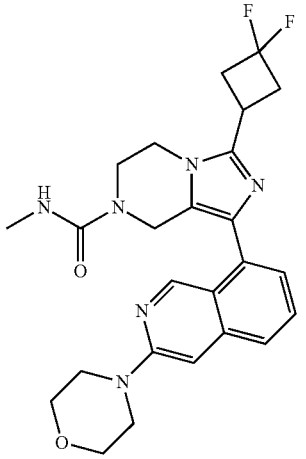 [SMILES: CNC(=O)N1CCn2c(C3CC(F)(F)C3)nc(-c3cccc4cc(N5CCOCC5)ncc34)c2C1] | 3-(3,3-difluorocyclobutyl)-N-methyl-1-(3-morpholinoisoquinolin-8-yl)-5,6-dihydroimidazo[1,5-a]pyrazine-7(8H)-carboxamide | 482/486 | 29 |
| 67 | 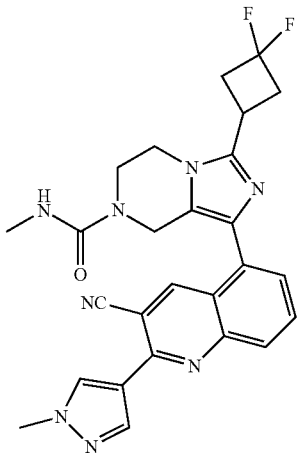 [SMILES: CNC(=O)N1CCn2c(C3CC(F)(F)C3)nc(-c3cccc4nc(-c5cnn(C)c5)c(C#N)cc34)c2C1] | 1-(3-cyano-2-(1-methyl-1H-pyrazol-4-yl)quinolin-5-yl)-3-(3,3-difluorocyclobutyl)-N-methyl-5,6-dihydroimidazo[1,5-a]pyrazine-7(8H)-carboxamide | 502/503 | 30 |

TABLE 1-continued

Example compounds 41 to 126

| Ex | Structure | IUPAC Name | MWt/ [M + H] | Ex. Method |
|---|---|---|---|---|
| 68 | 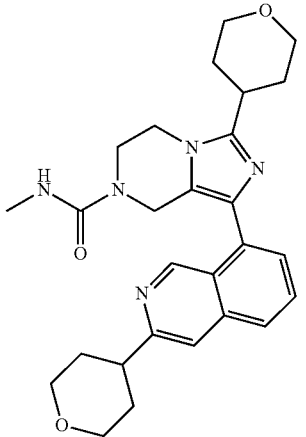 [SMILES: CNC(=O)N1CCn2c(C3CCOCC3)nc(-c3cccc4cc(C5CCOCC5)ncc34)c2C1] | N-methyl-3-(tetrahydro-2H-pyran-4-yl)-1-(3-(tetrahydro-2H-pyran-4-yl)isoquinolin-8-yl)-5,6-dihydroimidazo[1,5-a]pyrazine-7(8H)-carboxamide | 475/476 | 31 |
| 69 | 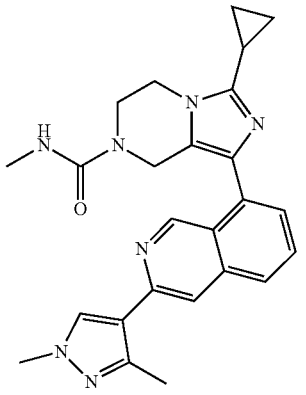 [SMILES: CNC(=O)N1CCn2c(C3CC3)nc(-c3cccc4cc(-c5cn(C)nc5C)ncc34)c2C1] | 3-cyclopropyl-1-(3-(1,3-dimethyl-1H-pyrazol-4-yl)isoquinolin-8-yl)-N-methyl-5,6-dihydroimidazo[1,5-a]pyrazine-7(8H)-carboxamide | 441/442 | 32 |
| 70 | 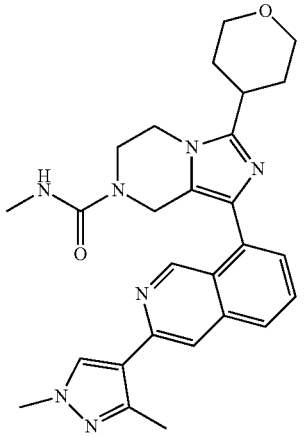 [SMILES: CNC(=O)N1CCn2c(C3CCOCC3)nc(-c3cccc4cc(-c5cn(C)nc5C)ncc34)c2C1] | 1-(3-(1,3-dimethyl-1H-pyrazol-4-yl)isoquinolin-8-yl)-N-methyl-3-(tetrahydro-2H-pyran-4-yl)-5,6-dihydroimidazo[1,5-a]pyrazine-7(8H)-carboxamide | 485/486 | 33 |

TABLE 1-continued

Example compounds 41 to 126

| Ex | Structure | IUPAC Name | MWt/ [M + H] | Ex. Method |
|---|---|---|---|---|
| 71 | 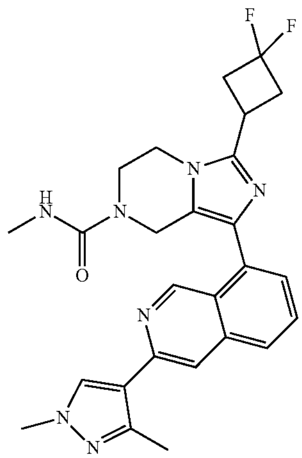 [SMILES: CNC(=O)N1CCn2c(C3CC(F)(F)C3)nc(-c3cccc4cc(-c5cn(C)nc5C)ncc34)c2C1] | 3-(3,3-difluorocyclobutyl)-1-(3-(1,3-dimethyl-1H-pyrazol-4-yl)isoquinolin-8-yl)-N-methyl-5,6-dihydroimidazo[1,5-a]pyrazine-7(8H)-carboxamide | 491/492 | 34 |
| 72 | 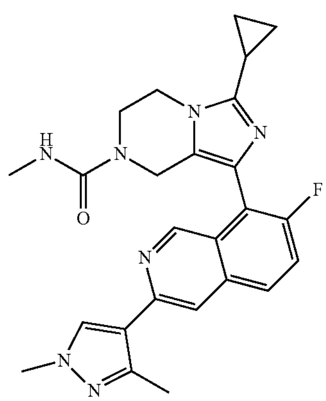 [SMILES: CNC(=O)N1CCn2c(C3CC3)nc(-c3c(F)ccc4cc(-c5cn(C)nc5C)ncc34)c2C1] | 3-cyclopropyl-1-(3-(1,3-dimethyl-1H-pyrazol-4-yl)-7-fluoroisoquinolin-8-yl)-N-methyl-5,6-dihydroimidazo[1,5-a]pyrazine-7(8H)-carboxamide | 459/460 | 35 |
| 73 | 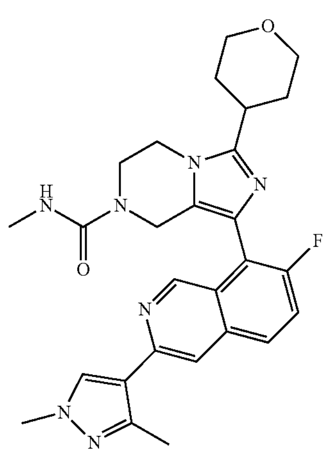 [SMILES: CNC(=O)N1CCn2c(C3CCOCC3)nc(-c3c(F)ccc4cc(-c5cn(C)nc5C)ncc34)c2C1] | 1-(3-(1,3-dimethyl-1H-pyrazol-4-yl)-7-fluoroisoquinolin-8-yl)-N-methyl-3-(tetrahydro-2H-pyran-4-yl)-5,6-dihydroimidazo[1,5-a]pyrazine-7(8H)-carboxamide | 503/504 | 36 |

TABLE 1-continued

Example compounds 41 to 126

| Ex | Structure | IUPAC Name | MWt/ [M + H] | Ex. Method |
|---|---|---|---|---|
| 74 | 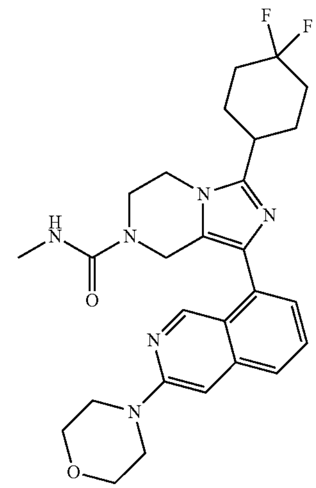 [SMILES: CNC(=O)N1CCn2c(C3CCC(F)(F)CC3)nc(-c3cccc4cc(N5CCOCC5)ncc34)c2C1] | 3-(4,4-difluorocyclohexyl)-N-methyl-1(3-morpholinoisoquinolin-8-yl)-5,6-dihydroimidazo[1,5-a]pyrazine-7(8H)-carboxamide | 510/511 | 37 |
| 75 | 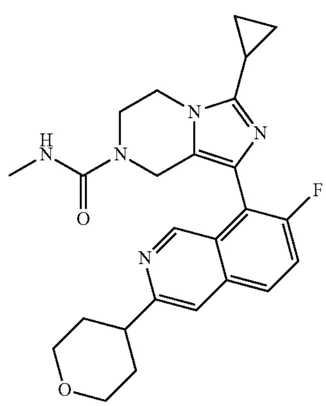 [SMILES: CNC(=O)N1CCn2c(C3CC3)nc(-c3c(F)ccc4cc(C5CCOCC5)ncc34)c2C1] | 3-cyclopropyl-1-(7-fluoro-3-(tetrahydro-2H-pyran-4-yl)isoquinolin-8-yl)-N-methyl-5,6-dihydroimidazo[1,5-a]pyrazine-7(8H)-carboxamide | 449/450 | 38 |
| 76 | 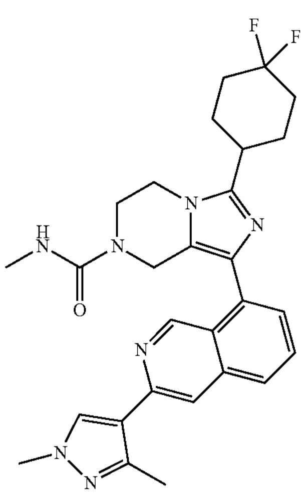 [SMILES: CNC(=O)N1CCn2c(C3CCC(F)(F)CC3)nc(-c3cccc4cc(-c5cn(C)nc5C)ncc34)c2C1] | 3-(4,4-difluorocyclohexyl)-1-(3-(1,3-dimethyl-1H-pyrazol-4-yl)isoquinolin-8-yl)-N-methyl-5,6-dihydroimidazo[1,5-a]pyrazine-7(8H)-carboxamide | 519/520 | 39 |

TABLE 1-continued

Example compounds 41 to 126

| Ex | Structure | IUPAC Name | MWt/ [M + H] | Ex. Method |
|---|---|---|---|---|
| 77 | 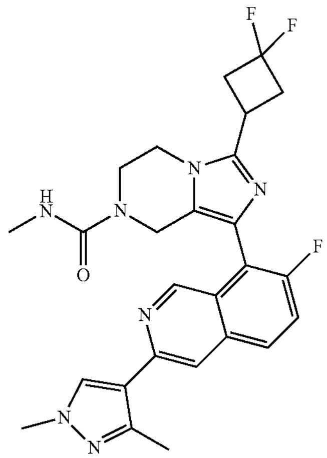 [SMILES: CNC(=O)N1CCn2c(C3CC(F)(F)C3)nc(-c3c(F)ccc4cc(-c5cn(C)nc5C)ncc34)c2C1] | 3-(3,3-difluorocyclobutyl)-1-(3-(1,3-dimethyl-1H-pyrazol-4-yl)-7-fluoroisoquinolin-8-yl)-N-methyl-5,6-dihydroimidazo[1,5-a]pyrazine-7(8H)-carboxamide | 509/510 | 40 |
| 78 | 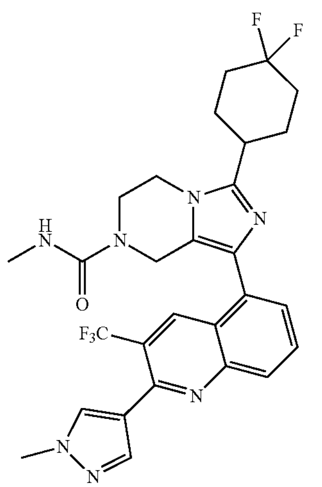 [SMILES: CNC(=O)N1CCn2c(C3CCC(F)(F)CC3)nc(-c3cccc4nc(-c5cnn(C)c5)c(C(F)(F)F)cc34)c2C1] | 3-(4,4-difluorocyclohexyl)-N-methyl-1-(2-(1-methyl-1H-pyrazol-4-yl)-3-(trifluoromethyl)quinolin-5-yl)-5,6-dihydroimidazo[1,5-a]pyrazine-7(8H)-carboxamide | 573/574 | 40 |
| 79 | 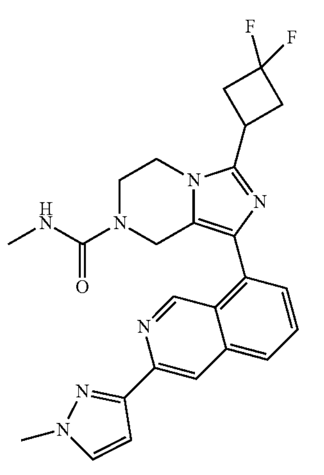 [SMILES: CNC(=O)N1CCn2c(C3CC(F)(F)C3)nc(-c3cccc4cc(-c5ccn(C)n5)ncc34)c2C1] | 3-(3,3-difluorocyclobutyl)-N-methyl-1-(3-(1-methyl-1H-pyrazol-3-yl)isoquinolin-8-yl)-5,6-dihydroimidazo[1,5-a]pyrazine-7(8H)-carboxamide | 477/478 | 40 |

TABLE 1-continued

Example compounds 41 to 126

| Ex | Structure | IUPAC Name | MWt/ [M + H] | Ex. Method |
|---|---|---|---|---|
| 80 | 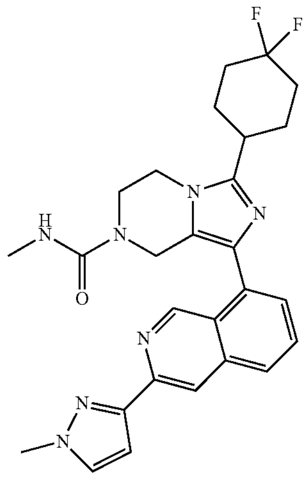 [SMILES: CNC(=O)N1CCn2c(C3CCC(F)(F)CC3)nc(-c3cccc4cc(-c5ccn(C)n5)ncc34)c2C1] | 3-(4,4-difluorocyclohexyl)-N-methyl-1-(3-(1-methyl-1H-pyrazol-3-yl)isoquinolin-8-yl)-5,6-dihydroimidazo[1,5-a]pyrazine-7(8H)-carboxamide | 505/506 | 40 |
| 81 | 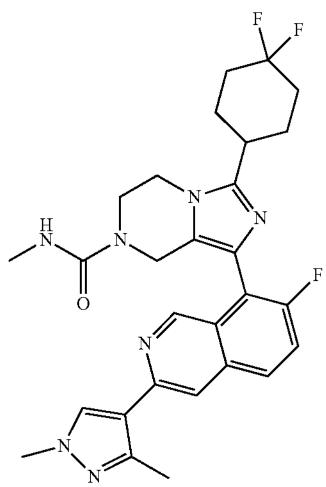 [SMILES: CNC(=O)N1CCn2c(C3CCC(F)(F)CC3)nc(-c3c(F)ccc4cc(-c5cn(C)nc5C)ncc34)c2C1] | 3-(4,4-difluorocyclohexyl)-1-(3-(1,3-dimethyl-1H-pyrazol-4-yl)-7-fluoroisoquinolin-8-yl)-N-methyl-5,6-dihydroimidazo[1,5-a]pyrazine-7(8H)-carboxamide | 537/538 | 40 |
| 82 | 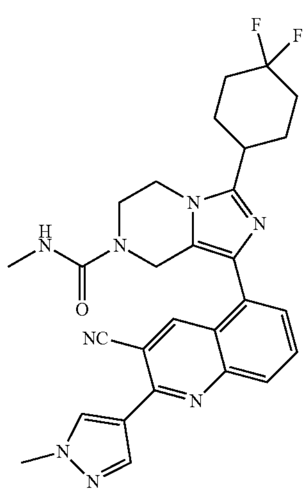 [SMILES: CNC(=O)N1CCn2c(C3CCC(F)(F)CC3)nc(-c3cccc4nc(-c5cnn(C)c5)c(C#N)cc34)c2C1] | 1-(3-cyano-2-(1-methyl-1H-pyrazol-4-yl)quinolin-5-yl)-3-(4,4-difluorocyclohexyl)-N-methyl-5,6-dihydroimidazo[1,5-a]pyrazine-7(8H)-carboxamide | 530/531 | 40 |

TABLE 1-continued

Example compounds 41 to 126

| Ex | Structure | IUPAC Name | MWt/ [M + H] | Ex. Method |
|---|---|---|---|---|
| 83 | 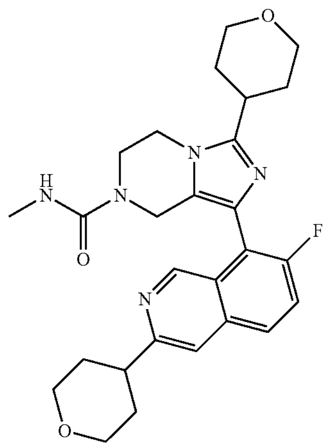 [SMILES: CNC(=O)N1CCn2c(C3CCOCC3)nc(-c3c(F)ccc4cc(C5CCOCC5)ncc34)c2C1] | 1-(7-fluoro-3-(tetrahydro-2H-pyran-4-yl)isoquinolin-8-yl)-N-methyl-3-(tetrahydro-2H-pyran-4-yl)-5,6-dihydroimidazo[1,5-a]pyrazine-7(8H)-carboxamide | 493/494 | 40 |
| 84 | 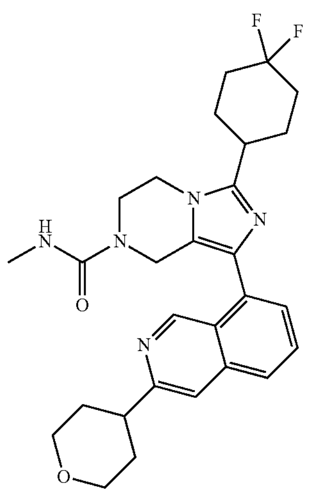 [SMILES: CNC(=O)N1CCn2c(C3CCC(F)(F)CC3)nc(-c3cccc4cc(C5CCOCC5)ncc34)c2C1] | 3-(4,4-difluorocyclohexyl)-N-methyl-1-(3-(tetrahydro-2H-pyran-4-yl)isoquinolin-8-yl)-5,6-dihydroimidazo[1,5-a]pyrazine-7(8H)-carboxamide | 509/510 | 7 |
| 85 | 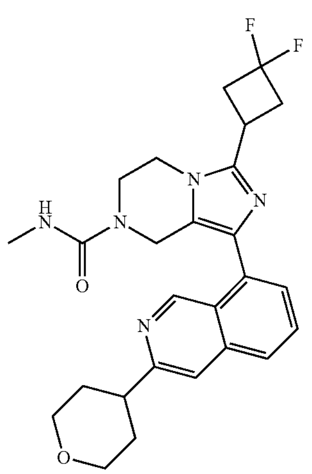 [SMILES: CNC(=O)N1CCn2c(C3CC(F)(F)C3)nc(-c3cccc4cc(C5CCOCC5)ncc34)c2C1] | 3-(3,3-difluorocyclobutyl)-N-methyl-1-(3-(tetrahydro-2H-pyran-4-yl)isoquinolin-8-yl)-5,6-dihydroimidazo[1,5-a]pyrazine-7(8H)-carboxamide | 481/482 | 40 |

TABLE 1-continued

Example compounds 41 to 126

| Ex | Structure | IUPAC Name | MWt/ [M + H] | Ex. Method |
|---|---|---|---|---|
| 86 | 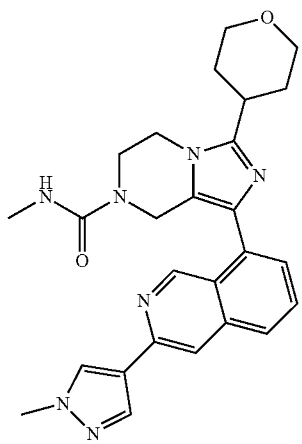 [SMILES: CNC(=O)N1CCn2c(C3CCOCC3)nc(-c3cccc4cc(-c5cnn(C)c5)ncc34)c2C1] | N-methyl-1-(3-(1-methyl-1H-pyrazol-3-yl)isoquinolin-8-yl)-3-(tetrahydro-2H-pyran-4-yl)-5,6-dihydroimidazo[1,5-a]pyrazine-7(8H)-carboxamide | 471/472 | 7 |
| 87 | 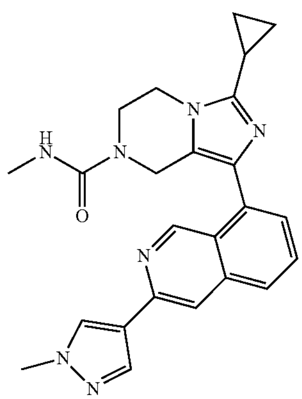 [SMILES: CNC(=O)N1CCn2c(C3CC3)nc(-c3cccc4cc(-c5cnn(C)c5)ncc34)c2C1] | 3-cyclopropyl-N-methyl-1-(3-(1-methyl-1H-pyrazol-3-yl)isoquinolin-8-yl)-5,6-dihydroimidazo[1,5-a]pyrazine-7(8H)-carboxamide | 427/428 | 13 |
| 88 | 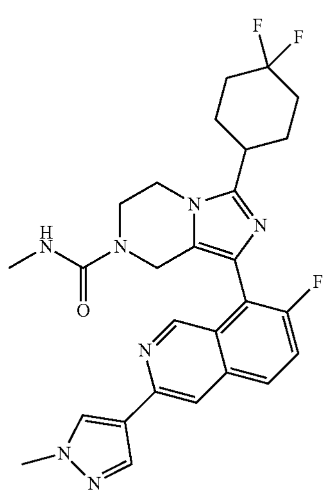 [SMILES: CNC(=O)N1CCn2c(C3CCC(F)(F)CC3)nc(-c3c(F)ccc4cc(-c5cnn(C)c5)ncc34)c2C1] | 3-(4,4-difluorocyclohexyl)-1-(7-fluoro-3-(1-methyl-1H-pyrazol-3-yl)isoquinolin-8-yl)-N-methyl-5,6-dihydroimidazo[1,5-a]pyrazine-7(8H)-carboxamide | 523/524 | 8 |

TABLE 1-continued

Example compounds 41 to 126

| Ex | Structure | IUPAC Name | MWt/ [M + H] | Ex. Method |
|---|---|---|---|---|
| 89 | 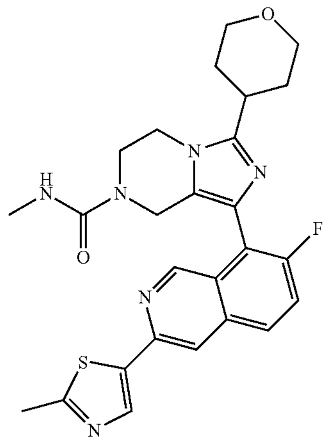 [SMILES: CNC(=O)N1CCn2c(C3CCOCC3)nc(-c3c(F)ccc4cc(-c5cnc(C)s5)ncc34)c2C1] | 1-(7-fluoro-3-(2-methylthiazol-5-yl)isoquinolin-8-yl)-N-methyl-3-(tetrahydro-2H-pyran-4-yl)-5,6-dihydroimidazo[1,5-a]pyrazine-7(8H)-carboxamide | 506/507 | 12 |
| 90 | 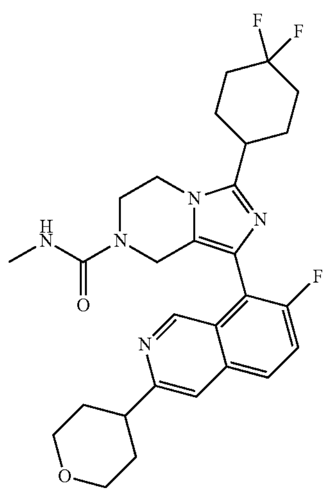 [SMILES: CNC(=O)N1CCn2c(C3CCC(F)(F)CC3)nc(-c3c(F)ccc4cc(C5CCOCC5)ncc34)c2C1] | 3-(4,4-difluorocyclohexyl)-1-(7-fluoro-3-(tetrahydro-2H-pyran-4-yl)isoquinolin-8-yl)-N-methyl-5,6-dihydroimidazo[1,5-a]pyrazine-7(8H)-carboxamide | 527/528 | 13 |
| 91 | 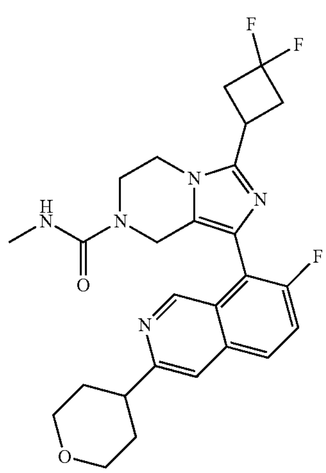 [SMILES: CNC(=O)N1CCn2c(C3CC(F)(F)C3)nc(-c3c(F)ccc4cc(C5CCOCC5)ncc34)c2C1] | 3-(3,3-difluorocyclobutyl)-1-(7-fluoro-3-(tetrahydro-2H-pyran-4-yl)isoquinolin-8-yl)-N-methyl-5,6-dihydroimidazo[1,5-a]pyrazine-7(8H)-carboxamide | 499/500 | 9 |

TABLE 1-continued

Example compounds 41 to 126

| Ex | Structure | IUPAC Name | MWt/ [M + H] | Ex. Method |
|---|---|---|---|---|
| 92 | 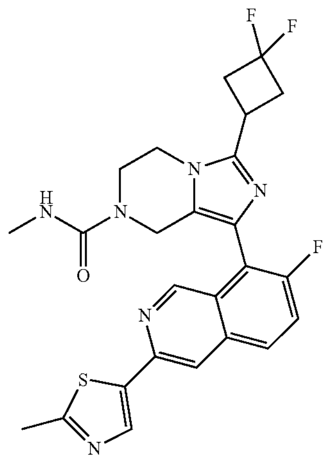 [SMILES: CNC(=O)N1CCn2c(C3CC(F)(F)C3)nc(-c3c(F)ccc4cc(-c5cnc(C)s5)ncc34)c2C1] | 3-(3,3-difluorocyclobutyl)-1-(7-fluoro-3-(2-methylthiazol-5-yl)isoquinolin-8-yl)-N-methyl-5,6-dihydroimidazo[1,5-a]pyrazine-7(8H)-carboxamide | 512/513 | 8 |
| 93 | 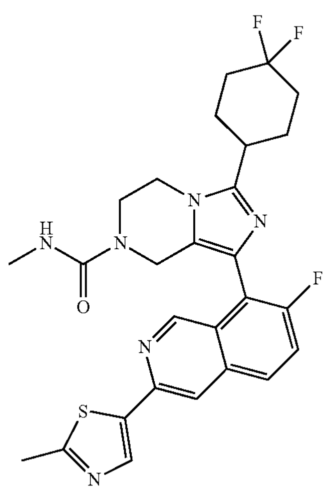 [SMILES: CNC(=O)N1CCn2c(C3CCC(F)(F)CC3)nc(-c3c(F)ccc4cc(-c5cnc(C)s5)ncc34)c2C1] | 3-(4,4-difluorocyclohexyl)-1-(7-fluoro-3-(2-methylthiazol-5-yl)isoquinolin-8-yl)-N-methyl-5,6-dihydroimidazo[1,5-a]pyrazine-7(8H)-carboxamide | 540/541 | 17 |
| 94 | 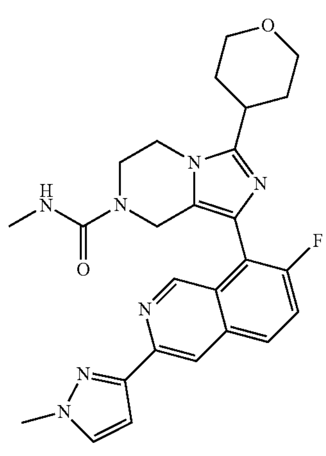 [SMILES: CNC(=O)N1CCn2c(C3CCOCC3)nc(-c3c(F)ccc4cc(-c5ccn(C)n5)ncc34)c2C1] | 1-(7-fluoro-3-(1-methyl-1H-pyrazol-3-yl)isoquinolin-8-yl)-N-methyl-3-(tetrahydro-2H-pyran-4-yl)-5,6-dihydroimidazo[1,5-a]pyrazine-7(8H)-carboxamide | 489/490 | 34 |

TABLE 1-continued

Example compounds 41 to 126

| Ex | Structure | IUPAC Name | MWt/ [M + H] | Ex. Method |
|---|---|---|---|---|
| 95 | 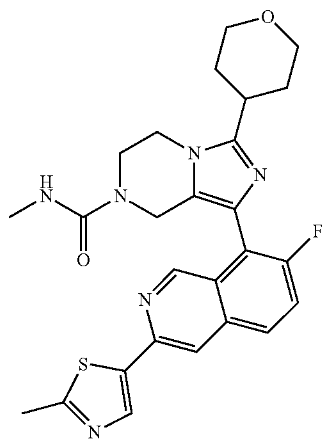 [SMILES: CNC(=O)N1CCn2c(C3CCOCC3)nc(-c3c(F)ccc4cc(-c5cnc(C)s5)ncc34)c2C1] | N-methyl-1-(3-(2-methylthiazol-5-yl)isoquinolin-8-yl)-3-(tetrahydro-2H-pyran-4-yl)-5,6-dihydroimidazo[1,5-a]pyrazine-7(8H)-carboxamide | 488/489 | 34 |
| 96 | 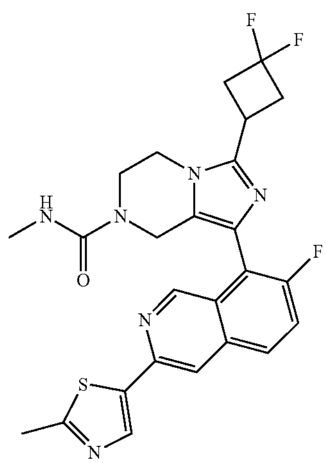 [SMILES: CNC(=O)N1CCn2c(C3CC(F)(F)C3)nc(-c3c(F)ccc4cc(-c5cnc(C)s5)ncc34)c2C1] | 3-(3,3-difluorocyclobutyl)-N-methyl-1-(3-(2-methylthiazol-5-yl)isoquinolin-8-yl)-5,6-dihydroimidazo[1,5-a]pyrazine-7(8H)-carboxamide | 494/495 | 34 |
| 97 | 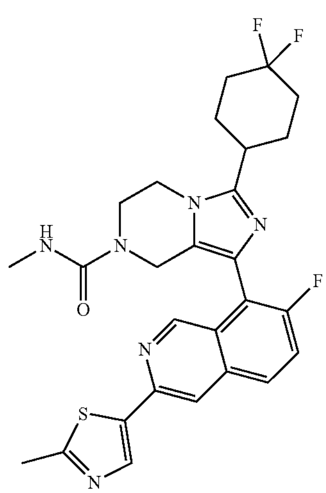 [SMILES: CNC(=O)N1CCn2c(C3CCC(F)(F)CC3)nc(-c3c(F)ccc4cc(-c5cnc(C)s5)ncc34)c2C1] | 3-(4,4-difluorocyclohexyl)-N-methyl-1-(3-(2-methylthiazol-5-yl)isoquinolin-8-yl)-5,6-dihydroimidazo[1,5-a]pyrazine-7(8H)-carboxamide | 522/523 | 34 |

TABLE 1-continued

Example compounds 41 to 126

| Ex | Structure | IUPAC Name | MWt/ [M + H] | Ex. Method |
|---|---|---|---|---|
| 98 | 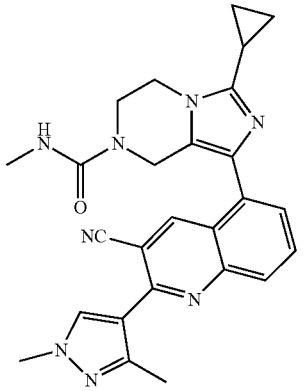 [SMILES: CNC(=O)N1CCn2c(C3CC3)nc(-c3cccc4nc(-c5cn(C)nc5C)c(C#N)cc34)c2C1] | 1-(3-cyano-2-(1,3-dimethyl-1H-pyrazol-4-yl)quinolin-5-yl)-3-cyclopropyl-N-methyl-5,6-dihydroimidazo[1,5-a]pyrazine-7(8H)-carboxamide | 466/467 | 20 |
| 99 | 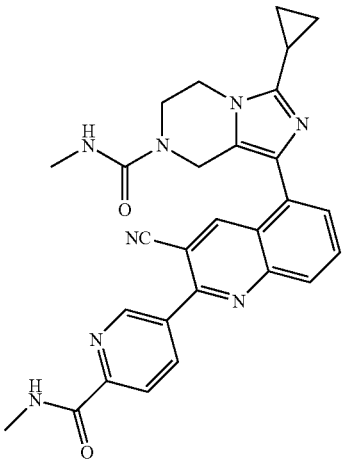 [SMILES: CNC(=O)c1ccc(-c2nc3cccc(-c4nc(C5CC5)n5c4CN(C(=O)NC)CC5)c3cc2C#N)cn1] | 1-(3-cyano-2-(6-(methylcarbamoyl)pyridin-3-yl)quinolin-5-yl)-3-cyclopropyl-N-methyl-5,6-dihydroimidazo[1,5-a]pyrazine-7(8H)-carboxamide | 506/507 | 18 |
| 100 | 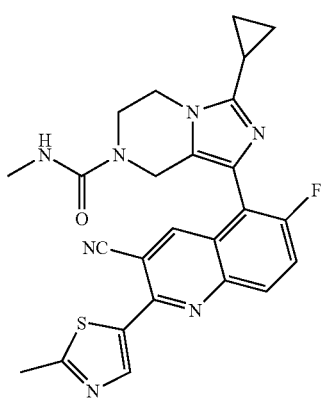 [SMILES: CNC(=O)N1CCn2c(C3CC3)nc(-c3c(F)ccc4nc(-c5cnc(C)s5)c(C#N)cc34)c2C1] | 1-(3-cyano-2-(2-methylthiazol-5-yl)quinolin-5-yl)-3-cyclopropyl-N-methyl-5,6-dihydroimidazo[1,5-a]pyrazine-7(8H)-carboxamide | 469/470 | 19 |

TABLE 1-continued

Example compounds 41 to 126

| Ex | Structure | IUPAC Name | MWt/ [M + H] | Ex. Method |
|---|---|---|---|---|
| 101 | 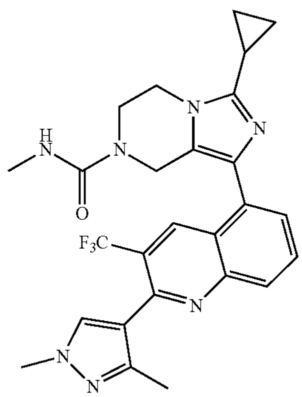 [SMILES: CNC(=O)N1CCn2c(C3CC3)nc(-c3cccc4nc(-c5cn(C)nc5C)c(C(F)(F)F)cc34)c2C1] | 3-cyclopropyl-1-(2-(1,3-dimethyl-1H-pyrazol-4-yl)-3-(trifluoromethyl)quinolin-5-yl)-N-methyl-5,6-dihydroimidazo[1,5-a]pyrazine-7(8H)-carboxamide | 509/510 | 20 |
| 102 | 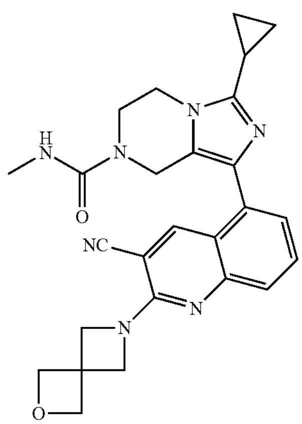 [SMILES: CNC(=O)N1CCn2c(C3CC3)nc(-c3cccc4nc(N5CC6(COC6)C5)c(C#N)cc34)c2C1] | 1-(3-cyano-2-(2-oxa-6-azaspiro[3.3]heptan-6-yl)quinolin-5-yl)-3-cyclopropyl-N-methyl-5,6-dihydroimidazo[1,5-a]pyrazine-7(8H)-carboxamide | 469/470 | 18 |
| 103 | 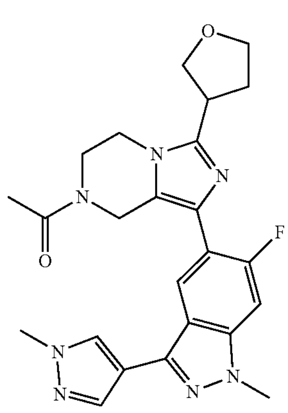 [SMILES: CC(=O)N1CCn2c(C3CCOC3)nc(-c3cc4c(-c5cnn(C)c5)nn(C)c4cc3F)c2C1] | 1-(1-(6-fluoro-1-methyl-3-(1-methyl-1H-pyrazol-4-yl)-1H-indazol-5-yl)-3-(tetrahydrofuran-3-yl)-5,6-dihydroimidazo[1,5-a]pyrazin-7(8H)-yl)ethan-1-one | 463/464 | 19 |

TABLE 1-continued

Example compounds 41 to 126

| Ex | Structure | IUPAC Name | MWt/ [M + H] | Ex. Method |
|---|---|---|---|---|
| 104 | 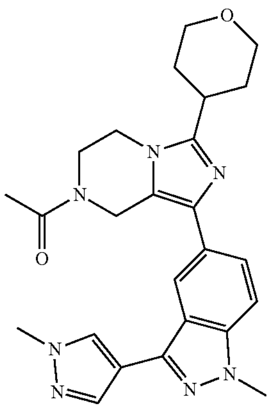 [SMILES: CC(=O)N1CCn2c(C3CCOCC3)nc(-c3ccc4c(c3)c(-c3cnn(C)c3)nn4C)c2C1] | 1-(1-(1-methyl-3-(1-methyl-1H-pyrazol-4-yl)-1H-indazol-5-yl)-3-(tetrahydro-2H-pyran-4-yl)-5,6-dihydroimidazo[1,5-a]pyrazin-7(8H)-yl)ethan-1-one | 459/460 | 21 |
| 105 | 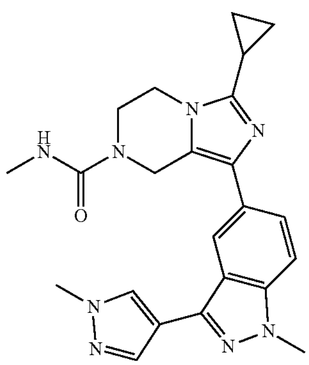 | 3-cyclopropyl-N-methyl-1-(1-methyl-3-(1-methyl-1H-pyrazol-4-yl)-1H-indazol-5-yl)-5,6-dihydroimidazo[1,5-a]pyrazine-7(8H)-carboxamide | 430/431 | 23 |
| 106 | 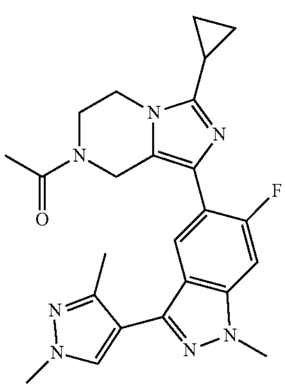 [SMILES: CC(=O)N1CCn2c(C3CC3)nc(-c3cc4c(-c5cn(C)nc5C)nn(C)c4cc3F)c2C1] | 1-(3-cyclopropyl-1-(3-(1,3-dimethyl-1H-pyrazol-4-yl)-1methyl-1H-indazol-5-yl)-5,6-dihydroimidazo[1,5-a]pyrazin-7(8H)-yl)ethan-1-one | 429/430 | 23 |
| 107 | 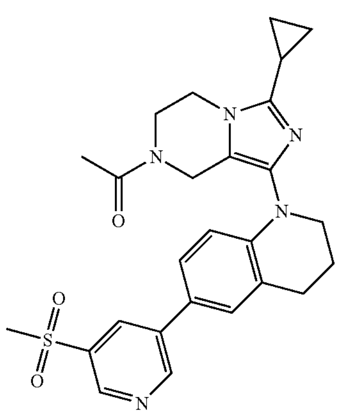 [SMILES: CC(=O)N1CCn2c(C3CC3)nc(N3CCCc4cc(-c5cncc(S(C)(=O)=O)c5)ccc43)c2C1] | 1-(3-cyclopropyl-1-(6-(5-(methylsulfonyl)pyridin-3-yl)-3,4-dihydroquinolin-1(2H)-yl)-5,6-dihydroimidazo[1,5-a]pyrazin-7(8H)-yl)ethan-1-one | 491/492 | 23 |

TABLE 1-continued

Example compounds 41 to 126

| Ex | Structure | IUPAC Name | MWt/ [M + H] | Ex. Method |
|---|---|---|---|---|
| 108 | 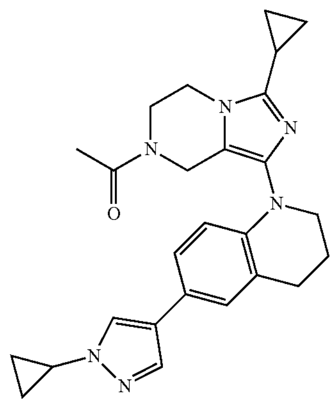 [SMILES: CC(=O)N1CCn2c(C3CC3)nc(N3CCCc4cc(-c5cnn(C6CC6)c5)ccc43)c2C1] | 1-(3-cyclopropyl-1-(6-(1-cyclopropyl-1H-pyrazol-4-yl)-3,4-dihydroquinolin-1(2H)-yl)-5,6-dihydroimidazo[1,5-a]pyrazin-7(8H)-yl)ethan-1-one | 442/443 | 22 |
| 109 | 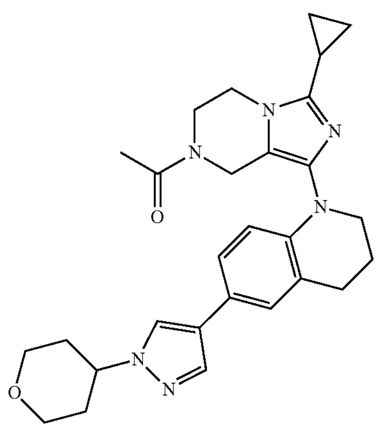 [SMILES: CC(=O)N1CCn2c(C3CC3)nc(N3CCCc4cc(-c5cnn(C6CCOCC6)c5)ccc43)c2C1] | 1-(3-cyclopropyl-1-(6-(1-(tetrahydro-2H-pyran-4-yl)-1H-pyrazol-4-yl)-3,4-dihydroquinolin-1(2H)-yl)-5,6-dihydroimidazo[1,5-a]pyrazin-7(8H)-yl)ethan-1-one | 486/487 | 22 |
| 110 | 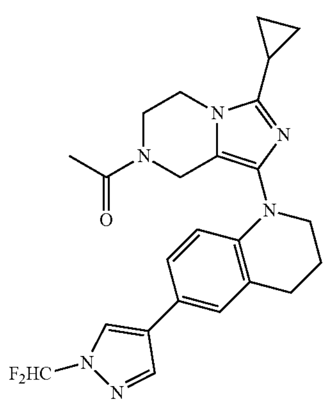 [SMILES: CC(=O)N1CCn2c(C3CC3)nc(N3CCCc4cc(-c5cnn(C(F)F)c5)ccc43)c2C1] | 1-(3-cyclopropyl-1-(6-(1-(difluoromethyl)-1H-pyrazol-4-yl)-3,4-dihydroquinolin-1(2H)-yl)-5,6-dihydroimidazo[1,5-a]pyrazin-7(8H)-yl)ethan-1-one | 452/453 | 18 |

TABLE 1-continued

Example compounds 41 to 126

| Ex | Structure | IUPAC Name | MWt/ [M + H] | Ex. Method |
|---|---|---|---|---|
| 111 | 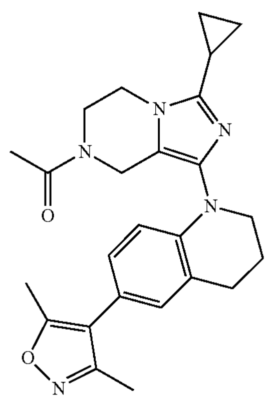 [SMILES: CC(=O)N1CCn2c(C3CC3)nc(N3CCCc4cc(-c5c(C)noc5C)ccc43)c2C1] | 1-(3-cyclopropyl-1-(6-(3,5-dimethylisoxazol-4-yl)-3,4-dihydroquinolin-1(2H)-yl)-5,6-dihydroimidazo[1,5-a]pyrazin-7(8H)-yl)ethan-1-one | 431/432 | IACS-015726 |
| 112 | 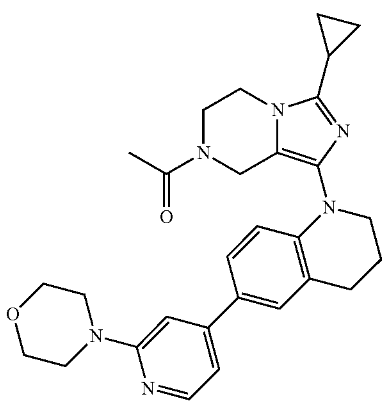 [SMILES: CC(=O)N1CCn2c(C3CC3)nc(N3CCCc4cc(-c5ccnc(N6CCOCC6)c5)ccc43)c2C1] | 1-(3-cyclopropyl-1-(6-(2-morpholinopyridin-4-yl)-3,4-dihydroquinolin-1(2H)-yl)-5,6-dihydroimidazo[1,5-a]pyrazin-7(8H)-yl)ethan-1-one | 498/499 | 23 |
| 113 | 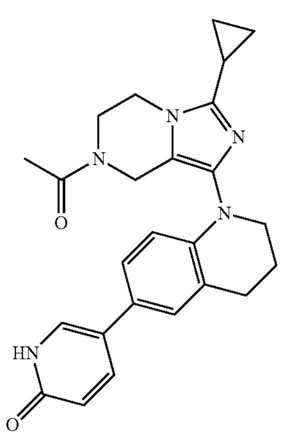 [SMILES: CC(=O)N1CCn2c(C3CC3)nc(N3CCCc4cc(-c5ccc(=O)[nH]c5)ccc43)c2C1] | 5-(1-(7-acetyl-3-cyclopropyl-5,6,7,8-tetrahydroimidazo[1,5-a]pyrazin-1-yl)-1,2,3,4-tetrahydroquinolin-6-yl)-1-methylpyridin-2(1H)-one | 443/444 | 22 |

TABLE 1-continued

Example compounds 41 to 126

| Ex | Structure | IUPAC Name | MWt/ [M + H] | Ex. Method |
|---|---|---|---|---|
| 114 | 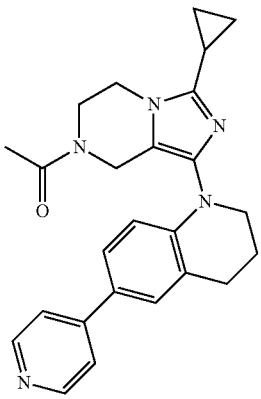 [SMILES: CC(=O)N1CCn2c(C3CC3)nc(N3CCCc4cc(-c5ccncc5)ccc43)c2C1] | 1-(3-cyclopropyl-1-(6-(pyridin-4-yl)-3,4-dihydroquinolin-1(2H)-yl)-5,6-dihydroimidazo[1,5-a]pyrazin-7(8H)-yl)ethan-1-one | 413/414 | 20 |
| 115 | 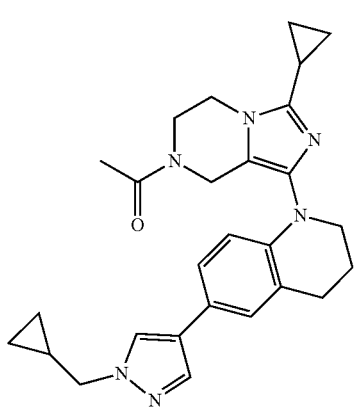 [SMILES: CC(=O)N1CCn2c(C3CC3)nc(N3CCCc4cc(-c5cnn(CC6CC6)c5)ccc43)c2C1] | 1-(3-cyclopropyl-1-(6-(1-(cyclopropylmethyl)-1H-pyrazol-4-yl)-3,4-dihydroquinolin-1(2H)-yl)-5,6-dihydroimidazo[1,5-a]pyrazin-7(8H)-yl)ethan-1-one | 456/457 | 23 |
| 116 | 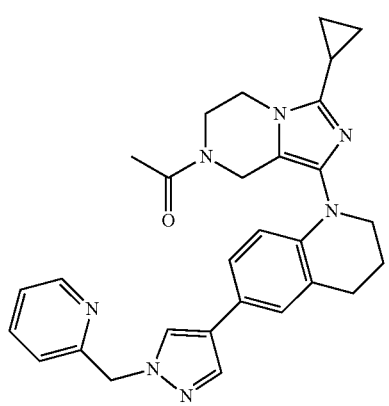 [SMILES: CC(=O)N1CCn2c(C3CC3)nc(N3CCCc4cc(-c5cnn(Cc6ccccn6)c5)ccc43)c2C1] | 1-(3-cyclopropyl-1-(6-(1-(pyridin-2-ylmethyl)-1H-pyrazol-4-yl)-3,4-dihydroquinolin-1(2H)-yl)-5,6-dihydroimidazo[1,5-a]pyrazin-7(8H)-yl)ethan-1-one | 493/494 | 23 |

TABLE 1-continued

Example compounds 41 to 126

| Ex | Structure | IUPAC Name | MWt/ [M + H] | Ex. Method |
|---|---|---|---|---|
| 117 | 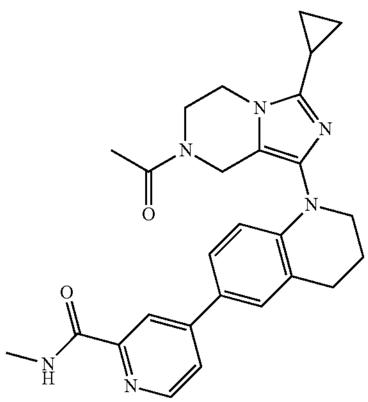 [SMILES: CNC(=O)c1cc(-c2ccc3c(c2)CCCN3c2nc(C3CC3)n3c2CN(C(C)=O)CC3)ccn1] | 4-(1-(7-acetyl-3-cyclopropyl-5,6,7,8-tetrahydroimidazo[1,5-a]pyrazin-1-yl)-1,2,3,4-tetrahydroquinolin-6-yl)-N-methylpicolinamide | 470/471 | 22 |
| 118 | 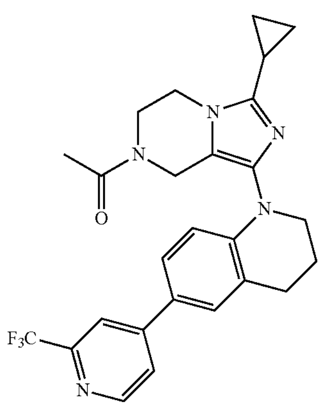 [SMILES: CC(=O)N1CCn2c(C3CC3)nc(N3CCCc4cc(-c5ccnc(C(F)(F)F)c5)ccc43)c2C1] | 1-(3-cyclopropyl-1-(6-(2-(trifluoromethyl)pyridin-4-yl)-3,4-dihydroquinolin-1(2H)-yl)-5,6-dihydroimidazo[1,5-a]pyrazin-7(8H)-yl)ethan-1-one | 481/482 | 19 |
| 119 | 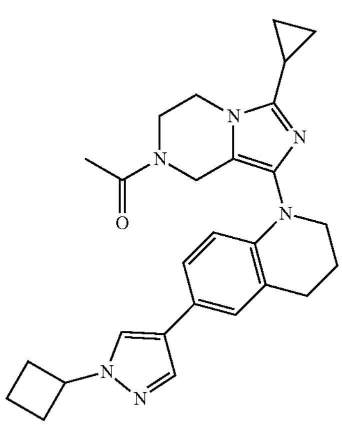 [SMILES: CC(=O)N1CCn2c(C3CC3)nc(N3CCCc4cc(-c5cnn(C6CCC6)c5)ccc43)c2C1] | 1-(1-(6-(1-cyclobutyl-1H-pyrazol-4-yl)-3,4-dihydroquinolin-1(2H)-yl)-3-cyclopropyl-5,6-dihydroimidazo[1,5-a]pyrazin-7(8H)-yl)ethan-1-one | 456/457 | IACS-015726 |

TABLE 1-continued

Example compounds 41 to 126

| Ex | Structure | IUPAC Name | MWt/ [M + H] | Ex. Method |
|---|---|---|---|---|
| 120 | 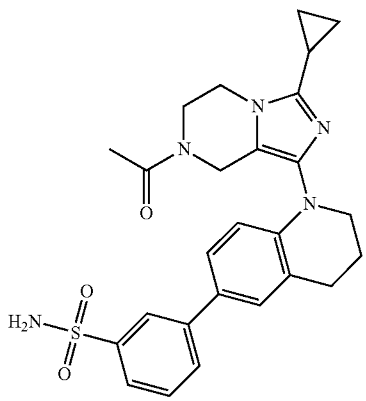 [SMILES: CC(=O)N1CCn2c(C3CC3)nc(N3CCCc4cc(-c5cccc(S(N)(=O)=O)c5)ccc43)c2C1] | 3-(1-(7-acetyl-3-cyclopropyl-5,6,7,8-tetrahydroimidazo[1,5-a]pyrazin-1-yl)-1,2,3,4-tetrahydroquinolin-6-yl)benzenesulfonamide | 491/492 | 21 |
| 121 | 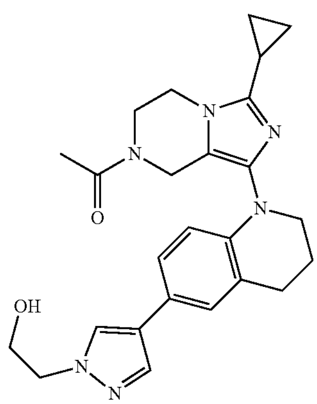 [SMILES: CC(=O)N1CCn2c(C3CC3)nc(N3CCCc4cc(-c5cnn(CCO)c5)ccc43)c2C1] | 1-(3-cyclopropyl-1-(6-(1-(2-hydroxyethyl)-1H-pyrazol-4-yl)-3,4-dihydroquinolin-1(2H)-yl)-5,6-dihydroimidazo[1,5-a]pyrazin-7(8H)-yl)ethan-1-one | 446/447 | 21 |
| 122 | 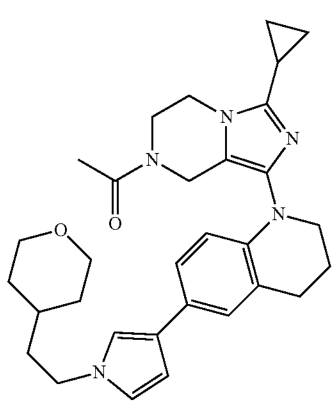 [SMILES: CC(=O)N1CCn2c(C3CC3)nc(N3CCCc4cc(-c5ccn(CCC6CCOCC6)c5)ccc43)c2C1] | 1-(3-cyclopropyl-1-(6-(1-(2-morpholinoethyl)-1H-pyrazol-4-yl)-3,4-dihydroquinolin-1(2H)-yl)-5,6-dihydroimidazo[1,5-a]pyrazin-7(8H)-yl)ethan-1-one | 515/516 | 23 |

TABLE 1-continued

Example compounds 41 to 126

| Ex | Structure | IUPAC Name | MWt/ [M + H] | Ex. Method |
|---|---|---|---|---|
| 123 | 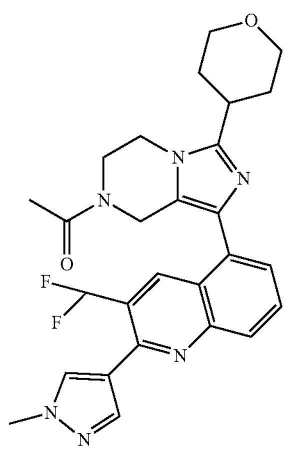 [SMILES: CC(=O)N1CCn2c(C3CCOCC3)nc(-c3cccc4nc(-c5cnn(C)c5)c(C(F)F)cc34)c2C1] | 1-(3-(difluoromethyl)-2-(1-methyl-1H-pyrazol-4-yl)quinolin-5-yl)-N-methyl-3-(tetrahydro-2H-pyran-4-yl)-5,6-dihydroimidazo[1,5-a]pyrazine-7(8H)-carboxamide | 521/522 | 23 |
| 124 | 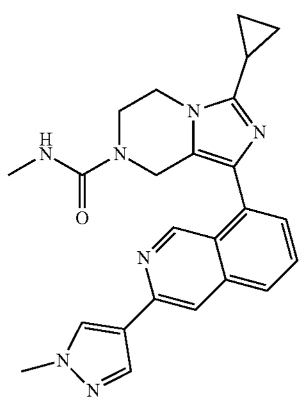 [SMILES: CNC(=O)N1CCn2c(C3CC3)nc(-c3cccc4cc(-c5cnn(C)c5)ncc34)c2C1] | 3-cyclopropyl-N-methyl-1-(3-(1-methyl-1H-pyrazol-4-yl)isoquinolin-8-yl)-5,6-dihydroimidazo[1,5-a]pyrazine-7(8H)-carboxamide | 427/428 | 11 |
| 125 | 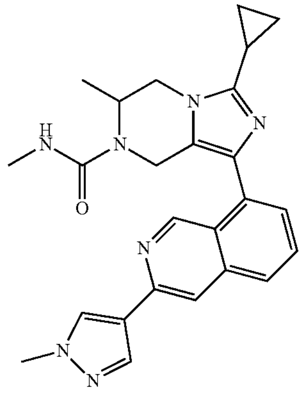 [SMILES: CNC(=O)N1Cc2c(-c3cccc4cc(-c5cnn(C)c5)ncc34)nc(C3CC3)n2CC1C] | 3-cyclopropyl-N,6-dimethyl-1-(3-(1-methyl-1H-pyrazol-4-yl)isoquinolin-8-yl)-5,6-dihydroimidazo[1,5-a]pyrazine-7(8H)-carboxamide | 441/442 | 11 |

TABLE 1-continued

Example compounds 41 to 126

| Ex | Structure | IUPAC Name | MWt/ [M + H] | Ex. Method |
|---|---|---|---|---|
| 126 | 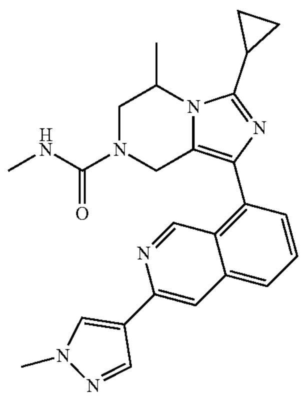 [SMILES: CNC(=O)N1Cc2c(-c3cccc4cc(-c5cnn(C)c5)ncc34)nc(C3CC3)n2C(C)C1] | 3-cyclopropyl-N,5-dimethyl-1-(3-(1-methyl-1H-pyrazol-4-yl)isoquinolin-8-yl)-5,6-dihydroimidazo[1,5-a]pyrazine-7(8H)-carboxamide | 441/442 | 11 |

The activity of the compounds in Examples 1-126 as inhibitors of CBP and BRD4 is illustrated in the following assays. The other compounds listed above, which have not yet been made and/or tested, are predicted to have activity in these assays as well.

Biological Activity Assays

Specific binding of the CBP or BRD4 bromodomain to the acetylated peptide derived from the H4 histone substrate (tetra acetylated H4(1-21) Ac-K5/8/12/16) was measured in absence or presence of inhibitors. The GST tagged bromodomains of CBP (1081-1197) and BRD4 (49-170) were obtained from BPS Bioscience and binding to the biotinylated H4(1-21) Ac-K5/8/12/16 (AnaSpec. 64989) was assessed via AlphaScreen technology (Perkin Elmer).

CBP AlphaScreen assay: 5 nM GST-CBP (1081-1197) and 20 nM biotin-H4(1-21) Ac-K5/8/12/16 (AnaSpec. 64989) were incubated with varying concentrations of CBP inhibitors in 15 µL of buffer containing 50 mM HEPES 7.5, 100 nM NaCl, 1 mM TCEP, and 0.003% Tween-20. After 30 minutes incubation at room temperature, 15 µL of detection buffer (BPS Bio. 33006) containing 7 µg/mL of Glutathione AlphaLisa acceptor beads (Perkin Elmer AL109) and 14 µg/mL of Streptavidin donor beads (Perkin Elmer 676002) was then added to the previous mixture. The reaction was incubated for an additional 2 hours at room temperature, and the AlphaScreen signal was quantified using the Envision Multilabel plate reader. As negative control, GST-CBP (1081-1197) was incubated with the non-acetylated biotin-H4(1-21) peptide (AnaSpec. 62555) and in presence of 0.25% of final DMSO concentration.

BRD4 AlphaScreen assay: The binding of 2.5 nM of BRD4(49-170) to 10 nM biotin-H4(1-21) Ac-K5/8/12/16 (AnaSpec. 64989) was assessed following the same procedure described for the CBP assay. The standard dose response curves were fitted by Genedata Screener software using the variable-slope model:

$$\text{Signal} = \text{Signal}_{negative\ control} + (\text{Signal}_{DMSO\ control} - \text{Signal}_{negative\ control})/(1+(IC_{50}/\text{Dose})^{\text{Hill slope}}).$$

Only Signal and Dose in the equation were treated as known values.

Results are given below in Table 1, which shows that the instant compounds inhibit CBP and are selective over BRD4.

TABLE 1

| | Biological Activity | |
|---|---|---|
| Ex. No | Avg CBP IC50, nM | Avg BRD4 IC50, nM |
| 1 | 47 | >10000 |
| 2 | 3 | 8900 |
| 3 | 5 | >10000 |
| 4 | 1262 | 15440 |
| 5 | 106 | 13903 |
| 6 | 24 | 8210 |
| 7 | 9 | >10000 |
| 8 | 115 | >10000 |
| 9 | 63 | >10000 |
| 10 | 197 | >10000 |
| 11 | 26 | >10000 |
| 12 | 341 | >10000 |
| 13 | 1382 | >10000 |
| 14 | 286 | >25000 |
| 15 | 46 | 21939 |
| 16 | 392 | >25000 |
| 17 | 1 | 5093 |
| 18 | 50 | >25000 |
| 19 | 5 | >25000 |
| 20 | 18 | 25000 |
| 21 | 20 | >25000 |
| 22 | 3 | 7060 |
| 23 | 1 | 3852 |
| 24 | 6 | 9106 |
| 25 | 57 | 15927 |
| 26 | 181 | >25000 |
| 27 | 1217 | >25000 |
| 28 | 33 | 18642 |
| 29 | 324 | >25000 |
| 30 | 1185 | >25000 |
| 31 | 611 | 7466 |
| 32 | 439 | >10000 |
| 33 | 40 | >10000 |
| 34 | 37 | 17305 |
| 35 | 79 | >25000 |
| 36 | 38 | 9713 |
| 37 | 16 | 14320 |
| 38 | 32 | 19824 |
| 39 | 33 | 14840 |
| 40 | 2 | 4779 |
| 41 | 4487 | >25000 |

TABLE 1-continued

Biological Activity

| Ex. No | Avg CBP IC50, nM | Avg BRD4 IC50, nM |
|---|---|---|
| 42 | 4261 | >25000 |
| 43 | 3191 | >25000 |
| 44 | 47 | 12148 |
| 45 | 124 | 6294 |
| 46 | 52 | >10000 |
| 47 | 153 | >10000 |
| 48 | 36 | >10000 |
| 49 | 67 | >10000 |
| 50 | 12 | >10000 |
| 51 | 149 | >10000 |
| 52 | 20 | >10000 |
| 53 | 176 | >10000 |
| 54 | 141 | >10000 |
| 55 | 18 | >10000 |
| 56 | 22 | >10000 |
| 57 | 1 | 5967 |
| 58 | 49 | >10000 |
| 59 | 5 | 18997 |
| 60 | 18 | 15810 |
| 61 | 25 | 13867 |
| 62 | 5 | 13494 |
| 63 | 14 | 23575 |
| 64 | 4 | 22766 |
| 65 | 4 | 13732 |
| 66 | 74 | >25000 |
| 67 | 36 | >25000 |
| 68 | 16 | >25000 |
| 69 | 17 | 10129 |
| 70 | 12 | 12289 |
| 71 | 38 | 13379 |
| 72 | 54 | 17139 |
| 73 | 40 | >25000 |
| 74 | 4 | >25000 |
| 75 | 22 | >25000 |
| 76 | 3 | 11884 |
| 77 | 45 | >25000 |
| 78 | 1 | 13471 |
| 79 | 6 | 14775 |
| 80 | 2 | 11947 |
| 81 | 11 | 10494 |
| 82 | 3 | 17862 |
| 83 | 16 | 19390 |
| 84 | 4 | 12111 |
| 85 | 15 | 18130 |
| 86 | 2 | 11188 |
| 87 | 3 | 8490 |
| 88 | 3 | 11322 |
| 89 | 2 | 6840 |
| 90 | 4 | 10171 |
| 91 | 48 | 22422 |
| 92 | 10 | >25000 |
| 93 | 2 | >25000 |
| 94 | 12 | >25000 |
| 95 | 1 | 3475 |
| 96 | 2 | 5539 |
| 97 | 1 | 3323 |
| 98 | 25 | 9579 |
| 99 | 11 | 8707 |
| 100 | 4 | 7949 |
| 101 | 19 | 24678 |
| 102 | 19 | >25000 |
| 103 | 147 | >25000 |
| 104 | 107 | 3734 |
| 105 | 15 | 7529 |
| 106 | 286 | >25000 |
| 107 | 510 | >25000 |
| 108 | 148 | 14329 |
| 109 | 349 | 13786 |
| 110 | 185 | 11187 |
| 111 | 1449 | 10288 |
| 112 | 270 | 20984 |
| 113 | 193 | 3459 |
| 114 | 615 | >25000 |
| 115 | 679 | >25000 |
| 116 | 1280 | >25000 |

TABLE 1-continued

Biological Activity

| Ex. No | Avg CBP IC50, nM | Avg BRD4 IC50, nM |
|---|---|---|
| 117 | 739 | >25000 |
| 118 | 715 | >25000 |
| 119 | 313 | >25000 |
| 120 | 358 | >25000 |
| 121 | 576 | >25000 |
| 122 | 500 | >25000 |
| 123 | 19 | >25000 |
| 124 | 2 | 6481 |
| 125 | 19 | >10000 |
| 126 | 39 | 17129 |

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this disclosure, and without departing from the spirit and scope thereof, can make various changes and modifications of the disclosure to adapt it to various usages and conditions.

What is claimed is:

1. A compound of structural Formula III

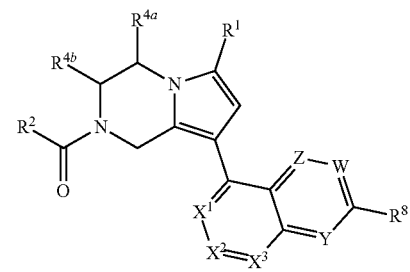

(III)

or a salt thereof, wherein:
$R^1$ is chosen from alkyl, cycloalkyl and heterocycloalkyl;
$R^2$ is chosen from —$CH_3$, —$CH_2F$, —$NH_2$, —$NHCH_3$, and —$OCH_3$;
$R^{4a}$ and $R^{4b}$ are H;
W is chosen from $C(R^{7a})$ and N;
$X^1$ is independently chosen from $C(R^{7b})$ and N;
$X^2$ and $X^3$ are independently chosen from C(H) and N;
Y and Z are independently chosen from C(H) and N;
$R^{7a}$ is chosen from H, alkyl, alkoxy, cyano, carboxy, halo, haloalkyl, hydroxy, and OXO;
$R^{7b}$ is chosen from H and fluoro;
$R^8$ is chosen from aryl, heteroaryl, and heterocycloalkyl, and is optionally substituted with 1, 2, or 3 $R^{10}$ groups; and
each $R^{10}$ is independently chosen from alkyl, cyclopropyl, methoxy, cyano, halo, difluoromethyl, trifluoromethyl, trifluoromethoxy, hydroxy, $CONH_2$, and $CONHCH_3$.

2. The compound as recited in claim 1, or a salt thereof, wherein:
$X^1$ is $C(R^{7b})$;
$X^2$ and $X^3$ are C(H); and
Z is C(H).

3. The compound as recited in claim 2, or a salt thereof, wherein $R^8$ is a monocyclic aryl or heteroaryl, and is optionally substituted with 1 or 2 $R^{10}$ groups.

4. The compound as recited in claim 3, or a salt thereof, wherein each $R^{10}$ is independently chosen from alkyl, cyclopropyl, methoxy, cyano, halo, difluoromethyl, trifluoromethyl, trifluoromethoxy, hydroxy, $CONH_2$, and $CONHCH_3$.

5. The compound as recited in claim 4, or a salt thereof, wherein $R^8$ is 5-membered monocyclic heteroaryl, and is optionally substituted with 1 or 2 $R^{10}$ groups.

6. The compound as recited in claim 5, or a salt thereof, wherein $R^{7a}$ is H.

7. The compound as recited in claim 6, or a salt thereof, wherein $R^{7b}$ is H.

8. The compound as recited in claim 7, or a salt thereof, wherein $R^1$ is chosen from:
—$CH_3$, —$CH(CH_3)_2$,

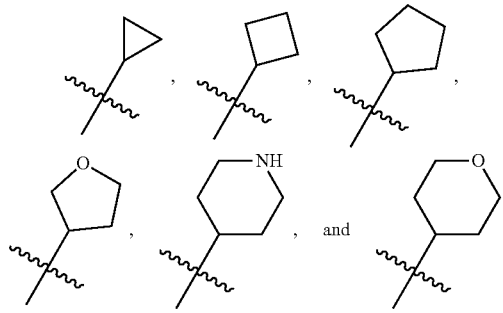

9. The compound as recited in claim 8, or a salt thereof, wherein $R^8$ is chosen from pyrrolyl, isoxazolyl, thiazolyl, imidazolyl, and pyrazolyl, any of which is optionally substituted with 1 or 2 $R^{10}$ groups.

10. The compound as recited in claim 9, or a salt thereof, wherein $R^8$ is substituted with 1 $R^{10}$ group.

11. The compound as recited in claim 10, or a salt thereof, wherein $R^8$ is

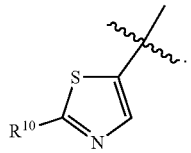

12. The compound as recited in claim 11, or a salt thereof, wherein $R^{10}$ is alkyl.

13. The compound as recited in claim 12, or a salt thereof, wherein $R^{10}$ is methyl.

14. The compound as recited in claim 12, or a salt thereof, wherein:

W is N; and
Y is C(H).

15. The compound as recited in claim 14, or a salt thereof, wherein $R^{10}$ is methyl.

16. The compound as recited in claim 12, or a salt thereof, wherein:
W is $C(R^{7a})$; and
Y is N.

17. The compound as recited in claim 16, wherein $R^{7a}$ is haloalkyl.

18. The compound as recited in claim 16, or a salt thereof, wherein $R^{10}$ is methyl.

19. The compound as recited in claim 14, wherein $R^2$ is —$CH_3$.

20. The compound as recited in claim 16, wherein $R^2$ is —$NHCH_3$.

21. A method of treatment of a cancer chosen from acute leukemia, acute lymphocytic leukemia, acute myelocytic leukemia, acute T-cell leukemia, breast cancer, chronic leukemia, chronic lymphocytic leukemia, chronic myelocytic leukemia, chronic myelogenous leukemia, diffuse large B-cell lymphoma, erythroleukemia, estrogen-receptor positive breast cancer, leukemia, lung cancer, lymphoblastic leukemia, lymphoma, lymphoid malignancies of T-cell or B-cell origin, melanoma, multiple myeloma, myelogenous leukemia, myeloma, non-small cell lung cancer, ovarian cancer, prostate cancer, renal cell carcinoma, and small cell lung cancer, comprising the administration of a therapeutically effective amount of a compound as recited in claim 1 to a patient in need thereof, wherein the treatment comprises the prevention of progression of the disease to a later stage.

22. The method as recited in claim 21, wherein said cancer is chosen from lung cancer, breast cancer, and melanoma.

23. The method as recited in claim 21, further comprising the administration of a cytotoxic agent.

24. The method as recited in claim 23, wherein said cytotoxic agent is chosen from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A, inhibitors of fatty acid biosynthesis, cell cycle signaling inhibitors, HDAC inhibitors, proteasome inhibitors, and inhibitors of cancer metabolism.

25. The method as recited in claim 21, further comprising the administration of a non-chemical method of cancer treatment.

26. The method as recited in claim 25, wherein said non-chemical method of cancer treatment is chosen from surgery, radiation therapy, thermoablation, focused ultrasound therapy, and cryotherapy.

* * * * *